US005605896A

United States Patent [19]
Leonardi et al.

[11] Patent Number: 5,605,896
[45] Date of Patent: *Feb. 25, 1997

[54] BICYCLIC HETEROCYCLIC DERIVATIVES HAVING $\alpha_1$ ADRENERGIC AND $5HT_{1A}$ ACTIVITIES

[75] Inventors: Amedeo Leonardi, Milan; Gianni Motta, Barlassina; Carlo Riva, Varese; Rodolfo Testa, Milan, all of Italy

[73] Assignee: Recordati S.A., Chemical and Pharmaceutical Company, Chiasso, Switzerland

[ * ] Notice: The term of this patent shall not extend beyond the expiration date of Pat. No. 5,474,994.

[21] Appl. No.: 299,188

[22] Filed: Aug. 31, 1994

Related U.S. Application Data

[63] Continuation-in-part of Ser. No. 67,861, May 26, 1993, Pat. No. 5,474,994, which is a continuation-in-part of Ser. No. 888,775, May 26, 1992, Pat. No. 5,403,842.

[30] Foreign Application Priority Data

Feb. 25, 1992 [IT] Italy .................................. MI92A0408

[51] Int. Cl.[6] ...................... C07D 243/08; C07D 413/00; C07D 215/16; C07D 235/04; A61K 31/395; A61K 31/47; A61K 31/38; A61K 31/335

[52] U.S. Cl. ........................ 514/218; 546/153; 546/169; 546/170; 546/171; 546/176; 546/174; 546/175; 546/196; 546/202; 546/204; 548/304.4; 548/491; 549/23; 549/49; 549/362; 549/398; 549/401; 549/403; 549/405; 514/234.5; 514/232.2; 514/233.5; 514/253; 514/314; 514/414; 514/443; 514/452; 514/394; 514/456; 514/469; 540/575; 544/143; 544/144; 544/146; 544/148; 544/151; 544/153; 544/363; 544/373; 544/376; 544/377

[58] Field of Search ........................ 540/575; 544/143, 544/144, 146, 148, 151, 153, 363, 373, 376, 377; 546/153, 169, 170, 121, 176, 174, 175, 196, 202, 204; 548/304.4, 991; 549/23, 49, 362, 398, 401, 403, 405; 514/218, 234.5, 232.2, 233.5, 253, 314, 414, 443, 452, 394, 456, 469

[56] References Cited

U.S. PATENT DOCUMENTS

| | | | |
|---|---|---|---|
| 2,921,070 | 1/1960 | Da Re | 260/247.2 |
| 3,277,094 | 10/1966 | Werner | 260/268 |
| 3,350,411 | 10/1967 | Da Re | 260/345.2 |
| 3,810,896 | 5/1974 | Witte et al. | 260/268 BC |
| 4,089,969 | 5/1978 | Muchowski et al. | 424/274 |
| 4,495,198 | 1/1985 | Wu | 514/456 |
| 4,539,318 | 9/1985 | Baldwin et al. | 514/222 |
| 4,668,804 | 5/1987 | Wu | 549/403 |
| 4,668,805 | 5/1987 | Wu | 549/403 |
| 4,684,651 | 8/1987 | Kikumoto et al. | 514/253 |
| 4,797,498 | 1/1989 | Albrecht et al. | 549/403 |
| 4,940,711 | 7/1990 | Nardi et al. | 514/255 |
| 5,091,182 | 2/1992 | Ong et al. | 424/400 |
| 5,403,847 | 4/1995 | Gluchowski | 514/318 |

FOREIGN PATENT DOCUMENTS

| | | |
|---|---|---|
| 38591/93 | 2/1994 | Australia . |
| 0017352 | 10/1980 | European Pat. Off. . |
| 0072620 | 7/1982 | European Pat. Off. . |
| 0064165 | 11/1982 | European Pat. Off. . |
| 0081621 | 6/1983 | European Pat. Off. . |
| 0100250 | 2/1984 | European Pat. Off. . |
| 0104614 | 4/1984 | European Pat. Off. . |
| 0107804 | 5/1984 | European Pat. Off. . |
| 0108986 | 5/1984 | European Pat. Off. . |
| 0206802 | 12/1985 | European Pat. Off. . |
| 0190015 | 8/1986 | European Pat. Off. . |
| 0288077 | 12/1987 | European Pat. Off. . |
| 0270342 | 6/1988 | European Pat. Off. . |
| 0333676 | 9/1989 | European Pat. Off. . |
| 0343961 | 11/1989 | European Pat. Off. . |
| 0364350 | 4/1990 | European Pat. Off. . |
| 0372305 | 6/1990 | European Pat. Off. . |
| 0430693 | 6/1991 | European Pat. Off. . |
| 0571243A1 | 11/1993 | European Pat. Off. . |
| 0435749 | 7/1991 | France . |
| 0401653 | 12/1990 | Germany . |
| 1166595 | 10/1969 | Great Britain . |
| 2073738A | 10/1981 | Great Britain . |
| 2161807 | 1/1986 | Great Britain . |
| 2193633 | 2/1988 | Great Britain . |
| 84143670/23 | 8/1984 | Japan . |
| 84143671/23 | 8/1984 | Japan . |
| 86064962/10 | 4/1986 | Japan . |
| 86322242/49 | 12/1986 | Japan . |
| 87104761/15 | 6/1987 | Japan . |
| 90019323/03 | 4/1990 | Japan . |
| 91055570/08 | 6/1991 | Japan . |
| 91153784/21 | 9/1991 | Japan . |
| 92064865/08 | 7/1992 | Japan . |
| 92077567/10 | 8/1992 | Japan . |
| WO91/19707 | 12/1991 | WIPO . |
| WO91/18597 | 12/1991 | WIPO . |
| WO9201-681 | 2/1992 | WIPO . |
| WO95/05169 | 2/1995 | WIPO ............................ A61K 31/35 |

OTHER PUBLICATIONS

Testa et al. "Rec 15/2739 (SB 216469) a novel prostate selective $\alpha$-adrenoceptor antagonist", *Pharmacology of Adrenoceptors*, Jul. 21–23, 1994.

G. Sironi et al. "Rec 15/2739, a new $\alpha_1$-antagonist selective for the lower urinary tract: in vivo studies", *Neurourology and Urodynamics* 13(4), pp. 471–474, 1994,–(with poster presentation).

A. Leonardi, "Synthesis and pharmacological evaluation of new 4H–1–benzopyran derivates, uro–selective $\alpha_1$–adrenoceptor antagonists", *XIIIth International Symposium on Medicinal Chem.* –Paris–Sep. 19–23, 1994, p. 152–Abstract.

(List continued on next page.)

*Primary Examiner*—Matthew V. Grumbling
*Attorney, Agent, or Firm*—Darby & Darby

[57] ABSTRACT

This invention provides bicyclic heterocyclic derivatives and their pharmaceutically acceptable salts useful for the treatment of hypertension, urethral and lower urinary tract contractions, and other disorders. The compounds are also useful for binding $\alpha_1$-adrenergic and $5HT_{1A}$ serotonergic receptors, in vitro or in vivo.

24 Claims, No Drawings

OTHER PUBLICATIONS

G. Motta et al, "Structural modification at the basic moiety of Rec 15/2739, a novel uro–selective $\alpha_1$ –adrenoceptor antagonist", *XIIIth International Symposium on Medicinal Chem.–Paris*–Sep. 19–23, 1994, p. 153–Abstract.

R. Testa et al., "Rec 15/2739, a novel $\alpha_{-1}$-antagonist selective for the lower urinary tract" *27° Congresso Nazionale della Società Italiana di Farmacologia, Torino*, 25–29 Sep. 1994,–Abstract.

Atassi et al., *Eur. J. Med. Chem.*, 20:393–402 (1985).
Augstein et al., *J. Med. Chem.*, 8:356–367 (1965).
Bagli, *J. Med. Chem.*, 19:876–882 (1976).
Bonte et al., *Eur. J. Med. Chem.*, 25:361–368 (1990).
Carroll et al., *J. of Med. Chem.*, 19(9): 1111–1119 (1976).
Cunico et al., *Org. Chem.*, 48:2780–2782 (1983).
Da Re, P. et al., *Jahrg*, 99:1962–1965, (1966).
Da Re, *Ann. Chim.*, pp. 506–513 (1962).
Da Re et al., *Eur. J. Med. Chem.*, 13;387–388 (1978).
Da Re, *Il Farmaco–Ed. Sc.*, vol. XI:670–675 (1960).
Da Re et al., *J. Med. Chem.*, 2(3): 263–269 (1960).
Engel et al., *J. Med. Chem.*, 33:2976–2981 (1990).
Farina et al., *Biochem. Pharm.*, 31:1887–1892 (1982).
Farina et al., *Biochem. Pharm.*, 35:209–215 (1986).
Frishman et al., *Cardiovascular Pharmacotherapy II*, 72(2):427–440 (1988).
Garcia–Sainz et al., *Biochemical and Biophysical Research Communications*, 186(2):760–767 (1992).
Gartside et al., *European Journal of Pharmacology*, 191:391–400 (1990).
Grewal et al., *J. Pharmac. Exp. Therap.*, 160(2):268–276 (1968).
Guarneri et al. *Neurourol. Urodyn.*, 11:340–41 (1992).
Hamon et al., *Annals New York Academy of Sciences*, pp. 114–131 (1960).
Hartig et al., *Drug Delivery Res.*, 26(3):215–224 (1992).
Laubie et al., *Arzheim–Forsch*, 19:1820–1826 (1969).
Leclerc et al., *Arzheim–Forsch Drug. Res.*, 35:1357–1367 (1985).
Lyon, R. A. et al. *J. Med. Chem.*, 29:630–634, (1986).
Martin, G. E. et al. *J. Med. Chem.*, 32:1052–1056, (1989).
Mielke et al., *Curr. Therap Res.*, 15(6):324–326 (1973).
Mull et al., *J. Med. Chem.*, 8:332–338 (1965).
Overberger et al., *J.A.C.S.*, 71:2661–2666 (1949).
Perez et al., *Molecular Pharmacology*, 40:876–883 (1991).
Ratouis et al., *J. Med. Chem.*, 8:271–273 (1965).
Ratouis et al., *J. Med. Chem.*, 8:104–107 (1965).
Romero et al., *Annual Reports in Medical Chemistry*, 27(3):21–30 (1992).
Saari et al., *J. Med. Chem.*, 33:97–101 (1990).
Silvestrini et al., *Arzheim–Forsch./Drug. Res.*, 32:668–673 (1982).
ten Hoeve, W. et al. *J. Org. Chem.*, 58:5101–5105, (1993).
Traber et al., *TIPS*, 8:432–437 (1987).
Uneyama et al., *Bull. Chem. Soc. Jpn.*, 58:2361–2365 (1985).
Valenti et al., *Boll. Chim. Farm.*, 114:294–300 (1975).
Vizi et al., *Medicinal Research Reviews*, 6:431–449 (1986).
Wu et al., *J. Med. Chem.*, 35:3519–3525 (1992).
Zifa et al., *Pharmacological Reviews*, 44(3): 401–458 (1992).
*Drugs of the Future*, 6:346–347 (1981).
*Chemical Abstracts* 55:5534a (1960).
*Chemical Abstracts* 59:2832b (1963).
*Chemical Abstracts* 63:11589h (1965).
*Chemical Abstracts* 66:37693s (1967).
*Chemical Abstracts* 66:85664e (1967).
*Chemical Abstracts* 67:64435m (1967).
*Chemical Abstracts* 74:22698p (1971).
*Chemical Abstracts* 76:14577z (1972).
*Chemical Abstracts* 78:584606 (1973).
*Chemical Abstracts* 98:107161d (1983).
*Chemical Abstracts* 83:131584c (1975).
*Chemical Abstracts* 84:59400u (1976).
*Chemical Abstracts* 100:103390q (1984).
*Chemical Abstracts* 104:109686v (1985).
*Chemical Abstracts* 104:19499g (1985).
*Chemical Abstracts* 105:78821z (1986).
*Chemical Abstracts* 107:236661v (1987).
*Chemical Abstracts* 108:15674v (1988).
*Chemical Abstracts* 108:37647r (1988).
*Chemical Abstracts* 108:150298r (1988).
*Chemical Abstracts* 109:128816g (1988).
*Chemical Abstracts* 110:135063h (1989).
*Chemical Abstracts* 111:153607p (1989).
*Chemical Abstracts* 112:216577x (1990).
*Chemical Abstracts* 113:109332n (1990).
*Chemical Abstracts* 116:262282c (1992).
*Chemical Abstracts* 59:10006g (1963).
*Chemical Abstracts* 81:20780e (1974).
*Derwent Abstract*, C93–164399 (1993).

BICYCLIC HETEROCYCLIC DERIVATIVES HAVING $\alpha_1$ ADRENERGIC AND $5HT_{1A}$ ACTIVITIES This is a continuation-in-part of U.S. patent application Ser. No. 08/067,861 filed May 26, 1993 now U.S. Pat. No. 5,474,994 which is a continuation-in-part of U.S. patent application Ser. No. 07/888,775, filed May 26, 1992 now U.S. Pat. No. 5,403,842. This invention relates to bicyclic heterocyclic derivatives, to pharmaceutical compositions containing them and to uses for such derivatives and compositions.

BACKGROUND OF THE INVENTION

Flavoxate, which is 8-(2-piperidinoethoxycarbonyl)-3-methyl-4-oxo-2-phenyl-4H-1-benzopyran, and has the formula

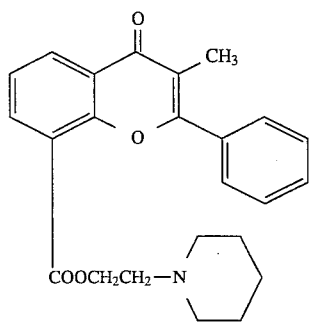

is used as a pharmaceutical agent for urinary tract disturbances as it possesses a smooth muscle relaxing activity attributable to its calcium antagonist activity. This activity is exerted on the bladder dome smooth muscles or can be related to an effect on the micturition center in the central nervous system.

The compounds of the invention, described below, essentially include more complex amino moieties in place of the piperidine group. Further changes include alternatives to the ethoxycarbonyl group which links the amino moiety to the benzopyran ring, alternative 2-, 3-, 6- and 7-substitution patterns in the benzopyran ring, replacement of the ring heteroatom by a sulfur atom or by a sulfinyl or sulfonyl group, or by a nitrogen atom or an amino group, and/or 2,3-hydrogenation of the benzopyran ring. Further variations of the heterocyclic ring, are described below. These structural variations give the new compounds the ability to interact with different biological systems, as supported by the affinity of the new compounds for the $\alpha_1$-adrenergic and $5HT_{1A}$-serotoninergic receptors. Flavoxate is practically devoid of affinity for these receptors.

SUMMARY OF THE INVENTION

In one aspect, the invention is directed to compounds of Formula I:

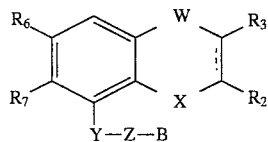

wherein

---- represents a single or double bond;

X represents a nitrogen, oxygen or sulfur atom, or an amino or alkylamino group, a sulfinyl or sulfonyl group;

W represents a carbonyl, thiocarbonyl, hydroxymethylene, or a methylene group or a bond;

when X is nitrogen and W is a methylene, the fused rings represent a quinoline; when X=NH and W=CO, the tautomer X=N and W=C(OH) is also considered to be included in the foregoing Formula I);

$R_2$ represents a hydrogen atom or an alkyl, alkenyl, alkynyl, carbocyclic or heterocyclic group, each of which groups may optionally be substituted by one or more substituents selected from the group consisting of alkyl, cyano, hydroxy, alkoxy, halogen, phenyl, phenoxy, trifluoromethyl, nitro, amino, acylamino, alkylamino, dialkylamino, alkylsulfonylamino and benzoyl; or $R_2$ itself represents a trifluoromethyl or an aroyl group;

$R_3$ represents a hydrogen atom or an alkyl, hydroxyalkyl, alkyl-O—$R_4$ phenyl, hydroxy, or O—$R_4$, wherein $R_4$ represents an alkyl group optionally substituted with an aryl group;

$R_6$ represents a hydrogen or halogen atom or a nitro, amino, acylamino, alkylsulfonylamino, alkylamino, dialkylamino, cyano, hydroxy, alkoxy or alkyl group;

$R_7$ represents a hydrogen atom or an alkoxy group;

Y represents one of the following groups, each of which is depicted with its left hand end being the end which attaches to the heterobicyclic ring and its right hand end being the end which attaches to the group Z:

| | |
|---|---|
| —CO—, | (Y1) |
| —COO—, | (Y2) |
| —CONH—, | (Y3) |
| —CON(CH$_3$)—, | (Y4) |
| —CON(OH)—, | (Y5) |
| —CH(OH)—, | (Y6) |
| —CH(OAlkyl)—, | (Y7) |
| —CH=CH—, | (Y8) |
| —CH=CH—COO—, | (Y9) |
| —CH=CH—CONH—, | (Y10) |
| —CH=NO—, | (Y11) |
| —CH$_2$—, | (Y12) |
| —CH$_2$COO—, | (Y13) |
| —CH$_2$CONH—, | (Y14) |
| —CH$_2$NH—, | (Y15) |
| —CH$_2$N(CH$_3$)—, | (Y16) |
| —CH$_2$N(COCH$_3$)—, | (Y17) |
| —CH$_2$N(CONH$_2$)—, | (Y18) |
| —CH$_2$NHCO—, | (Y19) |
| —CH$_2$N(CH$_3$)CO—, | (Y20) |
| —CH$_2$NH—CONH—, | (Y21) |

-CH₂NHSO₂—, (Y22)

-CH₂O—, (Y23)

-CH₂S—, (Y24)

-CH₂SO—, (Y25)

-CH₂SO₂—, (Y26)

-CH₂SO₂NH—, (Y27)

-CH₂SO₂N(CH₃)—, (Y28)

-NH—, (Y29)

-N(CH₃)—, (Y30)

-N(COCH₃)—, (Y31)

-N(CONH₂)—, (Y32)

-NHCO—, (Y33)

-N(CH₃)CO—, (Y34)

-NH-CONH—, (Y35)

-NHSO₂—, (Y36)

-O—, (Y37)

-S—, (Y38)

-SO—, (Y39)

-SO₂—, (Y40)

-SO₂NH—, (Y41)

-SO₂N(CH₃)—, (Y42)

-CONHO—, (Y43)

-CON(COCH₃)—, (Y44)

-CSNH—, (Y45)

-CSN(CH₃)—, (Y46)

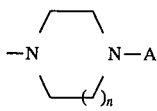 (Y47)

-NHCOO—, (Y48)

and

-COS— (Y49)

Z represents a linear or branched chain alkylene group having from 1 to 6 carbon atoms and optionally having one hydroxy substituent; and B represents one of the following groups:

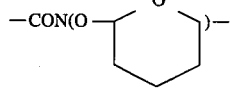 (B1)

wherein n is 1 or 2 and A represents a phenyl group substituted by one or more substituents (preferably at position 2) selected from the group consisting of alkoxy, alkyl, halogen, hydroxy, or A represents a 2-pyrimidinyl group or a bicyclic ring of formula

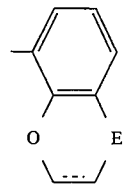

where --- represents a single or double bond and E represents an oxygen atom or a bond;

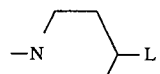 (B2)

wherein L represents one or two groups selected among phenyl, 4-fluorobenzoyl or a 2-oxo-1-benzimidazolinyl group or a group of the formula $(CH_2)_n$—O—A wherein n=0, 1, or 2 and A has the same meaning defined under B1;

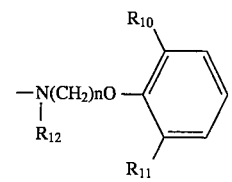 (B3)

wherein each of $R_{10}$ and $R_{11}$ independently represents a hydrogen atom or an alkoxy or alkylthio group, $R_{12}$ represents a hydrogen atom or an alkyl group and n is 2 or 3,

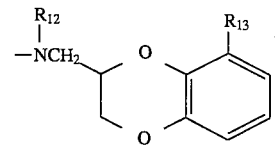 (B4)

wherein $R_{12}$ has the meaning defined under B3 and $R_{13}$ represents a hydrogen atom or an alkoxy group; and

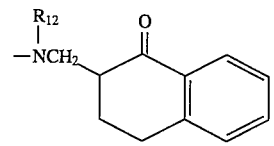 (B5)

wherein $R_{12}$ has the meaning defined under B3.

The invention further includes prodrugs of the formula I compounds, e.g., the derivatives of compounds of formula I bearing reactive groups such as NH, NH₂ and in particular OH (i.e., at positions W, $R_2$, $R_3$, $R_6$, Z, $B_1$, $B_2$) prepared for various purposes, e.g., to improve the pharmaco-kinetic properties (adsorption, distribution, metabolism, plasmatic half-life, etc.) of said compounds of formula I, which can be administered in this "masked" or prodrug form and are liberated, exerting their pharmacological action, in mammals receiving them. Examples of these prodrug derivatives have the following structure (Compound of Formula I)-OC(O,S)-J-F wherein J is a bond, an oxygen or sulfur atom, or a NH group, F represents an alkyl group (optionally containing hetero atoms such as O, S, N or substituted nitrogen), a carbocyclic group or heterocyclic group, optionally substituted with amino, alkylamino, dialkylamino, dialkylaminoalkyl, carboxy, alkoxycarbonyl, carboxamido.

Preferably, J is a bond and F is $CH_3$, $(CH_3)_3C$, $CH_3(CH_2)_3$, B'-$CH_2$-phenyl, B'-alkyl, B'-CO-alkyl, HOCO-alkyl, alkyl-OCO-alkyl, where B' represents a dialkylamino group or a cyclic amino group, optionally containing other heteroatoms such as N, O or S.

Also included in the invention are derivatives having the formula:

(Compound I)-OP(O)(OAlkyl)$_2$

Other examples of prodrug derivatives are those obtained by the derivatization of "acidic" NH groups (Ny) such as those present in Y3, Y10, Y14, Y19, Y22, Y27, Y33, Y36 and Y41, yielding derivatives having the formula:

(Compound I)-Ny-CH(Z)-O-C(O,S)-J-F wherein Z represents hydrogen atom or alkyl, phenyl or trichloromethyl group and J and F have the same meaning and preferred meaning as described above.

Additional prodrug examples are derivatives of the formula:

(Compound I)-Ny-CH$_2$-B' wherein B' has the same meaning as above.

The invention also includes the enantiomers, diastereoisomers, N-oxides and pharmaceutically acceptable salts of these compounds, as well as metabolites of these compounds having the same type of activity (hereafter sometimes referred to as "active metabolites" and prodrugs of said "active metabolites").

The invention further provides pharmaceutical compositions comprising a compound of Formula I or a prodrug, a metabolite, an enantiomer, diastereoisomer, N-oxide or pharmaceutically acceptable salt of such a compound or prodrug, in admixture with a pharmaceutically acceptable diluent or carrier.

In another aspect, the present invention is directed to methods for preventing contractions (including noradrenaline-related contractions) of the urethra and lower urinary tract, selectively preventing said contractions (without substantially affecting blood pressure), lowering blood pressure, and preventing potassium ion induced contractions of the bladder, all by administering one or more selected compounds of the Formula I to a mammal (including a human) in need of such treatment in an amount or amounts effective for the particular use.

In yet another aspect, the invention is directed to methods for blocking $\alpha 1$ and/or 5-HT$_{1A}$ receptors, by delivering to the environment of said receptors, e.g., to the extracellular medium (or by administering to a mammal possessing said receptors) an effective amount of a compound of the invention.

DETAILED DESCRIPTION OF THE INVENTION

All patents, patent applications, and literature references cited in this application are incorporated by reference in their entirety.

The adrenergic antagonistic activity of compounds of the invention renders them useful as agents acting on body tissues particularly rich in $\alpha_1$-adrenergic receptors (such as blood vessels, prostate, urethra, etc.). Accordingly, antiadrenergic compounds within the invention established as such on the basis of their receptor binding profile, can be useful therapeutic agents for the treatment, for example, of hypertension and of micturition problems associated with obstructive disorders of the lower urinary tract, including but not limited to benign prostatic hypertrophy (BPH).

The serotonergic activity of compounds within the present invention renders them useful as agents acting on tissues, particularly in the central nervous system, where 5HT$_{1A}$ receptors are functioning. 5HT$_{1A}$ receptors are believed to regulate the action and release of serotonin as well as the release of other neuromediators and are found both pre- and post-synaptically. The compounds of the invention have biological activity in blocking binding between these receptors and their various specific ligands (e.g., serotonin). Accordingly, the compounds of the invention that interact with the 5HT$_{1A}$ receptor (established as such on the basis of their receptor-binding profile) are useful for the treatment of anxiety disorders and depression.

Surprisingly, compounds within the invention (especially those displaying affinity for both the $\alpha_1$-adrenergic and the 5HT$_{1A}$ serotoninergic receptors) show high selectivity for the mammalian lower urinary tract, i.e., they are substantially more active in antagonizing urethral contractions than in lowering blood pressure. On the contrary, known $\alpha 1$-antagonists, such as prazosin(1-(4-amino-6,7-dimethoxy-2-quinazolinyl)-4-(2-furoyl)piperazine; GB 1,156,973) do not exhibit such selectivity (and in fact cause hypotension as a most common side-effect) while flavone derivatives structurally similar to flavoxate, such as terflavoxate (1,1-dimethyl-2-(1-piperidinyl)ethyl 3-methyl-4-oxo-2-phenyl-4H-1-benzopyran-8-carboxylate hydrochloride; EP 72 620) have no effect on urethral contractions. (Naturally, those compounds of the invention that are not selective for the lower urinary tract are preferred as antihypertensive agents, but even the selective compounds can often be used as antihypertensives because of their low toxicity.)

Compounds within the invention have also shown a good antagonist effect against contractions of rat bladder strip induced by potassium chloride. This effect can be attributed to a calcium antagonistic activity, which renders the new compounds useful as spasmolytics of the lower urinary tract (i.e., useful in the treatment of urinary incontinence, urge syndrome and other similar disorders).

The majority of the compounds of the invention exhibit low toxicity. Thus, they can be used in higher amounts, an advantage that often more than compensates for a relatively lower level of activity that some of these compounds have. Naturally, those compounds exhibiting both high activity and low toxicity are preferred.

The affinity of compounds of the invention for each receptor can be assessed by receptor binding assays, for example as follows:

(1) $\alpha_1$—adrenergic receptor: using the specific ligand $^3$H-prazosin, according to Morrow, A. L. et al., *Eur. J. Pharmacol.* 109: 285, 1985;

(2) 5HT$_{1A}$—serotonergic receptors using the specific ligand $^3$H-8-0H-DPAT according to Hoyer, D. et al., *Eur. J. Pharmacol.*, 118: 13, 1985.

It should be noted that identification and characterization of the foregoing receptors is still in progress and that their types and especially subtypes are subject to review and refinement. See, e.g., Perez, D. M., et al *Mol. Pharmacol.*, 40:876, 1991; Garcia-Sainz, J. A., et al, *Biochem. Biophys. Res. Comm.*, 186(2):760, 1992; Zifa, E., et al., *Pharmacol. Rev.*, 44(3):401, 1992; Hartig, P. R., et al., *Drug Delivery*

Res., 26(3), 215, 1992; Romero, A. G., et al., *Annual Reports in Medicinal Chemistry*, 27(3), 21, 1992, Academic Press.

The group

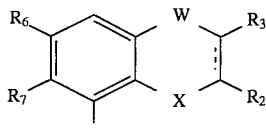

will be abbreviated hereinafter as Fl. The alphanumerics Y1 through Y49 and B1 through B5 will be used as abbreviations for the groups Y and B above to which they respectively apply.

Without limitation, alkyl groups within the definition of $R_2$ include $C_1$–$C_6$ alkyl; alkenyl groups include $C_2$–$C_4$ alkenyl; carbocyclic groups include cyclohexyl and aryl and heterocyclic groups include rings having one or two heteroatoms and 4 or 5 carbon atoms, such as thienyl, furyl, pyridinyl.

Without limitation, alkyl groups, as well as the alkyl moiety of other groups within the definition of $R_2$, $R_3$, $R_6$, $R_7$, $B_1$, $R_{10}$, $R_{11}$, $R_{12}$ and $R_{13}$, include $C_1$–$C_4$ alkyl.

The preferred values of the substituents in the group Fl are (most preferably simultaneously) as follows:

|  |  |
|---|---|
| ----: | a double bond, |
| X: | an oxygen atom, |
| W: | a carbonyl group, |
| $R_2$: | a phenyl group, |
| $R_3$: | a methyl group, |
| $R_6$: | a hydrogen atom, and |
| $R_7$: | a hydrogen atom. |

The group having all these preferred substituents, that is the 3-methyl-4-oxo-2-phenyl-4H-1-benzopyran-8-yl group, will be abbreviated hereinafter as Fl'.

The preferred (most preferably simultaneously with Fl') groups which Z may represent are trimethylene and tetramethylene. Y preferably represents one of the groups Y2, Y3, Y37, Y40, Y41 or Y42. B preferably represents one of the groups B1 or B3, especially the group 1-(2-methoxyphenyl)piperazinyl.

SYNTHESIS OF THE COMPOUNDS OF THE INVENTION

The compounds according to the invention may generally be prepared (except when the groups R6 and the substituents at $R_2$ are OH, $NH_2$ or aminoalkyl and Y=Y15 or Y29) as follows:

Path a:

By condensing compounds Fl-Y-Z-L, wherein L represents a halogen atom or a leaving group such as a tosylate group, with a compound H-B. The condensation is preferably, but not necessarily, carried out at a temperature within the range of 20°–140° C. in a polar solvent such as dimethylformamide or methanol, or without solvent, usually in the presence of a base such as potassium carbonate. Such condensations are illustrated in Examples 1 to 3, 7 to 9, 11, 13 to 16, 21, 23 to 31, 38 to 42, 46 to 49, 54 to 59, 69, 73, 77, 78, 84, 133, 141, 145–147, 152, 154, 158, 160, 161, 168, 172, 187, 189 and 190 below. See, also Gibson's chapter in Patai "The Chemistry of the Amino Group", p. 45 et seq. Wiley Interscience, New York, 1968.

An alternative method for the preparation of the present compounds is condensation (under the same conditions described in the preceding paragraph) of a compound Fl-Y-H with a compound L-Z-B wherein L is as above defined. This condensation is illustrated in Examples 5, 6, 66, 79 and 81 below. By this route, compounds having Y=Y15 or Y29 can also be prepared (see Gibson's chapter in Patai, supra).

Compounds of formula (I) bearing a $NH_2$ group in $R_6$ or as substituent in R2, may be prepared by reduction of the corresponding compounds (I) wherein R6 or the substituent in R2 are $NO_2$ groups.

Such reduction can be carried out:

with Ni-Raney catalyst in aprotic solvent selected from methanol, ethanol, isopropanol, water and mixtures of them; or with $SnCl_2$, $H_2O$, optionally in presence of hydrochloric acid, either in aprotic solvent such as methanol, ethanol, isopropanol, water, acetic acid and mixtures of them, or in an aprotic solvent such as ethyl acetate; or with Fe and aqueous hydrochloric acid in aprotic solvent such as methanol, ethanol, isopropanol, water and mixtures of them.

The temperatures of the above reactions will be chosen in a range between 20° C. and 100° C. (J. March, Advanced Organic Chemistry, IV Ed., page 1216, Wiley Interscience, 1992). Examples of this reduction are given in Examples 94 and 124.

Compounds of formula (I) having a NHAlk group as a $R_6$ substituent can be prepared by monoalkylation, starting from the corresponding parent compounds (I) where $R_6$=$NH_2$. For example, this may be done by first reacting the amino compound (I) with an excess of trifluoroacetic anhydride, then reacting the obtained trifluoroacetyl derivative with an alkyl-L reagent and finally deprotecting the thus-obtained trifluoroacetyl-alkylated derivative by treatment with $K_2CO_3$ in methanol or with sodium borohydride in methanol or dimethylsulfoxide.

These reactions are described in Examples 32 and 33, where they were carried out on Y groups.

Alternatively, compounds of formula I having a NHAlk or $N(Alk)_2$ groups as a $R_6$ substituent or as a substituent on the phenyl group in $R_2$ can be obtained by alkylation of the corresponding parent compounds (I) where $R_6$=$NH_2$ with the appropriate aldehydes in the presence of a reducing agent, such as sodium cyanobrohydride. Descriptions of these reactions are given in Examples 96, 97 and 131 below.

Compounds bearing a OH group as $R_6$ or as a substituent in $R_2$ may be prepared starting from the corresponding parent compounds (I) alkoxy-substituted at said positions. This can be accomplished by treating the parent compounds, for example, with $BBr_3$ in dichloromethane at 0°–40° C. (T. W. Greene "Protective Groups in Organic Synthesis", page 87, Wiley Interscience (1981)) or according to other methods described in the same reference.

Compounds of formula (I) having a saturated 2–3 bond (----=_____) can be alternatively obtained:

by selective hydrogenation of the corresponding compounds of formula (I) having a 2–3 double bond (----=___);

by conversion of the appropriate intermediates with a saturated 2–3 bond which, in turn, can be obtained according to Schemes 4, 6–9, 11, 12 and 14 in the Starting Materials section.

These last conversions are performed according to the methods described for compounds of formula (I) having a 2–3 double bond, in particular when a nitro group is already present in the molecule. This conversion is illustrated in Example 87.

The selective hydrogenations can be carried out using alternatively:

hydrogen in presence of a metal or metal oxide catalyst (e.g.: palladium on charcoal, or platinum dioxide) in a protic solvent at 20°–120° C. (E. H. Rodd, Chemistry of Carbon Compounds, Vol. IVB, page 903, Elsevier, 1959). This hydrogenation is described in Example 170. [Also, in this Example W=CO was transformed into W=CHOH and $R_2$=phenyl was transformed into $R_2$=cyclohexyl (Example 169).]

di-(isobutyl)aluminum hydride in an aprotic solvent (e.g.: tetrahydrofuran and/or methylene chloride) at –70°/0° C. (R. Sarges et al., *J. Med. Chem.* 33, 1859 (1990).

Compounds of formula I having W=CHOH and a 2–3 single bond (----=_____) can be obtained by reduction of the corresponding parent compounds of formula I having W=CO and ----=___, with sodium borohydride, as reported in Example 123 below.

In some cases, compounds of the Formula I may be prepared by conversion of other (parent) compounds of the invention. Such conversions include:

Path b:
Fl-CO-Z-B to Fl-CH(OH)-Z-B by reduction as illustrated in Examples 17 to 20 below, Path c:
Fl-CH(OH)-Z-B to Fl-(CHOAlkyl)-Z-B by etherification as illustrated in Example 22, Path d:
Fl-$(CH_2)$n-NH-Z-B→Fl-$(CH_2)$n-$NCH_3$-Z-B where n=0, 1, by methylation as illustrated in Example 35;

Path e:
Fl-$(CH_2)$n-NH-Z-B→Fl-$(CH_2)$n-N($COCH_3$)-Z-B where n=0, 1, by N-acetylation as illustrated in Example 36;

Path f:
Fl-$(CH_2)$n-NH-Z-B→Fl-$(CH_2)$n-N($CONH_2$)-Z-B where n=0, 1, by reaction with potassium isocyanate as illustrated in Example 50;

Path g:
Fl-CH(OH)-Z-B→Fl-CO-Z-B by oxidation, as illustrated in Example 51;

Path h:
Fl-Y-Z-B→Fl-Y-Z-B(N-oxide) by oxidation as illustrated in Example 43, 127, 139 and 140.

Path i:
$H_2$N-Fl-Y-Z-B→$CH_3$CONH-Fl-Y-Z-B (where in $H_2$N-Fl represents a Fl group bearing an amino group as the R6 group or as the substituent in $R_2$) using the N-acylation method described in Examples 36, 95 and 125.

Path j:
Fl (R6=$NH_2$)-Y-Z-B→Fl(R6=$CH_3SO_2$NH)-Y-Z-B by amidification using the method described in Example 112.

Path k:

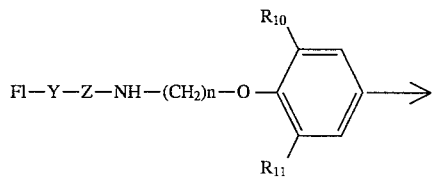

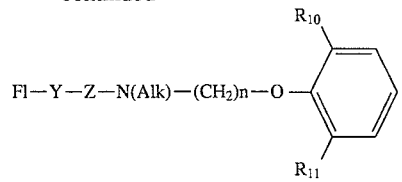

or

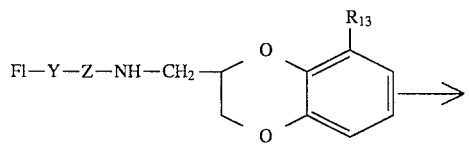

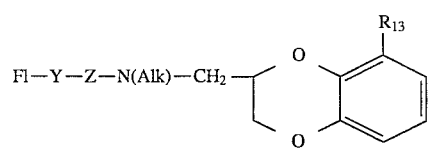

or

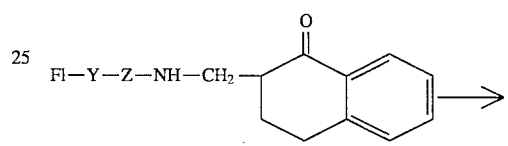

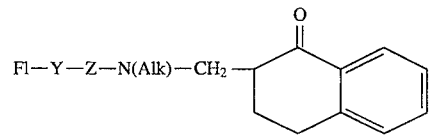

by N-alkylation using the procedure described in Examples 35 and 62.

Some compounds may be prepared by addition reactions. For example those in which Z contains a hydroxy substituent may be prepared by addition across an epoxy group Path l:

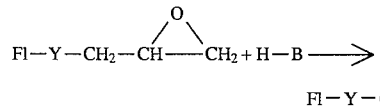

$Fl-Y-CH_2-CH(OH)-CH_2-B$ as illustrated in Example 45.

Addition across a double bond is also possible, e.g.:

Path m:
Fl-Y-CH=$CH_2$+H-B→Fl-Y-$CH_2$-$CH_2$-B as illustrated in Examples 37, 63 and 82.

Other synthetic schemes include the formation of Y, Z or B during the reaction, for example.

Path n:
Fl-(X)-(Q)-Cl+A-HN-Z-B→Fl-(X)-(Q)-N(A)-Z-B (wherein X=bond, $CH_2$ or CH=CH, Q=CO or $SO_2$, and A=H, alkyl or O$P_r$ wherein $P_r$ is a protective group) as illustrated in Example 12 (particularly preferred) and in Examples 60, 61, 64, 67, 68, 72, 87, 88, 93, 98, 116, 129, 130, 135 and 136.

The same compounds may also be prepared by other routes including:

Fl-(X)-COOH+A-NH-Z-B in presence of a coupling agent (e.g., dicyclohexylcarbodiimide, N,N'-carbonyl-diimidazole or diethyl cyanophosphonate) optionally in the presence of a promoting agent (e.g., N-hydroxysuccinimide, 4-dimethylaminopyridine in an aprotic or a chlorinated solvent (e.g., dimethylformamide, chloroform) at −10°/140° C. (Albertson, *Org. React.* 12, 205–218 (1962); Doherty et al., *J. Med. Chem.* 35:2 (1992); Staab et al., *Newer Methods Prep. Org. Chem.*, 5: 61 (1968); Ishihara, *Chem. Pharm. Bull.*, 39, 3236 (1991)); as illustrated in Examples 80, 86, 89, 90, 92, 99–111, 113–115, 117–119, 128, 132, 137, 142–144, 148–151, 153–155, 157, 159, 162–164, 167, 171, 176–180 and 183–186. In some cases the activated intermediate esters (such as N-hydroxysuccinimidyl esters) can be isolated (see for example Intermediate CXVII) and transformed into the corresponding amides by reacting with A-NH-Z-B in aprotic or chlorinated solvent at −10°/100° C., as illustrated in Example 138.

Fl-(X)-COOH+A-NH-Z-B without a solvent at 150°–220° C. (Mitchell et al., *J. Am. Chem. Soc.* 53: 1879 (1931) or in high-boiling ethereal solvents (e.g., diglyme);

Fl-(X)-COO-Alk+A-NH-Z-B optionally in the presence of a coupling agent (e.g.: trimethylaluminum) in an aprotic and/or a chlorinated solvent (e.g., hexane, dichloromethane) at −10°/80° C., or without solvents at 80°–180° C., (S. M. Weinreb et al., *Tetrahedron Lett.*, 1977, 4171); M. F. Lipton et al., *Org. Synth.* 59:49 (1979));

Fl-(X)-COOH+alkyl chloroformate in presence of a tertiary amine (e.g., triethylamine) followed by addition of A-NH-Z-B at 0°–80° C.; optionally a promoting agent (e.g.: 1-hydroxypiperidine) may be added before the amine addition (Albertson, *Org. React.* 12: 157 (1962).

Path o:
Fl-COCl+HS-Z-B→Fl-Y49-Z-B.

Path p:
Fl-COCl+HO-Z-B→Fl-Y2-Z-B as illustrated in Example 10.

Path q:
FlCHO+H$_2$NO-Z-B→Fl-Y11-Z-B, as illustrated in Example 70.

Path r:
Fl—CHO+A-HN-Z-B→Fl-CS-N(A)-Z-B (where A=H; CH$_3$) in presence of sulfur in an aprotic solvent (e.g., dimethylformamide or pyridine at 60°–120° C. (M. Carmack et al., *Org. Reaction* 3: 83 (1947) and R. Benassi et al., *Org. Magn. Res.* 15, 25 (1981)), as illustrated in Example 83.

Path s:
Fl-NH$_2$+HCO-Z-B→Fl-Y29-Z-B as illustrated in Example 43, 127, 139 and 140.

Path t:
Fl-Y-CH$_3$+HO-CH$_2$-B→Fl-Y-CH$_2$-CH$_2$-B as illustrated in Example 4, Path u:
Fl-CH=CH—CONH$_2$+HOCH$_2$-B→Fl-Y10-CH$_2$-B.

Path v:

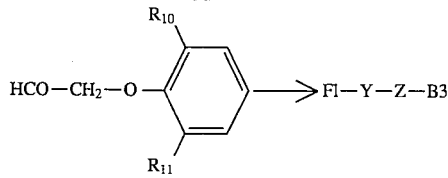

under reducing conditions as illustrated in Example 44.

Path w:
Fl—Y—Z—NH$_2$ +

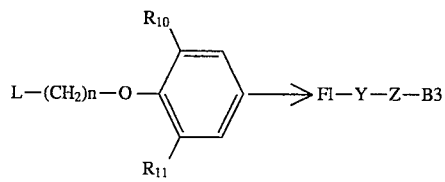

as illustrated in Examples 74, 75 and 76.

Fl—Y—Z—NH$_2$ +

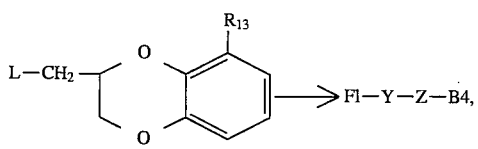

as illustrated in Example 52.

Path x:
Fl—Y—Z—HN$_2$ +

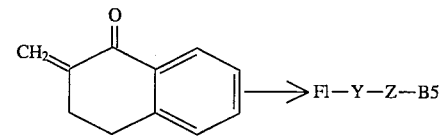

as illustrated in Example 65.

Path y:
Fl-Y-Z—CHO+HB→Fl-Y-Z-B as illustrated in Example 53 and 175.

Path z:
Fl-COOH+HO-Z-B→Fl-Y48-Z-B, in the presence of diphenylphosphorylazide and triethylamine in an aprotic solvent (e.g. dioxane) at 60°–100° C. (T. Shioiri et al., *J. Am. Chem. So.*, 94, 6203 (1972)), as illustrated in Example 166.

Path aa:
Fl—CHO+AHN-Z-B→Fl-Y15 -Z-B or Fl-Y16 -Z-B, under conditions of reductive amination as reported above and illustrated in Example 156.

Persons skilled in the art are aware that all the above synthetic paths b) to y) might be simplified provided that the reacting intermediate does not bear further groups sensitive to the same reactants (for example: CO, NH$_2$, NHAlk or OH groups).

Compounds of formula (I) bearing the above cited reactive groups can be prepared through paths b) to y) on condition that the reactive groups present in the starting materials are converted into non-reactive groups before reacting and then deprotected at the end of the reaction as illustrated in Example 71. Several examples of protection and deprotection for various reactive groups can be found in: T. W. Greene, "Protective Groups in Organic Synthesis"—Wiley Interscience (1991).

Alternatively, unreactive groups (e.g., $NO_2$) can be left unconverted during the first reaction and then converted to reactive ones (e.g.: $NH_2$) as a final step of the pathway. See, for example, path a).

Which synthetic technique will be preferred depends on the compound desired to be synthesized, but path n) is generally preferred for the compounds that can be made by it. Additional synthetic methods will be apparent to those skilled in the art.

Starting Materials

Intermediates, such as the compounds Fl-Y-Z-L and Fl-Y-H used in the preparation of compounds of the invention may themselves be prepared from simple compounds such as Fl-COOH, Fl—CHO, Fl-COCl, Fl-$NH_2$ Fl-OH and Fl$CH_2$CH=$CH_2$ by transformations known to those skilled in the art. Several such transformations are described in detail in the Examples.

When X is oxygen and W is carbonyl group, many of the aforesaid simple compounds are commercially available or their synthesis has been published in the literature. Those which are not available may be synthesized by cyclization according to the following Reaction Scheme 1 wherein the steps have the various meanings described below:

SCHEME 1

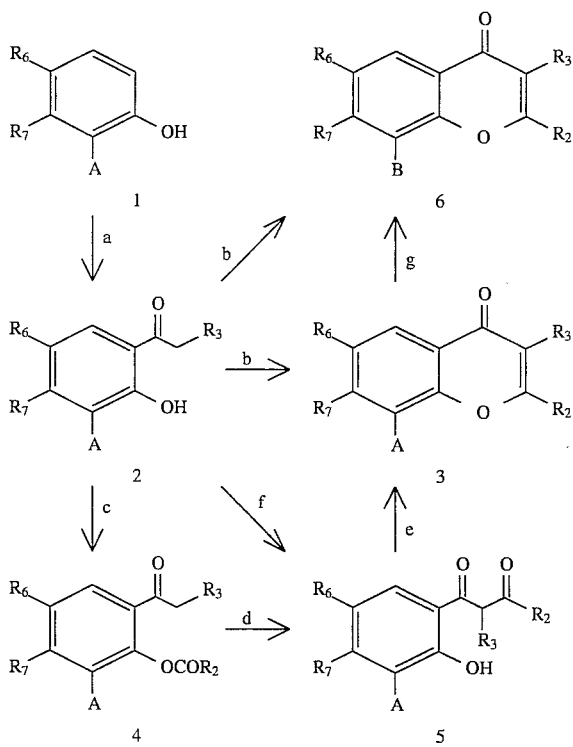

A = $CO_2CH_3$, $CO_2C_2H_5$, $NO_2$, CH=CHCH$_3$,
B = $CO_2H$, $NH_2$

Step 1a:
Procedure without isolation of the intermediate phenyl ester: $R_3CH_2COCl$ or $(R_3CH_2CO)_2O$ and a Lewis acid (e.g., $AlCl_3$ or $ZnCl_2$), without solvent or in aprotic solvent (e.g., nitrobenzene or chlorinated solvent) at 20°–180° C.;

procedure with isolation of the intermediate phenyl ester: $R_3CH_2COCl$ or $(R_3CH_2CO)_2O$ heated with the starting material or other esterification methods, such as the Schotten-Bauman procedure. The isolated ester is then heated in nitrobenzene or other non protic solvent (e.g., chlorinated solvent), or without any solvent, at 20°–180° C., in the presence of a Lewis acid (e.g., $AlCl_3$, or $ZnCl_2$). (A. M. Blatt, Org. React. 1: 342 (1942)).

Step 1b:
$R_2COCl$ or $(R_2CO)_2O$ and $R_2COONa$ alone or in high-boiling non-protic solvent (e.g., o-dichlorobenzene) at 150°–220° C.; this reaction also allows for the direct transformation of compounds 2 to 6, when compound 2 has A=COOH;

$R_2C(OAlk)_3$ in the presence of $HClO_4$ at 20°–40° C. or in pyridine as the reaction solvent in the presence of piperidine at 60°–80° C.;

$R_2COCl$ or $(R_2CO)_2O$ in a chlorinated solvent at −10°/120° C. in the presence of a base such as 1,8-diazabicycloundecene (DBU).

Step 1c:
$R_2COCl$ in pyridine at 20°–100° C. or in non-protic solvent at 0°–80° C., optionally in the presence of a base, such as triethylamine or 4-dimethylaminopyridine.

Step 1d:
Potassium carbonate in acetone or methyl ethyl ketone at 20°–80° C.;

Sodium hydride in dimethylsulfoxide or tetrahydrofuran at 0°–40° C.;

Potassium hydroxide or potassium tert-butoxide in pyridine at 20°–100° C.

Step 1e:
Hydrochloric acid or sulfuric acid in acetic acid solvent at reflux or an alcohol (methanol, ethanol, i-propanol) at 20° C.-reflux temperature;

Trifluoroacetic acid in dichloromethane at 20°–40° C;

p-toluenesulfonic acid in benzene or toluene at reflux.

Step 1f:
$R_2COCl$ and potassium carbonate or potassium hydroxide in water and a phase transfer catalyst in benzene or toluene at reflux;

$R_2COOAlk$ and lithium bis(trimethylsilyl)amide or lithium diisopropylamide in tetrahydrofuran at −78°/0° C.

Step 1g:
When A is a $COOCH_3$ or $COOC_2H_5$ group:

Sodium hydroxide in aqueous ethanol at 0°–75° C.;

Lithium hydroxide in aqueous dimethylformamide, methanol or tetrahydrofuran or a mixture thereof at 10°–100° C.;

Hydrochloric acid in aprotic solvent such as dioxane at 60°–120° C. When A is $NO_2$: Reduction with Ni-Raney catalyst in aprotic solvent (e.g., i-propanol) or a mixture of protic solvents at 20°–100° C.;

Reduction with hydrogen and a catalyst (e.g., Ni-Raney or Palladium/C) in a protic solvent (e.g., methanol, ethanol, i-propanol or mixtures thereof) at 20°–100° C.;

Reduction with $SnCl_2$ in the presence of aqueous hydrochloric acid in aprotic solvent (e.g., acetic acid) at 20°–100° C.;

Reduction in presence of Fe and aqueous hydrochloric acid in protic solvent at 20°–100° C.

When A is a CH=CHCH₃ group:

Oxidation with $Na_2Cr_2O_7$ or other oxidizing agents such as $KMnO_4$ in acetone/sulfuric acid at 0°–100° C. The cyclization reaction reported in step 1b (or steps 1c, 1d and 1e) can also be carried out on Intermediate 2 of Scheme 1 where A is represented by $Y_3$-Z-B. The final compounds of the invention corresponding to formula I can be produced directly with this approach. It is illustrated in Examples 173 and 174.

When X represents a sulfur atom or a sulfinyl or a sulfonyl group and W is carbonyl group, the simple starting materials may be prepared according to the following Reaction Scheme 2 wherein the steps have the following alternative meanings:

SCHEME 2

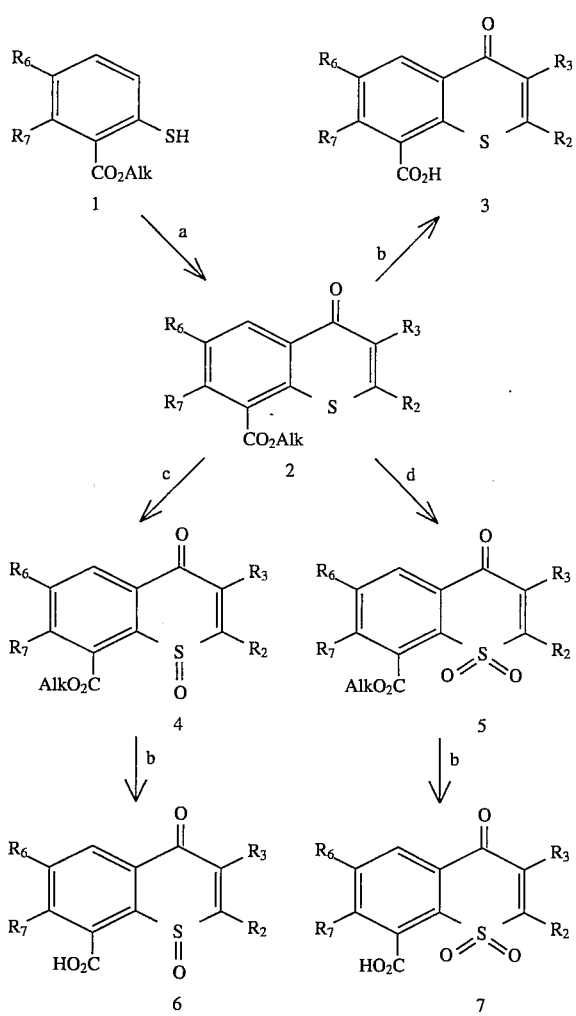

Step 2a:
R₂COCH(R₃)CN or R₂COCH(R₃)COOAlk in polyphosphoric acid at 50°–120° C.;
R2C≡C-COOAlk and $Al_2O_3$ in aprotic solvents (e.g., diethyl ether) at 0°–40° C.;
R₂C≡C-COOAlk and a base in aprotic solvents (e.g., tetrahydrofuran or dimethylformamide) at 20°–140° C.

The last two options are both followed by treatment with polyphosphoric acid at 50°–120° C.

Step 2b:
Sodium hydroxide in aqueous ethanol at 40°–75° C.
Lithium hydroxide in aqueous dimethylformamide at 40°–100° C.

Step 2c:
Stoichiometric 30% hydrogen peroxide in acetic acid, at 25°–60° C.;
m-chloroperbenzoic acid in chloroform at 0°–30° C.;

Step 2d:
30% hydrogen peroxide in acetic acid at 50°–80° C.

The starting ortho-mercaptobenzoates are commercially available or can be prepared by known methods: for example by transformation of the corresponding orthoalkoxycarbonylbenzenediazonium salts upon treatment with potassium ethylxanthate (M. S. Cohen et al., *J. Org. Chem.* 18: 1380 (1953)).

Simple starting materials having $R_7$=OCH₃, W=CO and X=O, S may be prepared according to Reaction Scheme 3 wherein the step 3a is:

Step 3a:
Formaldehyde and gaseous HCl in acetic acid containing aqueous HCl (d=1,18) at 50°–100° C. (P. Da Re et al., *Ann. Chim.*, 46:904 (1956)). This method can be used when $R_3$ is different from H or from a hydroxymethyl group.

SCHEME 3

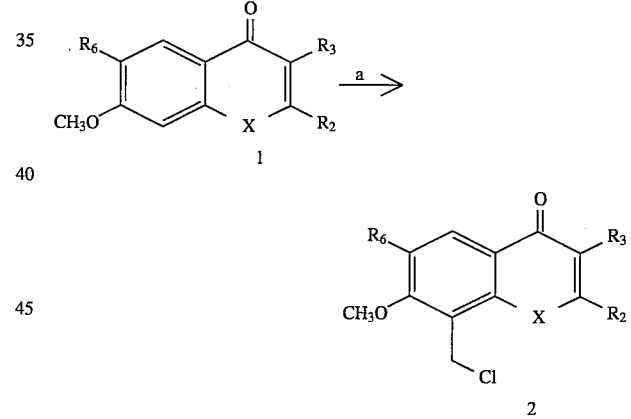

Intermediates (1) can be prepared according to Reaction Schemes 1 and 2 starting from the appropriate phenols or thiophenols (not substituted at position 2 or 6 with COOAlk or NO₂); then, the resulting Intermediates (2) can be converted using known methods to starting materials suitable for obtaining the desired compounds of the invention.

The synthesis of the simple 2,3-dihydro intermediates (----=_____), provided that other reactive groups possibly present (e.g., NH₂, OH) have been previously protected as described before, can be pursued using a method of the Reaction Scheme 4, wherein the steps 4a–4i have the following meanings:

SCHEME 4

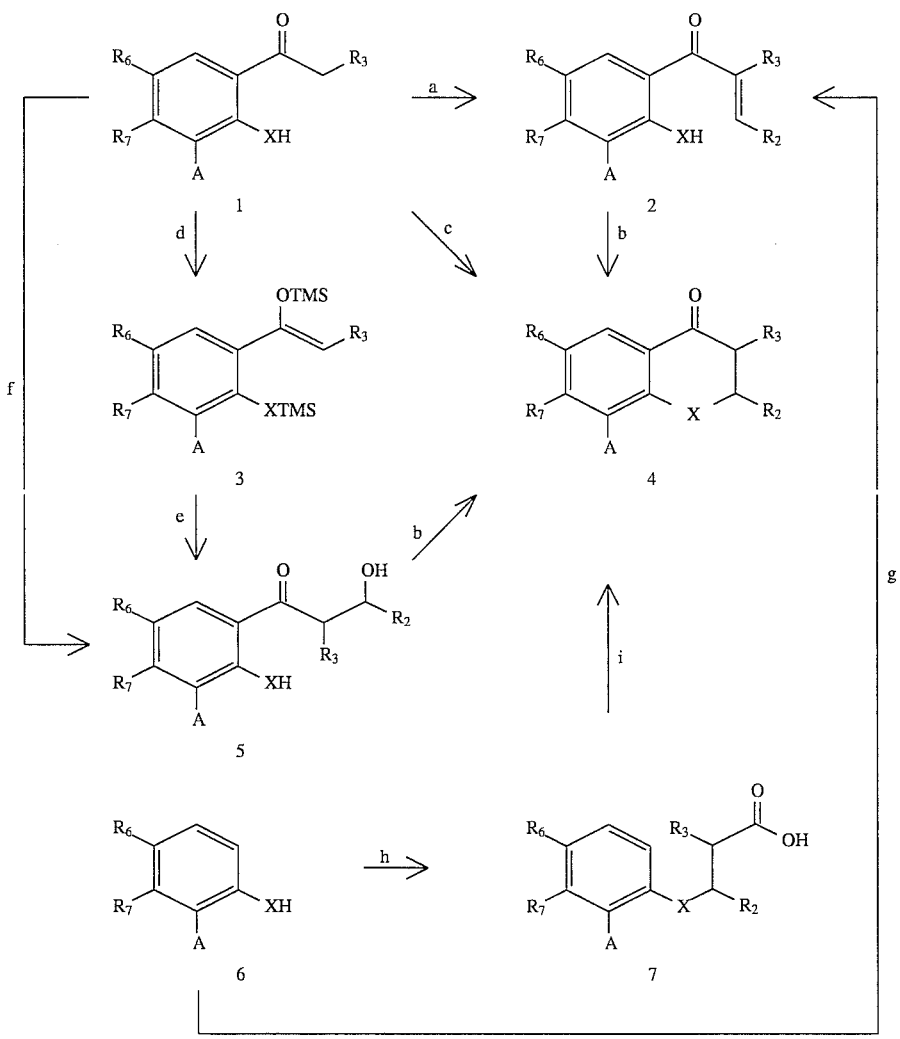

A = CO₂CH₃, CO₂C₂H₅, NO₂, CH=CHCH₃

Step 4a:
  R₂—CHO, aqueous sodium hydroxide in ethanol or other protic solvent;
  R₂—CHO, sodium hydride or potassium tert-butoxide in tetrahydrofuran (or other dipolar aprotic solvent) at 0°–150° C.;

Step 4b:
  Mineral acid (e.g., hydrochloric acid or sulfuric acid) in water or other protic solvents (e.g., ethanol, acetic acid) at 0°–100° C.;

Step 4c:
  R₂—CHO, 0.1–1N aqueous sodium hydroxide or other suitable base in aprotic solvent;
  R₂—CHO, pyrrolidine in aprotic (e.g., methanol) or polar aprotic solvent at 0°–100° C. (H. J. Kabbe, *Synthesis*, 1978, p.886);

Step 4d:
  Lithium diisopropylamide in tetrahydrofuran at 0°–20° C.; then trimethylsilylchloride and an organic base (e.g., triethylamine) (S. E. Kelly et al., *J. Org. Chem.* 56: 1325 (1991));

Step 4e:
  R₂—CHO in a chlorinated solvent (e.g., CH₂Cl₂) at −78° C. then TiCl₄ (or other Lewis acid) (S. E. Kelly, et al., *J. Org. Chem.*, 56: 1325 (1991));

Step 4f:
  Lithium diisopropylamide in tetrahydrofuran at −78° C. then R₂—CHO (A. Banerij et al., *Tetrahedron Letter*, 1979, 3685);

Step 4g:
  R₂—CH=CR₃COCl, a Lewis acid (e.g., AlCl₃) in a suitable solvent (e.g., nitrobenzene) or without solvent at 20°–180° C.;

Step 4h:
  R₂—CH=CR₃COOAlk, triethylbenzylammonium hydroxide in an aprotic solvent (e.g.: benzene) or without solvent at 50°–150° C.; then aqueous NaOH in methanol at 20°–50° C. or lithium hydroxide in aqueous dimethylformamide. (In this case compounds having A=COOCH₃ or COOC₂H₅ are also hydrolyzed to compounds having A=COOH);

Step 4i:
Concentrated sulfuric acid or phosphorus pentoxide or polyphosphoric acid or a Lewis acid in nitrobenzene or toluene or without solvent at 0°–180° C. (Also in this case, hydrolysis of A=COOAlk to A=COOH occurs).

The Intermediates (4) thus obtained can be converted to the corresponding derivatives having A=COOH or NH₂ according to the method of Scheme 1, step 1g.

SCHEME 5

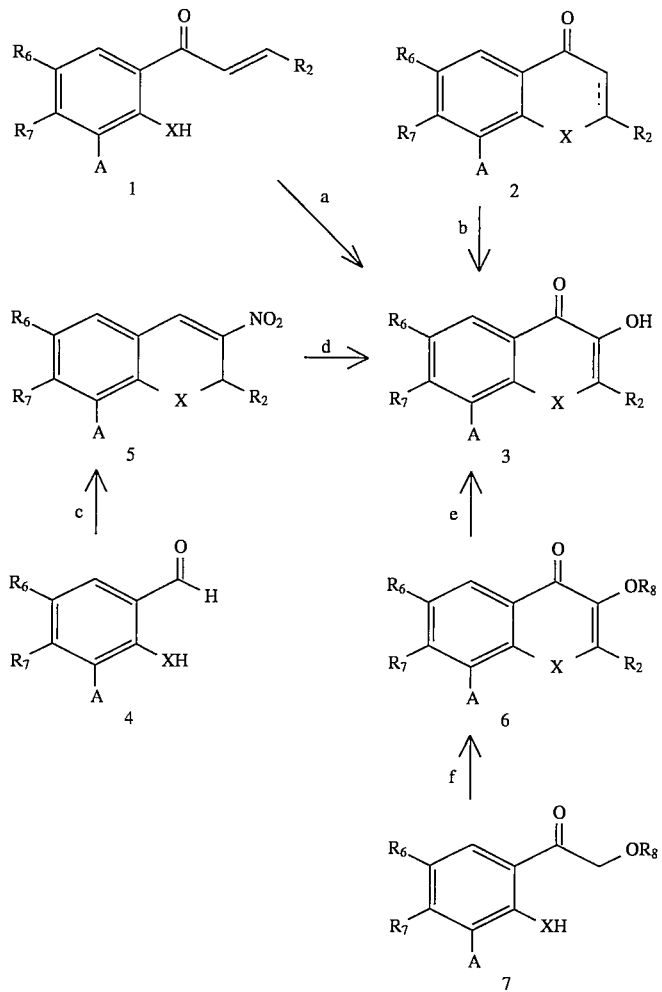

A = CO₂CH₃, CO₂C₂H₅, NO₂, CH=CHCH₃

SCHEME 6

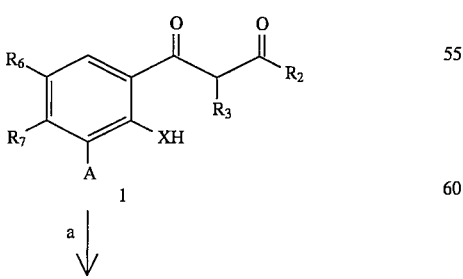

-continued
SCHEME 6

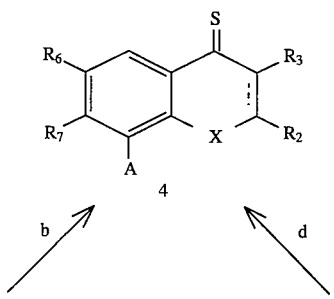

21
-continued
SCHEME 6
22
-continued
SCHEME 6
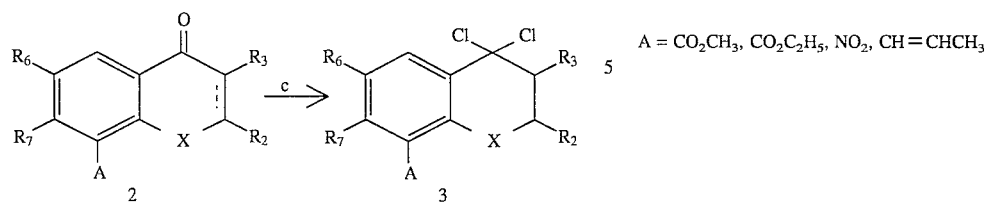
$A = CO_2CH_3, CO_2C_2H_5, NO_2, CH=CHCH_3$
SCHEME 7
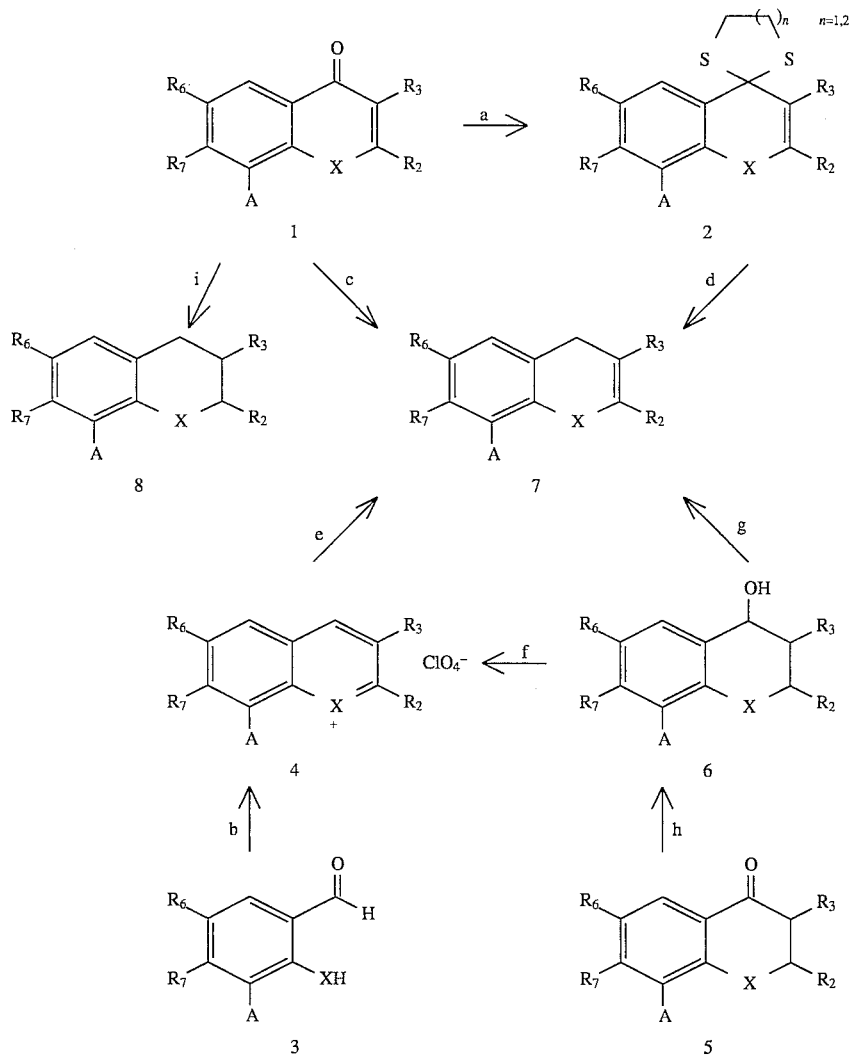
$A = CO_2CH_3, CO_2C_2H_5, NO_2, CH=CHCH_3$

SCHEME 8
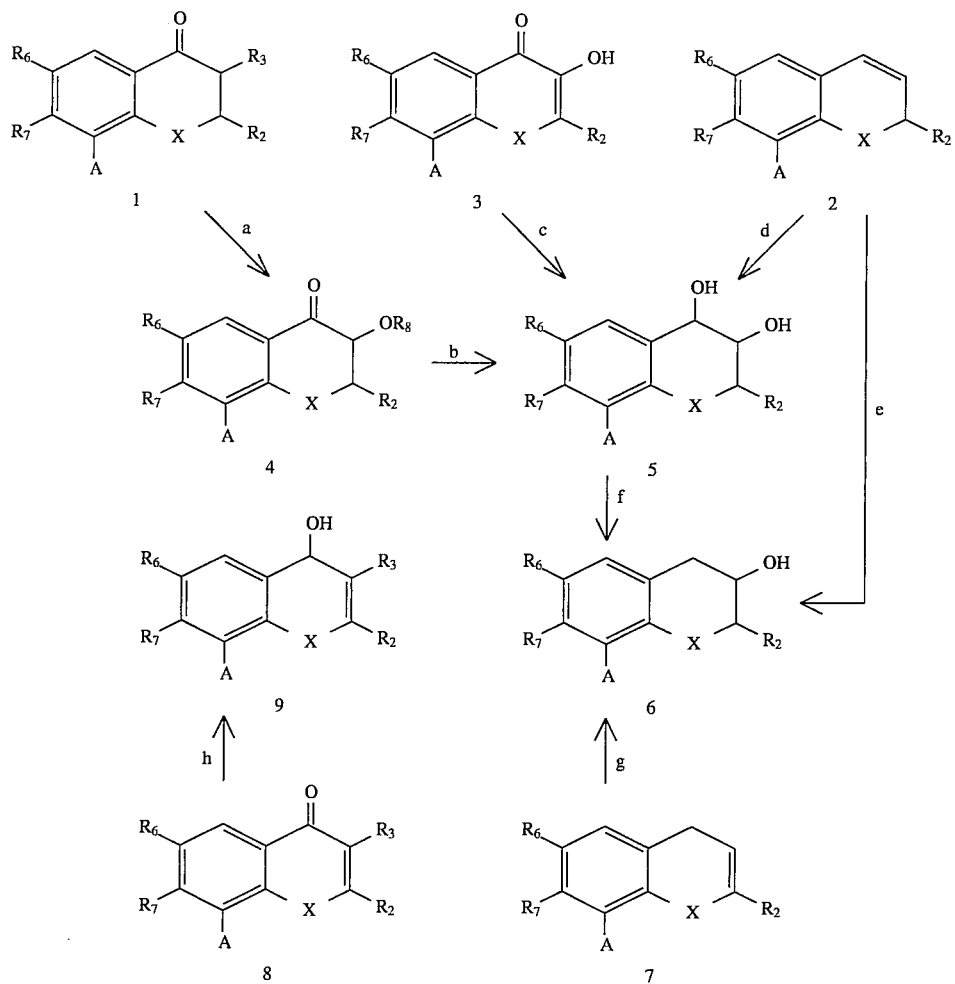
$R_8 = H, OAc$
$A = CO_2CH_3, CO_2C_2H_5, NO_2, CH=CHCH_3$
SCHEME 9
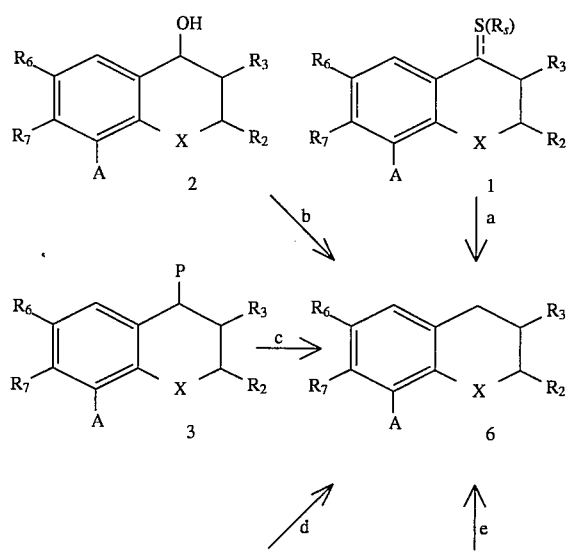
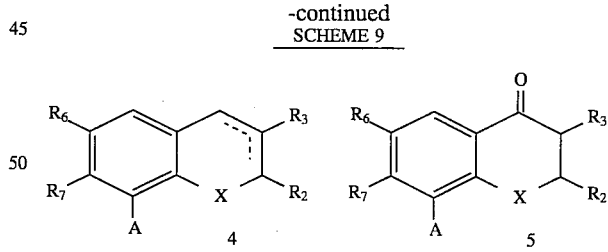
$A = CO_2CH_3, CO_2C_2H_5, NO_2, CH=CHCH_3$
$R_8 = $ Alkyl, aryl, heteroaryl, H or nothing
$P = $ halogen, O-tosyl, O-mesyl, OC(S)aryl, OC(S)heteroaryl
(e.g., OC(S)-1-imidazolyl), OC(S)O-aryl, OC(S)O-heteroaryl

SCHEME 10
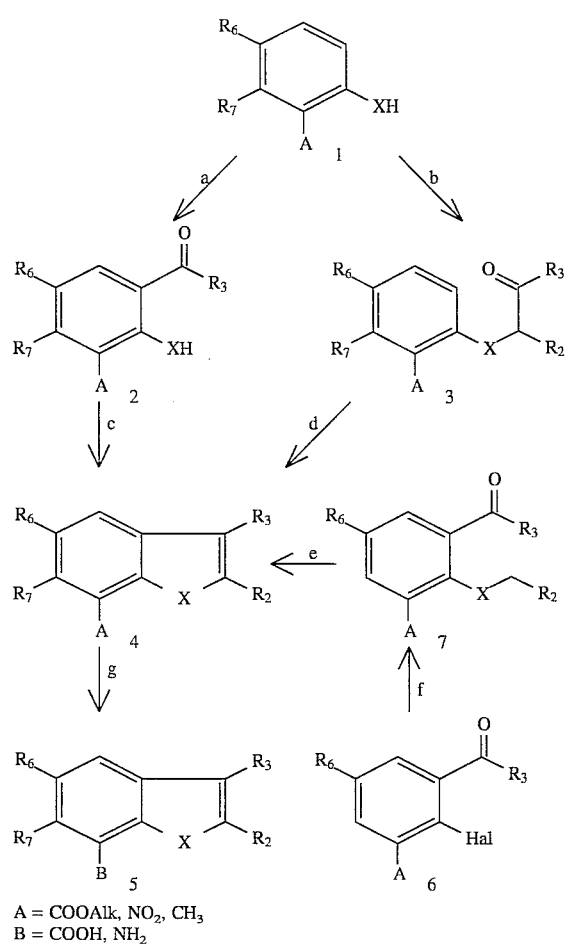
A = COOAlk, NO$_2$, CH$_3$
B = COOH, NH$_2$
SCHEME 11
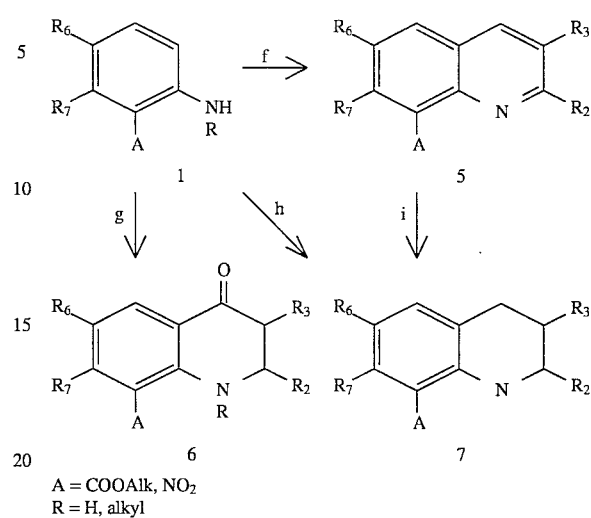
A = COOAlk, NO$_2$
R = H, alkyl
SCHEME 12
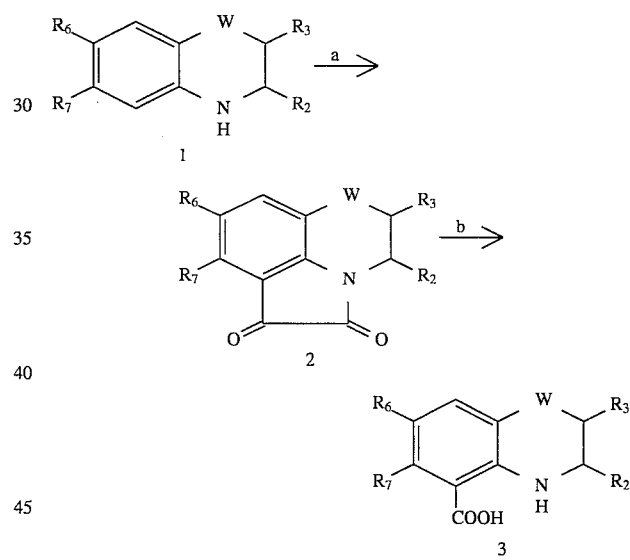
W = CH$_2$ or bond
SCHEME 11
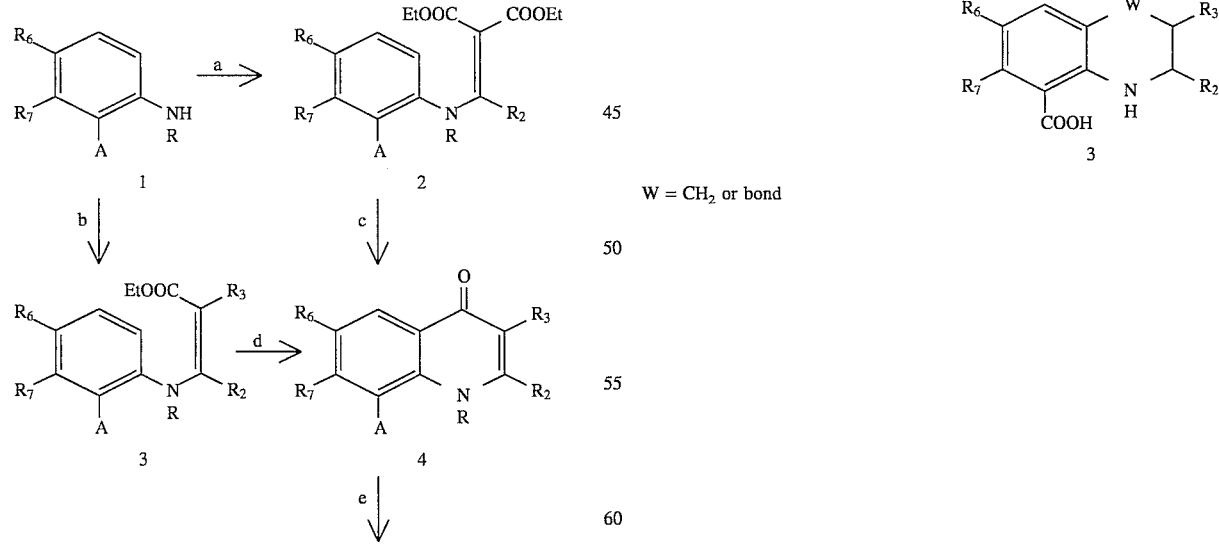

SCHEME 13
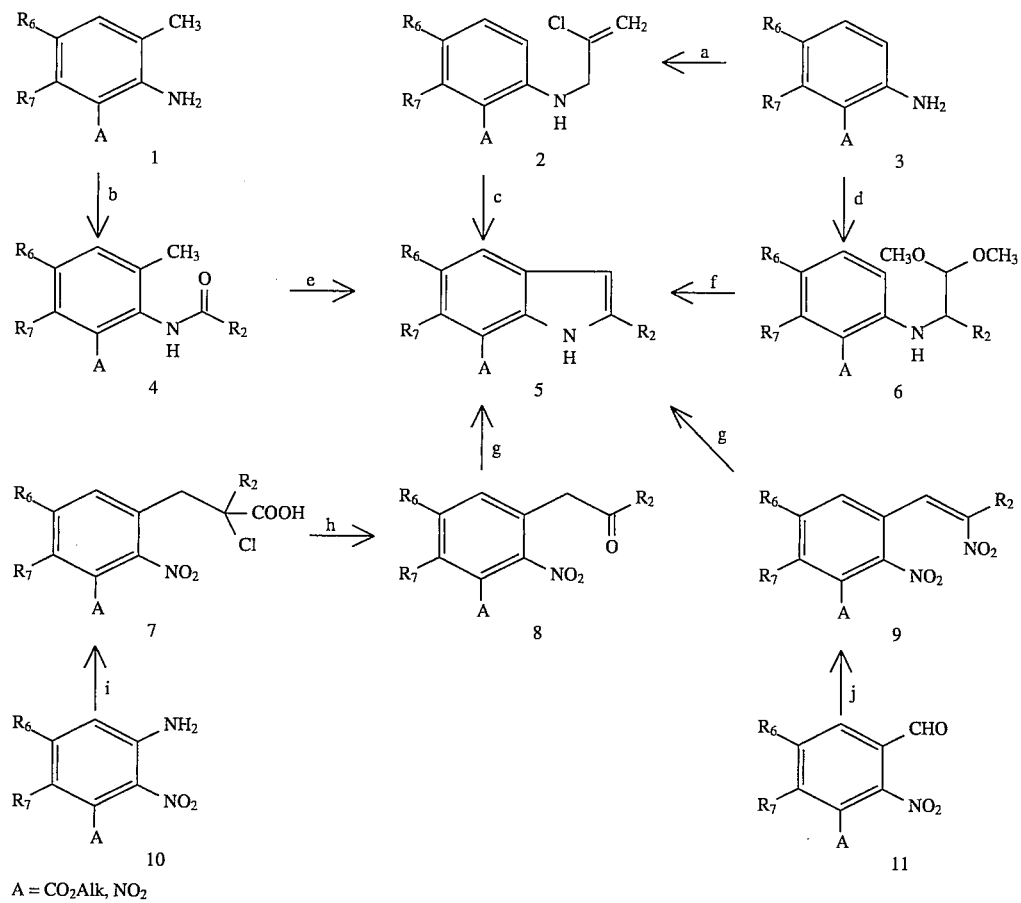
A = CO₂Alk, NO₂
SCHEME 14
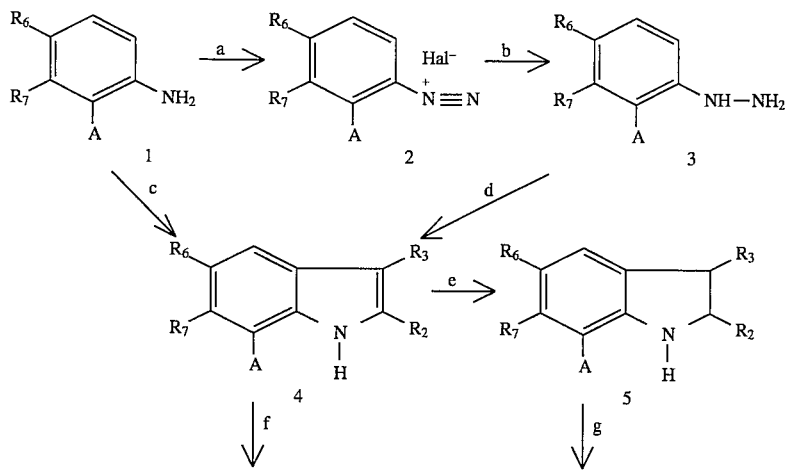

-continued
SCHEME 14
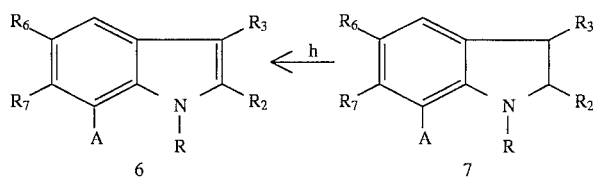
R = Alkyl
A = CO$_2$Alk, NO$_2$
SCHEME 15
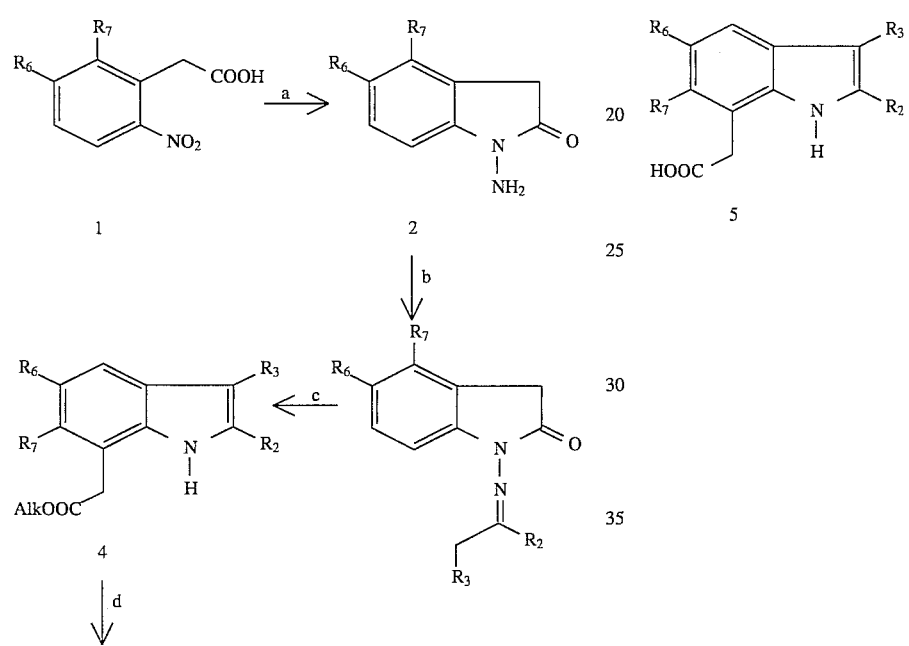
SCHEME 16
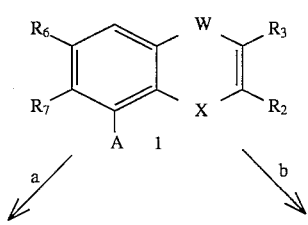

-continued
SCHEME 16

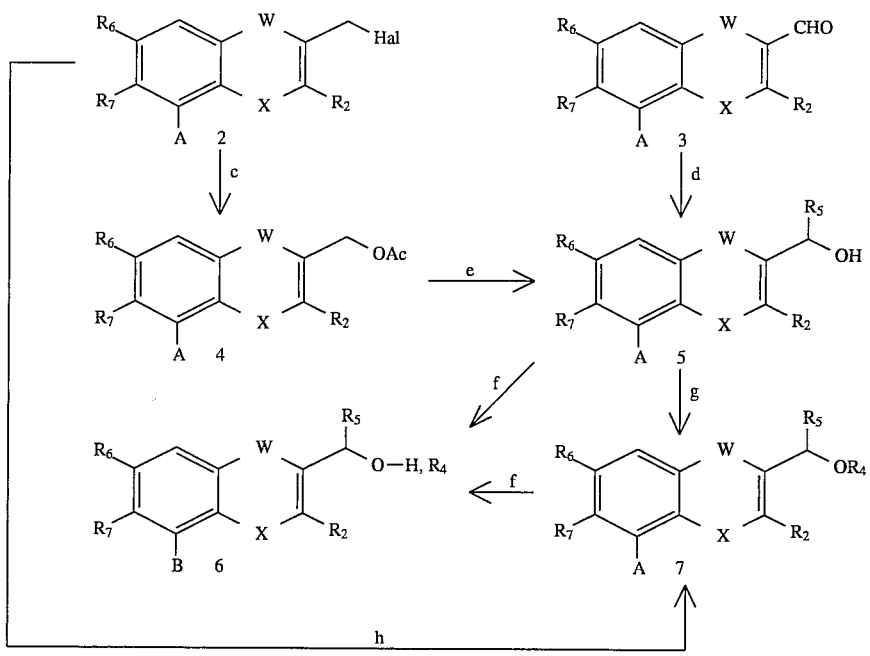

$R_5$ = H, Alk
A = $CO_2CH_3$, $CO_2C_2H_5$, $NO_2$, CH=CHCH$_3$
B = $CO_2H$, $NH_2$

Simple starting materials having $R_3$=OH or $OR_8$, where $R_8$ is alkyl or arylalkyl, may be prepared according to Reaction Scheme 5 where A has the same meaning as in Reaction Scheme 1. Intermediates (1) and (2) (which are the same as (2) and (3) in Reaction Scheme 4, but with $R_3$=H) can be prepared according to Reaction Scheme 4 starting from the appropriate phenols or thiophenols having $R_3$=H.

Steps 5a–5g have the following meanings:

Step 5a:

Aqueous sodium hydroxide in an alcoholic solvent (e.g., methanol or ethanol) followed by 30% $H_2O_2$ at −10°/−78° C. (N. D. Meyer et al., J. Med. Chem., 34,736, (1991) and references cited therein) (not when A is CH=CH—CH$_3$; when A=COOR it is simultaneously transformed into COOH).

Step 5b:

(----=_____) Amylnitrite or other alkylnitrite without solvent or in a suitable solvent (e.g., ethanol or benzene (in the presence of a catalyst (e.g., 37% hydrochloric acid) (Org. React., 7, 327 (1953)) and references cited therein), then aqueous sulfuric acid in aprotic solvent (e.g., acetic acid) at 10°–100° C. (Acheson R. M., "An Introduction to the Chemistry of Heterocyclic Compounds", 347 John Wiley end Sons, New York, 1976).

(----=___) lithium diisopropylamide in dry tetrahydrofuran at −78° C.; then trimethylborate at −50°/−20° C.; then acetic acid and 30% hydrogen peroxide (B. D. M. Cunningham et al., Anti-Cancer Drug Design, 7, 365 (1992).

Step 5c: Note: Intermediates (4) can be prepared by known methods from the corresponding salycilates or thiosalycilates (see J. March, "Advanced Organic Chemistry," 539, John Wiley and Sons, New York, 1992; L. Renè et al., Eur. J. Med. Chem. - Chim. Ther., 12, 385, (1977) and references cited therein) $R_2$—CH=CH—$NO_2$ (1–1,5 equivalent) in a suitable solvent (e.g., diisobutylether, dimethylsulfoxide or dimethylformamide) in the presence of a base (e.g., potassium or sodium hydroxide) in catalytic or stoichiometric quantity at 20°–150° C. (see L. Renè, above and T. Sakakibara et al., Bull. Chem. Soc. Jpn, 51, 3095, (1978)).

Step 5d:

$H_2O_2$ 15%, sodium hydroxide or other base (e.g., triethylamine) in a protic solvent (e.g., methanol) at 20°–100° C. (S. R. Deshpande et al., Synthesis, 835, (1983)) or photolysis and alkaline hydrolysis (Rao T. S. et al., Heterocycles, 22, 1377, (1984), or $KO_2$ in benzene containing 18-crown-6 ether at 20°–100° C. (Rao T. S., Heterocycles, 26, 2117, (1987)) (not when A is CH=CH—CH$_3$; when A=COOR it can be simultaneously transformed into COOH).

Step 5e:

$R_8L$, where L represents a leaving group (e.g., alkylsulphate, halogen, rosylate) and a base (e.g., potassium carbonate, sodium hydride, potassium or sodium or lithium hydroxide) in suitable solvent (e.g., tetrahydrofuran, dimethylsulfoxide, dimethylformamide, benzene) in the optional presence of a phase transfer catalyst (e.g., benzyltriethylammonium bromide) at 0°–180° C.

Step 5f:

performed as described for step 1b of Reaction Scheme 1.

Intermediates (3) and (6) of Reaction Scheme 6 can be transformed into the corresponding compounds having B (with the same meanings as for Reaction Scheme 1) instead of A, according to the step 1g.

Simple starting materials having a thiocarbonyl instead of a carbonyl group at position 4 of the heterocyclic ring may be prepared according to Reaction Scheme 6, where A has the same meaning as in Reaction Scheme 1. Intermediates (1) and (2) of this scheme can be prepared according to Reaction Schemes 1, 2, 4 and 5.

Steps 6a–6d have the following meanings:

Step 6a:
$P_2S_5$ in pyridine at 50°–100° C. (Stavaux et al., *Bull. Soc. Chim. Fr.*, 2082, (1967)).

Step 6b:
$P_2S_5$ or $B_2S_3$ or $SiS_2$ or Lawesson's reagent in a chlorinated solvent (e.g., chloroform) or in an aromatic solvent (e.g., benzene, toluene, xylene) at reflux. (Dean et al., *J. Chem. Soc. C*, 2192, (1963); R. K. Razdan et al., *J. Med. Chem.*, 21, 643, (1978); K, Clausen et al., *Tetrahedron*, 37, 3635 (1991)).

Step 6c:
$COCl_2$ without solvent or with an inert solvent (e.g., benzene) at 40°–90° C. (A. Schonberg et al., *Chem. Ber.*, 101, 701, (1968)).

Step 6d:
Thioacetic or thiobenzoic acid or potassium diethylxantogenate in a suitable solvent (e.g., benzene) at reflux (A. Schonberg, vide supra).

Intermediates (4) of Reaction Scheme 7 can be transformed into the corresponding compounds having B (with the same meanings as in Reaction Scheme 1) instead of A, according to step 1g.

Simple starting materials with a $CH_2$ or a CHOH group at the 4 position of the heterocyclic ring may be prepared according to Reaction Scheme 7, where A has the same meanings as in Reaction Scheme 1.

Intermediates (1), (2) and (4) can be prepared according to Reaction Schemes 1, 2, 5 and 6.

Steps 7a–7h have the following meanings:

Step 7a:
1,2-Ethanedithiol or 1,3-propanedithiol in an aprotic solvent (e.g., dichloromethane or benzene or toluene) at 0°–110° C. in the presence of a catalyst (e.g., p-toluenesulfonic acid or boron trifluoride etherate).

Step 7b:
$R_2COCH_2R_3$ in a suitable mixture of solvents (e.g., ethyl acetate or dichloromethane plus ethanol or methanol) saturated with gaseous hydrochloric acid at 0°–40° C.; then aqueous perchloric acid in acetic acid at 20°–100° C. (L. Jurd, *Tetrahedron*, 28, 493, (1972)).

Step 7c:
Lithium aluminum hydride in tetrahydrofuran at reflux (if A is other than COOR and $NO_2$);
Zinc iodide and sodium cyanoborohydride (6 equivalents) in a chlorinated solvent (e.g., 1,2-dichloroethane) at room temperature-reflux (C. K. Lau et al., *J. Org. Chem.*, 51, 3038, (1986)).

Step 7d:
Raney-Ni in an alcoholic solvent (e.g., isopropanol) at r.t. - reflux (Hilton et al., *J. Am. Chem. Soc.*, 90, 6887, (1968)).

Step 7e:
Sodium borohydride in a suitable solvent (e.g., methanol or ethanol or dimethylsulfoxide) at –10°/50° C. (L. Jurd, vide supra);
Lithium aluminum hydride in tetrahydrofuran (or other suitable solvent) at 0°–50° C. (when A is different from COOR or $NO_2$) (Degani et al., *Ann. Chim.*, 61, 793, (1971); Kurosawa, *Bull. Chem. Soc. Jpn.*, 51, 1175, (1978)).

Step 7f:
Trityl perchlorate in acetonitrile at room temperature (Degani et al., vide supra).

Step 7g:
Melting with $P_2O_5$ at 80°–180° C. (Hortmann et al., *J. Am. Chem Soc.*, 96, 6118, (1974)).

Step 7h:
Sodium borohydride in ethanol or other suitable solvent at 0° C. -reflux (K. Anaya, *Bull. Chem. Soc. Jpn.*, 40, 1884, (1967)).
Hydrogen (1–10 atm) in ethanol (or other suitable solvent) in the presence of a catalyst such as Pd-C 5 or 10% or Raney-Ni or $PtO_2$ at r.t./80° C. (K. Hanaya, vide supra). Not when A is $CH=CH-CH_3$; when $A=NO_2$, it is simultaneously reduced to $NH_2$.
Aluminum triisopropoxide in isopropanol at a range from room temperature to reflux.

Step 7i:
$PtO_2$ in an alcohol or a mixture of chlorinated solvent and an alcohol, under hydrogen pressure of 10 to 50 p.s.i. at a temperature rang of from 20° to 60° C. Also, under these conditions, when $R_2$=phenyl, this group may be reduced to the corresponding analogue where $R_2$=cyclohexyl [See Intermediate CXXXV].

Intermediates (6), (7) and (8) of Reaction Scheme 7 can be transformed into the corresponding compounds having B (with the same meanings as in Reaction Scheme 1) instead of A, according to step 1g.

Reaction Scheme 8 shows the preparation of simple starting materials such as (4), (5), (6) and (9), where A has the same meanings as in Reaction Scheme 1. Intermediates (1), (2), (3), (7), (8) can be prepared according to Reaction Schemes 1, 2, 4, 5, 7, 9, and 11.

Steps 8a–8h have the following meanings:

Step 8a:
$Pb(OAc)_4$ in a suitable solvent (e.g., benzene, toluene) at reflux (G. A. Russel et al., *J. Am. Chem. Soc.*, 1906, (1975)).

Step 8b:
Sodium borohydride in alcohol (see Reaction Scheme 7, step 7a) then alkaline hydrolysis (when A=COOR, it can be simultaneously converted into COOH);
aluminum isopropoxide as described in Reaction Scheme 7, step 7h;
diborane in tetrahydrofuran at –10° C./r.t. then aqueous hydrogen peroxide in the presence of sodium hydroxide (not when A is $CH=CH-CH_3$; when A=COOR, it can be simultaneously converted into COOH). (Kirkiacharian et al., *C.R. Hebd. Seances Acad. Sci. Ser. C*, 289, 227, (1979));
lithium aluminum hydride and aluminum trichloride in a suitable solvent (e.g., tetrahydrofuran) at 0° C./reflux (not for A=COOR or $NO_2$) (Bokadia et al., *J. Chem. Soc.*, 4663, (1961)).

Step 8c:
Hydrogen (100 atm), copper chromite in ethanol at 140° C. (M. A. Vickars, *Tetrahedron*, 20, 2873, (1964)). When A is $NO_2$ it is simultaneously converted into a $NH_2$ group.

Step 8d:
Potassium permanganate in tert-butanol (or other suitable solvent) in the presence of aqueous sodium hydroxide at –10°/0° C. (K. Hanaya, *Bull. Chem. Soc. Jpn.*, 40, 1884, (1967)) (not when A is $CH=CH-CH_3$). (See also A. H. Haines, "Methods for the Oxidation of Organic Compounds", Academic Press Inc, (London), 1985, chapter 3.2.2).

Osmium tetroxide (see A. H. Haines, vide supra, chapter 3.2.1) in a suitable solvent (e.g., diethyl ether) at room temperature (Baranton et al., *Bull. Soc. Chim. Fr,* 4203, (1968)) (not when A is CH=CH—CH$_3$);

aqueous hydrogen peroxide in formic acid or acetic acid at −20°/−50° C. then NaOH, H$_2$O, 45° C. (Baranton et al., vide supra; A. H. Haines, vide supra, chapter 3.2.7.) (not when A is CH=CH—CH$_3$; when A=COOR it can be simultaneously converted into COOH);

silver acetate and iodine in wet acetic acid at 0°–20° C. (K. Hanaya, vide supra; A. H. Haines, vide supra, chapters 3.2.3, 3.2.4, 3.2.9) (not when A is CH=CH—CH$_3$).

Step 8e:

30% Hydrogen peroxide in the presence of sodium hydrogencarbonate in benzonitrile at 0°–110° C., then lithium aluminum hydride in tetrahydrofuran at 0°–40° C. (not for A=COOR and CH=CH—CH$_3$) (Clark et al., *Austr. Journ. of Chem.,* 27, 865 (1974)).

Step 8f:

Hydrogen (1–50 atm) in a suitable solvent (e.g., ethanol) in the presence of a metallic catalyst (e.g., palladium dichloride) at r.t. 78° C. (when A=NO$_2$ it is simultaneously converted into NH$_2$), (Bolger et al., *Tetrahedron,* 23, 341, (1967)).

Step 8g:

see step 8e (Clark et al., vide supra).

Step 8h:

Cerium trichloride heptahydrate 0.4M in methanol, in a suitable solvent (e.g., methanol) then sodium borohydride at 0°/78° C. (W089/06650);

sodium borohydride in diglyme at 0° C./reflux (G. P. Thakar, *Indian J. Chem.,* 3, 74 (1965)) (when A=NO$_2$ it can be converted into NH$_2$);

sodium borohydride-aluminum trichloride in a suitable solvent (e.g., tetrahydrofuran or benzene) at 0° C./reflux (not with A=COOR) (G. P. Thakar, vide supra);

diborane in tetrahydrofuran at room temperature (not when A is CH=CH—CH$_3$) (G. P. Thakar, vide supra).

Intermediates (4), (5), (6), (9) of Reaction Scheme 8 can be transformed into the corresponding compounds having B (with the same meanings as in Reaction Scheme 1) instead of A, according to step 1g.

Simple starting materials having W=CH$_2$ and a single bond at position 2–3 may be prepared according to Reaction Scheme 9 (where A has the same meaning as in Reaction Scheme 1).

Intermediates (1) may be prepared according to Reaction Scheme 6 or from Intermediate (2) (obtainable following Reaction Scheme 7) converted into a 4-toluenesulfonic acid ester or a methanesulphonic acid ester or into a halogen derivative (3), which may be transformed into a thioether derivative (1) by nucleophilic substitution with a thiol. These simple conversions can be performed by techniques known to those skilled in the art. Intermediates (3) where P=OC(S)aryl or OC(S)heteroaryl or OC(S)O-alkyl, aryl or OC(S)S-alkyl may be obtained from (2) and the appropriate chlorothioformate or chlorothiocarbonate or 1,1'-thiocarbonildiimidazole as described in *J. Org. Chem.,* 55, 924 (1990) and *Synthesis,* 362, (1991) and references cited therein.

Intermediates (4) may be obtained from intermediates (1) or (3) by simple elimination reaction with bases.

Intermediates (5) may be obtained according to Reaction Scheme 4.

Step 9a–9e of Reaction Scheme 9 have the following meanings:

Step 9a:

Raney-Ni in a suitable solvent (e.g. isopropanol) at r.t./100° C. When A=NO$_2$ it is simultaneously converted into NH$_2$;

triethyltin hydride in benzene or other aromatic solvent at 30°–150° C. For other de-sulfurization methods, like, e.g., nickel chloride and sodium borohydride in methanol or borane-pyridine complex in trifluoroacetic acid or in dichloromethane in the presence of aluminum trichloride, see: J. March, "Advanced Organic Chemistry", pg. 728, J. Wiley & Sons, New York, 1992 and references cited therein. (not when A is CH=CH—CH$_3$).

Step 9b:

Hydrogen with a catalyst according to Reaction Scheme 8, step 8f. When A=NO$_2$, it is simultaneously converted into NH$_2$.

Step 9c: Where P is an O-C derivative:

tributyltin hydride or tris(trimethylsilyl)silane (Sc-hummer D., et al, SYNLETT, 11:705, 1990) in the presence of azobisisobutyronitrile ("AIBN" used as a radical reaction initiator and prepared according to C. G. Overberger et al, *J. Am. Chem. Soc.,* 71:2661, 1969) in a suitable solvent (e.g., toluene) at 80°–150° C.; (M. Drescher, *Synthesis,* 362, (1991). M. Sekine, *J. Org. Chem.,* 55, 924, (1990));

a silane (e.g., triethylsilane or diphenyl silane) in a suitable solvent (e.g., dichloromethane) at −20° C./reflux in the presence of trifluoroacetic acid or boron trifluoride (F. M. Mauser, *J. Org. Chem.,* 55, 555 (1990));

triethylchlorosilane, sodium iodide in acetonitrile then zinc powder in acetic acid and acetonitrile at r.t./80° C. (T. Morita et al., *Synthesis,* 32, (1981)) Where P is halogen or an O-S derivative:

a reducing agent (e.g., sodium cyanoborohydride in hexamethylphosphotriamide or sodium borohydride in dimethylsulfoxide) chosen from those cited in J. March, "Advanced Organic Chemistry", J. Wiley, New York, (1992) chapter 0–76 or 0–77.

Step 9d:

Hydrogen (1–5 atm) in a suitable solvent (e.g., ethanol) in the presence of a catalyst (e.g., palladium on carbon 10% at 50°–78° C.) (Sarcevic, *Helv. Chim. Acta,* 56, 1457, (1973)) (When A=NO$_2$ it is simultaneously converted into NH$_2$);

zinc and gaseous hydrochloride acid in diethyl ether or acetic anhydride in toluene at 0°–80° C. (M. Toda, *Bull. Chem. Soc. Jp.,* 45, 264, (1972)) (not when A is NO$_2$).

Step 9e:

Zinc and aqueous hydrochloric acid in a suitable solvent (e.g., ethanol) at 0°–78° C.;

according to step 9d above (when A=NO$_2$, it is simultaneously converted to NH$_2$);

hydrazine, sodium hydroxide in ethane-1,2-diol at 200° C. (CA 74 (1971): 22699) (not for A=COOR, NO$_2$) or other methods cited in J. March, vide supra) (not for A=COOR, NO$_2$);

according to step 7c of Reaction Scheme 7 (not for A=NO$_2$).

The intermediates (6) of Reaction Scheme 9 can be transformed into the corresponding compounds having B (with the same meanings as in Reaction Scheme 1) instead of A, according to step 1g.

When X represents an oxygen atom or a sulphur atom and W represents a bond, simple starting materials can be prepared according to the following Reaction Scheme 10, wherein the steps 10a–10g have the following alternative meanings:

Step 10a:
- using the same conditions described for step 1a of the Reaction Scheme 1 but utilizing $R_3COCl$ or $(R_3CO)_2O$ instead of $R_3CH_2COCl$ or $(R_3CH_2CO)_2O$, with or without isolation of the intermediate phenyl ester;
- hexamethylenetetramine in trifluoroacetic acid at reflux followed by aqueous hydrochloric acid addition. Such strong acid conditions might give Intermediates (2) having A=COOH, that need re-esterification with the appropriate alcohol (e.g., using thionyl chloride at reflux temperature) before Step 10c;

Step 10b:
- $R_2COCH(R_3)Hal$ in acetone or methyl ethyl ketone or dichloromethane or chloroform in the presence of a suitable base such as potassium carbonate, triethylamine or sodium hydride, at 20°–80° C.;

Step 10c:
- $R_2CH(Hal)COOAlk$ in an aprotic solvent (e.g., dimethylformamide) in the presence of a base (e.g., potassium carbonate) at 70°–100° C. followed by hydrolysis of the remaining intermediates with a strong base (e.g., potassium hydroxide) in aprotic solvent (e.g., ethyl alcohol) at reflux, and finally submitting to decarboxylation - dehydration conditions using a non-protic solvent (e.g., xylene) and an acid catalyst (e.g., p-toluenesulfonic acid) at reflux or simply heating at 240° C. in quinoline;
- $R_2CH_2Hal$ and potassium hydroxide in refluxing ethyl alcohol followed by cyclization of the isolated intermediate phenyl(thio)ether with sodium methoxide in a boiling dimethylformamide-methanol mixture; when A=COOAlk, intermediates (4) having A=COOH can be obtained.
- Using $ArCOCH_2Br$ and potassium carbonate in acetone at reflux, Intermediates (4), having $R_2$=ArCO, are obtained.

Step 10d:
- Vigorous stirring in preheated polyphosphoric acid at 90°–140° C.;
- Lewis acid (e.g., aluminum trichloride) in chlorobenzene at 70°–90° C. The cyclizations carried out on Intermediates (3) having $R_3$=Cl with a Lewis acid (e.g., aluminum trichloride) in o-dichlorobenzene at 45° C. or with boron trifluoride in diethyl ether at 20°–25° C. gives the Intermediates (4) where $R_3$=OH, as reported by K. Davies, *J. Chem. Soc.* (PT. 1), 2624, (1957) for compounds having X=S and $R_2$=H.

Step 10e:
- sodium alkoxide (1 equivalent) in the same alcohol used to prepare the alkoxide at 0°–90° C.; when A=COOAlk it may be suitable to use the corresponding AlkOH as solvent reaction.
- When $R_2$=COOAlk and X=S, Intermediates (4) can be hydrolyzed to the corresponding $R_2$=COOH with sulfuric-acetic acid mixture, (if A=COOAlk is present, it also can give A=COOH), and can be selectively decarboxylated with copper in anhydrous quinoline at 210°–220° C., to give Intermediates (4) where $R_2$=H according to J. Cooper et al., *J. Chem Soc.* (C), 3405 (1971).

Step 10f:
- $R_2CH_2XH$ and one equivalent of sodium in ethanol at reflux or $R_2CH_2XH$ with sodium hydrogencarbonate in ethanol-water mixture at 60°–90° C.

Step 10g:
- When A=COOAlk or $NO_2$, the same methods described in Reaction Scheme 1, step 1g can be used. It must be noted that reduction of the $NO_2$ group to the $NH_2$ group by catalytic hydrogenation can simultaneously afford hydrogenation of the double bond at position 2–3, as reported by S. L. Meisel et al., "Heterocyclic Compounds", Ed. Interscience Publ.: "Compounds with Condensed Thiophene Rings", pg 34, (1954) and M. Ahmed, ibidem, Ed. Wiley-Interscience: "Benzofurans", pg 56, (1974). When A=$NO_2$ and $R_2$=COAr, the reduction carried out with hydrogen in the presence of Pt on carbon as catalyst gives the 2,3-dihydro Intermediates (5) where B=$NH_2$ and $R_2$=$CH_2Ar$ as reported in WO 86 07,056 (1986); when A=$CH_3$ and $R_2$, $R_3$, $R_6$ are not $CH_3$ or $R_2$ does not bear a $CH_3$ group, the compounds can be transformed into the corresponding:
- A=$CH_2Br$ by reaction with N-bromosuccinimide in carbon tetrachloride and 2,2'-azobisisobutyronitrile (Griesbaum, supra) or benzoyl peroxide as catalysts at reflux;
- A=CHO by reaction of the above Intermediates with hexamethylenetetramine in refluxing chloroform followed by acid hydrolysis of the salt in boiling acetic acid or by reaction of Intermediates having A=$CH_3$ with tetrabutylammonium dichromate in refluxing chloroform according to Valenti et al, *Arzneim. Forsch.*, 40, 122 (1990);
- A=COOH by oxidation of the above Intermediates (A=CHO) with silver oxide in a mixture of protic aqueous solvent (e.g., ethanol-dimethylformamide at 0°–70° C. according to H. R. Rodriguez et al. *Tetrahedron*, 24, 6587 (1968) or with potassium permanganate in t-butyl alcohol in the presence of sodium di-H-orthophosphate aqueous solution at 70°–75° C. according to S. Masamune et al., *Tetrahedron Letters*, 27, 4537 (1986). Intermediates (4) of the above Reaction Scheme 10 having $R_3$=$C_6H_5$ or tert-butyl, $R_2$=H and X=O can be transformed into the corresponding intermediates having $R_2$=$C_6H_5$ or tert-butyl and $R_3$=H by reacting with polyphosphoric acid at 132° C. according to Davies et al. *J. Chem. Soc.*, 822 (1958). Intermediates (4) of the above Reaction Scheme 10 having $R_2$=COAr and A=COOAlk can be transformed into the corresponding intermediates having $R_2$=$CH_2Ar$ and A=COOAlk by hydrogenating with $H_2$ in presence of 10% Pd on carbon in protic solvents (e.g. ethanol, acetic acid) at 10–70 psi and at a temperature of 10°–60° C.

When X represents a nitrogen atom and W has all claimed meanings, except a bond, the simple starting materials may be prepared according to the following Reaction Scheme 11, wherein the steps have the following alternative meanings:

Step 11a:
- $EtOC(R_2)$=$C(COOEt)_2$ at 80°–140° C. without solvents or in a polar solvent (e.g., isopropanol);

Step 11b:
- $R_2COCH(R_3)COOAlk$ and p-toluenesulfonic acid or methanesulfonic acid in a chlorinated solvent (e.g., chloroform or dichloromethane) or aprotic solvent (e.g., benzene) at reflux under azeotropic conditions;

Step 11c:
- by heating Intermediates (2) in diphenyl ether in the presence of p-toluenesulfonic acid or phosphoric acid or zinc oxide as catalysts at 245°–255° C. according to Hung. Teljies 6251 (CA 79, 92026v (1973)); heating in a high boiling solvent (e.g., diphenyl ether) followed by hydrolysis of the remaining Intermediates (4) ($R_3$=COOEt) with a strong acid (e.g., hydrochloric acid) in a protic solvent (e.g., acetic acid) at reflux to give Intermediates (4) where $R_3$=COOH. The above isolated acids can be decarboxylated by heating in a high boiling solvent (e.g., diphenyl ether) to give Intermediates (4) where $R_3$=H according to R. Albrecht et al., Ber., 105, 3118 (1972);

Step 11d:

heating in a high-boiling solvent (e.g., diphenyl ether) at 255° C.;

when R=Alk Intermediates (4) are obtained directly from Intermediates (1), without isolation of Intermediates (3), by condensation with $R_2COCH(R_3)COOAlk$ in polyphosphoric acid at 90°–150° C. according to F. Piozzi et al., Gazz. Chim. It., 100, 678 (1970).

Step 11e:

Al/Hg amalgam in aqueous ethanol solution at reflux followed by acidification with a strong acid (e.g., hydrochloric acid) and treatment with iron trichloride at reflux according to W. A. Denny et al., J. Med. Chem., 32, 396 (1989).

When A=COOAlk Intermediates (4) should be hydrolyzed to the corresponding A=COOH before performing Step e.

When A=$NO_2$, intermediates (5) having A=$NH_2$ are obtained;

Step 11f:

$R_2CH$=CHCHO and arsenic acid in a strong acidic medium (e.g., concentrated sulfuric acid) and water at 105°–115° C. according to EP 206,802 (1986).

When A=COOAlk, Intermediates (1) should be hydrolyzed to the corresponding A=COOH before performing Step f. All Intermediates (1) have R=H and the obtained Intermediates (5) have $R_3$=H.

Step 11g:

$R_2CH$(Hal) - CH($R_3$)COOH in a protic solvent (e.g., water) in the presence of a strong base (e.g., sodium hydroxide) at 100°–125° C., followed by cyclization of the isolated Intermediates β-anilinopropionic acids with preheated polyphosphoric acid at 120°–125° C. or with phosphorous pentoxide in a high-boiling aprotic solvent (e.g., xylene) at 120°–140° C. In some cases, it is useful to start from Intermediates (1), where R=tosyl or other suitable protective groups; the obtained Intermediates (6), where R=tosyl, can be easily converted into Intermediates (6), where R=H, by hydrolysis with a strong acid (e.g., hydrochloric acid) in a protic solvent (e.g., acetic acid) at reflux. When A=COOAlk, Intermediates (6) having A=COOH, are obtained.

Step 11h:

$R_2$CHO and ethylene in acetic acid and hydrochloric acid at 25°–30° C. according to K. D. Hesse, Liebigs Ann. Chem., 741, 117 (1970). Where Intermediates (1) have R=H starting materials (7), having R=$R_3$=H are obtained. Epichlorohydrin followed by cyclization of the isolated anilinopropanol derivatives in refluxing N,N-diethylaniline or ortho-dichlorobenzene in the presence of a proton acceptor (e.g., triethylamine) according to S. D. Boyd et al., J. Org. Chem., 30, 2801 (1965). In this case, Intermediates (7) having R=$R_2$=H and $R_3$=OH are obtained;

Step 11i:

by hydrogenation in presence of a catalyst (e.g., platinum oxide) in a protic solvent (e.g., ethanol) at 20°–30° C. and 2–4 atm according to G. M. Coppola, J. Heter. Chem., 15, 645 (1978).

When A=$NO_2$, Intermediates (7), having A=$NH_2$ are obtained.

Intermediates (4),(5),(6) and (7) thus obtained can be converted to the corresponding derivatives having A=COOH or $NH_2$ according to the methods of Reaction Scheme 1, step 1g.

The synthesis of the simple Intermediates (7) of Reaction Scheme 11 having R=H and A=COOH can be also pursued using the method shown in the Reaction Scheme 12:

Step 12a:

oxalyl chloride in a polar solvent (e.g., tetrahydrofuran) at reflux followed by internal Friedel-Crafts acylation of the remaining chlorooxalylamide with a Lewis acid (e.g., aluminum trichloride) in a non polar solvent (e.g., carbon disulfide) at reflux, according to EP 402,859 (1989);

Step 12b:

30–35% aqueous hydrogen peroxide and a strong base (e.g., sodium hydroxide) in a polar solvent (e.g., water) at 20°–30° C. followed by addition of a strong acid (e.g., hydrochloric acid), as reported in EP 402,859 (1989).

When X represents an amino group and W is a bond, the simple starting materials may be prepared according to the following Reaction Schemes 13 and 14, wherein A has the same meanings as in Reaction Scheme 1 and the steps have the following alternative meanings:

Step 13a:

$ClCH_2C(Cl)$=$CH_2$ in the presence of potassium carbonate at 40°–80° C. according to L. Purdie, J. Chem. Soc. (C) 1970, 1126;

Step 13b:

$R_2$COHal in pyridine or in a chlorinated solvent (e.g., dichloromethane) in the presence of proton acceptor (e.g., triethylamine) at 20°–100° C. or in a polar solvent (e.g., acetone) in the presence of potassium carbonate at 20°–80° C.;

Step 13c:

boron trifluoride in methyl alcohol at 130°–155° C.; heating at 100°–110° C.

Intermediates (5) obtained by this route, have always $R_2$=$CH_3$.

Step 13d:

$R_2COCH(OAlk)_2$ in a non- polar solvent (e.g., toluene) in the presence of iodine as catalyst at reflux in azeotropic conditions followed by reduction of the isolated (or unisolated) imino intermediate with sodium borohydride in a polar solvent (e.g., methanol) in the presence of sodium hydroxide (as catalyst) at reflux. When A=COOAlk, Intermediates (6) having A=COOH can be obtained;

Step 13e:

sodium amide in a high boiling solvent (e.g., N,N-diethylaniline) at 220°–250° C. according to F. Piozzi et al., Gazz. Chim. It., 93, 1382 (1963);

potassium t-butoxide in a polar solvent (e.g., dimethylformamide) at 20°–100° C. according to EP 42,298 (1981);

Step 13f:

boron trifluoride in an apolar solvent (e.g., benzene) at 5°–10° C.;

Step 13g:

zinc or iron dust in acidic medium (e.g., acetic acid) and water at 70°–100° C.

When A=NO$_2$, Intermediates (5) having A=NH$_2$ are obtained.

Step 13h:
thionyl chloride at reflux followed by reaction of the isolated Intermediates (7) acyl chlorides with sodium azide in acidic medium (e.g., acetic acid) at 10°–20° C. and subsequent heating at 50°–70° C.;

Step 13i:
diazotation with sodium nitrite in concentrated sulfuric acid followed by aqueous zinc chloride addition at 5°–10° C. and by reaction of the isolated diazonium salts with CH$_2$=C(R$_2$) COOH in a polar solvent (e.g., acetone) in the presence of a copper salt (e.g., CuCl$_2$) at 25°–30° C.

Examples of steps 13g,h,i are reported by A. Allais et al., *Eur. J. Med. Chem.*, 10, 187 (1975).

Step 13j:
R$_2$CH$_2$NO$_2$ in a polar solvent (e.g., ethanol) in the presence of a base (e.g., n-butylamine) and catalytic amounts of an acid (e.g., acetic acid) at reflux.

The Intermediates (5) thus obtained can be converted to the corresponding derivatives having A=COOH or NH$_2$ according to the methods of Reaction Scheme 1 step 1g.

With regard to Reaction Scheme 14, it is intended that Intermediates (4) having R$_3$=H correspond to Intermediates (5) of Reaction Scheme 13.

Step 14a:
sodium nitrite in aqueous acidic medium (e.g., hydrochloric acid) at −5°/+5° C.;

isoamyl nitrite in a polar solvent (e.g., ethanol) at 5°–10° C.;

Step 14b:
aqueous solution of sulfur dioxide at 0°–10° C. according to Pfannstiel et al., *Ber.*, 75, 1096 (1942); triphenylphosphine and heating of the isolated phosphonium salt in an aqueous-alcoholic hydrogen chloride solution at reflux according to Horner et al., *Ber.*, 85, 1073 (1953).

Step 14c:
R$_2$COCH(R$_3$)Hal in a basic high boiling solvent (e.g., N,N-diethylaniline) at 160°–180° C. or by simply heating without solvents at 180° C.;

R$_3$COCH(R$_2$)Hal in a polar solvent (e.g., acetone) in the presence of a suitable proton acceptor (e.g., potassium carbonate) at reflux followed by cyclization of the isolated β-anilinoketone intermediates with freshly melted zinc chloride in aprotic solvent (e.g., ethanol) at reflux;

R$_2$CH(Hal)CN in the presence of boron trichloride and a Lewis acid (e.g., titanium tetrachloride) in an apolar solvent (e.g., benzene) at reflux followed by cyclization of the isolated 2-amino-α-haloacetophenones intermediates with a suitable reducing agent (e.g., sodium borohydride) in a polar medium (e.g., dioxanewater) at reflux, according to T. Sagusawa et al., *J. Org. Chem.*, 44, 578 (1979). By the above method, Intermediate (4), having R$_3$=H are obtained;

R$_2$COCH(R$_3$)Hal (half an equivalent) in a polar solvent (e.g., methanol) at reflux followed by cyclization of the isolated Schiff base intermediates with a strong acid (e.g., trifluoracetic acid) at 20°–30° C.;

Step 14d:
R$_2$COCH$_2$R$_3$ by heating at 100° C. without solvents or at reflux in a polar solvent (e.g., methanol) followed by cyclization of the isolated hydrazone intermediates with polyphosphoric acid at 100°–130° C. or by simply heating in ethyleneglycol or aqueous formic acid or ethanolic formic acid.

Cyclization can be also carried out by heating in ethanolic hydrogen chloride at reflux or in a mixture of acetic and hydrochloric acid at reflux or in orthophosphoric acid at 95°–105° C. or by simply heating with anhydrous zinc chloride at 100°–220° C. When A=COOAlk, Intermediates (4) having A=COOH can be obtained.

Step 14e:
borane-pyridine complex at 0°–30° C. followed by a protonating agent addition (e.g., hydrochloric acid);

tin or zinc and aqueous hydrochloric acid at 50°–100° C.;

sodium borohydride in the presence of a Lewis acid (e.g., aluminum trichloride) in pyridine at 0°–30° C. or alternatively in the presence of a salt like cobalt or zinc chloride;

sodium cyanoborohydride in acetic acid at 20°–80° C.;

hydrogen in the presence of a catalyst (e.g., Pt) in a polar solvent (e.g., ethanol) at 20°–80° C. Other general methods are reported by Houlihan in "Heterocyclic Compounds", part one, Ed. Wiley-Interscience: "Indoles", page 462 (1972). When A=NO$_2$, Intermediates (4) can be reduced to the corresponding Intermediates (5) having A=NH$_2$;

Step 14f:
sodium hydride and RHal in an anhydrous polar solvent (e.g., dimethylformamide) at 20°–80° C.;

RHal in the presence of potassium carbonate in a polar solvent (e.g., acetone) at reflux;

sodium amide and RHal in a polar anhydrous solvent (e.g., tetrahydrofuran) at low temperature (−70° C.). Intermediates (4), bearing other reactive groups such as NH$_2$ or OH, have to be protected using suitable protective groups which can be selectively cleaved at the end by deprotecting methods;

Step 14g:
RHal in the presence of alkaline metal carbonates (e.g., potassium carbonate) as reported by Houlihan in "Heterocyclic Compounds", part two, Ed. Wiley-Interscience: "Indoles", page 90 (1972) and references cited therein.

Intermediates (5), bearing other reactive groups such as NH$_2$ or OH, have to be protected as reported above;

Step 14h:
tetrachloro-[1,4]-benzoquinone in a polar solvent (e.g., ethylene glycol monomethyl ether) at reflux;

copper (II) chloride in pyridine at reflux according to Kikugawa et al., *J. Heter. Chem.*, 16, 1325 (1979). Intermediates (6) having R$_2$ and R$_3$ other than H, can be reduced to the corresponding starting materials (7) by lithium aluminum hydride according to H. C. Printy et al., *J. Am. Chem. Soc.*, 71, 3206 (1949).

Intermediates (4) of Reaction Scheme 14 having R$_2$=H and R$_3$=OH may be obtained from Intermediates (7) of Reaction Scheme 11 having R=R$_2$=H and R$_3$=OH by ring contraction using an oxidant (e.g., sodium periodate) and a base (e.g., sodium hydroxide) in aqueous ethanol at reflux according to S. D. Boyd et al., *J. Org. Chem.*, 30, 2801 (1965).

Starting materials (4), (5), (6) and (7) can be converted into the corresponding A=COOH or NH$_2$ according to the method of Reaction Scheme 1, step 1g, and from these into the alternative final products. When NH is present and might interfere on the following reactions, it can be protected as reported in T. W. Green's "Protective Groups in Organic Synthesis", Wiley Interscience (1981). Alternatively, unreactive groups (e.g., $NO_2$) can be converted to reactive ones (e.g., $NH_2$) as a final step of the pathway.

Starting materials having W=bond, X=amino and a carboxymethyl group at position 7, can be obtained according to Reaction Scheme 15, wherein the steps have the following alternative meanings:

Step 15a:

Hydrogen at 45 lbs. in the presence of 10% palladium on charcoal as catalyst in water containing one equivalent of sodium hydroxide, followed by diazotation with sodium nitrite in hydrochloric acid at 0°–5° C. and stannous chloride. Cyclization is performed during acidification of the tin salt with hydrogen sulfide and completed by refluxing in xylene according to H. E. Baumgarten et al., *J. Am. Chem. Soc.*, 82, 3977 (1960).

Step 15b:

$R_3CH_2COR_2$ in the presence of an acid (e.g., acetic acid) in a polar solvent (e.g., ethanol) at reflux as reported by W. J. Welstead et al., *J. Med. Chem.*, 22, 1074 (1979) for $R_2=CH_3$ and $R_3=C_6H_5$, where also step 15c and 15d are reported;

Step 15c:

AlkOH at reflux in the presence of an hydrogen chloride stream (AlkOH=lower alkanol, e.g., methanol, ethanol);

Step 15d:

a strong base (e.g., potassium hydroxide) in a polar solvent (e.g., water) at reflux.

The preparation of simple starting materials having $R_3$=hydroxyalkyl and/or the corresponding ethers can be carried out by reacting either Intermediates (3) of Reaction Scheme 1, Intermediates (2), (4) or (5) of Reaction Scheme 2, Intermediates (4) of Reaction Schemes 6, 10 and 15, Intermediates (4) and (5) of Reaction Scheme 11, Intermediates (5) of Reaction Scheme 13 and Intermediates (4) and (6) of Reaction Scheme 14 having $R_3$=H, $CH_3$ according to the Reaction Scheme 16, wherein A and B have the same meanings as in Reaction Scheme 1, $R_5$ represents an H or alkyl group and the steps 16a–16h have the following meanings:

Step 16a: $R_3$=H, W=CO, CS (and no activated phenyl rings present):

Formaldehyde and hydrogen chloride in water, ethanol or acetic acid at 50°–100° C.;

Chloromethyl methyl ether and fuming sulfuric acid at 50°–70° C. (H. Nakazumi et al., *Bull. Chem. Soc. Jap.*, 57, 2323 (1984));

$R_3=CH_3$, W=CO, CS, bond, (bicyclic ring=Quinoline) and no other methyl groups in the molecule:

N-bromosuccinimide in presence of benzoyl peroxide or 2,2'-azobisisobutyronitrile (Griesbaum, supra) in carbon tetrachloride at 50°–80° C.;

Step 16b:

$R_3$=H, W=bond, X=O, S, NH or N-Alk and no electron donating groups are present on the other rings of the molecule:

Phosphorous oxychloride and dimethylformamide at 50°–140° C., or other Viismeyer-Haack reagents (see Jutz, *Adv. Org. Chem.*, 9, 225 (1976));

$R_3=CH_3$, W=bond, X=O, S, NH or N-Alk and no other $CH_3$ groups are present

Irradiation with a Hg high-pressure lamp in a protic solvent (e.g., acetic acid) at 20°–100° C. as reported by Frasca et al., *Tetrahedron*, 23, 603 (1973);

Step 16c:

Sodium or potassium acetate in aprotic solvents (e.g., acetone, dimethylformamide) at 40°–120° C.;

Step 16d: $R_5$ in Intermediates (5)=H:

A reducing hydride (e.g., sodium borohydride) in a polar solvent (e.g., methanol or ethanol or dioxane) at 0°–80° C.; $R_5$ in Intermediates (5)=alkyl:

Alkyl magnesium bromide in aprotic solvents (e.g., diethyl ether, tetrahydrofuran) at 0°–60° C.;

Step 16e:

Sodium or lithium hydroxide in protic solvents (e.g., alcohols, water) or mixture thereof at 25°–50° C. (In this case, when A=COOAlk it can be simultaneously hydrolyzed to COOH);

Step 16f:

The same methods reported in step 1g of Reaction Scheme 1, but the oxidation of $CH=CHCH_3$ to COOH for compounds (5);

Step 16g:

A strong base (e.g., NaH) and an $R_4$-L reagent (where L is an halogen atom or a tosyloxy group) in anhydrous aprotic solvents (e.g., dimethylformamide or tetrahydrofuran) at 20°–140° C.;

Step 16h:

$R_4OH$ and a base (e.g., Na, NaH) in excess $R_4OH$ or in aprotic solvents (e.g., dimethylformamide or tetrahydrofuran) at 20°–140° C.

The simple Intermediates (6) having an hydroxyalkyl group at position 3 of the bicyclic heteroring, obtained in this way, can be reacted as such or, alternatively, derivatized at the hydroxymethyl group with known reagents and methods, so that said group does not interfere in the further reaction steps necessary to prepare those compounds of formula (I) which bear a protected hydroxyalkyl group such as $R_3$. The protected final compounds are finally converted by deprotecting methods to compounds of formula (I) having $R_3$=hydroxyalkyl group.

As used herein "prodrug" or "prodrug derivative" means a derivative of a compound disclosed herein which, once administered to a host, is converted into the compound disclosed herein. A "metabolite" of a compound disclosed herein is an active derivative of a compound disclosed herein which is formed when the compound is metabolized. A "prodrug of a metabolite" means a compound which is metabolized to the same metabolite as a compound disclosed herein.

Metabolites of compounds disclosed herein can be identified either by administration of compounds disclosed herein to a host and analysis of blood samples from the host, or by incubation of compounds disclosed herein with hepatic cells in vitro and analysis of the incubant. Both methods are well-known in the art.

Compounds defined as "prodrug derivatives" in the Summary of the Invention may be prepared, for example, starting from the corresponding hydroxy (method 1) or amidic (method 2) compounds by the following methods:

Method 1:

by reacting with a chloroformate, an isocyanate or isothiocyanate, a carbonyl chloride or bromide or another activated acid derivative (e.g., anhydride) in a suitable solvent (e.g., chlorinated solvents, dimethylformamide, tetrahydrofuran, dioxane, acetonitrile, pyridine) in the presence or absence of a base such as triethylamine, pyridine, 4-dimethylaminopyridine, sodium hydroxide, potassium carbonate or 1,10-diazabicycloundecene at −20°/100° C.;

by reacting with a carboxylic acid in the same solvents as above, in the presence of a condensing agent such as N,N'-carbonyldiimidazole, carbodiimides or others known to the people skilled in the art;

by reacting with a dialkyl or diaryl chlorophosphate or dialkyl cyanophosphonate in the same conditions described above (for examples of such derivatization methods see Examples 114, 120–122, 165 and S. O. Thorberg et al., *J. Med. Chem.*, 30, 2008 (1987)).

Method 2:

Prodrug derivatives of "acidic" NH groups according to the Summary of the Invention can be synthesized from the compounds of formula I considered in the Summary by preparing an N-hydroxy(substituted)methyl derivative and reacting the derivative under the same conditions as described above for oxygen derivatization. The intermediate N-hydroxy(substituted)methyl derivative can be isolated or directly reacted to give the desired compound. N-hydroxy(substituted)methyl derivatives of the type Ny-CH($R_1$)OH where $R_1$=H, $CCl_3$ can be obtained by reacting the appropriate compounds of formula I with formaldehyde or $CCl_3CHO$ as described in H. E. Zaugg, *Organic Reactions*, 14, Chapter 2, 52 J. Wiley and Sons New York, 1965 or in J. P. Chupp, *J. Org. Chem.*, 28, 2592 (1963). In the case where $R_1$=phenyl, said compounds can be synthesized by reacting with benzaldehyde and a cyclic amine (e.g., morpholine) in methanol or dichloromethane-methanol 1:1 at 0° C.-reflux and hydrolyzing the intermediate with 0.1N hydrochloric acid at pH=4. (O. Jacobseen, *Annalen*, 157, 243 (1884); H. Bundgaard et al., *Int. J. Pharm.*, 22, 45 (1984)).

Compounds of the type Ny-$CH_2$-B' (where B' has been described in the Summary of the Invention) can be prepared by reacting compounds of formula I with the appropriate secondary amine and formaldehyde in a suitable solvent (e.g., methanol, tetrahydrofuran) at 0°–100° C. (H. Bundgaard, Int. J. Pharm., 21, 251 (1984) or P. Tramontin, Synthesis, 1973, 736 and references cited therein).

Some examples of prodrugs can be found in Examples 114, 120–122 and 165. Examples of compounds that are considered metabolites (e.g. of the compound of Ex. 11) are in Example 59, 85, 91, 126, 133, 139, 140 and 158. The prodrugs of the former examples also qualify as prodrugs of the metabolites of the latter examples.

All the above described reaction pathways and steps are to be intended as examples and are not limiting the scope of the invention. A person skilled in the art would appreciate that reagents used in the chemical transformations of polyfunctional substrates may react with non-targeted groups present in the molecule. For example, catalytic hydrogenation can transform nitro groups into amino groups as desired, however, isolated double bonds might be hydrogenated and halogen atoms may be removed. Likewise, lithium aluminum hydride can reduce conjugated ketones to alkanes as desired (e.g., step 7c in Reaction Scheme 7), however, it may also reduce COOAlk groups to $CH_2OH$ or $NO_2$ groups to —N=N—. The undesired side-reactions can be avoided or minimized by choosing the appropriate conditions or by using alternative reagents or different synthetic pathways. Alternatively, the undesired intermediates may be transformed into useful ones using methods known in the art.

DETAILED SYNTHESIS OF INTERMEDIATES 8-(3-Bromopropoxycarbonyl)-3-methyl-4-oxo-2-phenyl-4H-1-benzopyran (Intermediate I)

30 g of 1,3-dibromopropane was added dropwise at ambient temperature to a suspension of 30 g of sodium3-methyl-4-oxo-2-phenyl-4H-1-benzopyran-8-carboxylate in 150 ml of dimethylformamide and 35 ml of water. The reaction mixture was stirred at ambient temperature for 5 days. 100 ml of water was added and stirring was continued for a further 15 minutes. The precipitate was filtered off by suction, washed with water and purified by flash chromatography on silica gel, eluting with chloroform:ethyl acetate 95:5. The collected fractions were evaporated to dryness in vacuo and the residue was recrystallized from ethanol to give 27.7 g of the title compound, m.p. 114°–115° C.

The benzopyran carboxylate salt used in the foregoing synthesis was prepared by dissolving the corresponding acid (104 g) in hot methanol (560 ml) and adding an aqueous solution (280 ml) of sodium hydrogen carbonate (31 g). The solution was added with acetone (850 ml) yielding the desired salt, collected by suction (62 g, m.p.>280° C.). The corresponding acid was prepared as per Da Re, P. et al., *J. Med. Pharm. Chem.* 2; 263, (1960).

8-Hydroxymethyl-3-methyl-4-oxo-2-phenyl-4H-1-benzopyran (Intermediate II)

467 ml of a 1.48N solution of sodium borohydride in anhydrous dimethyl formamide was added over a period of 30 minutes, under stirring at ambient temperature, to a solution of 100 g of 3-methyl-4-oxo-2-phenyl-4H-1-benzopyran-8-carbonyl chloride (prepared as described in Da Re, supra) in 1 liter of anhydrous dimethylformamide. The reaction mixture was stirred for 2.5 hours at ambient temperature. 88 ml of 2N aqueous hydrochloric acid solution was added while maintaining the temperature at 0°–5° C. 102 ml of 12.7N aqueous sodium hydroxide solution was then added. The mixture was poured into 6 liters of water, stirred for 3 hours, and filtered on a Buchner funnel. The filter cake was washed with 4N sodium hydroxide solution and then with water. The resultant white solid was crystallized from methanol to give 50 g of the title compound, m.p. 145°–147° C.

E-8-(2-carboxyvinyl)-3-methyl-4-oxo-2-phenyl-4H-1-benzopyran (Intermediate III)

A mixture of 7.92 g of 8-formyl-3-methyl-4-oxo-2-phenyl-4H-1-benzopyran (prepared as described in Uneyama, K. et al., *Bull. Chem. Soc. Jap.* 58.; 2361, (1985)) 3.75 g of malonic acid and 0.46 ml of piperidine in 15 ml of anhydrous pyridine was stirred at 100° C. for 3 hours. After cooling to 20°–25° C. the reaction mixture was poured into a mixture of 90 g of crushed ice and 33 ml of hydrochloric acid (d=1.18). The resultant precipitate was collected by suction filtration, washed with water and crystallized twice from 95% ethanol to give 5.5 g of the title compound, m.p. 226°–229° C.

E-8-(2-chlorocarbonylvinyl)-3-methyl-4-oxo-2-phenyl-4H-1-benzopyran (Intermediate IV)

A solution of 9.2 g of Intermediate III and 7.8 g of thionyl chloride in 75 ml of toluene was refluxed for 3 hours. After cooling to 20°–25° C. the resultant crystal was collected by suction filtration, washed with acetone and dried in vacuo to give 6.8 g of the title compound, m.p. (190) 196°–198° C. after recrystallization from toluene.

8-Acetyl-3-methyl-4-oxo-2-phenyl-4H-1-benzopyran (Intermediate V)

1.17 g of magnesium turnings, 7.4 ml of anhydrous ethanol and 0.2 ml of anhydrous carbon tetrachloride were placed in a round bottomed flask under a stream of nitrogen. When the temperature began to rise, 7.5 ml of anhydrous chlorobenzene was added, followed by the slow dropping (25 minutes) of a solution of 5.28 ml of anhydrous diethylmalonate and 3.5 ml of anhydrous chlorobenzene in 16 ml of anhydrous ethanol. The reaction flask was heated to 75°

C. for two hours, cooled to 25° C. and a solution of 8.8 g of 3-methyl-4-oxo-2-phenyl-4H-1-benzopyran-8-carbonyl chloride in 88 ml of anhydrous chlorobenzene was slowly added, without exceeding 35° C. The reaction mixture was further stirred for two hours at 35° C. and then cooled to 0° C. 13 ml of water and 1.9 ml of sulfuric acid (d=1.84) were added. The solution obtained was decanted from the insoluble inorganic matter and stripped in vacuo.

The crude acylmalonate obtained was refluxed for six hours with 10.4 ml of acetic acid, 7 ml of water and 1.3 ml of sulfuric acid (d=1.84). After cooling, the solution was poured into iced water and the precipitate was collected by suction filtration and washed with aqueous sodium carbonate. Crystallization from 90% ethanol gave 6.5 g of the title compound, m.p. 159°–161° C.

8-Bromoacetyl-3-methyl-4-oxo-2-phenyl-4H-1-benzopyran (Intermediate VI)

A solution of 11.2 g of bromine in 250 ml of chloroform was added, over a period of two hours at 20°–25° C., to a solution of 19.5 g of the Intermediate V in 700 ml of chloroform. After stirring for 1 hour at 20°–25° C., the solution was washed with 400 ml of 2N aqueous sodium hydroxide solution and then repeatedly with water, dried with anhydrous sodium sulfate and stripped in vacuo. The crude product was treated with diethyl ether, collected by suction filtration and crystallized from acetone, yielding 16 g of the title compound, m.p 134°–135° C.

8-(2-Hydroxyethylcarbamoyl)-3-methyl-4-oxo-2-phenyl-4H-1-benzopyran (Intermediate VII)

The title compound was prepared in the same manner as Intermediate XXXVI, but using 2-aminoethanol instead of 3-aminopropanol. m.p. 206°–208° C.

3-Methyl-4-oxo-2-phenyl-4H-1-benzopyran-8-sulfonyl chloride (Intermediate VIII)

A solution of 4.55 g of sodium nitrite in 12 ml of water was added dropwise to a stirred mixture of 15.1 g of 8-amino-3-methyl-4-oxo-2-phenyl-4H-1-benzopyran (prepared as described in Da Re, P. et al., *Il. Farmac* (Ed. Sci.) 11: 670, 1956) in 150 ml of hydrochloric acid (d=1.18) at −5° C. Stirring was continued at 0° C. for 30 minutes. The solution was poured, over a period of 10 minutes and at −5° to 0° C., into 120 ml of a 30% by weight solution of sulfur dioxide in acetic acid containing 1.53 g of cupric chloride dihydrate and 13 ml of water. After 1 hour at 0° C. and 1 hour at 20°–25° C., 300 ml of iced water was added to the mixture. A precipitate formed and was collected by suction filtration, washed with water and dried in a desiccator over sodium hydroxide until of constant weight to give 18 g of crude title product, m.p. 165°–170° C., for use without further purification.

8-(3-Chloropropoxy)-3-methyl-4-oxo-2-phenyl-4H-1-benzopyran (Intermediate IX)

This compound was prepared in the same manner as Intermediate XI, but using 1-bromo-3-chloropropane instead of 1-bromo-2-chloromethane (m.p. 98°–102° C.) after washing with petroleum ether:diethyl ether 7:3.

8-Acrylamido-3-methyl-4-oxo-2-phenyl-4H-1-benzopyran (Intermediate X)

A solution of 1.75 ml of acryloyl chloride in 15 ml of anhydrous tetrahydrofuran was added dropwise at −10° C. to a stirred mixture of 5 g of 8-amino-3-methyl-4-oxo-2-phenyl-4H-1-benzopyran and 3 ml of triethylamine in 60 ml of anhydrous tetrahydrofuran. After stirring at 0° C. for 1 hour and at ambient temperature for 1 hour, the reaction mixture was poured into water and filtered under suction. The filter cake was washed with water. Desiccation gave 5.5 g of the title compound, m.p. 229°–230° C.

8-(2-Chloroethoxy)-3-methyl-4-oxo-2-phenyl-4H-1-benzopyran (Intermediate XI)

A mixture of 7.52 g of 8-hydroxy-3-methyl-4-oxo-2-phenyl-4H-1-benzopyran (prepared as described in Da Re, P. et al., *Ann. Chim.*, 1962, p.506 et seq.), 6.22 g of anhydrous potassium carbonate and 25.5 ml of 1-bromo-2-chloromethane in 70 ml of dimethylformamide was stirred at 60° C. for 25 hours. The mixture was cooled to 20°–25° C. and poured into 600 ml of water. The organic solution, obtained by extraction with dichloromethane, was washed with aqueous sodium chloride solution and dried on anhydrous sodium sulfate. The solvents and excess 1-bromo-2-chloromethane were evaporated off in vacuo to yield 8.8 g of the title compound, m.p. 141°–142° C. after crystallization from chloroform: hexane.

8-(2-Azidoethoxy)-3-methyl-4-oxo-2-phenyl-4H-1-benzopyran (Intermediate XII)

A mixture of 15.2 g of Intermediate XI and 6.24 g of sodium azide in 150 ml of anhydrous dimethylformamide was stirred at 70°–75° C. for 12 hours. After cooling to 20°–25° C., the reaction mixture was poured into 1.5 liters of water and extracted with dichloromethane. The organic solution was washed with aqueous sodium chloride solution and dried on anhydrous sodium sulfate. The solvents were evaporated off in vacuo. The residue was taken up in water, collected by suction filtration and dried to give 14 g of the title compound, m.p. 119°–120° C.

8-[N-(2-hydroxyethyl)-N-methyl-carbamoyl]-3-methyl-4-oxo-2-phenyl-4H-1-benzopyran (Intermediate XIII)

A solution of 1.6 ml of 2-methylamino-ethanol in 10 ml of water was added dropwise over a period of 5 minutes to a suspension of 6 g of 3-methyl-4-oxo-2-phenyl-4H-1-benzopyran-8-carbonyl chloride and 1.52 g of potassium carbonate in 60 ml of acetone. After stirring for 2.5 hours at 20°–25° C., the solvent was removed in vacuo and the residue was taken up in 150 ml of acetone. The mixture was refluxed for 15 minutes, and was then filtered. The solvent was evaporated from the filtrate and the residue was dissolved in 20 ml of dimethylformamide, treated with 14 ml of 1.4% aqueous sodium carbonate solution, stirred for 30 minutes at 20°–25° C. and diluted by addition of 150 ml of water. The mixture was extracted with chloroform and the organic layer was washed with 0.5N aqueous hydrochloric acid solution and then with water. The solution was dried over anhydrous sodium sulfate and the chloroform was evaporated off. The resulting oil was taken up in 200 ml of diethyl ether and stirred for 2 hours at 20°–25° C. The solids were collected by filtration and crystallized from ethyl acetate to give 4.97 g of the title compound, m.p. 128°–130° C.

8-(2-Chloroethylcarbamoyl)-3-methyl-4-oxo-2-phenyl-4H-1-benzopyran (Intermediate XIV)

The title compound was prepared in the same manner as Intermediate XXXVII, but using Intermediate VII in place of Intermediate XXXVI and carrying out the reaction at ambient temperature, m.p. 181°–182° C. (ethyl acetate).

8-(N-methyl-2-chloro-ethylcarbamoyl)-3-methyl-4-oxo-2-phenyl-4H-1-benzopyran (Intermediate XV)

A solution of 1.1 ml of thionyl chloride in 2 ml of dichloromethane was added to a solution of 3.37 g of Intermediate XIII in 20 ml of dichloromethane, and the mixture was stirred for 4 hours at ambient temperature. Removal of the solvent gave an oil which was taken up in diethyl ether. The title compound precipitated as a white solid which was filtered off for use without further purification. m.p. (118) 126°–128° C. (diethyl ether).

8-(4-Bromobutoxy)-3-methyl-4-oxo-2-phenyl-4H-1-benzopyran (Intermediate XVI)

A mixture of 5 g of 8-hydroxy-3-methyl-4-oxo-2-phenyl-4H-1-benzopyran, 4.2 g of anhydrous potassium carbonate and 43.6 g of 1,4-dibromobutane in 45 ml of dimethylformamide was stirred at 75° C. for 2 hours. The mixture was cooled to 20°–25° C., poured into 100 ml of water and extracted with dichloromethane. The organic solution was washed with aqueous sodium chloride solution and dried on anhydrous sodium sulfate. The solvents and excess 1,4-dibromobutane were evaporated off in vacuo. The residue was rinsed with 55 ml of petroleum ether:diethyl ether (7:4) and collected by suction filtration to yield 5.6 g of the title compound, m.p. 91°–92° C.

8-(5-Bromopentyloxy)-3-methyl-4-oxo-2-phenyl-4H-1-benzopyran (Intermediate XVII)

This compound was prepared by the method described for the preparation of Intermediate XVI, but using 1,5-dibromopentane in place of 1,4-dibromobutane and purifying the crude product by column chromatography on silica gel (elution with dichloromethane:ethyl acetate (99:1). m.p. 75°–76° C., after rinsing with petroleum ether:diethyl ether (30:4).

8-(2-Chloroethoxymethyl)-3-methyl-4-oxo-2-phenyl-4H-1-benzopyran (Intermediate XVIII)

6 ml of thionyl chloride in 18 ml of chloroform was added at 0° C. to a stirred solution of 23 g of Intermediate XXII and 11 ml of triethylamine in 185 ml of chloroform. The reaction mixture was warmed to 70° C. and stirred for 2 hours. After cooling to ambient temperature, it was poured into water. The organic layer was separated, washed with aqueous sodium chloride solution, dried on anhydrous sodium sulfate and evaporated to dryness in vacuo. Yield: 24 g of the title compound. A sample crystallized from ethanol had a melting point of 102°–103° C.

8-Chloromethyl-3-methyl-4-oxo-2-phenyl-4H-1-benzopyran (Intermediate XIX)

53.4 g of Intermediate II and 38.8 ml of anhydrous triethylamine were dissolved in 440 ml of chloroform. Into this solution, maintained at −10° to −2° C., there was dropped a solution of 19.8 ml of thionyl chloride in 80 ml of anhydrous chloroform. The reaction mixture was stirred at room temperature for 4 hours, and then diluted with 400 ml of water. The aqueous phase was extracted with chloroform, and the extracts were added to the chloroform phase. The chloroform solution was washed with brine, dried on anhydrous sodium sulfate and evaporated to dryness in vacuo. Yield: 56 g of the title compound, which on recrystallization from ethanol was shown to have a melting point of 112°–113° C.

8-Methylaminomethyl-3-methyl-4-oxo-2-phenyl-4H-1-benzopyran (Intermediate XX)

A solution of 15.1 g of anhydrous zinc chloride and 14.5 g of sodium cyanoborohydride in 400 ml of anhydrous methanol was added dropwise at 0° C. into a stirred mixture of 58.8 g of 8-formyl-3-methyl-4-oxo-2-phenyl-4H-1-benzopyran, 60.7 g of methylamine hydrochloride and 125 ml of triethylamine in 600 ml of anhydrous methanol. After stirring for 5 hours at 20°–25° C., the solvent was evaporated off in vacuo and the residue was taken up in 200 ml of water and collected by suction filtration. The crude product was dissolved in aqueous acetic acid, washed with ethyl acetate and re-precipitated by addition of cold 6N aqueous sodium hydroxide solution. 49 g of the title compound was obtained. m.p. 97°–99° C., after crystallization from 75% ethanol.

8-(2-Chloroethylthiomethyl)-3-methyl-4-oxo-2-phenyl-4H-1-benzopyran (Intermediate XXI)

A solution of 37 g of Intermediate XIX and 10.5 g of thiourea in 370 ml of ethanol was refluxed for 1 hour. The reaction mixture was cooled to ambient temperature, and 42 g of 8-amidinothiomethyl-3-methyl-4-oxo-2-phenyl-4H-1-benzopyran hydrochloride spontaneously crystallized. A sample recrystallized from ethanol had a melting point of 233°–235° C.

48 ml of 35% aqueous sodium hydroxide solution was added to a vigorously stirred suspension of 35 g of the compound thus prepared and 1.05 g of benzyl triethylammonium chloride in 440 ml of 1,2-dichloroethane. The mixture was stirred for 2.5 hours and then poured into 300 ml of water. The aqueous layer was extracted with 1,2-dichloroethane and the extracts were added to the organic layer which was washed with sodium chloride solution, dried on anhydrous sodium sulfate, and evaporated to dryness in vacuo. The residue was crystallized from methanol, giving 22 g of the title compound, m.p. 82°–83° C.

8-(2-Hydroxyethoxymethyl)-3-methyl-4-oxo-2-phenyl-4H-1-benzopyran (Intermediate XXII)

A solution of 2.5 g of Intermediate XIX in 25 ml of xylene and 3 ml of dioxane was prepared. 0.15 g of sodium was dissolved in 3.10 ml of anhydrous ethylene glycol, and this solution was added dropwise at ambient temperature to the solution of Intermediate XIX. After refluxing for 5.5 hours, the reaction mixture was cooled to ambient temperature and poured into 50 ml of water. It was extracted with dichloromethane, and the extract was washed with sodium chloride solution, dried on anhydrous sodium sulfate and evaporated to dryness in vacuo. The solid residue was crystallized from ethanol, giving 2.1 g of the title compound, m.p. 132°–133° C.

8-Trifluoroacetamido-3-methyl-4-oxo-2-phenyl-4H-1-benzopyran (Intermediate XXIII)

A solution of 9.5 ml of trifluoroacetic anhydride in 20 ml of anhydrous dichloromethane was added dropwise at −5°–0° C. to a solution of 5 g of 8-amino-3-methyl-4-oxo-2-phenyl-4H-1-benzopyran in 50 ml of anhydrous dichloromethane. The reaction mixture was stirred for 2 hours at 20°–25° C. and then poured on to crushed ice. The organic solution obtained by extraction with dichloromethane was washed with cold 5% aqueous sodium bicarbonate solution and with water, and was dried on anhydrous sodium sulfate. The solvent was removed in vacuo and the residue was crystallized from ethanol to give 5.2 g of the title compound, m.p. 175°–176° C.

8-Aminomethyl-3-methyl-4-oxo-2-phenyl-4H-1-benzopyran (Intermediate XXIV)

A mixture of 21 g of Intermediate XXIX and 19 g of triphenylphosphine in 160 ml of tetrahydrofuran was stirred at ambient temperature for 8 hours. Thin layer chromatography showed the disappearance of Intermediate XXIX. 3 ml of water was added, and stirring was continued for a further 24 hours. The solvents were removed on a rotary evaporator, and the residue was dissolved in water as its acetate. The aqueous solution was washed with ethyl acetate, made basic with 37% aqueous sodium hydroxide solution and filtered on a Buchner funnel. The filter cake was washed with water and desiccated to give 18 g of the title compound. The hydrochloride, recrystallized from ethanol, had a melting point of 256°–258° C.

8-(2-Chloroethylsulfonylmethyl)-3-methyl-4-oxo-2-phenyl-4H-1-benzopyran (Intermediate XXV)

41.6 ml of aqueous 30% hydrogen peroxide was added dropwise at 40° C. over a period of 20 minutes to a solution of 26.2 g of Intermediate XXI in 300 ml of glacial acetic acid. The mixture was heated to 60° C., stirred at that temperature for 4.5 hours, cooled to ambient temperature and poured into 60 ml of water. Filtration on a Buchner funnel gave a filter cake which was washed with water and desiccated, yielding 29.4 g of the title compound. A sample was crystallized from ethanol. m.p. (89) 159°–161° C.

8-(2-Chloroethylsulfinylmethyl)-3-methyl-4-oxo-2-phenyl-4H-1-benzopyran (Intermediate XXVI)

36 ml of aqueous 30% hydrogen peroxide was quickly added dropwise at 10° C. to a solution of 12 g of Intermediate XXI in 84 ml of glacial acetic acid. The reaction mixture was stirred for 4 hours at ambient temperature, and then poured into 220 ml of water. The title compound was collected by suction filtration, washed with water and desiccated. Yield 12.4 g, m.p. 142°–145° C. (methanol).

8-[N-methyl-N-(2-chloroethyl)-aminomethyl]-3-methyl-4-oxo-2-phenyl-4H-1-benzopyran (Intermediate XXVII)

A mixture of 22 g of Intermediate XX, 66 ml of 1-bromo-2-chloroethane and 11 g of anhydrous potassium carbonate in 88 ml of dimethylformamide was stirred at 20°–25° C. for 12 hours. The reaction mixture was then poured into 600 ml of water and extracted with dichloromethane. The organic layer was washed with water, dried on anhydrous sodium sulfate and acidified with ethanolic hydrogen chloride. The solvent and the excess 1-bromo-2-chloroethane were distilled off in vacuo at 70°–80° C. The residue was taken up in cold 1N aqueous sodium hydroxide solution and extracted with dichloromethane. The organic solution was washed with water, dried on anhydrous sodium sulfate and evaporated to dryness in vacuo at 25°–30° C. The crude title product was purified by flash chromatography on silica gel, eluting with ethyl acetate:petroleum ether (7:3), to give 18 g of the title compound melting at 118°–120° C. after crystallization from ethanol.

1-(2-Hydroxy-2-methylpropyl)-4-(2-methoxyphenyl)-piperazine (Intermediate XXVIII)

A mixture of 7 g of 1-(2-methoxyphenyl)-piperazine, 7.33 g of anhydrous potassium carbonate, 1.75 g of potassium iodide and 5.6 ml of 1-chloro-2-methyl-2-propanol was stirred for 90 minutes at 70° C. and for a further 6 hours at 90° C. The reaction mixture was poured into iced water and extracted with ethyl acetate. The organic layer was washed with aqueous sodium chloride solution, dried on anhydrous sodium sulfate and evaporated to dryness in vacuo. The title product was obtained as an oil, and was characterized as its dihydrochloride, crystallized from ethanol, melting at 225°–227° C.

8-Azidomethyl-3-methyl-4-oxo-2-phenyl-4H-1-benzopyran (Intermediate XXIX)

A mixture of 22.8 g of Intermediate XIX and 6.8 g of sodium azide in 110 ml of dimethylformamide was stirred for 3 hours at 100° C. After cooling to ambient temperature, 130 ml of water and 88 ml of ethanol were added to the reaction mixture. After 1 hour, the crystals were collected by vacuum filtration, washed with water, and desiccated. Yield: 22 g of the title product. A sample recrystallized from ethanol had a melting point of 132°–134° C.

8-[N-(2-hydroxyethyl)-aminomethyl]-3-methyl-4-oxo-2-phenyl-4H-1-benzopyran (Intermediate XXX)

A solution of 2.38 g of anhydrous zinc chloride and 2.30 g of sodium cyanoborohydride in 71 ml of anhydrous methanol was added dropwise under stirring to a mixture of 9.24 g of 8-formyl-3-methyl-4-oxo-2-phenyl-4H-1-benzopyran and 9.12 g of ethanolamine in 90 ml of anhydrous methanol. Stirring was continued at 20°–25° C. for 5 hours, before removal of the solvent in vacuo. 250 ml of water was added to the residue, and the insoluble matter was collected by suction filtration and washed with water. The crude product was dissolved in 1N aqueous acetic acid solution and the solution was washed with ethyl acetate. The aqueous solution was then made alkaline by addition of 2N aqueous sodium hydroxide solution and the precipitate was collected by suction filtration and washed with water to give 8.5 g of the title compound, m.p. 117°–121° C. after drying at 60° C.

8-(N-methyl-N-chloracetyl-aminomethyl)-3-methyl-4-oxo-2-phenyl-4H-1-benzopyran (Intermediate XXXI)

A solution of 6 ml of chloracetyl chloride in 60 ml of 1,2-dichloroethane was added dropwise at −5° to 0° C. to a solution of 20 g of Intermediate XX and 10 ml of triethylamine in 200 ml of 1,2-dichloroethane. After stirring at 20°–25° C. for 2 hours, 150 ml of water was added to the reaction mixture and the phases were separated. The organic phase was washed with water and dried on anhydrous sodium sulfate. The solvent was removed in vacuo, and the residue was crystallized from ethanol to give 22.5 g of the title compound, m.p. 146°–148° C.

8-Chloracetamidomethyl-3-methyl-4-oxo-2-phenyl-4H-1-benzopyran (Intermediate XXXII)

A solution of 3.2 ml of chloracetyl chloride in 32 ml of 1,2-dichloroethane was added dropwise, under stirring at −5° C., to a mixture of 10 g of Intermediate XXIV and 5.5 ml of triethylamine in 80 ml of 1,2-dichloroethane. The reaction mixture was stirred at ambient temperature for 1 hour and then 150 ml of water was added. The phases were separated; the aqueous phase was extracted with 1,2-dichloroethane and the extracts were added to the organic phase which was then washed with a cold saturated solution of sodium bicarbonate, washed with water, dried on anhydrous sodium sulfate and evaporated to dryness in vacuo. The residue was crystallized from ethanol to give 10.7 g of the title compound, m.p. 152°–155° C.

8-[N-acetyl-N-(2-chloroethyl)-aminomethyl]-3-methyl-4-oxo-2-phenyl-4H-1-benzopyran (Intermediate XXXIII)

8.65 g of Intermediate XXX and 4.15 ml of triethylamine were dissolved in 70 ml of tetrahydrofuran. To this solution, at −10° C., there was added dropwise over a period of 40 minutes a solution of 2.35 ml of acetyl chloride in 23 ml of tetrahydrofuran. After stirring for 3 hours at 0°–10° C. and for 2 hours at 20°–25° C., the solvent was evaporated off in vacuo.

100 ml of water was added to the residue, and extraction with dichloromethane was effected, pooling the successive organic extracts and then removing the solvent in vacuo. The residue was dissolved in 50 ml of methanol and 3 g of potassium carbonate and 10 ml of water were added. After stirring at 50° C. for 20 minutes, to hydrolyse the N,O-diacetyl derivative which had formed, the solvent was removed in vacuo and the residue was treated with water and dichloromethane as above described. The dichloromethane solution was again evaporated to dryness, and 5.9 g of 8-[N-acetyl-N-(2-hydroxyethyl)-aminomethyl]-3-methyl-4-oxo-2-phenyl-4H-1-benzopyran, m.p. 171°–172° C., was obtained.

3.6 ml of thionyl chloride in 30 ml of dichloromethane was added dropwise at 0° C. to a solution of 6.1 g of the compound thus prepared in 70 ml of dichloromethane. After stirring for 90 minutes at 20°–25° C., the reaction mixture was washed with water and dried. The solvent was removed in vacuo to give the crude title product for use without further purification.

8-(3-Chloropropylthio)-3-methyl-4-oxo-2-phenyl-4H-1-benzopyran (Intermediate XXXIV)

A solution of 20.1 g of stannous chloride dihydrate in hydrochloric acid (d=1.18) was added over a period of 5 minutes at 65° C. to a solution of 6 g of Intermediate VIII in 70 ml of acetic acid. After 10 minutes, the reaction mixture was cooled to 30°–35° C. and the solvent was removed in vacuo. The residue was taken up in water, and the insoluble matter was collected by suction filtration, washed with water and dried. Yield 3.2 g of 8-mercapto-3-methyl-4-oxo-2-phenyl-4H-1-benzopyran, m.p. 115°–118° C. after crystallization from ethanol.

A mixture of 8 g of the compound so prepared, 27 ml of 1-bromo-3-chloro-propane, 0.2 g of tetrabutylammonium bromide and 6.2 ml of 35% sodium hydroxide in 80 ml of benzene was vigorously stirred for 4 hours at 20°–25° C. 100 ml of water and 40 ml of dichloromethane were added. The organic layer was separated off, washed with water and dried on anhydrous sodium sulfate. The solvents and excess 1-bromo-3-chloro-propane were removed in vacuo. The residue was purified by column chromatography on silica gel, eluting with petroleum ether:ethyl acetate 9:1, and 5.7 g of the title compound was obtained. After crystallization from methanol, it showed a melting point of 84°–86° C.

8-(3-Chloropropylsulfonyl)-3-methyl-4-oxo-2-phenyl-4H-1-benzopyran (Intermediate XXXV)

7 ml of 30% hydrogen peroxide was added at 20°–25° C. to a solution of 3.65 g of Intermediate XXXIV in 35 ml of acetic acid. After stirring for 4 hours at 60° C., the reaction mixture was cooled to 20°–25° C. 30 ml of water was added. A precipitate formed, and was collected by suction filtration, washed with water and dried, yielding 3.4 g of the title compound. After crystallization from acetone, it showed a melting point of 160°–163° C.

8-(3-Hydroxypropylcarbamoyl)-3-methyl-4-oxo-2-phenyl-4H-1-benzopyran (Intermediate XXXVI)

A solution of 7.6 ml of 3-aminopropanol in 50 ml of water was added dropwise over a period of 30 minutes to a suspension of 30 g of 3-methyl-4-oxo-2-phenyl-4H-1-benzopyran-8-carbonyl chloride and 15.2 g of potassium carbonate in 400 ml of acetone. The thick suspension was stirred for 3 hours at 20°–25° C. The solvents were removed in vacuo and the residue was taken up in 300 ml of water. After stirring for 1 hour, the precipitate was collected by suction filtration and washed with water. The crude product was purified by crystallization from 95% ethanol and 23.8 g of the title compound were obtained, m.p. 191°–193° C. An additional 4.7 g of the title compound was obtained by concentration in vacuo of the crystallization filtrate.

8-(3-Chloropropylcarbamoyl)-3-methyl-4-oxo-2-phenyl-4H-1-benzopyran (Intermediate XXXVII)

A solution of 1.1 ml of thionyl chloride in 2 ml of chloroform was added to a boiling solution of 3.37 g of Intermediate XXXVI in 20 ml of chloroform. After stirring for 90 minutes under reflux, the solvent was removed in vacuo and the residue was crystallized from acetonitrile to give 3 g of pure title compound, m.p. (188) 193°–194° C.

8-[1-Hydroxy-4-(4-methylphenylsulfonyloxy)-butyl]-3-methyl-4-oxo-2-phenyl-4H-1-benzopyran (Intermediate XXXVIII)

1.12 g of sodium cyanide in 3 ml of water was added at 20°–25° C. to a stirred mixture of 3.96 g of 8-formyl-3-methyl-4-oxo-2-phenyl-4H-1-benzopyran, 2.61 g of morpholine and 4.48 g of p-toluenesulfonic acid in 20 ml of tetrahydrofuran and 30 ml of 1,2-dichloroethane. The reaction mixture was refluxed for 4 hours, and then 10 ml of cold water was added. The tetrahydrofuran was distilled off at normal pressure, and 10 ml of 1,2-dichloroethane and 10 ml of chloroform were added. The organic phase was separated, washed with aqueous sodium chloride solution, dried over anhydrous sodium sulfate and evaporated to dryness in vacuo. The residue was suspended in diethyl ether, filtered off, and crystallized from chloroform:ethyl acetate. Yield: 3.55 g of 8-(N-morpholinyl)cyanomethyl-3-methyl-4-oxo-2-phenyl-4H-1-benzopyran, m.p. 236°–238° C.

3.5 ml of a 30% solution of potassium hydroxide in anhydrous methanol was added under stirring at ambient temperature to a suspension of 22.8 g of the compound thus prepared in 520 ml of anhydrous tetrahydrofuran. 6.3 ml of acrylonitrile in 20 ml of tetrahydrofuran was dropped into this suspension, and the reaction mixture was stirred at ambient temperatures for 1 hour. The solvents were evaporated off in vacuo. Crystallization of the residue from methanol gave 23.22 g of 8-(1,3-dicyano-1-morpholinopropyl)-3-methyl-4-oxo-2-phenyl-4H-1-benzopyran.

23.2 g of the compound thus prepared was dissolved in 250 ml of dioxane. 250 ml of 6M hydrochloric acid was added and the mixture was refluxed for $2\pi$ hours. After cooling to ambient temperature, the mixture was poured into 700 ml of aqueous sodium chloride solution and extracted with ethyl acetate. The extracts were washed with aqueous sodium chloride solution and treated with 700 ml of 1M sodium hydroxide solution. The aqueous layer was washed with ethyl acetate and acidified with 37% hydrochloric acid. The precipitate was collected by suction filtration and crystallized from ethanol to give 10.2 g of 8-(3-carboxy-1-oxopropyl)-3-methyl-4-oxo-2-phenyl-4H-1-benzopyran, m.p. 191°–192° C.

Diborane, generated by dropping a solution of 2.1 ml of freshly distilled boron trifluoride diethyl etherate in 10 ml of anhydrous diglyme into 19 ml of a 0.66M solution of sodium borohydride in diglyme, was bubbled into a suspension of 2.28 g of the compound thus prepared in 23 ml of anhydrous tetrahydrofuran, stirred at 0° C. under nitrogen flux. Stirring was continued for 20 minutes at 0° C. and for a further 20 minutes at ambient temperature. Methanol was cautiously dropped into the mixture at 0° C. to quench the reaction. The solvents were removed by evaporation in vacuo. The residue was purified by flash chromatography on silica gel, eluting with petroleum ether:ethyl acetate (3:7). The collected fractions were evaporated in vacuo to leave 2 g of 8-(1,4-dihydroxybutyl)-3-methyl-4-oxo-2-phenyl-4H-1-benzopyran, m.p. 133°–134° C.

2.8 g of p-toluenesulfonyl chloride was added at 0° C. to a stirred solution of 3.17 g of the compound thus prepared in 32 ml of anhydrous pyridine. The mixture was stirred for 6 hours at 0° C. and stood overnight at −4° C. without stirring. It was then poured into 200 ml of aqueous sodium chloride solution, acidified with 10 ml of 12N hydrochloric acid and filtered under suction. The filter cake was dissolved in chloroform, and the solution was washed with aqueous sodium chloride solution and dried on anhydrous sodium sulfate. The solvent was distilled off in a rotary evaporator. The residue was purified by flash chromatography on silica gel, eluting with petroleum ether:ethyl acetate (1:1). The collected fractions were evaporated to dryness in vacuo, yielding 3.04 g of pure title product, m.p. 123°–124° C.

4-[4-(2-Methoxyphenyl)-1-piperazinyl]-butyraldehyde (Intermediate XXXIX)

A solution of 5.4 g of 2-(3-chloropropyl)-dioxolan and 15.9 g of 1-(2-methoxyphenyl)-piperazine in 60 ml of dimethylformamide was stirred at 80° C. for 4 hours. After cooling to 20°–25° C., the reaction mixture was poured into 500 ml of ice cold 0.5N aqueous sodium hydroxide solution and extracted with dichloromethane. The organic phase was washed with water and dried on anhydrous sodium sulfate. The solvent was removed in vacuo, and the residue was purified by flash chromatography on silica gel, eluting with dichloromethane:ethanol (95:5). 9.8 g of 2-{3-[4-(2-methoxyphenyl)-1-piperazinyl]-propyl}-dioxolan was obtained as an oil.

NMR CDCl3 (δ) 1.5–2.0 (4H, m, $\underline{CH_2CH_2}$CH) 2.2–3.2 (10H, m, 5×$CH_2$N) 3.7–4.0 (7H, m, $OCH_3$ and 2×$OCH_2$) 4.8 (1H, t, OCHO) 6.7–6.9 (4H, m, aromatic protons)

A solution of 12.8 g of the compound thus prepared in 200 ml of tetrahydrofuran and 420 ml of 1N aqueous hydrochloric acid solution was maintained at 20°–25° C. for 24 hours. It was then made alkaline with 5N aqueous sodium hydroxide solution and immediately extracted with dichloromethane. The organic layer was washed with water and dried on anhydrous sodium sulfate. The solvent was evaporated off in vacuo, and the residue was purified by flash chromatography on silica gel, eluting with dichloromethane:methanol (97:3). 6.4 g of the title compound was obtained as an oil.

NMR CDCl3 (δ) 1.5–2.0 (2H, m, CH$_2$CH$_2$CH$_2$) 2.2–2.8 (8H, m, 3×CH$_2$N and CH$_2$CHO) 2.9–3.2 (4H, m, 2×CH$_2$NAr) 3.8 (3H, s, OCH$_3$) 6.8 (4H, s, aromatic protons) 9.3 (1H, s, CHO).

8-(2,3-Epoxypropoxy)-3-methyl-4-oxo-2-phenyl-4H-1-benzopyran (Intermediate XL)

7 ml of 2,3-epoxypropyl chloride was added dropwise at 20°–25° C. to a stirred mixture of 5 g of 8-hydroxy-3-methyl-4-oxo-2-phenyl-4H-1-benzopyran and 9.7 ml of 2N aqueous sodium hydroxide solution in 10 ml of ethanol. After 6 hours at 20°–25° C., the reaction mixture was poured into 100 ml of water and the precipitate which formed was collected by suction filtration. After drying and purifying by flash chromatography on silica gel (eluant petroleum ether: ethyl acetate (65:35), there was obtained 4.45 g of the title compound, m.p. 128°–129° C.

8-[N-methyl-2-(4-methylphenylsulfonyloxy)ethylsulfamyl]-3-methyl-4-oxo-2-phenyl-4H-1-benzopyran (Intermediate XLI)

A solution of 5 g of Intermediate VIII in 60 ml of dichloromethane and 20 ml of tetrahydrofuran was added dropwise at 0° C. to a mixture of 2.5 ml of 2-methylaminoethanol and 2.1 ml of triethylamine in 20 ml of dichloromethane. After stirring for 2 hours at 20°–25° C., 100 ml of water and 100 ml of dichloromethane were added to the reaction mixture. The phases were separated and the organic solution was dried on anhydrous sodium sulfate. The solvent was removed in vacuo, and the residue was purified by column chromatography on silica gel, eluting with petroleum ether:ethyl acetate (3:7). There was thus obtained 4.5 g of 8-(N-methyl-2-hydroxyethyl-sulfamyl)-3-methyl-4-oxo-2-phenyl-4H-1-benzopyran, melting at 146°–147° C. after crystallization from ethanol.

The compound thus prepared was converted to the title compound by p-toluene sulfonylation according to the second step of the procedure described below for the preparation of Intermediate 27469. The title compound was used without further purification.

8-[2-(4-Methylphenylsulfonyloxy)-ethylsulfamyl]-3-methyl-4-oxo-2-phenyl-4H-1-benzopyran (Intermediate XLII)

A solution of 5 g of Intermediate VIII in 37 ml of tetrahydrofuran was added dropwise at 0° C. to a mixture of 2.5 ml of ethanolamine and 2.5 ml of triethylamine in 25 ml of tetrahydrofuran. After stirring at 20°–25° C., the reaction mixture was poured into 400 ml of water. A precipitate formed, and was collected by suction filtration, washed with water and air dried, yielding 4.6 g of 8-(2-hydroxyethylsulfamyl)-3-methyl-4-oxo-2-phenyl-4H-1-benzopyran, melting at 186°–187° C. after crystallization from ethyl acetate.

2.1 g of p-toluenesulfonyl chloride was added portionwise at 0° C. to a solution of 3.6 g of the compound thus prepared in 25 ml of pyridine. After 6 hours at 20°–25° C., the reaction mixture was slowly poured on to crushed ice containing a slight excess of hydrochloric acid. A precipitate formed and was collected by suction filtration and washed with water. 4.9 g of the title compound was obtained, melting at (163) 166°–169° C. after crystallization from ethyl acetate.

8-(3-Aminopropylcarbamoyl)-3-methyl-4-oxo-2-phenyl-4H-1-benzopyran hydrochloride (Intermediate XLIII)

A solution of 21.6 g of 3-methyl-4-oxo-2-phenyl-4H-1-benzopyran-8-carbonyl chloride in 250 ml of anhydrous tetrahydrofuran was dropped at 0°–10° C. into a stirred solution of 17 g of 3-(2-methyl-2-propoxycarbamoyl)-propylamine (prepared as described in Saari, W. S. et al., J. Med. Chem. 33: 97, 1990) and 13 ml of triethylamine. After stirring for 2 hours at ambient temperature, the reaction mixture was poured into water and filtered to recover 12.3 g of N,3-(2-methyl-2-propoxycarbamoyl)-propyl- 3-methyl-4-oxo-2-phenyl-4H-1-benzopyran-8-carboxamide which was recrystallized from ethanol, m.p. 178°–180° C.

A solution of 4.3 g of trifluoroacetic acid in 15 ml of anhydrous dichloromethane was added dropwise at –5° C. under stirring to a solution of 3.3 g of the compound thus prepared in 35 ml of anhydrous dichloromethane. After warming to ambient temperature, the mixture was stirred for 8 hours. The dichloromethane and the excess trifluoroacetic acid were evaporated off at 20°–25° C. using a rotary evaporator. The oily residue was dissolved in dichloromethane and 1N aqueous sodium hydroxide solution was added. The organic layer was washed with water, dried on anhydrous sodium sulfate and filtered. Excess ethanolic hydrogen chloride was added to the filtrate, and the solvent was removed in vacuo. The residue was crystallized from ethanol to give 1.5 g of the title compound, m.p. 253°–255° C.

8-(2-Chloroethylureido)-3-methyl-4-oxo-2-phenyl-4H-1-benzopyran (Intermediate XLIV)

4 ml of 2-chloroethylisocyanate were added, under stirring at ambient temperature, to a solution of 3.9 g of 8-amino-3-methyl-4-oxo-2-phenyl-4H-1-benzopyran in 52 ml of anhydrous dimethylformamide. Stirring was continued at 70° C. for 5 hours. Water was added to the reaction mixture, which was then extracted with ethyl acetate. The organic phase was evaporated to dryness in vacuo. The residue was suspended in diethyl ether under stirring. The title product was then filtered off and recrystallized from methanol. Yield 3.74 g, m.p. 213°–214° C.

(Z,E)-8-{4-[2-(1,3-dioxanyl)]-1-butenyl}-3-methyl-4-oxo-2-phenyl-4H-1-benzopyran (Intermediate XLV)

1.6 ml of 2.5N butyl lithium in hexane was added dropwise at –20° C. to a solution of 1.53 g of 2-[2-(1,3-dioxanyl)]-ethyl triphenylphosphonium bromide in 10 ml of anhydrous tetrahydrofuran. The mixture was stirred for 20 minutes at –20° C. A solution of 0.8 g of 8-formyl-3-methyl-4-oxo-2-phenyl-4H-1-benzopyran in 11 ml of anhydrous tetrahydrofuran was dropped into the mixture, which was then warmed to 0° C. over a period of 90 minutes and then to ambient temperature over a period of 30 minutes. The reaction was quenched by addition of methanol. The solvents were evaporated off in vacuo and the residue was purified by flash chromatography on silica gel, eluting with ethyl acetate:petroleum ether (3:7), to give the title compound, as a mixture of diastereoisomers E and Z, m.p. (93) 98°–100° C. The ratio of the two isomers was determined by NMR spectroscopy and resulted E:Z=65:35.

NMR, CDCl$_3$ (δ) 8.1–8.2 (m, 1H) CH in position 5 of the benzopyran ring 7.2–7.8 (m, 7H) other aromatic CH groups of the benzopyran and phenyl rings 6.9 (dt, 1H) Fl'-CH of the E isomer 6.8 (dt, 1H) Fl'-CH of the Z isomer 6.4 (dt, 1H) Fl'—CH=CH of the E isomer 5.9 (dt, 1H) Fl'—CH=CH of the Z isomer 4.6–4.7 (m, 1H) OCHO 3.6–4.2 (m, 4H) CH$_2$O of the dioxane ring 2.4–2.7 (m, 2H) CHCH$_2$CH 1.9–2.3 (m, 5H) CH$_3$ and CH$_2$ in position 5 of the dioxane ring 8-{4-[2-(1,3-Dioxanyl)]-butyl}-3-methyl-4-oxo-2-phenyl-4H-1-benzopyran (Intermediate XLVI)

A mixture of 0.2 g of 10% palladium-on-carbon catalyst and of 1 g of Intermediate XLV in 24 ml of methanol was hydrogenated in a Parr apparatus at ambient temperature with a hydrogen pressure of 1.5 atmospheres. After the theoretical hydrogen consumption, the catalyst was filtered off and the solvent was removed by evaporation in vacuo. The residue was crystallized from cyclohexane to give the title compound, m.p. 118°–119.5° C.

8-Carboxymethyl-3-methyl-4-oxo-2-phenyl-4H-1-benzopyran (Intermediate XLVII)

4.5 g of potassium permanganate was added portionwise within 1.5 hours under stirring at 0°–10° C., to a mixture of 2.76 g of 8-allyl-3-methyl-4-oxo-2-phenyl-4H-1-benzopyran (P. Da Re, U.S. Pat. No. 3,350,411), 0.17 g of Aliquat 336® (methyltrioctylammonium chloride), 1.12 ml of acetic acid, 56 ml of dichloromethane, 3.2 ml of sulfuric acid (d=1.84) and 60 ml of water. Stirring was continued at room temperature for 5 hours. 3.4 g of sodium metabisulfite were added portionwise at 0°–5° C. within 15 minutes. The organic layer was separated, washed with water and extracted with 60 ml of 1N aqueous sodium hydroxide solution. The aqueous phase was acidified by addition of diluted hydrochloric acid and extracted with ethyl acetate. The organic phase was washed with water, dried on anhydrous sodium sulfate and, after filtration, evaporated to dryness in vacuo. The residue was treated with carbon tetrachloride and the solid was collected by suction to give 1 g of the title compound, m.p. 191°–192° C. (acetonitrile).

8-(4-Chlorobutyramido)-3-methyl-4-oxo-2-phenyl-4H-1-benzopyran (Intermediate XLVIII)

The title compound was prepared in the same manner as Intermediate X, but using 4-chlorobutyryl chloride instead of acryloyl chloride. The solid obtained, filtered from water and dried, was rinsed with hot diethyl ether and collected by suction to give the title compound. A sample, crystallized from 50% aqueous ethanol and washed with diethyl ether, melted at (153) 162°–164° C.

8-Methylamino-3-methyl-4-oxo-2-phenyl-4H-1-benzopyran (Intermediate XLIX)

A solution of 0.5 g of Intermediate XXIII in 1.5 ml of anhydrous dimethylformamide was added dropwise under stirring, at −5° C. to 0° C., to a suspension of 0.045 g of sodium hydride (80% in mineral oil). After stirring at room temperature for 1 hour, 0.092 ml of methyl iodide in 0.6 ml of anhydrous dimethylformamide was added dropwise. Then, the reaction mixture was stirred at 50° C. for 1 hour, cooled to 20° C., poured into water, filtered by suction and dried at 60° C. for 3 hours to recover 0.6 g of 8-(N-methyltrifluoroacetamido)-3-methyl-4-oxo-2-phenyl-4H-1-benzopyran.

NMR (CDCl3; (δ)) 8.15 (dd, 1H) benzopyran CH in 5 7.10–7.60 (m, 7H) other benzopyran and phenyl CHs 3.30 (s, 3H) CH$_3$—N 2.10 (s, 3H) benzopyran CH$_3$ in 3

A mixture of 0.44 g of the above compound and 0.05 g of sodium borohydride in 4 ml of ethanol and 1 ml of dimethylsulfoxide was stirred at room temperature for 1 hour, then quenched with An excess of 4N aqueous hydrochloric acid solution. After removal of ethanol by evaporation in vacuo, the residue was rinsed with water, then with 3N aqueous sodium hydroxide solution and extracted with ethyl acetate. The organic layer was washed with water, dried on anhydrous sodium sulfate and evaporated to dryness in vacuo. The solid residue was crystallized from ethanol to give 0.22 g of the title compound, melting at 143°–146° C.

8-(N-methylacrylamido)-3-methyl-4-oxo-2-phenyl-4H-1-benzopyran (Intermediate L)

This compound was prepared in the same manner as Intermediate X, but using Intermediate XLIX instead of 8-amino-3-methyl-4-oxo-2-phenyl-4H-1-benzopyran.

Instead of diluting with water, THF was removed by evaporation in vacuo and the crude residue was dissolved in ethyl acetate and washed with water. The organic solution was dried on anhydrous sodium sulfate and evaporated to dryness in vacuo to give the title compound. A sample was purified by column chromatography on silica gel (eluting with ethyl acetate - petroleum ether (4:6)) and crystallized from cyclohexane, melted at 136°–137° C.

1-[2-(1,3-Dihydro-1,3-dioxo-2H-isoindol-2-yloxy)ethyl]-4-(2-methoxyphenyl)piperazine (Intermediate LI)

A mixture of 6.73 g of N-hydroxyphthalimide, 3.73 g of sodium acetate and 10 g of 1-(2-chloroethyl)-4-(2-methoxyphenyl)piperazine in 100 ml of anhydrous dimethylsulfoxide was stirred at 100° C. for 4 hours. The reaction mixture was then cooled to room temperature, poured into water and extracted with ethyl acetate. The collected organic layers were washed with 1N aqueous sodium hydroxide solution, dried on anhydrous sodium sulfate and evaporated to dryness in vacuo to give 7.58 g of the title compound. A sample was crystallized from cyclohexane, m.p. (76) 80°–83° C.

1-(2-Aminooxyethyl)-4-(2-methoxyphenyl)piperazine hydrochloride (Intermediate LII)

A solution of 6.59 g of Intermediate LI and 1.10 ml of 85% hydrazine hydrate in 130 ml of 95% ethanol was refluxed for 4 hours. Ethanol was removed by evaporation in vacuo. The residue was rinsed with water then with an excess of 37% hydrochloric acid and filtered. The aqueous acid solution was made basic with 5% aqueous sodium hydroxide solution and extracted with chloroform. The organic layer was dried on anhydrous sodium sulfate and evaporated to dryness in vacuo to give 4.3 g of the title compound as an oil. A sample was converted to the hydrochloride by salification with ethanolic hydrochloric acid in dichoromethane. The solvents were removed by evaporation in vacuo and the crude residue was crystallized from ethanol, giving the title compound, m.p. 208°–209° C.

8-(4-Chlorobutylthio)-3-methyl-4-oxo-2-phenyl-4H-1-benzopyran (Intermediate LIII)

The title compound was prepared in the same manner as Intermediate XXXIV, but using 1-bromo-4-chlorobutane instead of 1-bromo-3-chloropropane. m.p. 81°–84° C. (ethanol).

8-(4-Chlorobutylsulfinyl)-3-methyl-4-oxo-2-phenyl-4H-1-benzopyran (Intermediate LIV)

The title compound was prepared in the same manner as Intermediate XXVI, but using Intermediate LIII instead of Intermediate XXI. A sample, crystallized from cyclohexane-benzene (0.5:1), melted at 124°–125° C.

8-Carboxy-4-oxo-3-phenyl-4H-1-benzopyran (Intermediate LV)

A solution of 38.22 g of silver nitrate in 75 ml of water was added dropwise, under stirring, at 20°–25° C., to a solution of 22.5 g of 8-formyl-4-oxo-3-phenyl-4H-1-benzopyran (prepared as described by G. Atassi et al., *Eur. J. Med. Chem. - Chim. Ter.* 20, 393 (1985)) in 150 ml of 85% ethanol and 450 ml of N,N-dimethylformamide. Then, a solution of 32.67 g of 85% potassium hydroxide in 195 ml of water was added dropwise under stirring at 15°–20° C. After additional stirring at room temperature, the reaction mixture was filtered by suction; the mother liquor was acidified with 37% hydrochloric acid and diluted with 1.2 l of water. Filtration by suction and washing with water to neutrality gave the title compound as a crude. The crude was suspended in 150 ml of ethyl acetate and stirred with 444 ml of 0.3M aqueous sodium hydrogen carbonate solution until clear layers were obtained. The aqueous layer was washed with 75 ml of ethyl acetate, then made acidic with 37% hydrochloric acid, filtered and dried at 60°–65° C. to give 19, 12 g of the title compound that melted at (215) 218° C. A sample, crystallized from ethanol, showed the same melting point, m.p. (215) 218° C.

8-Chlorocarbonyl-4-oxo-3-phenyl-4H-1-benzopyran (Intermediate LVI)

A mixture of 15.97 g of Intermediate LV and 15.6 ml of thionyl chloride in 75 ml of anhydrous toluene was stirred at 80°–85° C. for 4 hours. After removal of the solvent under vacuo, the residue was rinsed twice with 20 ml of toluene and evaporating to dryness in vacuo to give, after drying, 16 g of the title compound melting at (126) 138°–140° C. which was used without further purification. m.p. (130) 138°–140° C. (toluene).

8-(N-acetylcarbamoyl)-3-methyl-4-oxo-2-phenyl-4H-1-benzopyran Intermediate LVII

A mixture of 3.5 g of 8-carbamoyl-3-methyl-4-oxo-2-phenyl-4H-1-benzopyran (described in JP 61-238783, 1986), 4.8 ml of acetic anhydride and 0.25 ml of sulfuric acid (d=1,098) was stirred at 140° C. for 3 minutes. The reaction was cooled to ambient temperature, diluted with water and filtered by suction to give, after washing with water and desiccation, 3.88 g of the title compound.

$^1$H-NMR (CDCl$_3$; δ): 10.50 bs, 1H imidic NH 8.35–8.70 m, 2H CH in position 5 and 7 of the benzopyran ring 7.45–8.00 m, 6H other aromatic CHs 2.60 s, 3H CH$_3$CO 2.20 s, 3H CH$_3$ in position 3 of the benzopyran ring 2-(2-Methylthiophenoxy) acetaldehyde diethyl acetal Intermediate LVIII A mixture of 15.2 ml of 97% 2-bromoacetaldehyde diethyl acetal, 14 g of 2-(methylthio)phenol, 13.7 g of anhydrous potassium carbonate and 3.13 g of tricaprylmethylammonium chloride in 140 ml of anhydrous dimethylformamide was stirred at 95° C. for 38 hours.

After this period, the reaction mixture was cooled to room temperature, poured into 1 liter of water and extracted with diethyl ether; the organic layer was washed with water, dried on sodium sulfate and evaporated to dryness in vacuo. The oily residue was purified by column chromatography on silica gel eluting with petroleum ether-ethyl acetate (99:1). Evaporation in vacuo of the collected fractions yielded 12.9 g of pure title compound. A sample was crystallized from n-hexane and melted at 50°–52° C.

2-(2-Methylthiophenoxy)acetaldehyde Intermediate LIX

A mixture of 10.5 g of Intermediate LVIII and 140 ml of 2N hydrochloric acid in 85 ml of anhydrous tetrahydrofuran was stirred at 50° C. for 2 hours. After this period, the organic solvent was evaporated in vacuo and the aqueous residue was extracted with ethyl acetate.

The organic layer was washed with water, dried on sodium sulfate and evaporated to dryness in vacuo giving 9.5 g of the title compound as a solid which was used without further purification. A sample was crystallized from cyclohexane yielding the pure title compound, m.p. 102°–104° C.

8-(4-Chlorobutylsulfonyl)-3-methyl-4-oxo-2-phenyl-4H-1-benzopyran Intermediate LX The title compound was prepared by the same method as Intermediate XXV, but using Intermediate LIII instead of Intermediate XXI. It was crystallized from diisopropyl ether and melted at 112°–115° C.

Ethyl 4-oxo-4H-1-benzopyran-8-carboxylate Intermediate LXI 4.35 g of sodium metal was added in pieces at room temperature to a solution of 9.85 g of ethyl 3-acetyl-2-hydroxy benzoate (synthesized from 3-acetyl-2-hydroxybenzoic acid (prepared as described in R. E. Ford, *J. Med. Chem.*, 29, 538 (1986)) refluxing in 6N ethanolic hydrogen chloride for 1.5 hours, evaporating to dryness in vacuo and purifying the crude by column chromatography on silica gel (eluant ethyl acetate-petroleum ether 8:2)—m.p. 47° C. (hexane)) in 98 ml of ethyl formate.

The reaction mixture went spontaneously to reflux for 20 minutes; then it was stirred at room temperature for 4 hours and ethyl formate removed by evaporation to dryness in vacuo. The crude solid obtained was rinsed with 120 ml of ethanol and 67 ml of 5.6M ethanolic hydrogen chloride. The mixture was stirred at reflux for 30 minutes; after this period it was cooled to room temperature and evaporated to dryness in vacuo. The residue was purified by column chromatography on silica gel eluting with a ethyl acetate-petroleum ether gradient (3:7 to 6:4) to give 8.31 g of the title compound.

A sample crystallized from cyclohexane melted at 88°–89° C.

4-Oxo-4H-1-benzopyran-8-carboxylic acid Intermediate LXII 30 ml of 6N hydrochloric acid was added to a solution of 4.0 g of Intermediate LXI in 30 ml of dioxane and the resulting mixture was stirred at reflux for 5 hours.

After this period, the reaction mixture was cooled at room temperature and poured into 200 ml of water. After 12 hours at 0°–5° C., the title compound was filtered by suction and washed with water and diethyl ether yielding, after desiccation, 2.8 g of the title compound, used without further purification. A sample washed with boiling acetonitrile-methanol (25:1), filtered and crystallized from acetic acid melted at 253°–254° C.

6-Hydroxy-3-methyl-4-oxo-2-phenyl-4H-1-benzopyran-8-carboxylic acid Intermediate LXIII A mixture of 1.5 g of 6-methoxy-3-methyl-4-oxo-2-phenyl-4H-1-benzopyran-8-carboxylic acid (prepared as described in JP 61-15880) and 28 ml of 57% hydroiodic acid in 47 ml of acetic acid was stirred at reflux for 18 hours. The reaction mixture was cooled to room temperature and poured into water; the pH of the suspension was corrected to 4–5 by adding 1N aqueous sodium hydroxide solution. 2 g of sodium thiosulfate was added and stirring was continued for 15 minutes. After this period, the crude title compound was filtered by suction and dissolved in 0.5M aqueous sodium hydroxide solution; the basic solution was washed with ethyl acetate and acidified to pH=1 by adding 37% hydrochloric acid.

The title compound was collected by suction and desiccated to give 1.12 g of the title compound, used without further purification and melting at 279°–281° C. after crystallization from 50% ethanol.

2-Hydroxy-5-nitro-3-propionyl benzoic acid Intermediate LXIV 97.1 g of 2-hydroxy-3-propionyl benzoic acid (prepared as described in Brit 1, 343, 119 (1974)) were added in 5 minutes to 500 ml of sulfuric acid d=1.84 stirred at −25° C. A mixture of 40 ml of 65% nitric acid and 100 ml of sulfuric acid (d=1.84) was added in 40 minutes maintaining the temperature of the reaction mixture between −20° and −13° C. The mixture was stirred at −18° C. for additional 30 minutes. After this period, it was cautiously poured into a mixture of 2.0 kg of crushed ice and 500 ml of water, stirred for 10 minutes and filtered to give the title compound, after washing with water and drying at 50° C. for 6 hours. Crystallization of this solid from 50% aqueous ethyl alcohol solution yielded 91.5 g of title compound melting at 186°–189° C., used without further purification. A sample was recrystallized from 50% ethyl alcohol and melted at 189°–191° C.

Ethyl 2-hydroxy-5-nitro-3-propionyl benzoate Intermediate LXV

A solution of 93.3 g of Intermediate LXIV and 25 ml of sulfuric acid (d=1.84) in 490 ml of ethyl alcohol was refluxed for 17 hours.

After cooling to room temperature, 47.7 g of sodium carbonate was added portionwise and the ethyl alcohol was evaporated in vacuo. The residue was rinsed with 1.2 liter of water, made alkaline by adding 37% aqueous sodium hydroxide solution and stirred for 15 minutes. 37% hydrochloric acid was added to this suspension reaching pH=6. Filtration yielded 85.4 g of the title compound used without further purification (m.p. 75°–77° C.). A sample was crystallized twice from ethanol and melted at 76°–77° C.

Ethyl 3-methyl-6-nitro-4-oxo-2-phenyl-4H-1-benzopyran-8-carboxylate Intermediate LXVI A mixture of 48.1 g of Intermediate LXV, 63 ml of benzoyl chloride and 85.6 g of sodium benzoate was stirred at 180° C. (bath temperature) for 8 hours.

The pasty mixture was cooled to 60°–70° C.; 700 ml of 50% aqueous ethanol solution was added and the resulting mixture was stirred again at 50° C. for 30 minutes.

60 ml of 35% aqueous sodium hydroxide solution was added at 5° C. avoiding to exceed 15° C. Filtration by suction, followed by washing with 50% aqueous ethanol solution and water afforded a crude product, which was purified by double passage on column chromatography on silica gel eluting firstly with a dichloromethane-petroleum ether gradient (8:2 to 9:1) and then with dichloromethane followed by dichloromethane-ethyl acetate (95:5). Evaporation in vacuo of the collected fractions gave the title compound, washed with 140 ml of ethanol to give 43 g, melting at 132°–133° C. (ethanol).

3-Methyl-6-nitro-4-oxo-2-phenyl-4H-1-benzopyran-8-carboxylic acid Intermediate LXVII A mixture of 15.9 g of Intermediate LXVI and 48 ml of 1N sodium hydroxide in 320 ml of ethanol was stirred at reflux for 30 minutes. The organic solvent was removed by evaporation in vacuo and the resulting suspension was diluted with 200 ml of water and made acidic with 37% hydrochloric acid.

Filtration and washing with diethyl ether yielded 11.1 g of the title compound melting at (258) 286°–292° C. and used without further purification. After crystallization from dimethylformamide-water (6:4), the title compound exhibited the same melting point.

3-Methyl-6-nitro-4-oxo-2-phenyl-4H-1-benzopyran-8-carbonyl chloride Intermediate LXVIII A mixture of 6.2 g of Intermediate LVII, 5.2 ml of thionyl chloride, 0.1 ml of anhydrous dimethylformamide in 60 ml of toluene was stirred at 90° C. for 2 hours. Evaporation in vacuo to dryness and desiccation yielded 6.5 g of the title compound, melting at 161°–162° C., which was used without further purification. A sample was crystallized from toluene and had the same melting point.

7-Methoxy-3-methyl-4-oxo-2-phenyl-4H-1-benzopyran-8-carboxylic acid Intermediate LXIX 216 ml of a 0.3M solution of potassium permanganate in water was added dropwise in 40 minutes into a mixture of 7.94 g of 7-methoxy-3-methyl-4-oxo-2-phenyl-4H-1-benzopyran-8-carboxaldehyde (prepared as described in Da Re et al., *J. Org. Chem.*, 25, 1097, (1960)) and 54 ml of 5% aqueous sodium dihydrogen phosphate solution in 162 ml of tert-butanol, stirred at 75° C. After additional 2.5 hours stirring at the same temperature, the reaction mixture was cooled to room temperature and 81 ml of 1M aqueous sodium dithionite solution was dropped slowly therein. The mixture was extracted with ethyl acetate; the organic layer was washed four times with 160 ml of 0.5N aqueous sodium hydroxide solution. The collected basic aqueous layers were washed with diethyl ether and made acidic with 37% hydrochloric acid.

The title compound, that precipitated, was filtered and washed with water, yielding after desiccation, 3.3 g used in the following step without further purification and melting at 180°–181° C. after crystallization from 95% ethanol.

Ethyl 3-propionyl-2-(4-trifluoromethylbenzoyloxy)benzoate Intermediate LXX

A solution of 6.7 g of 4-trifluoromethylbenzoyl chloride (prepared from the corresponding benzoic acid and thionyl chloride in benzene at reflux and used as a crude) in 50 ml of chloroform was added dropwise to a solution of 7.13 g of ethyl 2-hydroxy-3-propionylbenzoate and 4.9 ml of triethylamine in 50 ml of chloroform.

The mixture was stirred at room temperature for 2 hours; the solvent was removed by evaporation in vacuo and the residue was purified by column chromatography on silica gel eluting with petroleum ether-ethyl acetate (85:15). Evaporation in vacuo to dryness of the collected fractions yielded 7.4 g of the title compound as on oil.

NMR spectrum at 60 MHz ( CDCl$_3$, ($\delta$)) 7.6–8.5 (m, 6H) aromatic CHs 7.5 (t,1H) phenol ring, CH in 5 4.2 (q,2H) COOCH$_2$ 2.9 (q,2H) COCH$_2$ 1–1.3 (2t, 6H) 2×CH$_3$ Ethyl 3-methyl-4-oxo-2-(4-trifluoromethylphenyl)-4H-1-benzopyran-8-carboxylate Intermediate LXXI A mixture of 6.96 g of Intermediate LXX and 2.58 g of potassium tert-butoxide in 35 ml of pyridine was stirred at 100° C. for 2 hours.

After this period, the reaction mixture was cooled to room temperature, poured into a solution of 50 ml of acetic acid in 600 ml of water and extracted with ethyl acetate. The organic layer was washed with 10% aqueous hydrochloric acid solution and with water, dried on sodium sulfate and evaporated to dryness in vacuo to give 6.9 g of 1-(2-hydroxy-3-ethoxycarbonyl)-2-methyl-3-(4-trifluoromethylphenyl)-1,3-propanedione.

A solution of the above Intermediate and 2.2 ml of 37% hydrochloric acid in 35 ml of glacial acetic acid was stirred at 100° C. for 1.5 hours.

After cooling to room temperature, the mixture was poured into 630 ml of 1N sodium hydroxide and extracted with ethyl acetate. The organic layer was washed with water, dried on sodium sulfate and evaporated to dryness in vacuo. The crude was purified by column chromatography on silica gel eluting with petroleum ether-ethyl acetate (85:15). Evaporation in vacuo to dryness yielded 2.95 g of the title compound, melting at 111°–113° C. after crystallization from cyclohexane.

3-Methyl-4-oxo-2-(4-trifluoromethylphenyl)-4H-1-benzopyran-8-carboxylic acid Intermediate LXXII A mixture of 2.95 g of Intermediate LXXI and 0.43 g of lithium hydroxide monohydrate in 12.5 ml of methanol and 12.5 ml of tetrahydrofuran containing 8 ml of water was stirred at room temperature for 1.5 hours. The mixture was poured into a solution of 30 ml of 1N aqueous hydrochloric acid solution in 300 ml of water and filtered by suction to give 2.47 g of the title compound used without further purification. A sample was crystallized from 60% aqueous ethanol solution and melted at 253°–254° C.

Ethyl 2-(4-benzoylphenyl)-3-methyl-4-oxo-4H-1-benzopyran-8-carboxylate Intermediate LXXIII The title compound was synthesized following the procedure of Intermediate LXX and LXXI in the established order but starting from 4-benzoylbenzoyl chloride instead of 4-trifluoromethylbenzoyl chloride and reacting this compound in 1,2-dichloroethane instead of chloroform in the presence of 4-dimethylaminopyridine instead of triethylamine.

After the usual workup, the residue was purified by column chromatography on silica gel eluting with dichloromethane-ethyl acetate (9:1). Evaporation in vacuo to dryness of the collected fractions yielded the title compound used without further purification. A sample was crystallized from cyclohexane and melted at 125°–136° C. (dec.).

2-(4-Benzoylphenyl)-3-methyl-4-oxo-4H-1-benzopyran-8-carboxylic acid Intermediate LXXIV The title compound was prepared in the same manner as Intermediate LXXII, but starting from Intermediate LXXIII instead of Intermediate LXXI. It was purified by dissolving the crude in 0,5M sodium hydroxide, washing the aqueous layer with ethyl acetate and precipitating the pure title compound by addition of 37% hydrochloric acid. A sample was crystallized from acetic acid and melted at 260°–262° C.

Ethyl 2-(4-phenoxybenzoyloxy)-3-propionylbenzoate Intermediate LXXV

The title compound was prepared according to the procedure of Intermediate LXX, but starting from 4-phenoxybenzoyl chloride instead of 4-trifluoromethylbenzoyl chloride. Evaporation of the solvent yielded the pure title Compound. NMR spectrum at 200 MHz (CDCl$_3$ (δ)) 8.17 (dd;3H) phenyl CHs in position or to the carboxylate groups 7.92 (dd;1H) phenyl CH in position ortho to the CO group 7.38–7.48 (m;3H) phenyl CHs in position meta to the carboxylate groups 7.25 (d;1H) CH in position 4 of the phenoxy ring 7.05; 7.10 (2d;4H) other CHs of the phenoxy ring 4.25 (q;2H) CH$_2$O 2.90 (q;2H) CH$_2$CO 1.05–1.20 (m;6H) 2×CH$_3$ Ethyl 3-methyl-4-oxo-2-(4-phenoxyphenyl)-4H-1-benzopyran-8-carboxylate Intermediate LXXVI The title compound was prepared according to the procedure of Intermediate LXXI, but starting from Intermediate LXXV instead of Intermediate LXX. The purification of the crude was performed by column chromatography on silica gel eluting with petroleum ether-ethyl acetate (6:4). Evaporation in vacuo yielded the pure title compound m.p. 98°–100° C.

3-Methyl-4-oxo-2-(4-phenoxyphenyl)-4H-1-benzopyran-8-carboxylic acid Intermediate LXXVII The title compound was obtained in the same manner as described for Intermediate LXXII, but starting from Intermediate LXXVI instead of Intermediate LXXI (m.p. 216°–218° C.).

2-tert-butyl-3-methyl-4-oxo-4H-1-benzopyran-8-carboxylic acid Intermediate LXXVIII 6 ml of pivaloyl chloride was added dropwise into a stirred solution of 8.9 g of ethyl 2-hydroxy-3-propionylbenzoate in 20 ml of anhydrous pyridine. The reaction mixture was stirred at 80° C. for 6 hours, cooled at room temperature and poured into a mixture of 200 g of crushed ice and 30 ml of 10N aqueous hydrochloric acid solution. After extraction with diethyl ether, the organic phase was washed with brine, dried on anhydrous sodium sulfate and evaporated to dryness in vacuo, yielding 11.4 g of crude ethyl 2-pivaloyloxy-3-propionylbenzoate.

2.4 g of this compound was dissolved in 4 ml of anhydrous pyridine and added with 1 g of anhydrous potassium tert-butoxide. The obtained mixture was heated for 15 minutes at 100° C., cooled to room temperature and poured into 50 g of iced water containing 8 ml of 10N aqueous hydrochloric acid solution. After extraction with diethyl ether, the organic phase was washed with brine, dried on anhydrous sodium sulfate and evaporated to dryness in vacuo, yielding 2.1 g of crude ethyl 2-hydroxy-3-(2-pivaloylpropionyl)benzoate, which was used without purification in the next step.

2 g of this Intermediate was heated at 100° C. for 15 minutes after dissolution in a mixture containing 15 ml of acetic acid and 1.5 ml of 37% hydrochloric acid. After cooling at room temperature, the mixture was poured into 100 ml of water and extracted with diethyl ether. The organic phase was washed with 5% aqueous sodium hydrogen carbonate solution followed by water, dried on sodium sulfate and evaporated in vacuo, yielding 1.6 g of crude ethyl 2-tert-butyl-3-methyl-4-oxo-4H-1-benzopyran-8-carboxylate.

1.5 g of the above ester was dissolved in 20 ml of methanol and slowly added with 3 ml of 10N aqueous sodium hydroxide solution, maintaining the temperature between 25° and 35° C. After 1.5 hours at room temperature, the reaction mixture was diluted with 100 ml of water and extracted with ethyl acetate. The aqueous layer was acidified with 3N aqueous hydrochloric acid solution. The precipitate was collected by suction, washed with water and crystallized from ethanol, yielding 0.8 g of the title compound, melting at 225°–228° C.

2-Cyclohexyl-3-methyl-4-oxo-4H-1-benzopyran-8-carboxylic acid Intermediate LXXIX This compound was prepared according to the reactions sequence and methods described for Intermediate LXXVIII, but starting from cyclohexylcarboxylic acid chloride instead of pivaloyl chloride and with other minor differences. Accordingly, ethyl 2-cyclohexylcarbonyloxy-3-propionylbenzoate was obtained after 8 hrs stirring at room temperature in pyridine and transposed to 1-(3-ethoxycarbonyl-2-hydroxyphenyl)-3-cyclohexyl-2-methyl-1,3-propanedione upon heating with potassium tertbutoxide for 2.5 hours at 100° C.

The cyclization of the above Intermediate to ethyl 2-cyclohexyl-3-methyl-4-oxo-4H-1-benzopyran-8-carboxylate was carried out by heating in the acetic-hydrochloric acids mixture at 100° C. for 1.5 hours and the hydrolysis to the title compound was performed in 20 minutes at room temperature.

The title compound melted at 224° C. after crystallization from 40% ethanol.

Ethyl 2-(2-furyl)-3-methyl-4-oxo-4H-1-benzopyran-8-carboxylate Intermediate LXXX A mixture of 3.2 g of Intermediate XC and 1.3 g of anhydrous potassium tert-butoxide in 8 ml of anhydrous pyridine was stirred at 60° C. for 15 minutes, cooled to room temperature and poured into 60 ml of iced water containing 15 ml of 10N aqueous hydrochloric acid solution. After extraction with ethyl acetate, the organic phase was washed with 5% aqueous sodium bicarbonate solution and water and dried on anhydrous sodium sulfate. Upon evaporation in vacuo 2.5 g of crude ethyl 3-(2-furoyl)propionyl-2-hydroxybenzoate was obtained.

2.5 g of the above crude was stirred at 100° C. for 30 minutes with 10 ml of acetic acid and 0.7 ml of 37% hydrochloric acid. After cooling to room temperature, the mixture was poured into 180 ml of water yielding the title compound as a precipitate, which was collected by suction, washed with water and crystallized with i-propanol. 1.5 g were obtained, m.p. 137°–139° C.

2-(2-Furyl)-3-methyl-4-oxo-4H-1-benzopyran-8-carboxylic acid Intermediate LXXXI

A mixture of 3.5 g of Intermediate LXXX and 6 ml of 10N sodium hydroxide in 40 ml of methanol was stirred at room temperature for 1 hour and poured into 500 ml of water. After extraction with ethyl acetate, the aqueous layer was acidified with 3N hydrochloric acid and the precipitated title compound was collected by suction, washed with water and crystallized from a 7:3 mixture of methanol/chloroform, yielding 2.55 g, m.p. 272°–277° C.

Ethyl 3-methyl-4-oxo-2-(2-thienyl)-4H-1-benzopyran-8-carboxylate Intermediate LXXXII This compound was prepared in two steps according to the method reported for Intermediate LXXX, but using Intermediate XCI instead of Intermediate XC. The title compound melted at 116°–118° C. after crystallization from i-propanol.

3-Methyl-4-oxo-2-(2-thienyl)-4H-1-benzopyran-8-carboxylic acid Intermediate LXXXIII This compound was prepared according to the method described for Intermediate LXXXI, but using Intermediate LXXXII instead of Intermediate LXXX. Melting point 287°–294° C. after crystallization from a 7:3 mixture of methanol and chloroform.

4-Oxo-2-phenyl-4H-1-benzothiopyran-8-carboxylic acid Intermediate LXXXIV

A mixture of 1 g of methyl 4-oxo-2-phenyl-4H-1-benzothiopyran-8-carboxylate (Intermediate XCII), 2.2 ml of 12.5N sodium hydroxide, 15 ml of methanol and 5 ml of dioxane was stirred at room temperature for 2.5 hours.

After evaporation in vacuo, water was added until complete solution and this solution was extracted with chloroform. The separated aqueous phase was acidified with diluted hydrochloric acid until Complete precipitation of the crude, that was filtered and purified by crystallization from acetic acid. Yield 0.62 g, m.p. 302° C.

(E)-ethyl 3-methyl-4-oxo-2-(2-phenylethenyl)-4H-1-benzopyran-8-carboxylate Intermediate LXXXV This compound was prepared in three steps according to the methods described for Intermediate XC (first step) and Intermediate LXXX (second and third steps). In the first step, (E)-cinnamoyl chloride was used instead of 2-furancarbonyl chloride and the obtained (E)-ethyl 2-hydroxy-3-[2-(2-phenylethenyl)propionyl]]benzoate was used without purification by column chromatography for the second step. The title compound melted at 129°–130° C. after crystallization from i-propanol.

(E)-3-methyl-4-oxo-2-(2-phenylethenyl)-4H-1-benzopyran-8-carboxylic acid Intermediate LXXXVI This compound was prepared according to the method described for Intermediate LXXXI, but starting from Intermediate LXXXV instead of Intermediate LXXX, and maintaining the reaction at room temperature for 10 hours. The title compound melted at 284°–286° C. after crystallization from ethanol.

3-Methyl-2-(4-methylphenyl)-4-oxo-4H-1-benzopyran-8-carboxylic acid Intermediate LXXXVII A mixture of 1.9 g of 2-hydroxy-3-propionylbenzoic acid (prepared as described in Brit. 1, 343, 119 (1974)), 5.2 g of anhydrous sodium 4-methylbenzoate and 3.9 ml of 4-methylbenzoyl chloride was stirred at 185°–195° C. for 8.5 hours. After cooling to room temperature, the solidified mass was added with 100 ml of chloroform and left standing overnight. The mixture was then shaken with 5% aqueous sodium carbonate solution, which was added until the pH of the aqueous phase reached pH=8.9. The organic phase was extracted again with 3% aqueous sodium carbonate solution and the aqueous phases were pooled, repeatedly extracted with diethyl ether and acidified with 10N aqueous hydrochloric acid solution. The precipitate was purified by flash chromatography on silica gel eluting with a chloroform-methanol gradient (100:2 to 100-20). The title compound, obtained by evaporating in vacuo the pooled fractions containing it, melted at 249°–251° C. after crystallization from ethanol.

Ethyl 2-(4-fluorophenyl)-3-methyl-4-oxo-4H-1-benzopyran-8-carboxylate Intermediate LXXXVIII This compound was prepared in three steps according to the methods described for Intermediate XC (first step) and Intermediate LXXX (second and third steps). In the first step, 4-fluorobenzoyl chloride was used instead of 2-furancarbonyl chloride and the reaction lasted 20 hours at room temperature, yielding ethyl 2-(4-fluorobenzoyloxy)-3-propionylbenzoate. This compound was used without purification by column chromatography for the second step. The title compound melted at 128°–130° C. after rinsing with diethyl ether and crystallization from ethanol.

2-(4-fluorophenyl)-3-methyl-4-oxo-4H-1-benzopyran-8-carboxylic acid Intermediate LXXXIX The solution of 3.3 g of Intermediate LXXXVIII and 0.6 g of lithium hydroxide hydrate in 50 ml of tetrahydrofuran, 10 ml of methanol and 10 ml of water was maintained at room temperature for 5 hours and poured into 300 ml of 1N aqueous hydrochloric acid solution. The precipitate formed was collected by suction, washed with water and dried, yielding 2.3 g of title compound, melting at 249°–250° C. after crystallization from 95% ethanol.

Ethyl 2-(2-furylcarbonyloxy)-3-propionylbenzoate Intermediate XC 4.35 ml of 2-furancarbonyl chloride were added dropwise at 10°–15° C. into a stirred mixture of 8.9 g of ethyl 2-hydroxy-3-propionylbenzoate and 5.4 g of 4-dimethylaminopyridine in 25 ml of dichloromethane. After 2 hours at room temperature, the reaction was quenched with 200 ml of water. The organic layer was washed with 5% sodium bicarbonate, dried on anhydrous sodium sulfate and evaporated in vacuo. The residue was purified by flash chromatography on silica gel eluting with petroleum ether-ethyl acetate 4:1, obtaining 9.4 g of the title compound as a low melting solid, used without further purification in the next step.

NMR Spectrum at 60 MHz (CDCl$_3$; (δ)) 8.2 (1H, dd, benzoate CH in 4) 8.0 (1H,dd,benzoate CH in 6) 7.7–7.8 (1H,dd,furane CH in 5) 7.43 (1H,t,benzoate CH in 5) 7.45 (1H,s,furane CH in 3) 6.6–6.8 (1H,m,furane CH in 4) 4.3 (2H, q,COOC$\underline{H}_2$CH$_3$) 2.9 (2H, q,COC$\underline{H}_2$CH$_3$) 0.95–1.35 (6H,m,2×CH$_3$)

Ethyl 3-propionyl-2-(2-thienylcarbonyloxy)benzoate Intermediate XCI

This compound was prepared according to the method of Intermediate XC, but using 2-thiophenecarbonyl chloride instead of 2-furancarbonyl chloride.

NMR Spectrum at 60 MHz (CDCl$_3$ (δ)) 7.1–8.35 (6H,m, aromatic CHs) 4.25 (2H,q,COOC$\underline{H}_2$CH$_3$) 2.9 (2H,q,COC$\underline{H}_2$CH$_3$) 0.95–1.3 (6H,m,2×CH$_3$)

Methyl 4-oxo-2-phenyl-4H-1-benzothiopyran-8-carboxylate Intermediate XCII

A mixture of 16.8 ml of methyl thiosalicylate, 25.6 ml of ethyl benzoylacetate and 360 g of polyphosphoric acid was stirred at 90° C. for 3 hours.

After cooling to room temperature, the mixture was poured into crushed ice and the crude was collected by filtration, washed with water and purified by crystallization from ethanol (m.p. 170°–171° C.).

Analysis (%) for $C_{17}H_{12}O_3S$, Calcd (Found): C, 68.90 (68.59); H,4.08(4.13); S,10.82(10.69).

NMR spectrum at 200 MHz (CDCl$_3$, (δ)) 8.83–8.95 (dd,1H) benzothiopyran CH in 5 8.45–8.53 (dd,1H) benzothiopyran CH in 7 7.68–7.80 (m,2H) 2-phenyl CHs in 2 and 6 7.55–7.65 (t,1H) benzothiopyran CH in 6 7.45–7.55 (m,3H) 2-phenyl CHs in 3,4 and 5 7.24 (s,1H) benzothiopyran CH in 3 4.00 (s,3H) COOCH$_3$ Ethyl 3-bromomethyl-4-oxo-2-phenyl-4H-1-benzopyran-8-carboxylate Intermediate XCIII A mixture of 9.2 g of ethyl 3-methyl-4-oxo-2-phenyl-4H-1-benzopyran-8-carboxylate (prepared as described by Da Re et al., *J. Med. Chem.*, 2, 263 (1960)), 6.4 g of N-bromosuccinimide and 0.04 g of benzoylperoxide in 80 ml of anhydrous carbon tetrachloride was stirred at reflux for 1.5 hours. After cooling to room temperature the formed succinimide was collected by suction and washed with cold carbon tetrachloride. The mother liquors were evaporated to dryness in vacuo and the residue was rinsed with diethyl ether and collected by suction yielding 9.2 g of the title compound melting at 133°–134° C. after crystallization from acetone-n-hexane.

Ethyl 3-acetoxymethyl-4-oxo-2-phenyl-4H-1-benzopyran-8-carboxylate Intermediate XCIV A solution of 10.2 g of sodium acetate. 3H$_2$O in 30 ml of water was added dropwise at room temperature into a solution of 29 g of Intermediate XCIII in 300 ml of dimethylformamide. After stirring at 50° C. for 1.5 hours, the reaction mixture was poured into 2 liters of water and the precipitated title compound was collected by suction and crystallized from acetone yielding 20 g (two crops collected), m.p. 151°–152° C.

3-Hydroxymethyl-4-oxo-2-phenyl-4H-1-benzopyran-8-carboxylic acid Intermediate XCV 116 ml of 1N sodium hydroxide were added over 10 minutes to a stirred suspension of 14.8 g of Intermediate XCIV in 300 ml of 95% ethanol. The reaction mixture was then heated at 60°–65° C. for 15 minutes obtaining a clear solution which was maintained at room temperature for one additional hour. After evaporation of the solvent in vacuo, the residue was dissolved in 200 ml of water and the solution acidified by slow addition of 10 ml of hydrochloric acid (d=1.18). After one hour stirring at room temperature the title compound was collected by suction, washed with water and crystallized from i-propanol, yielding 9.3 g, m.p. (225) 237°–240° C.

Ethyl 2-(4-nitrobenzoyloxy)-3-propionylbenzoate Intermediate XCVI

The title compound was prepared according to the procedure of Intermediate XC, but using 4-nitrobenzoylchloride instead of 2-furancarbonyl chloride. The product was obtained as a low-melting solid (m.p. (40) 78°–80° C.).

NMR Spectrum at 60 MHz (CDCl$_3$, (δ)) 7.85–8.50 (m,6H) aromatic CHs 7.50 (t,1H) CHs in position 5 of the phenol ring 4.25 (q,2H) CH$_2$O 3.95 (q,2H) CH$_2$ 0.95–1.30 (m, 6H) CH$_3$ Ethyl 3-methyl-2-(4-nitrophenyl)-4-oxo-4H-1-benzopyran-8-carboxylate Intermediate XCVII A mixture of 29.7 g of Intermediate XCVI and 10.18 g of anhydrous potassium tert-butoxide in 89 ml of anhydrous pyridine was stirred at 100° C. for 13 hours. The reaction mixture was cooled to room temperature, poured into 400 ml of 4N hydrochloric acid and extracted with dichloromethane. The organic layer was washed repeatedly with water, then with 2.5% sodium hydrogen carbonate, dried on sodium sulfate and evaporated to dryness in vacuo. The crude was purified by column chromatography on silica gel eluting with hexane-ethyl acetate (7:3). Evaporation in vacuo of the collected fraction yielded 7 g of the title compound, melting at (130) 145°–148° C.

3-methyl-2-(4-nitrophenyl)-4-oxo-4H-1-benzopyran-8-carboxylic acid Intermediate XCVIII A suspension of 7.07 g of Intermediate XCVII in 150 ml of dioxane and 100 ml of methanol was warmed under stirring at 50° C. 22.8 ml of 1N sodium hydroxide was added and stirring was continued for 0.75 hours at the same temperature. The reaction mixture was cooled to room temperature and 3N aqueous hydrochloric acid solution was added reaching pH=1. The suspension was filtered by suction giving 5.65 g of the title compound, which melted at 320°–321° C. after crystallization from dioxane.

Ethyl 3-methyl-4-oxo-2-trifluoromethyl-4H-1-benzopyran-8-carboxylate Intermediate XCIX 3.16 ml of 1,8-diazabicyclo[5.4.0]undec-7-ene was added dropwise at 0° C. by a syringe to a stirred mixture of 3 g of ethyl 2-hydroxy-3-propionyl benzoate and 5.53 ml of trifluoroacetic anhydride. The reaction mixture was stirred at 60° C. for 4 hours; after this period it was cooled to room temperature and diluted with ethyl acetate and water. The organic layer was washed with 1N sodium hydroxide and water, dried on sodium sulphate and evaporated to dryness in vacuo. The residue was purified by column chromatography on silica gel eluting with petroleum ether-ethyl acetate 95:5 yielding 0.8 g of the title compound. NMR spectrum at 200 MHz (CDCl$_3$; (δ)) 8.41;8.37 (2dd;2H) CHs in position 5 and 7 of the benzopyran ring 7.51 (t;1H) CH in position 6 of the benzopyran ring 4.46 (q;2H) COOCH$_2$ 2.22–2.27 (m;3H,JH-F=2.16 Hz) CH$_3$ in position 3 of the benzopyran ring 1.39 (t;3H ) CH$_2$CH$_3$ 3-Methyl-4-oxo-2-trifluoromethyl-4H-1-benzopyran-8-carboxylic acid Intermediate C The title compound was prepared by the same method as Intermediate LXII, but using Intermediate XCIX instead of Intermediate LXI and, after dilution with water, extracting with ethyl acetate instead of filtering.

After drying on sodium sulfate and evaporating in vacuo to dryness the organic layer, the title compound was obtained as a solid which melted at 175°–178° C.

3-[4-(2-Methoxyphenyl)-1-piperazinyl]-N-methylpropylamine Intermediate CI

A solution of 8.2 g of 3-[4-(2-methoxyphenyl)-1-piperazinyl]propyl chloride in 48 ml of dimethylformamide was added with 42 ml of 35% aqueous methylamine solution and heated at 60° C. in a closed vessel for 5 hours. After cooling to 30° C. and evaporation in vacuo, the residue was stirred for 30 minutes with 100 ml of diethyl ether and collected by suction. The obtained solid was dissolved in 200 ml of chloroform-5N methanolic ammonia 100:3. After 30 minutes stirring at room temperature, the obtained solution was adsorbed on a silica gel chromatographic column, which was eluted with a chloroform-5N methanolic ammonia gradient (100:5 to 100:15). The fractions containing the title compound were pooled and evaporated in vacuo, yielding 3 g of Intermediate CI as a thick oil.

NMR spectrum at 60 MHz (DMSO-d$_6$ (δ)) 6.80 (s,4H) aromatic CHs 3.75 (s,3H) OCH$_3$ 3.20–2.75 (m,4H) piperazinic CH$_2$s at pos. 3,5 2.75–2.10 (m,8H) piperazinic CH$_2$S at pos. 2,6 and C$\underline{H}_2$CH$_2$CH$_2$ 2.40 (s,1H) NH 2.30 (s,3H ) NCH$_3$ 1.80–1.40 (m,2H) CH$_2$C$\underline{H}_2$CH$_2$)

Ethyl 2-benzoyl-3-ethylbenzo[b]furan-7-carboxylate Intermediate CII

A mixture of 11.1 g of ethyl 2-hydroxy-3-propionylbenzoate, 9.9 g of phenacyl bromide, 6.9 g of anhydrous potassium carbonate and 200 ml of acetone was stirred at refluxing temperature for 7 hours. After cooling to room temperature, the inorganic salts were separated by filtration and the solution was evaporated in vacuo. The residue was purified by flash chromatography on silica gel eluting with toluene. The title compound, obtained by evaporating in vacuo the pooled fractions containing it, was crystallized from 90% ethanol. Yield 9.8 g, m.p. 64°–66° C.

2-Benzoyl-3-ethylbenzo[b]furan-7-carboxylic acid Intermediate CIII

A mixture of 7 g of Intermediate CII, 275 ml of 0.95N sodium hydroxide and 400 ml of dioxane was stirred at refluxing temperature for 4 hours. After cooling to room temperature, the dioxane was evaporated in vacuo and replaced with the same volume of water. After filtering with charcoal, the solution was acidified with diluted hydrochloric acid and the precipitate was filtered and purified by crystallization from acetone, Yield 4.94 g, m.p. 193°–195° C.

Methyl 3-methyl-2-(4-methylphenyl)-4-oxo-4H-1-benzopyran-8-carboxylate Intermediate CIV This compound was prepared in three steps according to the methods described for Intermediate XC (first step) and Intermediate LXXX (second and third steps). In the first step, 4-methylbenzoyl chloride was used instead of 2-furanecarbonyl chloride and methyl 2-hydroxy-3-propionylbenzoate was used instead of ethyl 2-hydroxy-3-propionylbenzoate. The reaction lasted 4 hours at room temperature, yielding methyl 2-(4-methylbenzoyloxy)3-propionylbenzoate. This compound was used without purification by column chromatography for the second step, that lasted 1.5 hours at 100° C. In the third step, 96% sulfuric acid was used instead of 37% hydrochloric acid. The title compound melted at 174°–175° C. after crystallization from ethanol.

Ethyl 2-(4-biphenylyl)-3-methyl-4-oxo-4H-1-benzopyran-8-carboxylate Intermediate CV This compound was prepared in three steps according to the methods described for Intermediate XC (first step) and Intermediate CIV (second and third steps). In the first step, 4-phenylbenzoyl chloride was used instead of 2-furanecarbonyl chloride and the reaction lasted 20 hours at room temperature and 13 hours at reflux. Purification was performed by column chromatography on silica gel eluting with a petroleum ether-ethyl acetate gradient (100:5 to 100:10), yielding ethyl 2-(4-biphenyl-yl)-3-propionylbenzoate. The title compound melted at 165°–167° C. after rinsing with 95% ethanol.

2-(4-Biphenylyl)-3-methyl-4-oxo-4H-1-benzopyran-8-carboxylic acid Intermediate CVI A mixture of 4.3 g of Intermediate CV and 35 ml of 35% hydrochloric acid in 50 ml of 1,4-dioxane and 15 ml of water was stirred at reflux for 16 hours. After cooling, the mixture was poured into 200 ml of water and extracted with ethyl acetate. The organic layer was separated and extracted with 20% aqueous sodium carbonate solution. The precipitate formed after acidifying the aqueous layer with diluted hydrochloric acid, was collected by suction, washed with water and dried, yielding 2.5 g of the title compound, melting at 242.5°–244° C.

2-(4-Hydroxyphenyl)-3-methyl-4-oxo-4H-1benzopyran-8-carboxylic acid Intermediate CVII A mixture of 3 g of ethyl 2-(4-methoxyphenyl)3-methyl-4-oxo-4H-1-benzopyran-8-carboxylate (prepared as described in JP 58,225,083; C.A. 100, 191648h (1984)) and 60 ml of 48% hydrobromic acid in 80 ml of acetic acid was stirred at reflux for 8 hours. After cooling, the mixture was poured into 500 ml of water and the precipitate was collected by suction and washed with water. The crude was purified by flash chromatography eluting with a chloroform-isopropyl alcohol gradient (9:1 to 7:3) followed by methanol elution, yielding 1 g the title compound, melting at 300° C.

1-(2-Methoxyphenyl)-4-(4-methylaminobutyl)piperazine Intermediate CVIII

A solution of 3.8 ml of trifluoroacetic anhydride in 25 ml of anhydrous dichloromethane was added dropwise under stirring at 0° C. to a solution of 2.53 g of 4-[4-2-methoxyphenyl)-1-piperazinyl]butylamine in 25 ml of anhydrous dichloromethane. After 2 hours stirring at room temperature, the reaction mixture was diluted with dichloromethane and washed with water. The organic layer was dried on sodium sulphate and evaporated to dryness in vacuo, yielding 3.3 g of pure 1-(2-methoxyphenyl)-4-(4-trifluoroacetylamino)butylpiperazine as by NMR spectrum.

NMR spectrum at 60 MHz (CDCl$_3$ ($\delta$)) 7.70–8.00 (bs, 1H) NH 6.80–7.20 (m, 4H) aromatic CHs 3.85 (s, 3H) CH$_3$O 2.90–3.80 (m, 12H) piperazine CH$_2$S, CH$_2$N and CH$_2$NHCO 1.50–2.05 (m, 4H) C-CH$_2$CH$_2$-C.

0.88 g of 50% sodium hydride was added portionwise under stirring at 0° C. to solution of 3.3 g of the above intermediate in 46 ml of anhydrous dimethylformamide. After stirring for one hour at the same temperature, 0.57 ml of methyl iodide was added.

The reaction mixture was stirred for an additional 1.5 hours and was then poured into water and extracted with ethyl acetate. The organic layer was washed with water, dried on sodium sulphate and evaporated to dryness in vacuo, yielding 1.13 g of crude 1-(2-methoxyphenyl)-4-[4-(N-methyltrifluoroacetylamino)butyl]piperazine, which was used in the following step without further purification. 0.18 g of sodium borohydride was added to a solution of 1.13 g of the intermediate in 30 ml of ethanol and the resulting mixture was stirred at 60° C. for 1 hour, After cooling to room temperature, the reaction mixture was poured into water, and extracted with dichloromethane. The organic layer was washed with water, dried on sodium sulfate and evaporated to dryness in vacuo, yielding 0.82 g of pure title compound.

NMR spectrum at 60 MHz (CDCl3, ($\delta$)) 6.80–7.20 (m, 4H) aromatic CHs 3.85 (s, 3H) CH$_3$O 2.90–3.20 (m, 4H) piperazine CH$_2$S, position 3 and 5 2.30–2.80 (m, 8H) piperazine CH$_2$S, position 2 and 6; 2×CH$_2$N 2.50 (s, 3H) CH$_3$N 1.80 (s, 1H) NH 1.40–1.80 (m, 4H) C-CH$_2$-CH$_2$-C (E,Z)-3-hydroxy-4-oxo-2-phenyl-8-(1-Propenyl)-4H-1-benzopyran Intermediate CIX 60 ml of 50% (w/v) sodium hydroxide was added dropwise during 30 minutes to a solution of 17.6 g of a 7:3 E-Z mixture of 2'hydroxy-3'-(1-propenyl)propiophenone (prepared as described in R. E. Ford. et al., *J. Med. Chem.*, 29, 538, (1986)) and 10.82 g of benzaldehyde in 73 ml of ethanol stirred at 0° C. The temperature of the reaction mixture was raised to 25° C. and stirring was continued for 4 hours. After standing at room temperature overnight, 150 ml of water was added, followed by dropwise addition of 95 ml of 37% hydrochloric acid under stirring at 0° C. The precipitated solid was filtered by suction, washed with water and desiccated, yielding 26.8 g of 1-[2-hydroxy-3-(1-propenyl)phenyl]-3-phenyl-2-propen-1-one. This material was used without further purification in the next step.

26.4 g of the above Intermediate was suspended in 470 ml of ethanol. The suspension was warmed to reflux till complete dissolution was reached. The oil bath was then removed and 366 ml of 10% (w/v) sodium hydroxide was quickly added, dropwise, at 50° C. into the solution, followed by addition of 15.5 ml of 35% hydrogen peroxide. After the reaction mixture reached room temperature, it was stirred for an additional 15 hours. Thereafter, the solution was diluted with water and acidified by adding at 0° C. 37% hydrochloric acid. The suspension was filtered by suction and the obtained solid was washed with water.

This crude material was purified by flash chromatography on silica gel eluting with dichloromethane. Evaporation in vacuo of the collected fractions, yielded 6.9 g of the title product, m.p. 165°–168° C., with the same E,Z diastereomeric composition as the starting compound.

(E,Z)-3-benzyloxy-4-oxo-2-phenyl-8-(1-propenyl)-4H-1-benzopyran Intermediate CX

A mixture of 2.22 g of Intermediate CIX, 0.2 g of benzyltriethylammonium chloride, 1.13 ml of 95% benzyl bromide, 11 ml of 50% (w/v) sodium hydroxide in 22 ml of toluene was stirred at 80° C. for 1 hour. The reaction mixture was cooled to room temperature and extracted with ethyl acetate. The organic layer was washed with water, dried on sodium sulfate and evaporated to dryness in vacuo. The crude was rinsed with petroleum ether and filtered by suction, yielding 1.72 g of the title compound as a 3:1 E-Z mixture, as determined by $^1$H-NMR spectrum at 200 MHz. It melted at 90°–98° C.

NMR spectrum at 200 MHz (CDCl$_3$; (δ)) 8.22 (0.25H, dd, CH in 5 of benzopyran ring; Z isomer) 8.18 (0.75H, dd, CH in 5 of benzopyran ring; E isomer) 7.95–8.10 (2H, m, CH$_S$ in 2,6 of 2-phenyl ring; Z+E isomers) 7.77 (0.75H, dd, CH in 7 of benzopyran ring; E isomer) 7.60 (0.25H, dd, CH in 7 of benzopyran ring; Z isomer) 7.43–7.55 (3H, m, CH$_S$ in 3,4,5 of 2-phenyl ring; E+Z isomers) 7.20–7.40 (6H, m, CH in 6 of benzopyran ring and CH$_S$ of benzyl ring; E+Z isomers) 6.91 (0.75H, dd, aryl—CH=, E isomer) 6.75 (0.25H, dd, aryl—CH=, Z isomer) 6.42 (0.75H, dq, C$\underline{H}$-CH$_3$, E isomer) 6.05 (0.25H, dq, C$\underline{H}$-CH$_3$, Z isomer) 5.13 (1H, s, CH$_2$, E+Z isomers) 1.98 (2.25H, dd, CH$_3$, E isomer) 1.87 (0.75H, dd, CH$_3$, Z isomer)

After crystallization from methanol, the pure E diastereoisomer (NMR) was obtained, melting at 98°–100° C.

3-Benzyloxy-4-oxo-2-phenyl-4H-1-benzopyran-8-carboxylic acid Intermediate CXI 4.1 ml of 70% aqueous sulfuric acid solution was added dropwise at 0°/5° C. to a stirred mixture of 1.62 g of Intermediate CX and 3.3 ml of 70% aqueous sodium dichromate solution in 44 ml of acetone. After the addition, the temperature was raised to room temperature and stirring was continued for 5.5 hours. 50 ml of cold water was added, followed by a 10% sodium bisulfite solution to destroy excess oxidizing agent. The mixture was then extracted three times with ethyl acetate. The combined ethyl acetate layers were extracted with 0.2N aqueous sodium hydroxide solution and the aqueous alkaline layer was separated, washed with diethyl ether and acidified (pH=1) with 37% hydrochloric acid. The obtained suspension was filtered to give, after desiccation, 0.62 g of the title compound, m.p. 171°–173° C. After crystallization from acetonitrile, the compound melted at 175°–176° C.

Ethyl 2-phenyl-4-thioxo-4H-1-benzopyran-8-carboxylate Intermediate CXII

A solution of 4.0g of 8-ethoxycarbonyl-2-phenyl-4-oxo-4H-1-benzopyran (prepared as described in Da Re et al., Ber. 1962, 99 (1966) and 3.55 g of 2,4-bis-(4-methoxyphenyl)-1,3-dithia-2,4-diphosphetane (Lawesson's reagent) in 68 ml of toluene was stirred at reflux for 2 hours. The reaction mixture was cooled to room temperature and evaporated to dryness in vacuo. The crude residue was rinsed with petroleum ether and filtered to give a solid. The material was purified by flash chromatography on silica gel, eluting with a petroleum ether - ethyl acetate gradient (9:1 to 7:3). Evaporation in vacuo of the collected fractions yielded 3.99 g of pure title compound, melting at 161°–163° C. after recrystallization from cyclohexane.

2-Phenyl-4-thioxo-4H-1-benzopyran-8-carboxylic acid Intermediate CXIII

The title compound was obtained according to the procedure described for Intermediate LXXII, but starting from Intermediate CXII instead of Intermediate LXXI and stirring for 5 hours instead of 1.5 hour.

The reaction mixture was poured into water containing an excess of 1N aqueous sodium hydroxide solution. The aqueous solution was washed with ethyl acetate and acidified with 37% HCl at 0° C. Suction filtration yielded the title compound.

$^1$H-NMR Spectrum at 60 MHz (DMSO-d$_6$ (δ)) 12.00–13.00 (br, 1H, COOH) 7.60–8.20 (m, 4H, CH$_S$ in 5, 7 of benzopyran ring and in 2, 6 of phenyl ring) 7.55 (s, 1H, CH in 3 of benzopyran ring) 7.20–7.55 (m, 3H, other phenyl CHs) 6.90 (t, 1H, CH in 6 of benzopyran ring)

2,2-Dimethyl-3-[4-(2-methoxyphenyl)-1-piperazinyl]propionaldehyde dihydrochloride Intermediate CXIV A mixture of 3 g of 1-(2-methoxyphenyl)piperazine dihydrochloride, 0.4 g of paraformaldehyde and 1 ml of isobutyraldehyde in 4 ml of ethanol was stirred at reflux for 1.5 hours. 0.4 g of paraformaldehyde was added and the mixture was stirred again for 1.5 hour at reflux. After cooling to room temperature, water was added and the resulting solution was washed twice with diethyl ether, made alkaline by adding 1N aqueous sodium hydroxide solution and extracted with diethyl ether. The organic layer was washed with water, dried on sodium sulfate and evaporated to dryness in vacuo. The crude was purified by flash chromatography on silica gel eluting with ethyl acetate. Evaporation in vacuo of the collected fractions yielded 2.1 g of the pure title compound as a base. 0.5 g of the base was dissolved in diethyl ether and 3.8N hydrochloric acid in diethyl ether was added. The title compound was recovered by suction filtration and melted at 181°–183° C.

Methyl 3-methyl-4-oxo-2-(2-phenylethyl)-4H-1-benzopyran-8-carboxylate Intermediate CXV This compound was prepared in three steps according to the method described for Intermediate XC (first step) and Intermediate LXXX (second and third steps). In the first step, 3-phenylpropionyl chloride was used instead of 2-furancarbonyl chloride and methyl 2-hydroxy-3-propionylbenzoate was used instead of the ethyl homolog, yielding methyl 2-(3-phenylpropionyloxy)-3-propionylbenzoate. This compound was used without purification for the second step. The title compound melted at 107.5°–109° C. after crystallization from ethanol.

3-Methyl-4-oxo-2-(2-phenylethyl)-4H-1-benzopyran-8-carboxylic acid Intermediate CXVI This compound was prepared according to the method described for Intermediate LXXXI, but using Intermediate CXV instead of Intermediate LXXX. The title compound was filtered by suction and melted at 181°–183° C. after crystallization from acetonitrile.

N-succinimido 4-oxo-2-phenyl-4H-1-benzothiopyran-8-carboxylate Intermediate CXVII A solution of 2.5 g of N,N'-dicyclohexylcarbodiimide in 35 ml of anhydrous dimethylformamide was added dropwise over 20 minutes at room temperature to a stirred mixture of 3.5 g of Intermediate LXXXIV and 1.4 g of N-hydroxysuccinimide in 70 ml of anhydrous dimethylformamide under a nitrogen atmosphere. After 4 hours at room temperature, the mixture was poured into 500 ml of water, the precipitate was filtered by suction and crystallized from ethanol, yielding 2.5 g of the title compound at 168°–171° C.

N-succinimido 2-phenyl-1,1,4-trioxo-4H-1-benzothiopyran-8-carboxylate Intermediate CXVIII A mixture of 2 g of the above Intermediate CXVII, 20 ml of acetic acid and 6.2 ml of 30% (w/v) hydrogen peroxide in water was stirred at 50° C. for 18 hours. After cooling to room temperature, the reaction mixture was poured into 100 ml of water and extracted with chloroform. The organic layer was separated, washed with 5% aqueous sodium hydrogen carbonate solution then with water and finally dried over anhydrous sodium sulfate. The solvent was evaporated to dryness in vacuo and the residue was crystallized from acetone, yielding 0.62 g of the title compound melting at 234.5°–238° C.

Ethyl 2-(4-cyanophenyl)-3-methyl-4-oxo-4H-1-benzopyran-8-carboxylate Intermediate CXIX A solution of 5.2 g of ethyl 2-hydroxy-3-propionylbenzoate in 30 ml of anhydrous pyridine was added dropwise over 20 minutes at room temperature into a stirred mixture of 4 g of 4-cyanobenzoyl chloride in 30 ml of anhydrous pyridine. The solution was stirred for 1 hour at the same temperature, then 2.6 ml of 1,8-diazabicyclo[5.4.0]undec-7-ene was added and the solution was heated at 100° C. for 2 hours. After cooling to room temperature, the solvent was evaporated in vacuo and the residue was quenched with 100 ml of water containing 40 ml of 6N aqueous hydrochloric acid solution. The mixture was extracted twice with 100 ml aliquots of dichloromethane, the organic layer was separated, washed with water, dried over sodium sulfate and evaporated in vacuo. The residue was purified by flash chromatography on silica gel eluting with n-hexane-ethyl acetate gradient (95:5 to 60:40), obtaining 3 g of the title compound after crystallization from ethanol, m.p. 181°–183° C.

4-Cyanophenyl-3-methyl-4-oxo-4H-1-benzopyran-8-carboxylic acid Intermediate CXX

The title compound was prepared according to the method described for Intermediate XCVIII, but using Intermediate CXIX instead of Intermediate XCVII. The reaction lasted 45 minutes and the crude was purified by crystallization from methanol, m.p. 286°–289° C.

Methyl 6-cyano-3-methyl-4-oxo-2-phenyl-4H-1-benzopyran-8-carboxylate Intermediate CXXI A mixture of 3.73 g of methyl 6-bromo-3-methyl-4-oxo-2-phenyl-4H-1-benzopyran-8-carboxylate (prepared as described in EP 107804), 2.69 g of cuprous cyanide and 30 ml of anhydrous N,N-dimethylformamide was heated at 175° C. under stirring for 4 hours, under nitrogen atmosphere. After cooling to room temperature, the mixture was poured into 200 ml of 7% aqueous ammonium hydroxide solution and extracted with chloroform. The organic layer was washed with water, dried over anhydrous sodium sulfate and evaporated to dryness in vacuo.

The crude was purified by flash chromatography on silica gel eluting with dichloromethane-methanol gradient (100:0 to 100:20). 1.9 g of the title compound was obtained, melting at 225°–227° C. after crystallization from methanol.

6-Cyano-3-methyl-4-oxo-2-phenyl-4H-1-benzopyran-3-carboxylic acid Intermediate CXXII The title compound was prepared according to the method described for Intermediate XCVIII, but using Intermediate CXXI instead of Intermediate XCVII. The title compound was obtained after crystallization from acetonitrile, m.p. 281°–283° C.

(E)-3-Methoxy-4-oxo-2-phenyl-8-(1-propenyl)-4H-1-benzopyran Intermediate CXXIII

A mixture of 2.68 g of Intermediate CIX, 1.2 ml of methyl iodide, 0.25 g of benzyltriethylammonium chloride and 40 ml of 25% (w/v) sodium hydroxide in 80 ml of toluene was stirred at 70° C. for 13 hours.

After this period, the reaction mixture was cooled to room temperature and diluted with water and ethyl acetate. The organic layer was then separated, and the aqueous layer extracted twice with ethyl acetate. The combined extracts were washed with water, dried on sodium sulfate and evaporated to dryness in vacuo to give 2.55 g of the title compound as a Z/E mixture with the same composition as Intermediate CIX, which was used in the next step without further purification. After washing with methanol, crystallization from the same solvent yielded the pure title compound, m.p. 121°–123° C.

3-Methoxy-4-oxo-2-phenyl-4H-1 benzopyran-8-carboxylic acid Intermediate CXXIV

The title compound was prepared by the same method as described for Intermediate CXI using Intermediate CXXIII instead of Intermediate CX. m.p. 216°–200° C.

Methyl 2-benzoyl-3-ethylbenzofuran-7-carboxylate Intermediate CXXV

The title compound was prepared according to the procedure of Intermediate CII, starting from methyl 2-hydroxy-3-propionylbenzoate instead of ethyl 2-hydroxy-3-propionylbenzoate and carrying out the reaction for 10 hours instead of 7 hours, m.p. 102.5°–104.5° C. (ethanol).

2-Benzyl-3-ethylbenzofuran-7-carboxylic acid Intermediate CXXVI

A mixture of 1.3 g of Intermediate CXXV, 26 ml of acetic acid and 0.25 g of 10% palladium on charcoal was hydrogenated at 46 p.s.i. in a Parr apparatus. After the theoretical consumption of hydrogen, the catalyst was separated by filtration and the solution was poured into 100 ml of water and extracted with ethyl acetate. The organic layer was dried over sodium sulphate and evaporated to dryness (in vacuo) and the crude product was purified by flash chromatography on silica gel eluting with n-hexane-ethyl acetate (9:1). The collected fractions containing the pure compound were evaporated to dryness (in vacuo) yielding 1.1 g of pure methyl 2-benzyl-3-ethylbenzofuran-7-carboxylate, as by NMR spectrum.

$^1$H-NMR spectrum at 60 MHz (CDCl$_3$, (δ)) 1.15 (t, 3H) CH$_2$CH$_3$ 2.65 (q, 2H) CH$_2$CH$_3$ 3.90 (s, 3H) OCH$_3$ 4.10 (s, 2H) benzyl CH$_2$ 7.10–7.35 (m, 6H) CHs of phenyl ring; CH in 5, benzofuran ring 7.55 (dd, 1H) CH in 4, benzofuran ring 7.80 (dd, 1H) CH in 6, benzofuran ring A mixture of intermediate, 0.234 g of lithium hydroxide hydrate, 10 ml of methanol, 10 ml of tetrahydrofuran and 1.6 ml of water was stirred at ambient temperature for 2 hours. After standing overnight, the mixture was poured into 100 ml of water and acidified with 3N hydrochloric acid. The precipitate was collected by suction filtration and washed with water. The yield of pure title compound was 0.63 g, m.p. 151°–153° C.

Methyl 2-(2-phenyl)benzoyloxy-3-propionylbenzoate Intermediate CXXVII

To a solution of 5.5 g of methyl 2-hydroxy-3-propionylbenzoate in 15 ml of anhydrous pyridine at room temperature was added 6.85 g of 2-phenylbenzoyl chloride. The mixture was stirred at 100° C. for 3 hours. After cooling to room temperature, the mixture was poured into 100 ml of water, acidified with hydrochloric acid and extracted with ethyl acetate. The organic layer was washed with dilute hydrochloric acid, water and 5% sodium bicarbonate solution, dried over anhydrous sodium sulfate and evaporated to dryness (in vacuo). The crude product was purified by flash chromatography on silica gel eluting with petroleum ether/ethyl acetate (4:1). Crystallization from ethanol yielded 7.6 g of the title compound, m.p. 110°–112° C.

Methyl 2-hydroxy-3-[2-(2-phenyl)benzoyl]propionylbenzoate Intermediate CXXVIII

A mixture of 8 g of Intermediate CXXVII, 2.62 g of potassium tert-butoxide and 30 ml of anhydrous pyridine was stirred at 60° C. under nitrogen atmosphere for 3 hours. After cooling, the mixture was poured into 150 ml of water and acidified by addition of 15% hydrochloric acid. The crude solid product was collected by filtration and crystallized from ethanol yielding 5.6 g of the title compound, m.p. 126°–127° C.

Methyl 2-(2-biphenylyl)-3-methyl-4-oxo-4H-1-benzopyran-8-carboxylate Intermediate CXXIX A mixture of 6.34 g of Intermediate CXXVIII, 3 ml of 37% hydrochloric acid and 50 ml of acetic acid was stirred at reflux temperature for 2.5 hours. After cooling, the mixture was poured into 200 ml of water. The precipitate was collected by filtration and crystallized from isopropyl alcohol to provide 3.55 g of the title compound, m.p. 115°–119° C.

Methyl 2-(3-nitrobenzoyloxy)-3-propionylbenzoate Intermediate CXXX

The title compound was prepared according to the procedure of Intermediate CXXVII, starting from 3-nitrobenzoyl chloride instead of 2-phenylbenzoyl chloride. The reaction lasted 7 hours at room temperature. The solvent was evaporated (in vacuo) and the residue was rinsed with water, acidified with 37% hydrochloric acid and extracted with ethyl acetate. The crude product was obtained by evaporation (in vacuo) of the organic phase. Crystallization from ethanol provided the title compound, m.p. 83°–84° C.

Methyl 2-(1-naphthoyloxy)-3-propionylbenzoate Intermediate CXXXI

The title compound was prepared according to the procedure of Intermediate CXXVII, starting from 1-naphthoyl chloride instead of 2-phenylbenzoyl chloride. The reaction lasted 3.5 hours at 60° C. then the mixture was poured into water and extracted with ethyl acetate. The crude product was purified by crystallization from ethanol to provide the title compound, m.p. 67°–70° C.

Methyl 3-methyl-2-(1-naphthyl)-4-oxo-4H-1-benzopyran-8-carboxylate Intermediate CXXXII The title compound was prepared according to the procedure of Intermediate LXXI, using Intermediate CXXXI instead of Intermediate LXX. The β-diketone intermediate methyl 2-hydroxy-3-[2-(1-naphthyl)carbonyl]propionylbenzoate was characterized by NMR spectrum as follows.

$^1$H-NMR spectrum at 60 MHz (CDCl$_3$, (δ)) 1.45–1.65 (d, 3H) COCH($\underline{CH}_3$) CO 4.00 (s, 3H) OCH$_3$ 5.50–5.95 (q, 1H) CO$\underline{CH}$(CH$_3$) CO 7.00 (t1H, CH in 5, phenyl ring 7.30–8.80 (m, 9H) all other aromatic CHs 11.00 (s, 1H) OH The crude product obtained after cyclization was purified by crystallization from ethanol to provide pure title compound, m.p. 155°–157° C.

3-Hydroxy-4-oxo-2-phenyl-4H-1-benzopyran-8-carboxylic acid Intermediate CXXXIII

A mixture of 1.12 g of Intermediate CXI and 14 ml of 37% hydrochloric acid (w/w) in 28 ml of glacial acetic acid was stirred at 60° C. for 2 hours. After this period, the reaction mixture was cooled to room temperature, diluted with 60 ml of water and stirred for 1 hour. The solid which precipitated was filtered and washed with water to neutrality. Desiccation yielded 0.77 g of the title compound, m.p. 293°–294° C.; (EtOH 95%).

1-(5-Hydroxy-2-methoxyphenyl)piperazine dihydrobromide Intermediate CXXXIV

A solution of 13 g of 1-(2,5-dimethoxyphenyl)piperazine dihydrochloride (prepared according to R. A. Lyon et al., J. Med. Chem. 29, 630–634 (1986)) in 67 ml of 48% hydrobromic acid was stirred at reflux for 2 hours. After cooling to 5° C., the reaction mixture was maintained at the same temperature for 12 hours. Afterwards, it was filtered and the mother liquor was evaporated to dryness (in vacuo). The residue was rinsed with 200 ml of ethanol and stirred at reflux for 30 min. After overnight cooling at 0° C. 11.48 g of the title compound was recovered by (in vacuo) filtration, m.p. 270°–272° C. (dec.); (water).

Ethyl 2-cyclohexyl-3,4-dihydro-2H-1-benzopyran-8-carboxylate Intermediate CXXXV

A solution of 4.38 g of ethyl 4-oxo-2-phenyl-4H-1-benzopyran-8-carboxylate, prepared as described by Da Re et al., Ber. 99, 1962 (1966), in 100 ml of methanol and 50 ml of chloroform was hydrogenated in the presence of 0.88 g of 70% platinum dioxide at an hydrogen pressure of 20 psi (Parr apparatus). After 3 hours stirring and standing overnight, the reaction mixture was degassed and the catalyst filtered off. The solvents were evaporated under vacuum and the crude product was purified by flash chromatography (eluant, petroleum ether/ethyl acetate, 98:2). A yield of 2.4 g of the title compound was obtained as a low-melting solid.

$^1$H-NMR Spectrum at 200 MHz (CDCl$_3$ (δ)): 7.59 (1H, dd) CH in 7(5), benzopyran 7.14 (1H, dd) CH in 5(7), benzopyran 6.80 (1H, dd) CH in 6, benzopyran 4.34 (2H, q) CH$_2$O 3.70–3.90 (1H, m) CHO 2.70–2.85 (2H, m) CH$_2$ in 4, benzopyran 1.10–2.20 (13H, m) cyclohexyl CH and CH$_2$s; CH$_2$ in 3, benzopyran 1.37 (3H, t) $\underline{CH}_3$CH$_2$ 2-Cyclohexyl-3,4-dihydro-2H-1-benzopyran-8-carboxylic acid Intermediate CXXXVI A mixture of 2.29 g of Intermediate CXXXV, 0.48 g of lithium hydroxide monohydrate and 6 ml of water in 38 ml of tetrahydrofuran/methanol (1:1) was stirred for 12 hours at room temperature. Afterwards, the reaction mixture was poured into 21 ml of 1N sodium hydroxide. The alkaline aqueous layer was washed with ethyl acetate, acidified (pH=1) with 1N hydrochloric acid and extracted with ethyl acetate. Evaporation (in vacuo) yielded 1.89 g of the title compound, m.p. 78°–88° C.

Ethyl 2-(1-adamantyl)-3-methyl-4-oxo-4H-1-benzopyran-8-carboxylate Intermediate CXXXVII To a solution of 4.35 g of 1-adamantoyl chloride and 3.31 g of ethyl 2-hydroxy-3-propionylbenzoate in 48 ml of anhydrous pyridine was added 4.6 g of 1,8-diazabicyclo[5.4.0]undec-7-ene. The reaction mixture was stirred at room temperature for 2 hours and at 60°–70° C. for 4 hours. After cooling the reaction mixture was poured into 6N hydrochloric acid and extracted with ethyl acetate. The organic layer was washed with water, dried on sodium sulfate and evaporated to dryness (in vacuo).

The residue was added with 100 ml of glacial acetic acid and 10 ml of 37% hydrochloric acid and heated at reflux for 3 hours. The reaction mixture was cooled, poured into 0.1N sodium hydroxide and filtered by suction. The gummy solid obtained was dissolved in chloroform, dried on sodium sulfate and evaporated to dryness (in vacuo). The crude product was purified by flash chromatography eluting with petroleum ether/ethyl acetate (9:1), yielding 1.64 g of the title compound, as a low-melting solid.

$^1$H-NMR Spectrum at 200 MHz (CDCl$_3$ (δ)) : 8.37 (1H, dd) CH in 5(7), benzopyran 8.16 (1H, dd) CH in 7(5), benzopyran 7.39 (1H, dd) CH in 6, benzopyran 4.46 (2H, q) CH$_3$$\underline{CH}_2$O 2.30 (3H, s) CH$_3$C 2.20–2.26 and 1.90–1.94 (15H, m) adamantane CHs and CH$_2$s 1.43 (3H, t) $\underline{CH}_3$CH$_2$ 2-(1-Adamantyl)-3-methyl-4-oxo-4H-1-benzopyran-8-carboxylicacid Intermediate CXXXVIII The title compound was prepared according to the procedure described for Intermediate LXXXIX starting from Intermediate CXXXVII instead of Intermediate LXXXVIII.

$^1$H-NMR Spectrum at 200 MHz (CDCl$_3$, (δ)) 9.50–12.00 (1H, bb) COOH 8.47 (1H, dd) CH in 7 (5), benzopyran 8.32

(1H, dd) CH in 5 (7), benzopyran 7.41 (1H, dd) CH in 6, benzopyran 2.31 (3H, s) CH$_3$ 2.20–2.30 and 1.90–2.00 (15H, m) adamantane CHs and CH$_2$s 8-(5-Bromopentylthio)-3-methyl-4-oxo-2-phenyl-4H-1-benzopyran Intermediate CXXXIX The title compound was obtained according to the procedure described for Intermediate XXXIV using 1,5-dibromopentane instead of 1-chloro-3-bromopropane. The crude product was purified by flash chromatography by eluting with a petroleum ether-ethyl acetate mixture (8:2). The residue was crystallized from 2-propanol to provide the title compound, m.p. 68°–70° C.

8-(5-Bromopentylsulfonyl)-3-methyl-4-oxo-2-phenyl-4H-1-benzopyran Intermediate CXL The title compound was prepared by the same method as Intermediate XXXV, using Intermediate CXXXIX instead of Intermediate XXXIV. The product was crystallized from ethanol, m.p. 94°–96° C.

3-Ethoxymethyl-2-phenyl-4-oxo-4H-1-benzopyran-8-carboxylic acid Intermediate CXLI To a stirred solution of sodium ethoxide, prepared by dissolving 0.23 g of sodium into 20 ml of ethanol, under nitrogen atmosphere was added 1.94 g of Intermediate XCIII. The mixture was heated at reflux for 4 hours. After cooling to room temperature the reaction mixture was diluted with 50 ml of water and the ethanol was evaporated (in vacuo). The aqueous solution was extracted with diethyl ether. The extracts were acidified by addition of 37% hydrochloric acid. The precipitate which formed was collected by suction, washed with water and crystallized from acetonitrile yielding 1.15 g of the title compound, m.p. 194°–198° C.

3-Benzyloxymethyl-2-phenyl-4-oxo-4H-1-benzopyran-8-carboxylic acid Intermediate CXLII A mixture of 3.15 ml of benzyl alcohol, 1.25 g of 50% sodium hydride in mineral oil and 120 ml of tetrahydrofuran was stirred at reflux temperature under nitrogen atmosphere. After 5 hours, 5.03 g of Intermediate XCIII and 0.35 g of tetrabutylammonium bromide were added. Stirring was continued for 12 hours at the reflux temperature. After cooling to room temperature, the mixture was poured into 200 ml of water and 37% hydrochloric acid was added cautiously until the reaction mixture was acidic. The mixture was extracted with ethyl acetate. The organic layer was washed with water, dried over sodium sulfate and evaporated to dryness (in vacuo). Crystallization of the crude product from ethanol provided 2.55 g of the title compound, m.p. 218°–220° C.

3-Methyl-2-(1-naphthyl)-4-oxo-4H-1-benzopyran-8-carboxylic acid Intermediate CXLIII The title compound was prepared according to the procedure of Intermediate LXVII, starting from Intermediate CXXXI instead of Intermediate LXVI and carrying out the reaction at 30° C. After crystallization from ethanol, the title compound melted at 254°–256° C.

2-(2-Biphenylyl)-3-methyl-4-oxo-4H-1-benzopyran-8-carboxylic acid Intermediate CXLIV The title compound was prepared according to the procedure of Intermediate LXVII, starting from Intermediate CXXIX instead of Intermediate LXVI. The reaction was carried out at 30° C. After crystallization from isopropanol, the product melted at 245°–250° C.

(Z,E)-8-{4-[2-(1,3-Dioxolanyl)]-1-butenyl}-3-methyl-4-oxo-2-phenyl-4H-1-benzopyran Intermediate CXLV The title compound was prepared according to the procedure described for Intermediate XLV using 3-[2-(1,3-dioxolanyl)]propyl triphenylphosphonium iodide (prepared as described by E. Bertele et al., Helvetica Chimica Acta 50, 2445–2456 (1967)) instead of 2-[2-(1,3-dioxanyl)]ethyl triphenylphosphonium bromide. Chromatographic purification provided the title compound as a mixture of E and Z diastereoisomers (oil). The ratio of the two isomers was determined by NMR spectroscopy. The ratio was E:Z=6:4.

$^1$H-NMR Spectrum at 200 MHz (CDCl$_3$ (δ)) 8.18; 8.12 (1H; 2dd) benzopyran, CH in 7 (E+Z) 7.55–7.78 (3H; m) benzopyran, CH in 5; phenyl CHs in 2, 6 7.45–7.55 (3H; m) phenyl CHs in 3, 4, 5 7.37; 7.31 (1H; 2dd) benzopyran, CH in 6 (E+Z) 6.85 (0.6H; d) Aryl—CH=(E) 6.70 (0.4H; d) Aryl CH=(Z) 6.45 (0.6H; dt) CH=CH—CH$_2$(Z) 5.87 (0.4H; dt) CH=CHCH$_2$(E) 4.92; 4.87 (1H; 2t) dioxolanyl CH(Z+E) 3.75–4.20 (4H; m) dioxolanyl CH$_2$s 2.35–2.50 (2H; m) CH$_2$CH 2.19; 2.18 (3H; 2s) CH$_3$ (Z+E) 1.75–1.95 (2H; m) CH$_2$—CH=

8-{4-[2-(1,3-Dioxolanyl)]butyl}-3-methyl-4-oxo-2-phenyl-4H-1-benzopyran Intermediate CXLVI The title compound was prepared following the procedure described for Intermediate XLVI starting from Intermediate CXLV instead of Intermediate XLV. Evaporation of the reaction solvent (in vacuo) provided a white solid, which was crystallized from cyclohexane, m.p. 69°–71° C.

3-Methyl-4-oxo-8-(5-oxopentyl)-2-phenyl-4H-1-benzopyran Intermediate CXLVII

The title compound was prepared following the procedure described for the last step of Intermediate XXXIX starting from Intermediate CXLVI instead of 2-{3-[4-(2-methoxyphenyl)-1-piperazinyl]-propyl}dioxolane. The compound was obtained as a solid, m.p. 46°–50° C.

$^1$H-NMR Spectrum at 200 MHz (CDCl$_3$, (δ)) : 9.71 (1H; t) CHO 8.15 (1H; dd) benzopyran, CH in 5 7.60–7.75 (2H; m) phenyl CHs in 2, 6 7.40–7.60 (4H; m) benzopyran CH in 7; phenyl CHs in 3, 4, 5 7.31 (1H; dd) CH of benzopyran in 6 2.90 (2H; t) aryl-CH$_2$ 2.35–2.55 (2H; m) CH$_2$CHO 2.18 (3H; s) CH$_3$ 1.55–1.85 ( 4H; m) CH$_2$CH$_2$CH$_2$CH$_2$ Ethyl 3-methyl-2-(4-methylcyclohexyl)-4-oxo-4H-1-benzopyran-8-carboxylate Intermediate CXLVIII A mixture of 4.26 g of 4-methylcyclohexanecarboxylic acid, 2.19 ml of thionyl chloride and 0.16 ml of pyridine in 60 ml of diethyl ether was stirred at room temperature for 12 hours. Then the solvent was removed (in vacuo). The crude 4-methylcyclohexanecarbonyl chloride obtained was mixed with 6.17 g of ethyl 2-hydroxy-3-propionylbenzoate and 9 ml of 1,8-diazabicyclo[5,4,0]-undec-7-ene in 90 ml of pyridine. The solution was stirred for hours at room temperature and at 70° C. for 6 hours. After cooling to room temperature, the reaction mixture was poured into water, acidified to pH=1, with 37% hydrochloric acid and extracted with chloroform. After the usual workup, the residue was purified by flash chromatography eluting with petroleum ether/ethyl acetate (9:1) to provide 6.64 g of the title compound.

$^1$H-NMR spectrum at 200 MHz (CDCl3 (δ)) : 8.40 (dd, 1H) benzopyran CH in 7 8.20 (dd, 1H) benzopyran CH in 5 7.38 (dd, 1H) benzopyran CH in 6 4.46 (q, 2H) CH$_2$O 2.75–2.95 (m, 1H) CH-C-O cyclohexyl C$_1$ 2.10 (s, 3H) benzopyran CH$_3$ in 3 1.60–1.95 (m, 6H) cyclohexyl protons 1.45–1.60 (m, 1H) CHCH$_3$ cyclohexyl C4 1.45 (t, 3H) CH$_3$CH$_2$ 1.00–1.20 (m, 2H) cyclohexyl protons 0.96 (d, 3H) CH$_3$CH 3-Methyl-2-(4-methylcyclohexyl)-4-oxo-4H-1-benzopyran-8-carboxylic acid Intermediate CXLIX The title compound was prepared as described for Intermediate CXXXVI starting from Intermediate CXLVIII instead of Intermediate CXXXV. Evaporation of the solvent (in vacuo) was followed by dilution with water. Acidification of the solution with 1N hydrochloric acid provided the pure title compound. This was collected by filtration, m.p. 220°–224° C.

Ethyl 3-(2-cyclopentylcarbonyl)propionyl-2-hydroxybenzoate Intermediate CL

This compound was prepared in 2 steps. The first step was carried out according to the procedure of Intermediate CXXVII starting from ethyl 2-hydroxy-3-propionylbenzoate instead of methyl 2-hydroxy-3-propionylbenzoate and from cyclopropylcarbonyl chloride (prepared as described by G. B. Payne et al., J. Org. Chem. 22, 1680 (1957)) instead of 2-phenylbenzoyl chloride. The reaction was carried for 2 hours at 80° C. After cooling, to room temperature, the mixture was concentrated (in vacuo) to a small volume and added to water. The crude methyl 2-cyclopropylcarbonyloxy-3-propionylbenzoate so obtained was used for the second step without further purification.

The second step was carried out according to the procedure of Intermediate CXXVIII, using the ester intermediate prepared above instead of Intermediate CXXVII. After acidification, the mixture was extracted with ethyl acetate and the organic extracts were dried over sodium sulfate. The solvent was removed (in vacuo). The title compound was crystallization from ethanol, m.p. 87°–90° C.

Ethyl 2-cyclopentyl-3-methyl-4-oxo-2-phenyl-4H-1-benzopyran-8-carboxylate Intermediate CLI This compound was prepared according to the procedure of Intermediate CXXIX, using Intermediate CL instead of Intermediate CXXVIII. The reaction was stirred at 100° C. for 15 minutes. The crude product was purified by flash chromatography on silica gel eluting with n-hexane/ethyl acetate (4:1). After crystallization from ethanol, the title compound melted at 79°–80° C.

2-Cyclopentyl-3-methyl-4-oxo-4H-1-benzopyran-8-carboxylic acid Intermediate CLII This compound was prepared according to the procedure of Intermediate LXVII, starting from Intermediate CLI instead of Intermediate LXVI. The reaction was carried out at room temperature for 1 hour using methanol as co-solvent, in place of ethanol. The title compound was crystallized from acetonitrile, m.p. 193°–196° C.

Methyl 2-hydroxy-3-[2-(1-phenylcyclopentyl)carbonyl]propionylbenzoate Intermediate CLIII This compound was prepared in 2 steps. The first step was carried out according to the procedure of Intermediate CXXVII starting from 1-phenylcyclopentylcarbonyl chloride (prepared as described in S. L. Calderon et al., J. Med. Chem. 34, 3163 (1991)) instead of 2-phenylbenzoyl chloride. The reaction was conducted for 2 hours at 70° C. and 12 hours at room temperature and the mixture was concentrated (in vacuo) to a small volume before adding to water. The precipitate was extracted with ethyl acetate. The organic layer was washed, in succession, with dilute hydrochloric acid, 5% sodium bicarbonate solution, and water. This was followed by drying over anhydrous sodium sulfate. The crude methyl 2-(1-phenylcyclopentylcarbonyloxy)-3-propionylbenzoate was obtained by evaporation of the solvent. The product was used for the second step without further purification.

The second step was carried out according to the procedure of Intermediate CXXVIII, using the ester intermediate prepared above instead of Intermediate CXXVII and 1.1 eq of 1,8-diazabicyclo[5.4.0]undec-7-ene instead of potassium t-butoxide. The reaction was conducted for 2 hours at 100° C. After cooling to room temperature, the mixture was concentrated (in vacuo) to a small volume and added to water. The precipitate was extracted with ethyl acetate. The organic layer was washed, in succession, with dilute hydrochloric acid, 5% sodium bicarbonate solution, and water. This was followed by drying over anhydrous sodium sulfate.

The crude product was purified by flash chromatography on silica gel, eluting with n-hexane-ethyl acetate (4:1). Crystallization from ethanol provided the pure title compound, m.p. 114°–116° C.

Methyl 3-methyl-2-(1-phenylcyclopentyl)-4-oxo-4H-1-benzopyran-8-carboxylate Intermediate CLIV This compound was prepared according to the procedure of Intermediate CXXIX, using Intermediate CLIII instead of Intermediate CXXVIII and stirring at 100° C. for 4.5 hours. After crystallization from ethanol, the title compound melted at 95°–97° C.

3-Methyl-2-(1-phenylcyclopentyl)-4-oxo-4H-1-benzopyran-8-carboxylic acid Intermediate CLV This compound was prepared according to the procedure of Intermediate LXVII, starting from Intermediate CLIV instead of Intermediate LXVI and carrying out the reaction at room temperature for 10 hours using a mixture of methanol/1,4-dioxane (5:3) instead of ethanol. After crystallization from ethanol, the title compound melted at 218°–220° C.

3-Methyl-2-(1-methylcyclohexyl)-4-oxo-4H-1-benzopyran-8-carboxylic acid Intermediate CLVI A solution of 6.25 g of methyl 2-hydroxy-3-propionylbenzoate in 15 ml of anhydrous pyridine was prepared and maintained at room temperature. 1-Methylcyclohexylcarbonyl chloride, 4.85 g, (prepared as described in Rouzaud J. et al., Bull. Soc. Chim. Fr. 7, 2030 (1965); (Chem. Abst. 63, 11378e (1963)) was added to the solution. The mixture was stirred at 70° C. for 2 hours, concentrated to small volume (in vacuo) and poured into water. The precipitate was extracted with ethyl acetate. The organic layer was washed, in succession, with dilute hydrochloric acid, 5% sodium bicarbonate solution and water. This was followed by drying over anhydrous sodium sulfate. The solvent was evaporated to dryness to give 8.75 g of the crude methyl 2-(1-methylcyclohexylcarbonyloxy)-3-propionylbenzoate This compound was utilized without further purification.

A mixture of 7.18 g of the ester intermediate prepared above, 5 ml of 1,8-diazabicyclo[5.4.0]undec-7-ene and 24 ml of anhydrous pyridine was stirred at 100° C. for 3 hours and then concentrated to small volume (in vacuo) and poured into water. The precipitate was extracted with ethyl acetate. The organic layer was washed, in succession, with dilute hydrochloric acid, 5% sodium bicarbonate solution and water. This was followed by drying over anhydrous sodium sulfate. The solvent was evaporated to dryness to give 6.48 g of methyl 2-hydroxy-3-[2-(1-methylcyclohexylcarbonyl)]propionylbenzoate. This compound was utilized without further purification.

A mixture of 4.4 g of the methyl benzoate intermediate prepared above, 0.5 ml of 37% hydrochloric acid and 18 ml of acetic acid was stirred at 100° C. for 3.5 hours. After cooling, the mixture was poured into 100 ml of water and the precipitate was extracted with ethyl acetate. The organic layer was washed with 2N aqueous sodium hydroxide solution and water, dried over anhydrous sodium sulfate and evaporated to dryness (in vacuo) to provide 2.89 g of crude methyl 3-methyl-2-(1-methylcyclohexyl)-4-oxo-4H-1-benzopyran-8-carboxylate. This compound was used without further purification for the final step.

The title compound was prepared according to the procedure of the Intermediate LXVII, starting from 2.42 g of intermediate prepared above instead of Intermediate LXVI and carrying out the reaction at room temperature for 5 hours. Crystallization from acetonitrile provided 1.2 g of the title compound, m.p. 195°–198° C.

$^1$H-NMR spectrum at 200 MHz (DMSO-$d_6$, ($\delta$)) 1.33 (s, 3H) CH$_3$ in 1, cyclohexane ring 1.20–1.65 (m, 8H) CHs of cyclohexane ring 2.14 (s, 3H) CH3 in 3, benzopyran ring 2.45–2.60 (m, 2H) CHs of cyclohexane ring 7.50 (dd, 1H) CH in 6, benzopyran ring 8.10 and 8.25 (2dd, 2H) CHs in 5 and 7, benzopyran ring 13.40 (bs, 1H) COOH Methyl 2-(bicyclo[2.2.1]hept-5-en-2-yl)-3-methyl-4-oxo-4H-1-benzopyran-8-carboxylate Intermediate CLVII A solution of 12.9 g of bicyclo[2.2.1]hept-5-en-2-carbonyl chloride (prepared as described in Parham, W. E. et al., J. Am. Chem. Soc. 73, 5068 (1951)) in 20 ml of anhydrous pyridine was added dropwise, at room temperature, over about 15 minutes, into a stirred solution of 14.6 g of methyl 2-hydroxy-3-propionylbenzoate in 50 ml of anhydrous pyridine. After 3 hours stirring and 24 hours standing at room temperature, 24.5 ml of 1,8-diazabicyclo[5.4.0]-undec-7-ene was added and stirring was continued for 2 hours at room temperature followed by 3.5 hours at 80° C. After cooling to room temperature, the mixture was poured into 500 ml of ice-water, acidified with 37% hydrochloric acid and extracted with chloroform. The organic layer was washed with water, dried over anhydrous sodium sulfate, and evaporated to dryness (in vacuo). The crude product was purified by flash chromatography on silica gel eluting with petroleum ether/ethyl acetate (9:1) to provide 11.5 g of the title compound as on oily mixture (from the NMR spectrum mixture of endo-exo isomers), m.p. 91°–93° C. (n-hexane).

$^1$H-NMR spectrum at 200 MHz (CDCl$_3$, ($\delta$)) 1.35–1.65 (m, 2H) CH$_2$ in 7 of bicycloheptene ring 1.90–2.25 (m, 2H) CH$_2$ in 3 of bicycloheptene ring 2.11 (s, 3H) CH$_3$ in pos. 3 of benzopyran ring 2.80–3.15 (m, 3H) CHs in 1, 2 and 4 of bicycloheptene ring 6.10–6.35 (m, 2H) CHs in 5 and 6 of bicycloheptene ring 7.40 (dd, 1H) CH in 6 of benzopyran ring 8.20 (dd, 1H) CH in 7(5) of benzopyran ring 8.42 (dd, 1H) CH in 5(7) of benzopyran ring 2-(Bicyclo[2.2.1]hept-5-en-2-yl)-3-methyl-4-oxo-4H-1-benzopyran-8-carboxylic acid Intermediate CLVIII This compound was prepared according to the procedure of Intermediate LXVII, starting from Intermediate CLVII instead of Intermediate LXVI. The reaction was carried out at 50°–55° C. for 3 hours using 1,4-dioxane as the solvent instead of methanol. The crude product was purified by flash chromatography on silica gel eluting with chloroform/methanol (10:1). After crystallization from acetonitrile, the title compound melted at 199°–200° C. This was a mixture of endo-exo isomers, determined from the NMR spectrum.

$^1$H-NMR spectrum at 200 MHz (CDCl$_3$, ($\delta$)) 1.45–1.70 (m, 2H) bicycloheptene ring, CH$_2$ in 7 1.90–2.30 (m, 5H) CH$_2$ in 3, bicycloheptene ring and CH$_3$ in 3, benzopyran ring 2.85–3.75 (m, 3H) CHs in 1,2,4 of bicycloheptene ring 5.80–6.40 (m, 2H) CHs in 5 and 6 of bicycloheptene ring 7.40–7.55 (m, 1H) CH in 6 of benzopyran ring 8.30–8.40 (m, 1H) CH in 7(5) of benzopyran ring 8.45–8.55 (m, 1H) CH in 5 (7) of benzopyran ring 10.10–12.10 (bb, 1H) COOH 2-Cycloheptyl-3-methyl-4-oxo-4H-1-benzopyran-8-carboxylic acid Intermediate CLIX A mixture, of 7.3 g of methyl 2-hydroxy-3-propionylbenzoate, 4.7 g of 4-dimethylaminopyridine and 50 ml of dichloromethane was stirred at room temperature. Cycloheptanecarbonyl chloride, 56 g, in 10 ml of dichloromethane, (prepared as described in P. W. Collins et al., J. Med. Chem. 32, 1001–1006 (1989)) was added to the solution using dropwise addition. The mixture was stirred at room temperature for 5 hours and allowed to stand overnight. The reaction mixture was washed, in succession, with 3% hydrochloric acid, saturated aqueous sodium bicarbonate solution and water. This was followed by drying over anhydrous sodium sulfate and evaporation to dryness to provide 9.8 g of crude methyl 2-cycloheptanecarbonyloxy-3-propionylbenzoate. This product was utilized without further purification.

A mixture of 7.66 g of the ester prepared above and 1 ml of 1,8-diazabicyclo[5,4,0]-undec-7-ene in 20 ml of anhydrous pyridine was stirred for 1 hour at 100° C. After cooling to room temperature, the solvent was evaporated (in vacuo) and 60 ml of water was added to the residue. The mixture was extracted with ethyl acetate. The organic layer was washed, in succession, with 3% hydrochloric acid, saturated aqueous sodium bicarbonate solution and water. This was followed by drying over anhydrous sodium sulfate. Evaporation to dryness (in vacuo) provided the crude methyl ester of the title compound. It was purified by flash chromatography on silica gel eluting with petroleum ether/ethyl acetate (9:1) and used for the following hydrolysis.

The purified intermediate prepared above (2 g) was hydrolyzed according to the procedure of Intermediate LXVII. The reaction was carried out at room temperature for 4.5 hours using a mixture of 1,4-dioxane-methanol (3:7) instead of ethanol. The title compound was purified by crystallization from acetonitrile to provide 1.6 g of solid, m.p. 212°–215° C.

$^1$H-NMR Spectrum at 200 MHz (DMSO-d6, ($\delta$)) 1.48–1.75 (m, 6H) CH$_2$s of cycloheptane ring 1.75–1.95 (m, 6H) CH$_2$s of cycloheptane ring 2.00 (s, 3H) CH$_3$ in 3, benzopyran ring 3.05–3.20 (m, 1H) CH in 1, cycloheptane ring 7.49 (dd, 1H) CH in 6, benzopyran ring 8.15 (dd, 1H) CH in 7(5), benzopyran ring 8.20 (dd, 1H) CH in 5 (7), benzopyran ring 13.10–13.60 (bs, 1H) COOH Methyl 4-chloro-2-phenylquinoline-8-carboxylate Intermediate CLX A mixture of 7 g of 2-phenyl-4(1H)-quinolone-8-carboxylic acid (prepared as described by W. A. Denny et al., J. Med. Chem., 32, 396 (1989)) and 60 ml of phosphorus oxychloride was stirred at reflux temperature for 40 minutes. After cooling to room temperature, the mixture was poured into 500 g of ice water, neutralized with 12N sodium hydroxide solution and extracted with chloroform. The organic layer was washed with water, dried over anhydrous sodium sulfate and evaporated to dryness (in vacuo) to provide the crude product. The product was purified by flash chromatography on silica gel eluting with petroleum ether/ethyl acetate (9:1). Crystallization from ethanol provided 3.6 g of the title compound, m.p. 98°–101° C.

Methyl 2-phenyl-1,2,3,4-tetrahydroquinoline-8-carboxylate Intermediate CLXI

Chloro-ester Intermediate CLX, (3.63 g) was reduced, in a Parr apparatus in a hydrogen atmosphere at 45 psi, in a mixture of 1.21 g of anhydrous sodium acetate, 30 ml of methanol, 0.73 g of Raney nickel and 91 ml of ethyl acetate. After the theoretical hydrogen absorption, the insoluble material was separated by suction filtration, the filtrate was concentrated to a small volume (in vacuo), diluted with water and extracted with ethyl acetate. The organic layer was separated, washed with saturated aqueous sodium bicarbonate solution and water. The crude product was obtained by evaporation of the solvent. Crystallization from ethanol provided 2.1 g of the title compound, characterized by NMR spectrum as follows.

$^1$H-NMR Spectrum at 200 MHz (CDCl$_3$, ($\delta$)) 1.85–2.25 (m, 2H) CH$_2$ in 3, tetrahydroquinoline ring 2.65–2.95 (m, 2H) CH$_2$ in 4, tetrahydroquinoline ring 3.82 (s, 3H) CH$_3$ 4.62 (m, 1H) CH in 2, tetrahydroquinoline ring 6.50 (dd, 1H) CH in 6, tetrahydroquinoline ring 7.10 (dd, 1H) CH in 5, tetrahydroquinoline ring 7.20–7.40 (m, 5H) CHs of phenyl ring 7.75 (dd, 1H) CH in 7, tetrahydroquinoline ring 8.08 (s, 1H) NH Methyl 1-methyl-2-phenyl-1,2,3,4-tetrahydroquinoline-8-carboxylate Intermediate CLXII A mixture of 0.21 g of Intermediate CLXI, 0.23 g of paraformaldehyde, 0.15 g of sodium borohydride and 7.8 ml of tetrahydrofuran was stirred and maintained at room temperature. Trifluoroacetic acid 3.8 ml was added, using dropwise addition to the solution. The mixture was stirred at room temperature for 26 hours, then poured into 100 ml of cooled water and alkalinized by addition of 7 ml of 12N sodium hydroxide solution. After saturation with sodium chloride, the mixture was extracted with diethyl ether, the organic layer was separated, dried over anhydrous sodium sulfate and evaporated to dryness to provide 0.25 g of the title compound as an oily residue, characterized by NMR spectrum as follows.

$^1$H-NMR Spectrum at 200 MHz (CDCl3, (δ)) 1.80–2.00 (m, 1H) CH in 3, tetrahydroquinoline ring 2.20–2.40 (m, 1H) CH in 3, tetrahydroquinoline ring 2.60–2.95 (m, 2H) CH$_2$ in 4, tetrahydroquinoline ring 2.71 (s, 3H) NCH$_3$ 3.86 (s, 3H) OCH$_3$ 4.25–4.40 (m, 1H) CH in 2, tetrahydroquinoline ring 6.65 (dd, 1H) CH in 6, tetrahydroquinoline ring 7.05 (dd, 1H) CH in 5, tetrahydroquinoline ring 7.20–7.45 (m, 5H) CHs of phenyl ring 7.50 (dd, 1H) CH in 7, tetrahydroquinoline ring 1-Methyl-2-phenyl-1,2,3,4-tetrahydroquinoline-8-carboxylic acid Intermediate CLXIII This compound was prepared according to the procedure used for Intermediate LXVII, starting from Intermediate CLXII instead of Intermediate LXVI and using potassium hydroxide instead of sodium hydroxide. The reaction was continued for 12 hours at 90° C. using a mixture of ethanol/1,4-dioxane (5:3) instead of ethanol. The title compound was characterized by NMR spectrum as follows.

$^1$H-NMR Spectrum at 200 MHz (CDCl$_3$, (δ)) 2.30–2.45 (m, 2H) CH$_2$ in 3, tetrahydroquinoline ring 2.60 (s, 3H) NCH$_3$ 2.95–3.05 (m, 2H) CH$_2$ in 4, tetrahydroquinoline ring 4.30–4.40 (m, 1H) CH in 2, tetrahydroquinoline ring 7.25 (dd, 1H) CH in 6, tetrahydroquinoline ring 7.30–7.45 (m, 6H) CH in 5, tetrahydroquinoline ring and CHs of phenyl ring 8.05 (dd, 1H) CH in 7, tetrahydroquinoline ring 14.90–15.50 (bs, 1H) COOH (Trans)-methyl 2-(4-methoxycyclohexyl)-3-methyl-4-oxo-4H-1-benzopyran-8-carboxylate Intermediate CLXIV and (Cis)-methyl 2-(4-methoxycyclohexyl)-3-methyl-4-oxo-4H-1-benzopyran-8-carboxylate Intermediate CLXV The title compounds were prepared following the procedure described for Intermediate CXLVIII, starting from 4.9 g of 4-methoxycyclohexancarboxylic acid (cis-trans mixture). Purification and resolution of the crude products by flash chromatography (eluent petroleum ether/ethyl acetate 8:2) provided 1.54 g of trans Intermediate CLXIV and 1.10 g of cis Intermediate CLXV as amorphous solids characterized by NMR as follows.

$^1$H-NMR Spectra at 200 MHz (CDCl$_3$ (δ)):

Intermediate CLXIV (trans) 8.40 (1H, dd) CH in 7(5), benzopyran 8.22 (1H, dd) CH in 5(7), benzopyran 7.39 (1H, dd) benzopyran, CH in 6 4.00 (3H, s) COOCH$_3$ 3.41 (3H, s) OCH$_3$ eq. 3.20–3.40 (1H, m) CHOCH$_3$ ax. 2.80–3.00 (1H, m) cyclohexyl, CH in 1, ax. 2.18–2.32 (2H, m) cyclohexyl, CHs 2.10 (3H, s) CH$_3$C 1.88–2.03 (4H, m) cyclohexyl, CHs 1.22–1.48 (2H, m) cyclohexyl, CHs Intermediate CLXV (cis,) 8.40 (1H, dd) CH in 7(5), benzopyran 8.22 (1H, dd) CH in 5(7), benzopyran 7.39 (1H, dd) benzopyran, CH in 6 4.05 (3H, s) COOCH3 3.52–3.62 (1H, m) CHOCH3 eq. 3.37 (3H, s) OCH3 ax. 2.85–3.05 (1H, m) cyclohexyl, CH in 1, ax. 2.05–2.32 (7H, m) CH3C and cyclohexyl CHs 1.43–1.78 (4H, m) cyclohexyl CHs (Trans)-2-(4-methoxycyclohexyl)-3-methyl-4-oxo-4H-1-benzopyran-8-carboxylic acid Intermediate CLXVI The title compound was prepared as described for Intermediate CXXXVI starting from Intermediate CLXIV instead of Intermediate CXXXV. Filtration of the solid after acidification of the alkaline solution, provided the title compound, m.p. 202°–209° C.

(Cis)-2-(4-methoxycyclohexyl)-3-methyl-4-oxo-4H-1-benzopyran-8-carboxylic acid Intermediate CLXVII The title compound was prepared as described for Intermediate CXXXVI starting from Intermediate CLXV instead of Intermediate CXXXV. After acidification of the alkaline solution, filtration of the solid provided the title compound m.p. 195°–197° C.

2-Hydroxy-N,3-[4-(2-methoxyphenyl)-1-piperazinyl]propyl-3-propionylbenzamide dihydrochloride Intermediate CLXVIII A solution of 7.48 g of 1-(3-aminopropyl)-4-(2-methoxyphenyl)piperazine in 30 ml of dichloromethane was added dropwise within 45 minutes at 4° C. into a stirred mixture of 6.37 g of 2-hydroxy-3-propionylbenzoyl chloride (prepared as described in DE 2,631,248) and 4.2 ml of triethylamine in 80 ml of dichloromethane. The reaction mixture was stirred for 2 hours at 4° C. and for 8 hours at room temperature, then it was extracted with 5% aqueous sodium hydrogen carbonate solution followed by water and the organic layer was dried over anhydrous sodium sulfate. The residue obtained by evaporation in vacuo of the solvent was purified by flash chromatography on silica gel eluting with dichloromethane-methanol 98:2 to 95:5. The fractions containing the pure base were confined, the solvent were evaporated (in vacuo), the residue was dissolved in ethanol and an excess of ethanolic hydrogen chloride was added. This was followed by addition of diethyl ether until the salt crystallized. Crystallization from methanol provided 7.6 g of the title compound, m.p. 215°–217° C. (decompose).

8-Trifluoroacetamidomethyl-3-methyl-4-oxo-2-phenyl-4H-1-benzopyran

This compound can be prepared according to the procedure described for Intermediate XXIII, but using Intermediate XXIV instead of 8-amino-3-methyl-4-oxo-2-phenyl-4H-1-benzopyran.

It can be used as starting material instead of Intermediate XXIII, in the same reaction as that described in Example 32 to yield 8-{2[4-(2-methoxyphenyl)-1-piperazinyl]ethylamino}-methyl-3-methyl-4-oxo-2-phenyl-4H-1-benzopyran.

8-(2-Chloroethylureido)methyl-3-methyl-4-oxo-2-phenyl-4H-1-benzopyran

This intermediate can be prepared operating as described for Intermediate XLIV by using Intermediate XXIV instead of 8-amino-3-methyl-4-oxo-2-phenyl-4H-1-benzopyran.

It can be reacted with a compound of formula H-B, according to Path (a) to give the desired final compounds.

8-Ethenylsulfonylaminomethyl-3-methyl-4-oxo-2-phenyl-4H-1-benzopyran

This compound can be prepared by reacting Intermediate XXIV with 2-chloroethylsulfonylchloride in an halogenated solvent (e.g., dichloromethane) in presence of triethylamine at 0°–40° C., according to A. A. Goldberg, Jr., *J. Chem. Soc.*, 464 (1945).

It can be reacted with the appropriate compounds H-B, according to Path (m) to yield the desired final compounds.

8-Chlorosulfonylmethyl-3-methyl-4-oxo-2-phenyl-4H-1-benzopyran

This intermediate can be prepared by reacting amidinothiomethyl-3-methyl-4-oxo-2-phenyl-4H-1-benzopyran (whose synthesis is described in Intermediate XXI) with chlorine gas in water at −10°/10° C. according to T. B. Johnson et al., *J. Am. Chem. Soc.*, 61, 2548 (1939). By reaction of this intermediate with the appropriate compounds A-NH-Z-B(A=H,OR,CH$_3$) according to Path (n) the final desired compounds can be obtained.

DETAILED SYNTHESIS OF EXAMPLES

Example 1

8-{2-[4-(2-Methoxyphenyl)-1-piperazinyl]-1-oxoethyl}-3-methyl-4-oxo-2-phenyl-4H-1-benzopyran hydrochloride A solution of 11.5 g of 1-(2-methoxyphenyl)-piperazine in 30 ml of methanol was added dropwise at 20°–25° C. to a stirred mixture consisting of 21.4 g of Intermediate VI and 4.1 g of potassium carbonate in 120 ml of methanol. After 4 hours stirring at the same temperature, the reaction mixture was stripped in vacuo. The residue was extracted with chloroform and the organic solution was washed with water, dried on anhydrous sodium sulfate/calcium chloride, filtered and stripped in vacuo. The obtained crude product was dissolved in acetone and a slight excess of ethanolic hydrogen chloride was added. After collection by suction filtration and recrystallization from 95% ethanol, 16.3 g of the title compound was obtained (m.p. (189) 195°–199° C.).

Example 2

8-{2-[4-(2-Methylphenyl)-1-piperazinyl]-1-oxoethyl}-3-methyl-4-oxo-2-phenyl-4H-1-benzopyran hydrochloride This compound was prepared according to Example 1, but using 1-(2-methylphenyl)-piperazine instead of 1-(2-methoxyphenyl)-piperazine and carrying out the reaction in dimethylformamide for 1 hour instead of in methanol for 4 hours, m.p. (194) 203°–206° C. (2-propanol).

Example 3

8-{2-[4-(2-Ethoxyphenyl)-1-piperazinyl]-1-oxoethyl}-3-methyl-4-oxo-2-phenyl-4H-1-benzopyran hydrochloride This compound was prepared according to Example 1, but using 1-(2-ethoxyphenyl)-piperazine instead of 1-(2-methoxyphenyl)-piperazine and carrying out the reaction in dimethylformamide for 2 hours instead of in methanol for 4 hours. m.p. 208°–210° C. (2-propanol).

Example 4

8-{3-[4-(2-Methoxyphenyl)-1-piperazinyl]-1-oxopropyl}-3-methyl-4-oxo-2-phenyl-4H-1-benzopyran hydrochloride A solution of 10 ml of 37% formaldehyde in 15 ml of methanol was dropped, over a period of 3 minutes at 0° C., into a solution of 5.75 g of 1-(2-methoxyphenyl)piperazine in 10 ml of methanol. After 12 hours at 0° C., the mixture was stripped in vacuo and redissolved in 15 ml of methanol. 20 ml of 3.6N hydrogen chloride in diethyl ether was added at 0° C. After stripping in vacuo, the residue was suspended in 15 ml of 1,4-dioxane. A solution of 8.3 g of Intermediate V in 100 ml of 1,4-dioxane was added under stirring at 20°–25° C. After stirring for 8 hours at reflux the reaction mixture was cooled to 30°–40° C. 50 ml of methanol was added and the mixture was refluxed for a further 2 hours. After cooling to 20°–25° C., the resultant solution was diluted with 300 ml of diethyl ether. Stirring was continued for a further 3 hours at the same temperature. The title compound was collected by suction filtration and recrystallization from ethanol. Yield 4 g, m.p. 209°–210° C.

Example 5

8-{3-[4-(2-Methoxyphenyl)-1-piperazinyl]-propoxycarbonyl}-3-methyl-4-oxo-2-phenyl-4H-1-benzopyran dihydrochloride A mixture of 4.24 g of 8-carboxy-3-methyl-4-oxo-2-phenyl-4H-1-benzopyran and 6.3 g of anhydrous potassium carbonate in 60 ml of dimethylformamide was stirred at 80° C. for 30 minutes. 5.23 g of 1-(3-chloropropyl)-4-(2-methoxyphenyl)-piperazine was then added and stirring was continued at 80° C. for 3.5 hours. The reaction mixture was cooled to ambient temperature, poured on to iced water and extracted with ethyl acetate. The organic extracts were washed with aqueous sodium chloride solution, dried on anhydrous sodium sulfate, and evaporated to dryness in vacuo. The residue was taken up in ethanol and excess ethanolic hydrogen chloride was added to the solution. Yield: 8.16 g of the title compound, m.p. 198°–203° C.

Example 6

8-{2-[4-(2-Methoxyphenyl)-1-piperazinyl]-ethoxycarbonyl}-3-methyl-4-oxo-2-phenyl-4H-1-benzopyran dihydrochloride Operating as described in Example 5, but using 1-(2-chloroethyl)-4-(2-methoxyphenyl)-piperazine instead of 1-(3-chloropropyl)-4-(2-methoxyphenyl)-piperazine, the title compound was obtained, m.p. 200°–203° C. from ethanol.

Example 7

8-{3-[4-(2-Chlorophenyl)-1-piperazinyl]-propoxycarbonyl}-3-methyl-4-oxo-2-phenyl-4H-1-benzopyran dihydrochloride A mixture of 2.8 g of 1-(2-chlorophenyl)-piperazine hydrochloride and 4.2 g of anhydrous potassium carbonate in 25 ml of dimethylformamide was stirred at ambient temperature for 15 minutes. 4.81 g of Intermediate I was added, and stirring was continued for 2 days. The reaction mixture was then poured into 200 ml of cold water, and extracted with diethyl ether and ethyl acetate. The organic extracts were washed in turn with aqueous sodium chloride solution, 0.1N aqueous acetic acid solution, aqueous sodium chloride solution, aqueous 4% sodium carbonate solution and water, and were then dried on anhydrous sodium sulfate. After evaporation to dryness in vacuo, the residue was dissolved in 160 ml of acetonitrile and excess hydrogen chloride in diethyl ether was added. The insoluble title compound. was recrystallized from acetonitrile. Yield 3.6 g, m.p. 138°–143° C.

Example 8

8-[3-(4-Phenyl-1-piperazinyl)-propoxycarbonyl]-3-methyl-4-oxo-2-phenyl-4H-1-benzopyran dihydrochloride The title compound was prepared by the method described in Example 7, but using 1-phenyl-piperazine in place of 1-(2-chlorophenyl)-piperazine hydrochloride. Recrystallization was from methanol; the melting point was 229°–231° C.

Example 9

8-{3-[4-(2-Methoxyphenyl)-1-piperazinyl]-propoxycarbonyl}-3-methyl-4-oxo-2-phenyl-4H-1-benzopyran dihydrochloride Operating as described in Example 7, but using 1-(2-methoxyphenyl)-piperazine hydrochloride instead of 1-(2-chlorophenyl)-piperazine hydrochloride, the title compound was obtained. This represents an alternative route to the product of Example 5.

Example 10

8-{3-[4-(2-Methoxyphenyl)-1-piperazinyl]-2-methyl-2-propoxycarbonyl}-3-methyl-4-oxo-2-phenyl-4H-1-benzopyran dihydrochloride 5.29 g of Intermediate XXVIII in 25 ml of 1,2-dichloroethane was added dropwise at 60° C. to a solution of 6 g of 3-methyl-4-oxo-2-phenyl-4H-1-benzopyran-8-carbonyl chloride in 22 ml of 1,2-dichloroethane. The reaction mixture was refluxed for 16 hours, and then cooled to ambient temperature and poured into cold 0.5N aqueous sodium hydroxide solution. Water and dichloromethane were added. The organic phase was separated off, washed with aqueous sodium chloride solution and dried on anhydrous sodium sulfate. The solvents were evaporated off and the oily residue was purified by flash chromatography on silica gel, eluting with petroleum ether:ethyl acetate (85:15). The collected fractions were evaporated to dryness in vacuo and the residue was dissolved in ethanol. Excess ethanolic hydrogen chloride was added to give 6.71 g of the title compound, m.p. 203°–204° C.

Example 11

8-{3-[4-(2-Methoxyphenyl)-1-piperazinyl]propylcarbamoyl}-3-methyl-4-oxo-2-phenyl-4H-1-benzopyran dihydrochloride hemihydrate A mixture of 6.28 g of 1-(2-methoxyphenyl)-piperazine and 5.34 g of Intermediate XXXVII was heated at 180° C. for 5 hours. After cooling, the dark mass was purified by flash chromatography on silica gel, eluting with dichloromethane: methanol (100:3). The fractions containing the title compound were pooled. The solvents were removed in vacuo and the residue was dissolved in boiling ethanol. The solution was filtered, acidified with ethanolic hydrogen chloride, and stood overnight at 20°–25° C. The crude product was collected by filtration and crystallized from ethanol to give 5 g of the title compound, m.p. (177) 182°–186° C.

Example 12

8-{3-[4-(2-methoxyphenyl)-1-piperazinyl]propylcarbamoyl}-3-methyl-4-oxo-2-phenyl-4H-1-benzopyran dihydrochloride hemihydrate A solution of 4.48 g of 3-methyl-4-oxo-2-phenyl-4H-1-benzopyran-8-carbonyl chloride in 40 ml of chloroform was added dropwise over a period of 10 minutes at ambient temperature to a solution of 3.74 g of 3-[4-(2-methoxyphenyl)-1-piperazinyl]propylamine (prepared as in British Patent No. 2,161,807) and 1.97 g of triethylamine in 50 ml of chloroform. After stirring for 2 hours, the solution was washed first with 0.5N aqueous hydrochloric acid solution, secondly with a saturated aqueous sodium bicarbonate solution and finally with water. The chloroform solution was dried on anhydrous sodium sulfate and the solvent was evaporated off in vacuo. The residue was worked up as described in Example 11 to give 6.67 g of the title compound, m.p. (177) 182°–186° C. This represents an alternative route to the product of Example 11.

The following salts were also prepared:

monohydrochloride hydrate, m.p. 151°–154° C., monomethanesulfonate, m.p. 162°–164° C., and monomethanesulfonate, monohydrate m.p. 136°–141° C., (±)-hemimalate hydrate, m.p. 110°–112° C.

The title compound was isolated as the anhydrous base, m.p. 133°–136° C. (2-propanol or ethyl acetate). Recrystallization of the anhydrous base from an acetonitrile-water mixture (2:1) provided the base contained 0.25 molar equivalents of water, m.p. 104°–106° C.

This example has described the condensation of the amine, 3-[4-(2-methoxyphenyl)-1-piperazinyl]-propylamine, with the carbonyl chloride, 3-methyl-4-oxo-2-phenyl-4H-1benzopyran-8-carbonyl chloride. It should be noted that the amine can be condensed with the corresponding free acid or the corresponding ethyl ester by heating equimolar amounts thereof with or without a solvent. If a solvent is used, a high boiling point hydrophilic or hydrophobic solvent is appropriate. The amine can also be condensed at room temperature with an equimolar amount of the corresponding free acid in the presence of N,N'-dicyclohexylcarbodiimide and 4-dimethylaminopyridine in a solvent such as dichloromethane, chloroform, tetrahydrofuran, or dimethylformamide.

Example 13

8-{2-[4-(2-Methoxyphenyl)-1-piperazinyl]ethylcarbamoyl}-3-methyl-4-oxo-2-phenyl-4H-1-benzopyran monohydrochloride hemihydrate The title compound was prepared by the method described in Example 16, but using Intermediate XIV instead of Intermediate XV and heating at 55°–60° C. for 32 hours. Also, work up was varied as follows. After collecting the base by filtration, purification was by flash chromatography on silica gel, eluting with a chloroform:methanol gradient (100:0.5 and then 100:1). The fractions containing the title compound were pooled and the solvents were removed in vacuo. The residue was crystallized from ethanol. After filtration, the solids were taken up in boiling water and sufficient dilute hydrochloric acid was added to effect solution. The crystalline salt separated on cooling and was collected by suction filtration. m.p. 119°–123° C.

Example 14

8-{3-[2-(2-Methoxyphenoxy)-ethylamino]-propylcarbamoyl}-3-methyl-4-oxo-2-phenyl-4H-1-benzopyran hydrochloride Operating as described in Example 11, but using 2-(2-methoxyphenoxy)-ethylamine (prepared according to Augstein, J. et al., *J. Med. Chem.* 8: 356, 1965) instead of 1-(2-methoxyphenyl)piperazine, heating for 2 hours instead of 5 hours, and using dichloromethane:methanol (100:5) as eluant, the title compound was obtained, m.p. 200°–202° C. (ethanol).

Example 15

8-[3-(4-Phenyl-1-piperazinyl)-propylcarbamoyl]-3-methyl-4-oxo-2-phenyl-4H-1-benzopyran monohydrochloride hemihydrate Operating as described in Example 11, but using 1-phenylpiperazine instead of 1-(2-methoxyphenyl)-piperazine and heating for 2 hours instead of 5 hours, and using dichloromethane:methanol 100:4 as eluant, the title compound was obtained. m.p. (251) 255°–258° C. with decomposition (87% ethanol).

Example 16

8-{N-methyl-2-[4-(2-methoxyphenyl)-1-piperazinyl]-ethyl-carbamoyl}-3-methyl-4-oxo-2-phenyl-4H-1-benzopyran monohydrochloride A mixture of 3.56 g of Intermediate XV, 2.35 g of 1-(2-methoxyphenyl)-piperazine, 2.76 g of anhydrous potassium carbonate and 1.66 g of potassium iodide in 25 ml of dimethylformamide was stirred at 100° C. for 6 hours. After cooling, the solvent was removed in vacuo and the residue was taken up in 50 ml of water, stirred for 1 hour at room temperature, collected by filtration, washed with water and crystallized from 95% ethanol in the presence of a small amount of activated charcoal (for decoloring). The base was dissolved in 105 ml of boiling 0.086N aqueous hydrochloric acid solution. After cooling, the crystallized salt was collected by filtration, giving 4.3 g of the title compound (m.p. 201°–203° C.).

Example 17

8-{1-Hydroxy-2-[4-(2-methoxyphenyl)-1-piperazinyl]-ethyl}-3-methyl-4-oxo-2-phenyl-4H-1-benzopyran hydrochloride 1.36 g of sodium borohydride was added portionwise at 0° to +5° C. to a solution of 15.5 g of the compound prepared in Example 1 in 1500 ml of methanol. After stirring for 90 minutes at 0° to +5° C., 3N aqueous hydrochloric acid solution was added in order slightly to acidify the reaction mixture, which was then stripped in vacuo. The residue was shaken with 2N aqueous sodium hydroxide solution and extracted with chloroform. The organic layer was dried on anhydrous sodium sulfate/calcium chloride, filtered, acidified with ethanolic hydrogen chloride and stripped in vacuo. After washing with diethyl ether, the crude product was crystallized from ethanol to give 9.5 g of title compound, m.p. 248°–249° C.

Example 18

8-{1-Hydroxy-2-[4-(2-methylphenyl)-1-piperazinyl]-ethyl}-3-methyl-4-oxo-2-phenyl-4H-1-benzopyran hydrochloride This compound was prepared according to Example 17, but starting from the compound prepared in Example 2, rather than that prepared in Example 1. m.p. 257°–258° C. (ethanol).

Example 19

8-{1-Hydroxy-2-[4-(2-ethoxyphenyl)-1-piperazinyl]-ethyl}-3-methyl-4-oxo-2-phenyl-4H-1-benzopyran hydrochloride This compound was prepared according to Example 17, but starting from the compound prepared in Example 3 rather than that prepared in Example 1. m.p. 241°–242° C. (methanol).

Example 20

8-{1-Hydroxy-3-[4-(2-methoxyphenyl)-1-piperazinyl]-propyl}-3-methyl-4-oxo-2-phenyl-4H-1-benzopyran hydrochloride This compound was prepared according to Example 17, but starting from the compound prepared in Example 4 rather than that prepared in Example 1. The crude base was purified by flash chromatography (silica gel, eluant - ethyl acetate: chloroform (4:1). The fractions containing the pure base were pooled, acidified with ethanolic hydrogen chloride and stripped in vacuo. The residue was crystallized from ethanol. m.p. (126) 156°–160° C.

Example 21

8-{1-Hydroxy-4-[4-(2-methoxyphenyl)-1-piperazinyl]-butyl}-3-methyl-4-oxo-2-phenyl-4H-1-benzopyran hydrochloride monohydrate A solution of 3.04 g of Intermediate XXXVIII and 2.45 g of 1-(2-methoxyphenyl)-piperazine in 21 ml of anhydrous dimethylformamide was stirred for 5 hours at ambient temperature. A further 1.22 g of 1-(2-methoxyphenyl)-piperazine was added, and the mixture was stirred for 4 hours, poured into 300 ml of water, and extracted with ethyl acetate. The combined organic extracts were washed with aqueous sodium bicarbonate solution and then with aqueous sodium chloride solution, and evaporated to dryness in vacuo. The residue was purified by flash chromatography on silica gel, eluting with ethyl acetate:methanol (95:5). The collected fractions were stripped on a rotary evaporator, and the residue was dissolved in 0.81M ethanolic hydrogen chloride and stripped again in vacuo. The solid residue was crystallized from water:ethanol (9:1) to give 2.43 g of the title compound, m.p. 144°–146° C.

Example 22

8-{1-Ethoxy-2-[4-(2-methoxyphenyl)-1-piperazinyl]-ethyl}-3-methyl-4-oxo-2-phenyl-4H-1-benzopyran hydrochloride 6 ml of anhydrous dimethylsulfoxide was added to 6.55 g of sodium hydride (50% in mineral oil, repeatedly washed with hexane) under nitrogen. A solution of 3 g of the compound prepared in Example 17 in 50 ml of anhydrous dimethylsulfoxide was added to the mixture at 20°–25° C. After stirring for 1 hour at 20° C., 0.66 g of ethyl bromide was added. The reaction mixture was stirred for an additional 20 minutes at the same temperature and then poured into iced water. The crude product obtained after suction filtration was purified by flash chromatography (silica gel, eluant - chloroform:ethyl acetate (8:2). The fractions containing the pure title compound were pooled, acidified with ethanolic hydrogen chloride, and stripped in vacuo. The residue was crystallized from chloroform:diethyl ether and dried in vacuo at 140° C. to give 1.6 g of the title compound, m.p. (155) 209° C.

Example 23

8-{N-methyl-2-[4-(2-methoxyphenyl)-1-piperazinyl]-ethylaminomethyl}-3-methyl-4-oxo-2-phenyl-4H-1-benzopyran dihydrochloride A mixture of 5.2 g of Intermediate XXVII, 3.1 g of 1-(2-methoxyphenyl)-piperazine and 2.2 g of anhydrous potassium carbonate in 50 ml of dimethylformamide was stirred at 70° C. for 7 hours. After cooling to 20°–25° C., the reaction mixture was poured into 500 ml of water, and extracted with dichloromethane. The organic phase was washed with water and dried on anhydrous sodium sulfate. The solvent was removed in vacuo. The residue was purified by flash chromatography on silica gel, eluting with ethyl acetate:petroleum ether (98:2). The title compound was obtained by salification with ethanolic hydrogen chloride. m.p. 217°–219° C.

Example 24

8-{N-acetyl-2-[4-(2-methoxyphenyl)-1-piperazinyl]-ethylaminomethyl}-3-methyl-4-oxo-2-phenyl-4H-1-benzopyran hydrochloride A mixture of 5 g of Intermediate XXXIII and 5.3 g of 1-(2-methoxyphenyl)-piperazine in 75 ml of dimethylformamide was stirred at 95° C. for 2 hours. After cooling to 20°–25° C., the reaction mixture was poured into 200 ml of water, made alkaline with potassium carbonate and extracted with ethyl acetate. The organic phase was washed with water and dried on anhydrous sodium sulfate. The solvent was removed in vacuo. The residue was purified by flash chromatography on silica gel, eluting with dichloromethane:methanol (100:0.2). Salification of the pure base with ethanolic hydrogen chloride and recrystallization from methanol gave 4.4 g of the title compound, melting at (200) 227°–228° C. and containing one equivalent of methanol.

Example 25

8-[4-(2-Methoxyphenyl)-1-piperazinylacetamidomethyl]-3-methyl-4-oxo-2-phenyl-4H-1-benzopyran hydrochloride A mixture of 3.42 g of Intermediate XXXII, 2.74 g of 1-(2-methoxyphenyl)-piperazine and 0.71 g of anhydrous potassium carbonate in 34 ml of anhydrous dimethylformamide was stirred at 0° C. for 2 hours. The reaction mixture was poured into water and filtered under suction. The resultant solid was purified by flash chromatography on silica gel, eluting with ethyl acetate:petroleum ether (6:4). The collected fractions were evaporated to dryness in vacuo, and the residue was crystallized from ethyl methyl ketone. The base obtained was treated in ethanolic solution with a molar equivalent of aqueous 2.25N hydrochloric acid to give the title compound, m.p. 168°–170° C.

Example 26

8-{N-methyl-[4-(2-methoxyphenyl)-1-piperazinyl]-acetamido-methyl}-3-methyl-4-oxo-2-phenyl-4H-1-benzopyran hydrochloride hydrate A mixture of 5 g of Intermediate XXXI, 2.9 g of 1-(2-methoxyphenyl)-piperazine and 2 g of anhydrous potassium carbonate in 50 ml of dimethylformamide was stirred at 20°–25° C. for 3 hours. The reaction mixture was then poured into 500 ml of water and extracted with dichloromethane. The organic phase was washed with water and dried on anhydrous sodium sulfate. The solvent was removed in vacuo. The residue was purified by flash chromatography on silica gel, eluting with ethyl acetate: petroleum ether (6:4), and crystallized from acetone to give 3.6 g of the base of the title compound, melting at 144°–145° C. The base was dissolved in ethanol, and 8N hydrochloric acid and water were added, yielding the title compound, m.p. 218°–220° C. after drying at 100° C. in vacuo.

Example 27

8-{2-[4-(2-Methoxyphenyl)-1-piperazinyl]-ethoxymethyl}-3-methyl-4-oxo-2-phenyl-4H-1-benzopyran dihydrochloride A mixture of 4 g of Intermediate XVIII, 2.4 g of 1-(2-methoxyphenyl)piperazine, 1.96 g of potassium iodide and 1.65 g of anhydrous potassium carbonate in 40 ml of anhydrous dimethylformamide was stirred at 90° C. for 7 hours. After cooling to ambient temperature, the mixture was poured into water and extracted with dichloromethane. The combined extracts were washed with aqueous sodium chloride solution, dried on anhydrous sodium sulfate and evaporated to dryness in vacuo. The residue was crystallized from ethyl acetate and the collected crystals were dissolved in ethanol and treated with excess ethanolic hydrogen chloride to give 5.21 g of the title compound, m.p. 199°–201° C.

Example 28

8-{2-[2-(2-Ethoxyphenoxy)-ethylamino]-ethoxymethyl}-3-methyl-4-oxo-2-phenyl-4H-1-benzopyran hydrochloride Operating as described in Example 27, but using 2-(2-ethoxyphenoxy)-ethylamine in place of 1-(2-methoxyphenyl)piperazine and including a purification step of flash chromatography on silica gel eluted with ethyl acetate::methanol (97:3), 4.25 g of the title compound was obtained. m.p. 191°–193° C.

Example 29

8-{2-[4-(2-Methoxyphenyl)-1-piperazinyl]-ethylthiomethyl}-3-methyl-4-oxo-2-phenyl-4H-1-benzopyran hydrochloride 2.5 g of potassium carbonate, 2.13 g of potassium iodide and 3.15 g of 1-(2-methoxyphenyl)-piperazine were added to a solution of 5 g of Intermediate XXI in 50 ml of dimethylformamide, and the mixture was stirred at 90° C. for 4.5 hours. After cooling to ambient temperature, the reaction mixture was poured into 450 ml of water and extracted with ethyl acetate. The organic extracts were washed with water, dried on anhydrous sodium sulfate and evaporated to dryness in vacuo. A solution of the residue in acetone was treated with a molar equivalent of 3.8N hydrogen chloride in diethyl ether, filtered and recrystallized from ethanol to yield 6.15 g of the title compound, m.p. (218) 223°–224° C.

Example 30

8-{2-[4-(2-Methoxyphenyl)-1-piperazinyl]-ethylsulfinylmethyl}-3-methyl-4-oxo-2-phenyl-4H-1-benzopyran dihydrochloride hemihydrate The title compound was prepared by the method described in Example 29, using Intermediate XXVI instead of Intermediate XXI and stirring for 2.5 hours rather than for 4.5 hours. After the usual work up, the residue was purified by flash chromatography on silica gel, eluting with ethyl acetate:methanol (97:3). The collected fractions were acidified with excess ethanolic hydrogen chloride, evaporated to dryness in vacuo. The residue was crystallized from ethanol, giving 5.2 g of the title compound, m.p. 170°–172° C. This compound contains 1 equivalent of ethanol.

Example 31

8-{2-[4-(2-Methoxyphenyl)-1-piperazinyl]-ethylsulfonylmethyl}-3-methyl-4-oxo-2-phenyl-4H-1-benzopyran hydrochloride A mixture of 4.5 g of Intermediate XXV, 2.36 g of 1-(2-methoxyphenyl)-piperazine and 0.84 g of potassium carbonate in 45 ml of anhydrous dimethylformamide was stirred at ambient temperature for 2.5 hours. The reaction mixture was poured into 300 ml of water and filtered under suction, washing with water. The solid base was crystallized from ethanol and had a melting point of 143°–146° C. The crystals were dissolved in 1,2-dichloroethane and acidified with ethanolic hydrogen chloride. 4.4 g of the title compound, m.p. 229°–233° C., was obtained by recrystallization from methanol:water (1:3.5).

Example 32

8-{2-[4-(2-Methoxyphenyl)-1-piperazinyl]-ethylamino}-3-methyl-4-oxo-2-phenyl-4H-1-benzopyran dihydrochloride A solution of 3.7 g of Intermediate XXIII in 10 ml of dimethylformamide was added dropwise at 0° C. to a suspension of 0.9 g of sodium hydride (50% in mineral oil) in 9 ml of dimethylformamide. The cooling bath was removed, and after 30 minutes at 20°–25° C. a solution of 4.1 g of 1-(2-chloroethyl)-4-(2-methoxyphenyl)-piperazine in 10 ml of dimethylformamide was added. The mixture was stirred at 90° C. for 5 hours and then cooled to 20°–25° C. A further addition of 0.25 g of sodium hydride (50% in mineral oil) followed by 1.36 g of 1-(2-chloroethyl)-4-(2-methoxyphenyl)-piperazine in 5 ml of dimethylformamide was made. The mixture was stirred at 90° C. for 8 hours and again cooled to 20°–25° C. 200 ml of water was cautiously added, and the mixture was extracted with ethyl acetate. The organic layer was washed with water and dried on anhydrous sodium sulfate. The solvent was evaporated off in vacuo and the residue was purified by flash chromatography on silica gel, eluting with n-hexane:ethyl acetate (3:2). This gave a mixture of the base of the title compound and the corresponding N-trifluoroacetyl compound.

3.8 g of this mixture was dissolved in 35 ml of ethanol and 35 ml of dimethylsulfoxide. To this solution, 0.55 g of sodium borohydride was added portionwise at 20°–25° C. The mixture was stirred for 3 hours at this temperature, and then poured into 200 ml of water and extracted with ethyl acetate. The organic extracts were washed with water, dried on anhydrous sodium sulfate and evaporated to dryness in vacuo. The residue was dissolved in dichloromethane. 2 equivalents of ethanolic hydrogen chloride were added to give the title compound, which was recrystallized from ethanol. Yield 3.8 g, m.p. 231°–234° C.

Example 33

8-{3-[4-(2-Methoxyphenyl)-1-piperazinyl]-propylamino}-3-methyl-4-oxo-2-phenyl-4H-1-benzopyran hydrochloride 2.75-hydrate Using 1-(3-chloropropyl)-4-(2-methoxyphenyl)-piperazine instead of 1-(2-chloroethyl)-4-(2-methoxyphenyl)-piperazine, but otherwise operating as described in Example 32, the title compound was obtained. m.p. 206°–208° C. (10% ethanol).

Example 34

8-{4-[4-(2-Methoxyphenyl)-1-piperazinyl]-butylamino}-3-methyl-4-oxo-2-phenyl-4H-1-benzopyran hydrochloride hemihydrate A mixture of 4.5 g of Intermediate XXXIX, 3.9 g of 8-amino-3-methyl-4-oxo-2-phenyl-4H-1-benzopyran, 8.3 g of sodium triacetoxyborohydride and 3.4 ml of acetic acid in 40 ml of 1,2-dichloroethane was stirred for 6 hours at 20°–25° C. 15 ml of 5% aqueous sodium bicarbonate solution was then added, and the mixture was stirred for 10 minutes. The mixture was then made alkaline by addition of 0.5N aqueous sodium hydroxide solution and extracted with dichloromethane. The organic extracts were washed with water and dried on anhydrous sodium sulfate. The solvent was evaporated off in vacuo and the residue was purified by flash chromatography on silica gel, eluting with ethyl acetate: petroleum ether 9:1. The base obtained was dissolved in dichloromethane and 1 equivalent of ethanolic hydrogen chloride was added. After removing the solvent in vacuo, the residue was crystallized from 50% ethanol to give 1.6 g of the title compound, m.p. (140) 151°–153° C.

Example 35

8-{N-methyl-3-[4-(2-methoxyphenyl)-1-piperazinyl]-propylamino}-3-methyl-4-oxo-2-phenyl-4H-1-benzopyran hydrochloride hemihydrate A mixture of 4 g of the compound prepared in Example 33, in the form of its base, 4.35 ml of 37% aqueous formaldehyde and 1.15 g of sodium cyanoborohydride in 25 ml of acetonitrile was stirred at 20°–25° C., maintaining the pH in the range 5–6 by the addition of acetic acid during the reaction. After 4 hours the solvent was evaporated off in vacuo. 80 ml of ethyl acetate and 200 ml of ice cooled 1N aqueous sodium hydroxide solution were added to the residue. The organic phase was washed with water, dried on anhydrous sodium sulfate and evaporated to dryness in vacuo. The residue was purified by flash chromatography on silica gel, eluting with ethyl acetate:petroleum ether (3:1). The pure base which was obtained was dissolved in diethyl ether. 1 equivalent of ethanolic hydrogen chloride was added and the solvent was removed in vacuo. The residue was crystallized from water to give 2 g of the title compound, m.p. 186°–187° C.

Example 36

8-{N-acetyl-3-[4-(2-methoxyphenyl)-1-piperazinyl]-propylamino}-3-methyl-4-oxo-2-phenyl-4H-1-benzopyran hydrochloride hydrate A mixture of 4.8 g of the compound prepared in Example 33, in the form of its base, 2.8 ml of acetic anhydride and 33 ml of pyridine was stirred at 80° C. for 4 hours. After cooling to 20°–25° C., the reaction mixture was poured into 200 g of iced water containing 40.8 ml of 10N aqueous hydrochloric acid solution and extracted with dichloromethane. The organic extracts were washed with water, dried on anhydrous sodium sulfate and evaporated to dryness in vacuo. The residue was purified by flash chromatography on silica gel, eluting with ethyl acetate:methanol (95:5). The pure base which was obtained was dissolved in dichloromethane. 1 equivalent of ethanolic hydrogen chloride was added and the solvent was removed in vacuo. The residue was crystallized from acetonitrile to give 3 g of the title compound containing 0.33 equivalents of acetonitrile, m.p. 208.5°–210.5° C.

Example 37

8-{3-[4-(2-Methoxyphenyl)-1-piperazinyl]-propionamido}-3-methyl-4-oxo-2-phenyl-4H-1-benzopyran hydrochloride A mixture of 3.97 g of Intermediate X and 3.07 g of 1-(2-methoxyphenyl)-piperazine in 40 ml of dimethylformamide was stirred at 60° C. for 6 hours. The reaction mixture was then cooled to ambient temperature and poured into water. Following. extraction with dichloromethane, the organic phase was washed with water and dried on anhydrous sodium sulfate. The solvent was removed in vacuo. The crude residue was crystallized from ethanol to give the base of the title compound, which was then dissolved in hot ethanol. 1 molar equivalent of 0.81M ethanolic hydrogen chloride was added to the solution. 4 g of the title compound, m.p. 255°–257° C., was obtained.

Example 38

8-{2-[4-(2-Methoxyphenyl)-1-piperazinyl]-ethylureido}-3-methyl-4-oxo-2-phenyl-4H-1-benzopyran methanesulfonate A mixture of 3.34 g of Intermediate XLIV and 7.22 g of 1-(2-methoxyphenyl)-piperazine was stirred at 100° C. for 5 hours. An additional 1.8 g of 1-(2-methoxyphenyl)-piperazine was then added and stirring was continued for a further 2 hours at 100° C. After cooling to ambient temperature, the reaction mixture was poured into water and extracted with ethyl acetate. The organic phase was washed with aqueous sodium hydroxide solution, dried on anhydrous sodium sulfate and evaporated to dryness in vacuo. The crude residue was purified by flash chromatography on silica gel, eluting with ethyl acetate: methanol (98:2). The collected fractions were evaporated to dryness in vacuo and crystallized from water:ethanol (4:6). The crystals were redissolved in dichloromethane and treated with 1 molar equivalent of methanesulfonic acid. The crude methanesulfonate obtained by evaporation in vacuo was crystallized from ethyl acetate:ethanol (1:1) to yield 2.35 g of the title compound, melting at 191°–193° C.

Example 39

8-{2-[4-(2-Methoxyphenyl)-1-piperazinyl]-ethoxy}-3-methyl-4-oxo-2-phenyl-4H-1-benzopyran hydrochloride hydrate A mixture of 6.61 g of the Intermediate XI, 8.34 g of 1-(2-methoxyphenyl)-piperazine and 1.26 g of sodium iodide in 70 ml of dimethylformamide was stirred at 80° C. for 17 hours. After cooling to 20°–25° C., the reaction mixture was poured into 600 ml of water, made alkaline with 5% aqueous sodium bicarbonate solution and extracted with dichloromethane. The organic extracts were washed with aqueous sodium chloride solution, dried on anhydrous sodium sulfate and evaporated to dryness in vacuo. The residue was purified by flash chromatography on silica gel, eluting with a dichloromethane:methanol gradient (99:1, then 98:2). The fractions containing the base of the title compound were pooled, and the solvent was removed in vacuo. The residue was dissolved in ethanol and ethanolic hydrogen chloride was added. The title compound crystallized and was collected by suction filtration. It was recrystallized from 95% ethanol. Yield 6.5 g, m.p. 224°–225° C.

Elemental analysis: Found % : C=66.38, H=6.34, N=5.35, Cl=6.76, $H_2O$=3.35 Calculated %: 66.34, 6.14, 5.33, 6.75, 3.43

NMR Spectrum at 60 MHz ($CDCl_3$-$CD_3OD$) 7.8–7.1 (m,8H) aromatic protons of the benzopyran ring 7.1–6.6 (m,4H) aromatic protons of the 2-methoxyphenyl group 4.8–4.4 (m,2H) $OCH_2$ 4.4–4.1 (m,3H) $H_2O$ and $N^+H$ 3.9–3.0 (m,10H) 5×$CH_2N$ 3.8 (s, 3H) $OCH_3$ 2.1 (s, 3H) $CH_3$ Example 40

8-{3-[4-(2-Methoxyphenyl)-1-piperazinyl]-propoxy}-3-methyl-4-oxo-2-phenyl-4H-1-benzopyran dihydrochloride This compound was prepared by the method described in Example 39, but using Intermediate IX instead of Intermediate XI. Purification by flash chromatography was omitted as unnecessary in this case. m.p. 226°–227° C.

Example 41

8-{4-[4-(2-Methoxyphenyl)-1-piperazinyl]-butoxy}-3-methyl-4-oxo-2-phenyl-4H-1-benzopyran dihydrochloride A mixture of 7.75g of Intermediate XVI, 4.7 g of 1-(2-methoxyphenyl)-piperazine, 3.3 g of potassium iodide and 2.8 g of anhydrous potassium carbonate in 78 ml of dimethylformamide was stirred at 75° C. for 2 hours. After cooling to 20°–25° C., the reaction mixture was poured into 600 ml of water and extracted with dichloromethane. The organic extracts were washed with water and dried on anhydrous sodium sulfate, and the solvent was then evaporated off in vacuo. The residue was purified by column chromatography on silica gel, eluting with ethyl acetate. The pure title compound thus obtained as its base was transformed into its dihydrochloride by treatment with ethanolic hydrogen chloride. After crystallization from ethanol, 6.5 g of title compound was obtained. m.p. 217°–219° C.

Example 42

8-{5-[4-(2-Methoxyphenyl)-1-piperazinyl]-pentyloxy}-3-methyl-4-oxo-2-phenyl-4H-1-benzopyran hydrochloride This compound was prepared by the method described in Example 41, but using Intermediate XVII instead of Intermediate XVI. m.p. 173° C. (ethanol). The corresponding base melts at 117°–118° C. (ethanol).

Example 43

8-{3-[4-(2-Methoxyphenyl)-1-oxo-1-piperazinyl]-propoxy}-3-methyl-4-oxo-2-phenyl-4H-1-benzopyran 1.75-hydrate 2.93 g of magnesium monoperoxyphthalate in 10 ml of water was added dropwise at −15° C. to a solution of 4.34 g of the compound prepared in Example 40 and 0.1 g of benzyl(triethyl) ammonium chloride in 20 ml of dichloroethane and 20 ml of methanol. The mixture was stirred for 2 hours at 0° C. and then warmed to ambient temperature. It was poured into water and made basic by addition of aqueous sodium hydroxide solution. Extraction with dichloromethane gave, after the usual work up, a solid which was purified by flash chromatography, eluting with dichloromethane:methanol (9:1). The collected fractions containing the pure compound were evaporated to dryness in vacuo and the residue was crystallized from acetonitrile to give 0.5 g of the title compound, m.p. 89°–92° C.

Example 44

8-{2-[2-(2,6-Dimethoxyphenoxy)-ethylamino]-ethoxy}-3-methyl-4-oxo-2-phenyl-4H-1-benzopyran hydrochloride A mixture of 4.5 g of Intermediate XII, 3.7 g of triphenyl phosphine and 2.85 g of 2,6-dimethoxyphenoxy-acetaldehyde (prepared as per Nelson, W. L. et al., *J. Med. Chem.* 22: 1125, 1979) in 45 ml of benzene was stirred at 20°–25° C. for 18 hours and at reflux for 5 hours. The solvent was evaporated off in vacuo and the residue was dissolved in 80 ml of anhydrous methanol containing 3Å molecular sieves at 0° C. The mixture was stood for 1 hour at 0° C. and for 1 hour at 20°–25° C., and then poured into iced water and extracted with dichloromethane. The organic extracts were washed with water and dried on anhydrous sodium sulfate. The solvent was removed in vacuo and the residue was purified by flash chromatography on silica gel, eluting with dichloromethane: methanol (49:1). The base obtained was treated with ethanolic hydrogen chloride. After crystallization from ethanol, the title compound was obtained. Yield 40%, m.p. 200°–202° C.

Example 45

8-{2-Hydroxy-3-[4-(2-methoxyphenyl)-1-piperazinyl]-propoxy}-3-methyl-4-oxo-2-phenyl-4H-1-benzopyran hydrochloride A solution of 3.7 g of Intermediate XL and 4.64 g of 1-(2-methoxyphenyl)-piperazine in 40 ml of dimethylformamide was stirred at 80° C. for 3 hours. After cooling to 20°–25° C., the reaction mixture was poured into 400 ml of water and extracted with dichloromethane. The aqueous phase was made alkaline with 1N aqueous sodium hydroxide solution and extracted with ethyl acetate. The combined organic extracts were washed with water and dried on anhydrous sodium sulfate. The solvents were evaporated off in vacuo. The residue was purified by flash chromatography on silica gel, eluting with ethyl acetate. The fractions containing the title compound in the form of its base were pooled, and stripped in vacuo. The residue was dissolved in dichloromethane and one equivalent of ethanolic hydrogen chloride was added. The solvents were removed in vacuo and the residue was crystallized from ethanol. 5 g of the title compound containing one molar equivalent of ethanol were obtained. m.p. (122) 126°–128° C. with decomposition.

Example 46

8-{3-[4-(2-Methoxyphenyl)-1-piperazinyl]-propylthio}-3-methyl-4-oxo-2-phenyl-4H-1-benzopyran A mixture of 4.4 g of Intermediate XXXIV, 2.5 g of 1-(2-methoxyphenyl)-piperazine, 1 g of potassium iodide and 1.8 g of anhydrous potassium carbonate in 40 ml of dimethylformamide was stirred at 100° C. for 3 hours. After cooling to 20°–25° C., the reaction mixture was poured into 350 ml of water and extracted with dichloromethane. The organic extracts were washed with water and dried on anhydrous sodium sulfate, and the solvent was then evaporated off in vacuo. The residue was purified by column chromatography on silica gel, eluting with ethyl acetate: petroleum ether 3:2, and by crystallization from ethanol, yielding 3.9 g of the title compound, m.p. (70) 96°–99° C.

Example 47

8-{3-[4-(2-Methoxyphenyl)-1-piperazinyl]-propylsulfonyl}-3-methyl-4-oxo-2-phenyl-4H-1-benzopyran hydrochloride A solution of 3.8 g of Intermediate XXXV and 4 g of 1-(2-methoxyphenyl)-piperazine in 40 ml of dimethylformamide was heated at 60° C. for 7 hours. After cooling to 20°–25° C., the reaction mixture was poured into 500 ml of water and extracted with dichloromethane. The organic extracts were washed with water and dried on anhydrous sodium sulfate, and the solvent was then evaporated off in vacuo. The residue was purified by flash chromatography on silica gel, eluting with ethyl acetate: petroleum ether (1:1). The base of the title compound was obtained. It was dissolved in ethanol and one equivalent of ethanolic hydrogen chloride was added to give 4.5 g of the title compound, m.p. (215) 226°–228° C.

Example 48

8-{2-[4-(2-Methoxyphenyl)-1-piperazinyl]-ethylsulfamyl}-3-methyl-4-oxo-2-phenyl-4H-1-benzopyran hydrochloride A solution of 4.5 g of Intermediate XLII and 3.8 g of 1-(2-methoxyphenyl)-piperazine in 40 ml of dimethylformamide was heated at 70° C. for 7 hours. After cooling to 20°–25° C., the reaction mixture was poured into 150 ml of water and extracted with dichloromethane. The organic solution was washed with water and dried on anhydrous sodium sulfate, and the solvent was then evaporated off in vacuo. The residue was purified by flash chromatography on silica gel, eluting with ethyl acetate: petroleum ether (3:7), and the title compound was obtained by salification with ethanolic hydrogen chloride. Yield 2.9 g, m.p. 236°–238° C.

Example 49

8-{N-methyl-2-[4-(2-methoxyphenyl)-1-piperazinyl]-ethylsulfamyl}-3-methyl-4-oxo-2-phenyl-4H-1-benzopyran hydrochloride The title compound was obtained by the method described in Example 48, but using Intermediate XLI instead of Intermediate XLII. m.p. 194°–198° C. (ethanol).

Example 50

8-{N-aminocarbonyl-3-[4-(2-methoxyphenyl)-1-piperazinyl]-propylamino}-3-methyl-4-oxo-2-phenyl-4H-1-benzopyran methanesulfonate hemihydrate A mixture of 4.06 g of the compound of Example 33 and 1.5 g of potassium cyanate in 42 ml of glacial acetic acid is stirred at 50° C. for 4 hours. The reaction mixture is poured into iced water and made alkaline. The precipitate is collected by suction filtration, dried and purified by flash chromatography using a silica gel column, eluting with ethyl acetate:methanol (98:2). The fractions, containing the title product as a base, are evaporated to dryness in vacuo and an equivalent of methane-sulfonic acid is added to the residue dissolved in 30 ml of dichloromethane. The solvent is evaporated off in vacuo and the residue is crystallized from ethanol to give 3.1 g of the title compound (m.p. 157°–160° C., with decomposition). This compound contains one molar equivalent of ethanol.

Example 51

8-{4-[4-(2-Methoxyphenyl)-1-piperazinyl]-1-oxobutyl}-3-methyl-4-oxo-2-phenyl-4H-1-benzopyran methanesulfonate A solution of 1.33 ml of anhydrous dimethylsulfoxide in 9 ml of dichloromethane is added at −70° C. to a solution of 0.74 ml of oxalyl chloride in 6 ml of dichloromethane. After stirring at −70° C. for 15 minutes, a solution of 2.8 g of the compound of the Example 21 (as a base) in 14 ml of dichloromethane is added. After 15 minutes at the same temperature, 4.7 ml of anhydrous triethylamine is added and the temperature is raised to −30° C. over a period of 30 minutes. Stirring is continued at −30° C. for another 30 minutes. After letting the temperature rise to 0° C., the mixture is diluted with 120 ml of water and extracted with dichloromethane. The organic phase is washed with water, dried on anhydrous sodium sulphate and evaporated to dryness in vacuo. The residue is purified by flash chromatography in a silica gel column, eluting with ethyl acetate:dichloromethane (9:1). The fractions, containing the title product, are evaporated to dryness in vacuo and one equivalent of methanesulphonic acid is added to the residue dissolved in 30 ml of dichloromethane. The solvent is evaporated off in vacuo and the residue is crystallized from ethanol to give 2.9 g of the title compound (m.p. 194°–195° C.).

Example 52

8-{3-[2-(1,4-Benzodioxanyl)methylamino]propylcarbamoyl}-3-methyl-4-oxo-2-phenyl-4H-1-benzopyran methanesulfonate A mixture of 5.56 g of the Intermediate XLIII, as a base, 4.58 g of 2-(4-toluenesulfonyloxymethyl)-1,4-benzodioxane and 1.9 g of anhydrous potassium carbonate in 80 ml of anhydrous dimethylformamide is stirred at 110° C. for 5 hours. The reaction mixture is cooled to ambient temperature, poured into water and extracted with dichloromethane. The organic phase is washed with water, dried on anhydrous sodium sulphate, filtered and evaporated to dryness in vacuo. The residue is purified by flash chromatography using a silica gel column, eluting with ethyl acetate:methanol (95:5). The fractions containing the title product as a base are evaporated to dryness in vacuo and one equivalent of methanesulfonic acid dissolved in ethyl acetate is added to the residue dissolved in ethanol. The crystallized product is filtered and recrystallized from ethanol to give 2.4 g of the title compound (m.p. 172°–174° C.).

Example 53

8-{4-[4-(2-Methoxyphenyl)-1-piperazinyl]butyl}-3-methyl-4-oxo-2-phenyl-4H-1-benzopyran methanesulfonate A solution of 2.8 g of the Intermediate XLVI and 0.13 g of p-toluenesulfonic acid in 150 ml of methanol is refluxed for 5 hours. After cooling to 20°–25° C., 0.8 g of anhydrous potassium carbonate is added and stirring is continued for 3 hours. After filtration, the reaction mixture is evaporated to dryness in vacuo to give 2.5 g of 8-(4,4-dimethoxybutyl)-3-methyl-4-oxo-2-phenyl-4H-1-benzopyran.

NMR CDCl$_3$ ($\delta$) 1.6–1.9 (4H, m, CH$\underline{CH_2CH_2}$CH) 2.2 (3H, s, flavone CH$_3$) 2.9 (2H, t, Fl'-CH$_2$) 3.3 (6H, s, 2×OCH$_3$) 4.4 (1H, t, $\underline{CH}$(OCH$_3$)$_2$) 7.3 (1H, dd, flavone CH in 6) 7.5–7.8 (6H, m, flavone CH in 7, and 5×phenyl CH) 8.1 (1H, dd, flavone CH in 5)

A solution of 2.5 g of the above compound in 10 ml of water and 30 ml of acetic acid are heated at 50° C. for 2.5 hours. The reaction mixture is cooled to ambient temperature, diluted with iced water, basified with aqueous sodium carbonate, and extracted with chloroform. The organic phase is dried on anhydrous sodium sulphate, filtered and evaporated to dryness in vacuo. The residue is purified by flash chromatography on silica gel, eluting with petroleum ether:ethyl acetate (3:1). 2.1 g of 8-(4-oxobutyl)-3-methyl-4-oxo-2-phenyl-4H-1-benzopyran is obtained (>75% yield) and is used with no further purification in the next step.

NMR CDCl$_3$ ($\delta$) 1.9–2.1 (2H, dd, CH$_2$$\underline{CH_2}$CH$_2$CHO) 2.2 (3H, s, flavone CH$_3$) 2.5 (2H, t, $\underline{CH_2}$CHO) 2.9 (2H, t, Fl'-CH$_2$) 7.3 (1H, dd, flavone CH in 6) 7.5–7.7 (6H, m, flavone CH in 7, and 5×phenyl CH) 8.1 (1H, dd, flavone CH in 5) 9.7 (1H, s, CHO)

2.3 ml of 6N hydrochloric acid in ethanol, a solution of 2.1 g of the above compound in 40 ml of methanol and 0.45 g of sodium cyanoborohydride are added in succession to a solution of 8 g of 1-(2-methoxyphenyl)piperazine in 30 ml of methanol. After stirring the reaction at ambient temperature for 24 hours, the mixture is poured into 500 ml of iced water and extracted with dichloromethane. The organic phase is washed with water, dried on anhydrous sodium sulphate and evaporated to dryness in vacuo. The residue is purified by flash chromatography using a silica gel column, eluting with ethyl acetate:petroleum ether (9:1). The fractions, containing the title product as a base, are evaporated to dryness in vacuo and an equivalent of methanesulphonic acid is added to the residue dissolved in 30 ml of dichloromethane. The solvent is evaporated off in vacuo and the residue is crystallized from acetone to give 2.35 g of the title compound (m.p. 141°–143° C.).

Example 54

8-[3-(4-Phenyl-1-piperidinyl)propylcarbamoyl]-3-methyl-4-oxo-2-phenyl-4H-1-benzopyran methanesulfonate This compound is prepared by the method described in Example 11, using 4-phenylpiperidine instead of 1-(2-methoxyphenyl)piperazine and conducting the reaction for 1 hour instead of 5 hours. Purification is carried out by flash chromatography using a silica gel column, eluting with dichloromethane:methanol (100:5). m.p. 157°–159° C. (ethyl acetate). The respective base melts at (127) 147°–149° C. (ethanol).

Example 55

8-[3-(4,4-Diphenyl-1-piperidinyl)propylcarbamoyl]-3-methyl-4-oxo-2-phenyl-4H-1-benzopyran methanesulfonate This compound is prepared by the method described in Example 11, using 4,4-diphenylpiperidine instead of 1-(2-methoxyphenyl)piperazine and conducting the reaction for 2 hours instead of 5 hours. m.p. 221°–223° C. (ethyl acetate).

Example 56

8-{3-[4-(4-Fluorobenzoyl)-1-piperidinyl]propylcarbamoyl}-3-methyl-4-oxo-2-phenyl-4H-1-benzopyran This compound is prepared by the method described in Example 11, using 4-(4-fluorobenzoyl)piperidine instead of 1-(2methoxyphenyl)piperazine and conducting the reaction for 30 minutes instead of 5 hours. Purification is carried out by flash chromatography using a silica gel column, eluting with a dichloromethane:5N ammonia in methanol gradient (100:1 to 100:20). m.p. 181°–183° C. (ethanol).

Example 57

8-{3-[4-(2-oxo-1-Benzimidazolinyl)-1-piperidinyl]-propylcarbamoyl}-3-methyl-4-oxo-2-phenyl-4H-1-benzopyran This compound is prepared by the method described in Example 11, using 4-(2-oxo-1-benzimidazolinyl) piperidine instead of 1-(2-methoxyphenyl)piperazine. Purification is carried out by flash chromatography using a silica gel column, eluting with chloroform: 5N ammonia in methanol (100:3). m.p. 238°–241° C. (ethanol).

Example 58

8-{-[4(2-Pyrimidinyl)-1-piperazinyl]propylcarbamoyl}-3-methyl-4-oxo-2-phenyl-4H-1-benzopyran methanesulfonate This compound is prepared by the method described in Example 11, using 1-(2-pyrimidinyl)piperazine instead of 1-(2-methoxyphenyl)piperazine and conducting the reaction for 2 hours. The product is purified by flash chromatography using a silica gel column, eluting with chloroform:methanol (100:3). The desired fractions are dissolved in dichloromethane and an equivalent of methanesulfonic acid is added to the solution. After evaporation of the solvent in vacuo, the residue is boiled for 1 hour with ethyl acetate and then collected by filtration, m.p. 209°–210° C. The product so obtained contains 0.2 equivalents of ethyl acetate and 0.1 equivalents of water. The respective base melts at 178°–180° C. (ethanol).

Example 59

8-{3-[4-(2-Hydroxyphenyl)-1-piperazinyl]propyl carbamoyl}-3-methyl-4-oxo-2-phenyl-4H-1-benzopyran Operating as described in Example 11, but using 1-(2-hydroxyphenyl)-piperazine instead of 1-(2-methoxyphenyl)piperazine, heating for 1.5 hours instead of 5 hours, and using a dichloromethane - methanol gradient (100:3 to 100:10) as eluant for column chromatography, the title compound is obtained. m.p. 118°–120° C. (ethanol 95%).

Example 60

8-{4-[4-(2-Methoxyphenyl)-1-piperazinyl]butylcarbamoyl}-3-methyl-4-oxo-2-phenyl-4H-1-benzopyran methanesulfonate This compound was prepared by the method used in Example 12, but using 4-[4-(2-methoxyphenyl)-1-piperazinyl]butylamine instead of 3-[4-(2-methoxyphenyl)-1-piperazinyl]propylamine. The reaction mixture was stirred at room temperature for 22 hours, diluted with water and filtered by suction, washing the insoluble solid with water. The crude residue was dried and purified by column chromatography on silica gel, eluting with ethyl acetate - methanol (9:1). The fractions containing the pure product as a base were collected, evaporated to dryness in vacuo and dissolved in dichloromethane. Methanesulfonic acid was added to the solution and the salt was precipitated by adding two volumes' of ethyl acetate, filtered and recrystallized from ethanol to give the title compound, m.p. 230°–232° C. This product was showed to contain 0.3 molar equivalent of ethanol.

Example 61

8-{3-[4-(2-Methoxyphenyl)-1-piperazinyl]propylsulfamyl}-3-methyl-4-oxo-2-phenyl-4H-1-benzopyran methanesulfonate This compound was obtained operating as described in Example 12 but using Intermediate VIII instead of 8-chlorocarbonyl-3-methyl-4-oxo-2-phenyl-4H-1-benzopyran and stirring for 24 hours instead of 2.5 hours. The crude was purified by column chromatography on silica gel, eluting with ethyl acetate - methanol (98.5:1.5). The collected fractions containing the pure product as a base, were evaporated to dryness in vacuo and dissolved in dichloromethane. Methanesulfonic acid was added to the solution and the solvent was removed by evaporation in vacuo. The crude salt was crystallized from ethanol to give the title compound, m.p. (196) 198°–200° C.

Example 62

8-{3-[N-methyl-2-(2-methoxyphenoxy)-ethylamino]propylcarbamoyl}-3-methyl-4-oxo-2-phenyl-4H-1-benzopyran hydrochloride A solution of 10.5 ml of formaldehyde 40% in water was added to a suspension of 6.66 g of the compound prepared in Example 14 in 55 ml of acetonitrile and 20 ml of water. After stirring for 15 minutes at room temperature, 2.70 g of sodium cyanoborohydride (95%) was added to the red solution and after an additional 15 minutes in the same conditions, 1.38 ml of acetic acid was added. After stirring for 3 hours, the solvents are removed in vacuo and the residue was rinsed with 250 ml of water and 250 ml of chloroform. After addition of 3N aqueous sodium hydroxide solution, the organic phase was separated off and the aqueous phase was extracted twice with chloroform. The solvent of the collected organic phases was evaporated in vacuo and the residue was purified by flash chromatography on silica gel, eluting with a chloroform: 5.2N methanolic ammonia gradient (100:0.5 to 100:2). The Collected fractions containing the pure title compound as a base were evaporated to dryness in vacuo and the residue was dissolved in hot ethanol. The solution was acidified with ethanolic hydrogen chloride and, after evaporation of the solvent in vacuo, the residue was rinsed with diethyl ether and stirred at room temperature. The crude product was collected by filtration and crystallized from acetonitrile to give 3.1 g of the title compound, m.p. 146°–148° C.

Example 63

8-{N-methyl-3-[4-(2-methoxyphenyl)-1-piperazinyl)propionamido}-3-methyl-4-oxo-2-phenyl-4H-1-benzopyran methanesulfonate Operating as described in Example 37, but using Intermediate L instead of Intermediate X and stirring at 90° C. for 4 hours instead of 60° C. for 6 hours, the title compound was obtained as a crude base. After purification by column chromatography on silica gel, eluting with ethyl acetate-methanol (95:5), a crude methanesulfonate was obtained as described in Example 61 and crystallized from acetone to give the title compound, m.p. 200°–202° C.

Example 64

8-{3-[4-(2-Methoxyphenyl)-1-piperazinyl]propylcarbamoyl}-3-phenyl-4-oxo-4H-1-benzopyran dimethanesulfonate The title compound was prepared operating as described in Example 12, but using Intermediate LVI instead of 8-chlorocarbonyl-3-methyl-4-oxo-2-phenyl-4H-1-benzopyran and stirring for 24 hours instead of 2.5 hours. The crude was purified by column chromatography, eluting with ethyl acetate-methanol 92:8, and the pure base, obtained by evaporation in vacuo of the collected fractions, was dissolved in dichloromethane and added with two equivalents of methanesulfonic acid. The crude dimethanesulfonate, obtained after evaporation of the solvent, was recrystallized from acetone, m.p. (153–156) 200° C.

Example 65

8-{3-[2-(3,4-Dihydro-1, (2H)-naphthalenonyl)methylaminolpropyl-carbamoyl}-3-methyl-4-oxo-2-phenyl-4H-1-benzopyran methanesulfonate A mixture of 6 g of Intermediate XLIII, 2.4 g of 2-methylene-α-tetralone [prepared as described in Org. Synth., 60, 88 (1981)] and 3.14 ml of triethylamine in 48 ml of anhydrous dimethylformamide was stirred at room temperature for 6 hours, then at 50° C. for additional 1 hour. The reaction mixture was diluted with water and extracted with dichloromethane. The organic layers were washed with water, dried on anhydrous sodium sulfate and evaporated to dryness in vacuo. The crude residue was purified twice by column chromatography eluting firstly with dichloromethane - methanol (95:5) and then with dichloromethane methanol - 5.8N methanolic ammonia (98:2:0.2), to give 1.74 g of the title compound as a base. The base was converted into the methanesulfonate by the procedure described in Example 61. The salt was recrystallized first from acetone and then from acetonitrile to give the title compound, m.p. (69) 157°–159° C.

Example 66

8-{2-[4-(2-Methoxyphenyl)-1-piperazinyl]ethoxycarbonylmethyl}-3-methyl-4-oxo-2-phenyl-4H-1-benzopyran dihydrochloride The title compound was prepared by the method described in Example 5, but using Intermediate XLVII in place of 8-carboxy-3-methyl-4-oxo-2-phenyl-4H-1-benzopyran and 1-(2-chloroethyl)-4-(2-methoxyphenyl)-piperazine instead of 1-(3-chloropropyl)-4-(2-methoxyphenyl)piperazine. m.p. 193°–196° C. from ethanol/diethyl ether.

Example 67

8-{4-[4-(2-Methoxyphenyl)-1-piperazinyl]butylsulfamyl}-3-methyl-4-oxo-2-phenyl-4H-1-benzopyran dimethanesulfonate The title compound was prepared as described in Example 61 but using 4-[4-(2-methoxyphenyl)-1-piperazinyl]butylamine instead of 3-[4-(2-methoxyphenyl)-1-piperazinyl] propylamine. The crude dimethanesulfonate was crystallized first from acetonitrile and then from ethanol, m.p. 172°–174° C.

Example 68

8-{N,2-tetrahydropyranyloxy-3-[4-(2-methoxyphenyl)-1-piperazinyl]propylcarbamoyl}-3-methyl-4-oxo-2-phenyl-4H-1-benzopyran methanesulfonate hemihydrate A solution of 3.6 g of 1-(3-chloropropyl)-4-(2-methoxyphenyl)piperazine in 30 ml of anhydrous dimethylformamide was added dropwise, under stirring at 0° C., to a mixture of 3.92 g of 0,2-tetrahydropyranyl hydroxylamine [prepared as described by R. N. Watrener et al., *Angewandte Chem. Int. Ed.*, 5, 511 (1966)] and 9.2 g of anhydrous potassium carbonate in 100 ml of DMF. Stirring at 0° C. was continued for 2 hours, and then for 12 hours at 110° C. The reaction mixture was cooled to room temperature and dimethylformamide removed by distillation in vacuo. The residue was rinsed with water and extracted with ethyl acetate. The combined organic layers were washed with water, dried on anhydrous sodium sulfate and the solvent was evaporated to dryness in vacuo to give 4.39 g of 1-[3-(2-tetrahydropyranyloxyamino)propyl]-4-(2-methoxyphenyl)piperazine.

1H-NMR (CDCl3; (δ)) 6.50–6.75 (m; 4H) aromatic protons 5.20 (bs; 1H) NH 4.60 (m; 1H) O—CH—O 3.30–4.00 (m; 5H) OCH$_3$ and tetrahydropyran CH$_2$O 2.80–3.20 (m; 6H) piperazine 2×CH$_2$ alkyl chain CH$_2$N 2.20–2.80 (m; 6H) piperazine 2×CH$_2$, alkyl chain CH$_2$N 1.30–2.00 (m; 8H) tetrahydropyran 3×CH$_2$, alkyl chain C–CH$_2$C A solution of 2.79 g of 8-chlorocarbonyl-3-methyl-4-oxo-2-phenyl-4H-1-benzopyran in 47 ml of chloroform was added dropwise at room temperature to a mixture of 3.26 g of the above-described Intermediate and 1.42 g of potassium carbonate in 47 ml of chloroform. The reaction mixture was stirred for 3 hours, then diluted with 75 ml of chloroform and washed three times with 1M aqueous sodium hydroxide solution; the organic layer was washed with water, dried on anhydrous sodium sulfate and evaporated to dryness in vacuo. The crude residue was purified by column chromatography on silica gel eluting with ethyl acetate - methanol (98:2). The collected fractions were evaporated to dryness in vacuo to give 2.99 g of pure title compound as a base, which was dissolved in dichloromethane. Methanesulfonic acid was added to the solution and the solvent was removed by evaporation in vacuo. The crude salt was crystallized from ethyl acetate to yield the title compound, m.p. 159°–160° C.

Example 69

8-{4-[4-(2-Methoxyphenyl)-1-piperazinyl]butyramido}-3-methyl-4-oxo-2-phenyl-4H-1-benzopyran methanesulfonate hemihydrate The title compound was prepared operating as described in Example 38, but using Intermediate XLVIII instead of Intermediate XLIV and stirring 1 hour at 70° C. and 2 hours at 130° C. instead of 7 hours at 100° C. After the usual workup, the crude residue was purified by column chromatography on silica-gel eluting with ethyl acetate - methanol (95:5). The fractions containing the pure title compound as a base were collected and evaporated to dryness in vacuo. The residue was dissolved in methylene chloride and one equivalent of methanesulfonic acid was added to the solution. After evaporation of the solvent to dryness in vacuo, the crude salt was crystallized from acetone, m.p. 175°–176° C.

Example 70

E-8-{2-[4-(2-methoxyphenyl)-1-piperazinyl]ethoxyaminomethyl}-3-methyl-4-oxo-2-phenyl-4H-1-benzopyran A solution of 5.4 g of 8-formyl-3-methyl-4-oxo-2-phenyl-4H-1-benzopyran and 5.13 g of Intermediate LII in 10 ml of chloroform, containing molecular sieves 3A, was stirred at reflux for 6 hours. Molecular sieves were removed by filtration and the solvent evaporated to dryness in vacuo. The crude product was purified by column chromatography on silica gel, eluting with ethyl acetate - petroleum ether (7:3); two groups of fractions were collected and the solvent evaporated in vacuo. The first eluted group of fractions (less polar) containing almost pure title compound; the second group (more polar) was a 1:1 mixture of the E and Z diastereomers, as determined as by 1H-NMR at 200 MHz..

1H-NMR (CDCl3, (δ)) 8.75 (dd, 0.5H) benzopyran CH in 7 (Z) 8.65 (s, 0.4H) iminic CH (E) 8.30 (dd, 1H) benzopyran CH in 5 (E+Z) 8.15 (dd, 0.5H) benzopyran CH in 7 (E) 8.00 (s, 0.5H) iminic CH (Z) 7.60–7.75 (m, 2H) phenyl CH in 2' and 6' (E+Z) 7.50–7.60 (m, 3H) phenyl CH in 3', 4' and 5' (E+Z) 7.45 ( dd, 0.5H) benzopyran CH in 6 (Z) 7.41 (dd, 0.5H) benzopyran CH in 6 (E) 6.70–7.10 (m, 4H) phenyl protons (E+Z) 4.41 (t, 2H) CH$_2$O (E+Z) 3.86 (s, 3H) CH$_3$O (E+Z) 3.05–3.20 (m, 4H) piperazine 2×CH$_2$ (E+Z) 2.70–2.90 (m, 6H) piperazine 2×CH$_2$ and CH$_2$N (E+Z) 2.20 (s, 1.5H) benzopyran CH$_3$ in 3 (Z) 2.18 (s, 1.5H) benzopyran CH$_3$ in 3 (E)

The E diastereoisomer was crystallized from ethanol-water 2:1 to give 2.5 g of pure title compound, m.p. 107°–109° C.

Example 71

8-{N-hydroxy-3-[4-(2-methoxyphenyl)-1-piperazinyl]-propyl-carbamoyl}-3-methyl-4-oxo-2-phenyl-4H-1-benzopyran methanesulfonate×0.25 H$_2$O A solution of 2.04 g of compound of Example 68 as a base in 104 ml of 1.6N ethanolic hydrochloric acid was stirred for 12 hours at room temperature. Ethanol was removed by evaporation in vacuo and the residue was rinsed with 1N aqueous sodium hydroxide solution and dichloromethane. The organic layer was collected, washed with water, dried on anhydrous sodium sulfate and evaporated to dryness in vacuo. One molar equivalent of methanesulfonic acid was added to a solution of the residue in dichloromethane. The solvent was removed and the crude methanesulfonate crystallized from acetone to give 1.02 g of the title compound, m.p. 211°–213° C. The product contained 0.25 mole of water.

Example 72

E-8-{2-[2-[4-(2-methoxyphenyl)-1-piperazinyl]ethylcarbamoyl}-ethenyl}-3-methyl-4-oxo-2-phenyl-4H-1-benzopyran methanesulfonate×1.2 H$_2$O The title compound was obtained operating as described in Example 61 but using Intermediate IV instead of Intermediate VIII and 2-[4-(2-methoxyphenyl)-1-piperazinyl] ethylamine instead of the corresponding propylamine, in 1,1,2,2,-tetrachloroethylene as solvent. At the end, the reaction mixture was diluted with water and chloroform and washed with 1N aqueous sodium hydroxide solution, then with water. To the organic layer, after drying on anhydrous sodium sulfate, was added methanesulfonic acid and the solvents were evaporated to dryness in vacuo. The crude product was crystallized twice from isopropanol to give the title compound containing 1.2 molar equivalent of water (m.p. 124°–127° C.).

Example 73

8-{4-[4-(2-Methoxyphenyl)-1-piperazinyl]butylsulfinyl}-3-methyl-4-oxo-2-phenyl-4H-1-benzopyran methanesulfonate The title compound was prepared according to Example 38, but using Intermediate LIV instead of Intermediate XLIV, stirring at 70° C. for 3 hours and again at 90° C. for 3 hours after adding catalytic quantity of potassium iodide (0.01 equivalents). Purification by column chromatography on silica gel, eluting with ethyl acetate - methanol (9:1), gave the title compound as base. To the crude base, dissolved in dichloromethane, was added one molar equivalent of methanesulfonic acid. After removal of the solvent by evaporation in vacuo, the resulting saint was crystallized from acetone to give the title compound (m.p. 183°–184° C.).

Example 74

8-{3-[3-(2-Methoxyphenoxy)propylamino]propylcarbamoyl}-3-methyl-4-oxo-2-phenyl-4H-1-benzopyran methanesulfonate hemihydrate The title compound was prepared according to the method described in Example 76 but using 3-(2-methoxyphenoxy)propyl chloride (prepared as described in B. Willhalm, *Tetrahedron*, 20, 1185, (1964)) instead of 2-(2,6-dimethoxyphenoxy) ethyl bromide. The residue from dichloromethane extraction was purified by column chromatography on silica gel eluting with dichloromethane-methanol-5N methanolic ammonia (9:1:0.3); the pure base was converted into the methanesulfonate, which was crystallized twice from ethyl acetate-acetonitrile (9:1) to give the title compound, melting at (60) 87°–90° C.

Example 75

3-Methyl-8-{3-[2-(2-methylthiophenoxy)ethylamino]propyl carbamoyl}-4-oxo-2-phenyl-4H-1-benzopyran methanesulfonate 0.75 $H_2O$ 1.85 g of 95% sodium borohydride was added to a solution of 7 g of Intermediate LIX in 70 ml of methanol stirred at 0° C. After 1 hour stirring at the same temperature, the solvent was removed by evaporation in vacuo; the residue was diluted with water and 2N aqueous hydrochloric acid solution and extracted with ethyl acetate. The organic layer was washed with water, dried on sodium sulfate and evaporated to dryness in vacuo, giving 6.6 g of pure 2-(2-methylthiophenoxy)ethanol as an oil. 8.57 g of p-toluenesulfonyl chloride was added portionwise to a solution of the above Intermediate in 35 ml of pyridine stirred at 0° C.

After 14 hours stirring at room temperature, the reaction mixture was poured into cold 2N aqueous hydrochloric acid solution and extracted with dichloromethane; the organic layer was washed twice with water, dried on sodium sulfate and evaporated to dryness in vacuo yielding 7.8 g of a 3:1 mixture of 2-(2-methylthiophenoxy)ethyl p-toluenesulfonate and 1-chloro-2-(2-methylthiophenoxy)ethane (assessed by NMR) as a low melting solid which was used without further purification.

A homogeneous mixture of 3.3 g of the above mixture and 8 g of the Intermediate XLIII was kept in an oil bath at 140° C. for 20 minutes. After this period the melted mass was cooled to room temperature and solidified. The solid residue was rinsed with dichloromethane and 4N aqueous sodium hydroxide solution; the organic layer was washed with water, dried on sodium sulfate and evaporated to dryness in vacuo.

The crude was purified by column chromatography on silica gel eluting with dichloromethane-methanol (9:1) giving 2.07 g of the title compound as a base. This was converted by the usual method into a crude methanesulfonate, which was crystallized firstly from acetone, then from acetonitrile and melted at 143°–146° C.

Example 76

8-{3-[2-(2,6-Dimethoxyphenoxy)ethylamino]propylcarbamoyl}-3-methyl-4-oxo-2-phenyl-4H-1-benzopyran hydrochloride A homogeneous mixture of 3.3 g of 2-(2,6-dimethoxyphenoxy)ethyl bromide (prepared as described in J. Augstein et al., *J. Med. Chem.*, 8, 356 (1965)) and 8.4 g of Intermediate XLIII was heated in an oil bath at 150° C. for 10 minutes.

The melted mass was cooled to room temperature and solidified; the solid residue was rinsed with ethyl acetate and 2N sodium hydroxide; the organic layer was washed with water, dried on sodium sulfate and evaporated to dryness in vacuo. The oily residue was purified twice by column chromatography on silica gel eluting firstly with ethyl acetate-methanol-5N methanolic ammonia (97:3:0.3) then with dichloromethane-methanoltriethylamine (90:10:0.3) yielding 3.3 g of pure title compound. The crude hydrochloride obtained by the usual method, was crystallized from acetone followed by acetonitrile (m.p. 179°–181° C.).

Example 77

8-{3-[4-(5-Chloro-2-methoxyphenyl)-1-piperazinyl]propylcarbamoyl}-3-methyl-4-oxo-2-phenyl-4H-1-benzopyran This compound was prepared by the method described in Example 11, but using 1-(5-chloro-2-methoxyphenyl)-piperazine instead of 1-(2-methoxyphenyl)piperazine and carrying out the reaction for 6 hours instead of 5 hours. Purification was carried out by flash chromatography on silica gel, eluting with chloroform: 5N ammonia in methanol (100:1). The title compound melted at 163°–166° C. after crystallization from 95% ethanol.

Example 78

(E)-8-{4-[4-(2-Methoxyphenyl)-1-piperazinyl]-1-butenyl}-3-methyl-4-oxo-2-phenyl-4H-1-benzopyran 33.4 ml of a 1 molar solution of lithium bis(trimethylsilyl)amide in anhydrous tetrahydrofuran was added dropwise during 15 minutes to a suspension of 6.4 g of 3-hydroxypropyltriphenylphosphonium bromide in 60 ml of anhydrous tetrahydrofuran cooled to −15° C.

Thereafter, a solution of 4 g of 8-formyl-3-methyl-4-oxo-2-phenyl-4H-1-benzopyran in 40 ml of tetrahydrofuran was added dropwise. The reaction mixture was stirred at 0° C. for 0.5 hour, then at room temperature for 1.5 hours.

Quenching with methanol, followed by evaporation to dryness in vacuo of the solvents gave a residue which was purified by column chromatography on silica gel using a mixture of ethyl acetate-petroleum ether (6:4). The collected fractions were evaporated in vacuo giving 4.17 g of 8-(4-hydroxy-1-butenyl)-3-methyl-4-oxo-2-phenyl-4H-1-benzopyran as a E-Z diastereomers mixture having a 3.5:1 ratio, determined by 1H-NMR spectroscopy at 200 MHZ.

1H-NMR (CDCl$_3$, (δ)) 8.10–8.20 (d,1H) benzopyran CH in 5 (E+Z) 7.30–7.80 (m,7H) other aromatics (E+Z) 6.80; 7.00 (2d, 1H) aryl—CH=(E+Z) 6.41 (dt,0.78H) CH—CH$_2$ (E) 5.90 (dt,0.22H) CH—CH$_2$ (Z) 3.60–3.80 (m,2H) CH$_2$O (E+Z) 2.45–2.60 (m,2H) CH—CH$_2$ (E+Z) 2.18 (s,3H) benzopyran CH$_3$ in 3 (E+Z) 1.60–1.90 (sa,1H) OH (E+Z)

1.65 g of p-toluenesulfonyl chloride was added to a solution of 2.2 g of the above mixture in 24 ml of anhydrous pyridine stirred at 0° C. Stirring was continued for 48 hours at the same temperature, then the reaction mixture was poured into cold 1N aqueous hydrochloric acid solution and filtered by suction. The gummy solid was washed with water and rinsed with dichloromethane. The solution was dried on sodium sulfate and evaporated to dryness in vacuo to give 2.30 g of (E,Z)-4-{8-[3-methyl-4-oxo-2-phenyl-4H-1-benzopyranyl}-3-butenyl p-toluenesulfonate having the same diastereoisomer composition as the above Intermediate.

A solution of 2.85 g of the p-toluenesulfonic acid ester above and of 2.98 g of 1-(2-methoxyphenyl)piperazine in anhydrous dimethylformamide was stirred at room temperature for 48 hours.

After this period, the mixture was poured into 250 ml of water and extracted with ethyl acetate.

The organic layer was washed with water, dried on sodium sulfate and evaporated to dryness in vacuo giving a residue which was purified by column chromatography on silica gel eluting with ethyl acetate-petroleum ether 6:4. The collected fractions were evaporated to dryness in vacuo and the crude was crystallized from 70% ethanol yielding 1.48 g of the title compound that melted at 119°–121° C.

1H-NMR spectrum at 200 MHz (CDCl$_3$, (δ)) 8.14 (dd, 1H) benzopyran CH in 5 7.85 (dd,1H) benzopyran CH in 7 7.41–7.70 (m,5H) phenyl CHs 7.34 (dd,1H) benzopyran CH in 6 6.70–7.10 (m,5H) aryl - CH= and methoxyphenyl CHs 6.30–6.50 (dt, 1H, J$_{trans}$=16.5 Hz) C$\underline{H}$-CH$_2$ 3.86 (s,3H) CH$_3$O 3.00–3.15 (m,4H) 2 piperazine CH$_2$ 2.50°–2.80 (m,8H) 2 piperazine CH$_2$, CHC$\underline{H_2}$CH$_2$N 2.18 (s,3H) benzopyran CH$_3$ in 3

Example 79

(E)-8-{2-[2-[4-(2-methoxyphenyl)-1-piperazinyl]ethoxycarbonyl]ethenyl}-3-methyl-4-oxo-2-phenyl-4H-1-benzopyran methanesulfonate The title compound was prepared according to Example 6, but using Intermediate III instead of 8-carboxy-3-methyl-4-oxo-2-phenyl-4H-1-benzopyran.

After the usual workup, the residue was crystallized twice from ethanol; the solid obtained was purified by column chromatography on silica gel eluting with chloroform-ethyl acetate (8:2) to give the pure base, which was dissolved in chloroform-ethyl alcohol (1:1). Methanesulfonic acid was added to the solution and the solvents were removed by evaporation in vacuo. The crude salt was crystallized from isopropyl alcohol yielding the title compound, melting at 193°–195° C. This compound contained 0.33 equivalents of isopropanol and 0.25 equivalents of water.

Example 80

8-{{2-[4-(2-Methoxyphenyl)-1-piperazinyl]ethylcarbamoyl}methyl}-4-oxo-2-phenyl-4H-1-benzopyran methanesulfonate hydrate A mixture of 2.8 g of Intermediate XLVII and 1.28 g of 1-hydroxybenzotriazole in 20 ml of anhydrous dimethylformamide was stirred ar 0°/5° C. for 15 minutes and added dropwise, in about 40 minutes, with a solution of 1.96 g of dicyclohexylcarbodiimide in 20 ml of anhydrous dimethylformamide. After 8 hours stirring at room temperature, a solution of 2.24 g of 1-(2-aminoethyl)-4-( 2-methoxyphenyl)piperazine in 15 ml of anhydrous dimethylformamide was added.

After 5 hours stirring and overnight standing at the same temperature, the insoluble was filtered and the filtrate was poured into about 300 ml of water and made alkaline by addition of 1N aqueous sodium hydroxide solution. The mixture was extracted with dichloromethane and the organic layer was separated, dried on anhydrous sodium sulfate and evaporated in vacuo. The crude was purified by flash chromatography on silica gel eluting with a mixture of chloroform-methanol (95:5). One molar equivalent of methanesulfonic acid was added to the solution of the crude base in ethanol, followed by diethyl ether until crystallization of the salt. This one was filtered and recrystallized from a 1:2 mixture of ethanol and diethyl ether to give 1.15 g of the title compound, m.p. 160°–162° C.

Example 81

8-{N-acetyl-N-3-[4-(2-methoxyphenyl)-1-piperazinyl]propylcarbamoyl}-3-methyl-4-oxo-2-phenyl-4H-1-benzopyran A solution of 2.86 g of Intermediate LVII, 5.04 g of 1-(3-chloropropyl)-4-(2-methoxyphenyl)piperazine and 2.58 g of anhydrous potassium carbonate in 50 ml of dimethylformamide was stirred at 90° C. for 7 hours. After cooling to room temperature, the reaction mixture was poured into 500 ml of water and extracted with dichloromethane; the organic layer was washed with water, dried on sodium sulfate and evaporated to dryness in vacuo.

The residue was purified by column chromatography on silica gel eluting with ethyl acetate-petroleum ether (7:3) to give 1.89 g of the title compound melting at (55) 62°–63° C.

Example 82

8-{2-[4-(2-Methoxyphenyl)-1-piperazinyl]ethylsulfonylamino}-3-methyl-4-oxo-2-phenyl-4H-1-benzopyran methanesulfonate 1.05 ml of 2-chloroethanesulfonyl chloride was added dropwise to a solution of 5 g of 8-amino-3-methyl-4-oxo-2-phenyl- 4H-1-benzopyran and 1.4 ml of triethylamine stirred at 0° C. The reaction mixture was stirred at room temperature for 2 days. After filtering the precipitated solid, the solution was evaporated to dryness in vacuo to give a crude residue containing 8-(ethenYlsulfonylamino)-3-methyl-4-oxo-2-phenyl-4H-1-benzopyran used without further purification. A mixture of 7.54 g of this residue and 5.8 g of 1-(2-methoxyphenyl)piperazine and 4.15 g of potassium carbonate in 100 ml of dimethylformamide was stirred at room temperature for 4 hours, poured into 600 ml of water and extracted with ethyl acetate. The organic layer was evaporated to dryness in vacuo and the residue was purified by column chromatography on silica gel eluting with petroleum ether-acetone 8:2. The collected fractions were evaporated to dryness in vacuo and crystallized from 70% ethanol to give 0.75 g of the title compound as a base. This solid was dissolved in dichloromethane and 1 equivalent of methanesulfonic acid was added to the solution. The crude methanesulfonate, obtained by evaporation in vacuo, was crystallized from acetone, yielding 0.6 g of the title compound melting at 202°–203° C.

Example 83

8-{3-[4-(2-Methoxyphenyl)-1-piperazinyl]propylthiocarbamoyl}-3-methyl-4-oxo-2-phenyl-4H-1-benzopyran methanesulfonate A stirred mixture of 0.8 g 8-formyl-3-methyl-4-oxo-2-phenyl-4H-1-benzopyran, 0.75 g of 1-(3-aminopropyl)-4-(2-methoxyphenyl)piperazine and 0.14 g of sulfur in 5 ml of pyridine was refluxed for 6 hours.

After solvent evaporation in vacuo, the residue was purified by flash chromatography on silica gel, eluting with chloroform. The obtained title compound (as the base) was dissolved in dichloromethane and added with an equivalent of methanesulfonic acid. The title compound was obtained

Example 84

8-{4-[4-(2-Methoxyphenyl)-1-piperazinyl]butylsulfonyl}-3-methyl-4-oxo-2-phenyl-4H-1-benzopyran methanesulfonate · 0.25 H$_2$O The title compound was prepared according to Example 73, but using Intermediate LX instead of Intermediate LIV. Its purification was performed by column chromatography on silica gel, eluting with ethyl acetate-petroleum ether (7:3). One molar equivalent of methanesulfonic acid was added to a solution of the crude base in dichloromethane.

After removal of the solvent by evaporation in vacuo, the resulting salt was crystallized from acetone to give the title compound, m.p. 212°–214° C.

Example 85

3-Hydroxymethyl-8-{3-[4-(2-methoxyphenyl)-1-piperazinyl]propyl carbamoyl}-4-oxo-2-phenyl-4H-1-benzopyran. 0.4 ethanol A mixture of 3.6 g of Intermediate XCV and 1.65 g of 1-hydroxybenzotriazole in 35 ml of anhydrous dimethylformamide was stirred at 0°/5° C. for 15 minutes and added dropwise with a solution of 2.5 g of dicyclohexylcarbodiimide in 35 ml of anhydrous dimethylformamide. After 1 hour stirring at the same temperature, a solution of 1-(3-aminopropyl)-4-(2-methoxyphenyl)piperazine was added.

After 2 hours stirring at the same temperature and overnight standing at room temperature, the reaction mixture was evaporated to dryness in vacuo. The residue was purified by flash chromatography eluting with a mixture of dichloromethane-methanol (100:3), followed by crystallization from ethanol. 2.5 g of the title compound was obtained, m.p. 152°–154° C.

Example 86

8-{3-[4-(2-Methoxyphenyl)-1-piperazinyl]propylcarbamoyl}-4-oxo-2-phenyl-4H-1-benzopyran methanesulfonate. 0.25 H$_2$O 3.6 ml of diethyl cyanophosphonate were added dropwise at 0°/5° C. into a stirred solution of 4 g of 4-oxo-2-phenyl-4H-1-benzopyran-8-carboxylic acid (prepared as described in Da Re et al., Ber., 99, 1962 (1966)) and 3.75 g of 1-(3-aminopropyl)-4-(2methoxyphenyl)piperazine in 35 ml of anhydrous dimethylformamide. Immediately afterwards, 2.5 ml of triethylamine was added dropwise at the same temperature. After 30 minutes stirring at 0°/5° C. and 1 hour at room temperature, the reaction mixture was poured into 350 ml of 2.5% aqueous sodium carbonate solution. The precipitate formed was stirred for 1 hour at room temperature, collected by suction and crystallized from ethanol. The title compound obtained in this way as the base was dissolved in dichloromethane and added with one equivalent of methanesulfonic acid. After evaporation in vacuo, a glassy solid was obtained, which was crushed and refluxed for 1 hour in acetone, yielding 5 g of the title compound melting at 191°–194° C.

Example 87

2,3-Dihydro-8-{3-[4-(2-methoxyphenyl)-1-piperazinyl]propylcarbamoyl}-4-oxo-4H-1-benzopyran methanesulfonate A solution of 0.84 ml of thionyl chloride in 17 ml of anhydrous dichloromethane was added dropwise to a solution of 2.0 g of 2,3-dihydro-4-oxo-4H-1-benzopyran-8-carboxylic acid (prepared as described in Lichtenberger et al., Bull. Chem. Soc. Fr., 275 (1963)) and 1.75 ml of triethylamine in 17 ml of dichloromethane stirred at room temperature.

Stirring was continued for 1.5 hour at the same temperature; after this period the reaction mixture was evaporated to dryness in vacuo giving 8-chlorocarbonyl-2,3-dihydro-4-oxo-4H-1-benzopyran as a crude.

Using the above Intermediate instead of 8-chlorocarbonyl-3-methyl-4-oxo-2-phenyl-4H-1-benzopyran, the title compound was prepared according to Example 10. The crude was purified by column chromatography eluting with ethyl acetate-methanol (85:15) yielding 1.91 g of the pure base, which was dissolved in dichloromethane and converted into its methanesulfonate salt by addition of methanesulfonic acid. This solution was evaporated to dryness in vacuo and the crude salt was crystallized from acetonitrile giving 1.57 g of the title compound (m.p. 175°–177° C.).

Example 88

8-{3-[4-(2-methoxyphenyl)-1-piperazinyl]propylcarbamoyl}-4-oxo-4H-1-benzopyran methanesulfonate 1.25 H$_2$O The title compound was prepared by the method described in Example 87, but using Intermediate LXII instead of 2,3-dihydro-4-oxo-4H-1-benzopyran-8-carboxylic acid.

The crude methanesulfonate was rinsed with diethyl ether, filtered and repeatedly crystallized from acetonitrile (m.p. 155°–157° C.).

Example 89

6-Bromo-8-{3-[4-(2-methoxyphenyl)-1-piperazinyl]propylcarbamoyl}-3-methyl-4-oxo-2-phenyl-4H-1-benzopyran This compound was prepared according to Example 86, but using 6-bromo-3-methyl-4-oxo-2-phenyl-4H-1-benzopyran-8-carboxylic acid (prepared as described in EP 107804 (1983)) instead of 4-oxo-2-phenyl-4H-1-benzopyran-8-carboxylic acid. It was purified as a base by flash chromatography on silica gel eluting with dichloromethane-methanol (100:3), and crystallized from 95% ethanol (m.p. (150) 154°–159° C.).

Example 90

6-Methoxy-8-{3-[4-(2-methoxyphenyl)-1-piperazinyl]propylcarbamoyl}-3-methyl-4-oxo-2-phenyl-4H-1-benzopyran methanesulfonate 1.01 ml of diethylcyanophosphonate and 0.85 ml of triethylamine were added to a solution of 1.7 g of 6-methoxy-3-methyl-4-oxo-2-phenyl-4H-1-benzopyran-8-carboxylic acid (prepared as described in JP 61°–15880) and 1.51 g 1-(2-methoxyphenyl)-4-(3aminopropyl)piperazine in 20 ml of anhydrous dimethylformamide stirred at 0° C.

After 1 hour stirring at 0° C. to room temperature, the reaction mixture was poured into a mixture of 100 ml of water and 10 ml of 1N aqueous sodium hydroxide solution. The title compound precipitated as a base and was filtered and washed with water. After desiccation it was converted in the usual way to the methanesulfonate, which was crystallized from acetonitrile yielding 1.7 g melting at 185°–186° C.

Example 91

6-Hydroxy-8-{3-[4-(2-methoxyphenyl)-1-piperazinyl]propylcarbamoyl}-3-methyl-4-oxo-2-phenyl-4H-1-benzopyran methanesulfonate 0.8 g of compound of Example 114 and 5.8 ml of 1N sodium hydroxide in 10 ml of methanol was stirred at room temperature for 4 hours.

After standing overnight, 15 ml of 1N sodium hydroxide and 15 ml of methanol was added and the mixture was stirred at room temperature for 1 hour. Methanol was evaporated in vacuo and water was added to the residue. The suspension was filtered by suction to give 0.48 g of the title compound as a base which was converted by the usual procedure into its methanesulfonate salt, recrystallized from acetonitrile (m.p. 200°–202° C.).

Example 92

3,6-Dimethyl-8-{3-[4-(2-methoxyphenyl)-1-piperazinyl]propyl carbamoyl}-4-oxo-2-phenyl-4H-1-benzopyran methanesulfonate The title compound was prepared according to Example 90 but using 3,6-dimethyl-4-oxo-2-phenyl-4H-1-benzopyran-8-carboxylic acid (prepared as described in Da Re et al., *Arch. Pharm.*, 296, 714 (1963)) instead of 6-methoxy-3-methyl-4-oxo-2-phenyl-4H-1-benzopyran-8-carboxylic acid.

The crude methanesulfonate was crystallized from acetonitrile (m.p. 196°–197° C.).

Example 93

8-{3-[4-(2-Methoxyphenyl)-1-piperazinyl]propylcarbamoyl}-3-methyl-6-nitro-4-oxo-2-phenyl-4H-1-benzopyran This product was obtained operating as described in Example 12 but using Intermediate LXVIII instead of 3-methyl-4-oxo-2-phenyl-4H-1-benzopyran-8-carbonyl chloride and 1,1,2-trichloroethane instead of chloroform.

After the usual workup, the crude was purified by column chromatography eluting with dichloromethane-methanol 98:2. Evaporation in vacuo to dryness of the collected fractions and crystallization from ethanol yielded the title compound (m.p. 159.5°–161° C.).

Example 94

6-Amino-8-{3-[4-(2-methoxyphenyl)-1-piperazinyl]propyl carbamoyl}-3-methyl-4-oxo-2-phenyl-4H-1-benzopyran A mixture of 33 g of compound of Example 93, 109 ml of 1N hydrochloric acid, 105 ml of water and 8.78 g of Raney-Ni in 950 ml of ethanol was hydrogenated in a Parr apparatus ($PH_2$=2 atm) stirring at 40° C. for 12 hours. After this period, the catalyst was filtered off and washed with 80% ethanol. The mother liquors were evaporated in vacuo, reaching a volume of 80 ml and filtered, washing the crude with water.

The crude was suspended in water; 37% hydrochloric acid was added up to pH=1. The insoluble was filtered by suction and the filtrate was alkalinized by adding 35% aqueous sodium hydroxide solution. The title compound that precipitated was recovered by filtration and washed with water. Desiccation yielded 26 g melting at (108) 215°–217.5° C. This compound was used as an Intermediate without further purification. 4.7 g were crystallized firstly from ethanol and then from 85% ethanol, to give 3 g of the title compound (m.p. 218°–219° C.).

Example 95

6-Acetylamino-8-{3-[4-(2-methoxyphenyl)-1-piperazinyl]propylcarbamoyl}-3-methyl-4-oxo-2-phenyl-4H-1-benzopyran The title compound was obtained according to the procedure described in Example 36, but using the compound prepared in Example 94 instead of that one of Example 33. The reaction mixture was diluted with water and filtered by suction, washing the solid with water. After desiccation at 80° C., this solid was purified by column chromatography on silica gel eluting with chloroform-methanol (95:5). Evaporation in vacuo of the collected fractions and crystallization from 95% ethanol of the residue gave the title compound, m.p. (150) 218°–220° C.

Example 96

6-Ethylamino-8-{3-[4-(2-methoxyphenyl)-1-piperazinyl]propylcarbamoyl}-3-methyl-4-oxo-2-phenyl-4H-1-benzopyran A mixture of 8.42 g of the compound of Example 94, 0.45 ml of acetaldehyde, 0.59 g of 85% sodium cyanoborohydride and 3.3 ml of 4.85N ethanolic hydrochloric acid in 73 ml of methanol was stirred at room temperature for 5 days.

After this period, the reaction mixture was poured into cold 1.5N sodium hydroxide; the suspension was diluted with water and filtered by suction. After desiccation, the residue was purified by column chromatography on silica gel eluting with chloroform-methanol 100:3. Evaporation in vacuo of the collected fractions yielded 6 g of the compound of Example 94 and 2.67 g of the title compound, which melted at 198°–201° C., after recrystallization from ethanol.

Example 97

6-Dimethylamino-8-{3-[4-(2-methoxyphenyl)-1-piperazinyl]propylcarbamoyl}-3-methyl-4-oxo-2-phenyl-4H-1-benzopyran The title compound was prepared according to Example 35, but using the compound prepared in Example 94 instead of that prepared in Example 33, reacting 10 molar equivalents of 40% formaldehyde instead of 7 molar equivalents and 3 moles of sodium cyanoborohydride instead of 2 moles and stirring at room temperature for 18 hours instead of 4.5 hours. After the usual workup, the crude was purified by column chromatography on silica gel eluting with chloroform-methanol 97:3. Evaporation in vacuo of the collected fractions and crystallization of the residue from ethanol yielded the title compound which melted at 183°–186° C.

Example 98

7-Methoxy-8-{3-[4-(2-methoxyphenyl)-1-piperazinyl]propylcarbamoyl}-3-methyl-4-oxo-2-phenyl-4H-1-benzopyran The title compound was prepared according to the procedure described in Example 87, but using Intermediate LXIX instead of 2,3-dihydro-4-oxo-4H-1-benzopyran-8-carboxylic acid. After the usual workup, the solid residue was purified by column chromatography on silica gel eluting with ethyl acetate-methanol (8:2). The collected fractions were evaporated to dryness in vacuo and the residue was crystallized from acetonitrile to give the title compound, melting at 151°–152° C.

Example 99

8-{3-[4-(2-Methoxyphenyl)-1-piperazinyl]propylcarbamoyl}-3-methyl-4-oxo-2-(4-trifluoromethylphenyl)-4H-1-benzopyran methanesulfonate 1.5 $H_2O$ The title compound was prepared following the procedure described in Example 90 starting from Intermediate LXXII instead of 6-methoxy-3-methyl-4-oxo-2-phenyl-4H-1-benzopyran-8-carboxylic acid. The methanesulfonate melted at

Example 100

2-(4-Benzoylphenyl)-8-{3-[4-(2-methoxyphenyl)-1-piperazinyl]propylcarbamoyl}-3-methyl-4-oxo-4H-1-benzopyran methanesulfonate hemihydrate The title compound was prepared following the procedure described in Example 90, but starting from Intermediate LXXIV instead of 6-methoxy-3-methyl-4-oxo-2-phenyl-4H-1-benzopyran-8-carboxylic acid. The crude methanesulfonate was crystallized from acetonitrile and melted at 208°–210° C.

Example 101

8-{3-[4-(2-Methoxyphenyl)-1-piperazinyl]propylcarbamoyl}-3-methyl-4-oxo-2-(4-phenoxyphenyl)-4H-1-benzopyran methanesulfonate. 0.25 H$_2$O The title compound was prepared following the procedure described in Example 90 but starting from Intermediate LXXVII instead of 6-methoxy-3-methyl-4-oxo-2-phenyl-4H-1-benzopyran-8-carboxylic acid. The crude methanesulfonate was crystallized from acetonitrile, m.p. 200°–202° C.

Example 102

2,3-Dimethyl-8-{3-[4-(2-methoxyphenyl)-1-piperazinyl]propylcarbamoyl}-4-oxo-4H-1-benzopyran This compound was prepared according to Example 86, but using 2,3-dimethyl-4-oxo-4H-1-benzopyran-8-carboxylic acid (prepared as described in Da Re, *Farmaco Ed. Sci.*, 11, 678 (1956)) instead of 4-oxo-2-phenyl-4H-1-benzopyran-8-carboxylic acid and carrying out the reaction at room temperature for 5 hours. It was purified as a base by flash chromatography on silica gel eluting with chloroform-methanol (98:2), and crystallized from acetone (m.p. 155°–158.5° C.).

Example 103

2-tert-Butyl-8-{3-[4-(2-methoxyphenyl)-1-piperazinyl]propylcarbamoyl}-3-methyl-4-oxo-4H-1-benzopyran dihydrochloride dihydrate This compound was prepared according to Example 86, but using Intermediate LXXVIII instead of 4-oxo-2-phenyl-4H-1-benzopyran-8-carboxylic acid.

The base was purified by flash chromatography on silica gel eluting with a mixture of chloroform-methanol (49:1) and converted into the dihydrochloride in methanol-diethyl ether. It melted at 226°–229.5° C. after recrystallization from methanol-diethyl ether (1:1).

Example 104

2-Cyclohexyl-8-{3-[4-(2-methoxyphenyl)-1-piperazinyl]propylcarbamoyl}-3-methyl-4-oxo-4H-1-benzopyran This compound was prepared according to Example 86, but using Intermediate LXXIX instead of 4-oxo-2-phenyl-4H-1-benzopyran-8-carboxylic acid, and carrying out the reaction for 5 hours at room temperature.

It was purified as a base by flash chromatography on silica gel eluting with a mixture chloroform-methanol (49:1), and crystallized from acetonitrile (m.p. 155°–157° C.).

This compound was also isolated as its monomethanesulfonate salt by addition of one equivalent methanesulfonic acid to a solution of the base in boiling ethanol, cooling to ambient temperature, and filtering. Recrystallization from ethanol provided the pure product, m.p. 210°–211° C.

Example 105

2-(2-Furyl)-8-{3-[4-(2-methoxyphenyl)-1-piperazinyl]propylcarbamoyl}-3-methyl-4-oxo-4H-1-benzopyran This compound was prepared according to Example 86 but using Intermediate LXXXI instead of 4-oxo-2-phenyl-4H-1-benzopyran-8-carboxylic acid, and completing the reaction at room temperature for 5 hours. After quenching, the title compound was isolated by extraction with chloroform and purified by flash chromatography on silica gel eluting with the mixture chloroform-methanol 49:1, followed by crystallization from acetonitrile (m.p. 151°–153° C.).

Example 106

8-{3-[4-(2-Methoxyphenyl)-1-piperazinyl]propylcarbamoyl}-3-methyl-4-oxo-2-thienyl-4H-1-benzopyran This compound was obtained according to Example 86, but using Intermediate LXXXIII instead of 4-oxo-2-phenyl-4H-1-benzopyran-8-carboxylic acid. It was purified by stirring in water (to completely remove dimethylformamide), followed by column chromatography on silica gel eluting with the mixture chloroform-methanol (49:1), and crystallized from acetonitrile (m.p. 174°–175° C.).

Example 107

8-{3-[4-(2-Methoxyphenyl)-1-piperazinyl]propylcarbamoyl}-4-oxo-2-phenyl-4H-1-benzothiopyran A mixture of 2.8 g of Intermediate LXXXIV and 3.4 g of 1,1-carbonyldiimidazole in 60 ml of anhydrous dimethylformamide was stirred under N$_2$ at room temperature for 1.5 hours. Afterwards, 2.7 g of 1-(3-aminopropyl)-4-(2-methoxyphenyl)piperazine was added. After further 2 hours stirring at room temperature, the reaction mixture was poured into 300 ml of water and extracted with chloroform. The organic layer was dried on anhydrous sodium sulfate and evaporated in vacuo. The residue was purified by flash chromatography on silica gel eluting with chloroform-methanol (49:1), washed with water and crystallized from acetonitrile, yielding 2 g of the title compound melting at 144°–146° C.

Example 108

(E)-8-{3-[4-(2-methoxyphenyl)-1-piperazinyl]propylcarbamoyl}-3-methyl-4-oxo-2-(2-phenylethenyl)-4H-1-benzopyran This compound was prepared according to Example 86, but using Intermediate LXXXVI instead of 4-oxo-2-phenyl-4H-1-benzopyran-8-carboxylic acid. It was purified by crystallization from acetonitrile (m.p. 191°–194° C.).

Example 109

8-{3-[4-(2-methoxyphenyl)-1-piperazinyl]propylcarbamoyl}-3-methyl-2-(4-methylphenyl)-4-oxo-4H-1-benzopyran This compound was prepared according to Example 86, but using Intermediate LXXXVII instead of 4-oxo-2-phenyl-4H-1-benzopyran-8-carboxylic acid and completing the reaction at room temperature for 4 hours.

After quenching, the title compound was isolated by extraction with ethyl acetate, drying on sodium sulfate and evaporation in vacuo, followed by rinsing with diethyl ether and crystallization from acetonitrile (m.p. 161°–163° C.).

Example 110

2-(4-Methoxyphenyl)-8-{3-[4-(2-methoxyphenyl)-1-piperazinyl]propylcarbamoyl}-3-methyl-4-oxo-4H-1-benzopyran This compound was prepared according to Example 86, but using 2-(4-methoxyphenyl)-3-methyl-4-oxo-4H-1-benzopyran-8-carboxylic acid (prepared as described in EP 108986 (1984)) instead of 4-oxo-2-phenyl-4H-1-benzopyran-8-carboxylic acid, and completing the reaction at room temperature for 3.5 hours. It was purified by flash chromatography on silica gel eluting with chloroform-methanol (49:1), followed by crystallization from acetonitrile (m.p. 158°–161° C.).

Example 111

2-(4-Fluorophenyl)-8-{3-[4-(2-methoxyphenyl)-1-piperazinyl]propyl carbamoyl}-3-methyl-4-oxo-4H-1-benzopyran This compound was prepared according to Example 86, but using Intermediate LXXXIX instead of 4-oxo-2-phenyl-4H-1-benzopyran-8-carboxylic acid. It was purified by flash chromatography on silica gel eluting with a chloroform-methanol gradient (100:2 to 100:6) and crystallized from 95% ethanol (m.p. 166°–168° C.).

Example 112

8-{3-[4-(2-Methoxyphenyl)-1-piperazinyl]-propylcarbamoyl}-3-methyl-6-methanesulfonylamino-4-oxo-2-phenyl-4H-1-benzopyran hydrochloride 0.032 ml of methanesulfonyl chloride in 1 ml of dimethylformamide was added dropwise in 10 minutes to a solution of 0.21 g of compound of Example 94 and 0.062 ml of triethylamine in 4 ml of dimethylformamide, stirred at –20° C. Stirring was continued at the same temperature for 3.5 hours. After this period, the reaction mixture was poured into water and the suspension was filtered by suction, yielding 0.1 g of the title compound which was recrystallized from 80% ethanol (m.p. 272°–275° C.).

Example 113

8-{3-[4-(2-Methoxyphenyl)-1-piperazinyl]propylcarbamoyl}-3-methyl-2-(4-nitrophenyl)-4-oxo-4H-1-benzopyran The title compound was prepared following the procedure described in Example 90, but starting from Intermediate XCVIII instead of 6-methoxy-3-methyl-4-oxo-2-phenyl-4H-1-benzopyran-8-carboxylic acid. After 1 hour stirring at room temperature, the reaction mixture was poured into cold 2% aqueous sodium carbonate solution and the precipitated solid was collected by suction. After desiccation and crystallization from ethanol, the title compound melted at (60) 185°–187° C.

Example 114

6-Diethoxyphosphonyloxy-8-{3-[4-(2-methoxyphenyl)-1-piperazinyl]propylcarbamoyl}-3-methyl-4-oxo-2-phenyl-4H-1-benzopyran The title compound was prepared following the procedure described in Example 90, but starting from Intermediate LXIII instead of 6-methoxy-3-methyl-4-oxo-2-phenyl-4H-1-benzopyran-8-carboxylic acid and using 2 equivalents of diethyl cyanophosphate instead of 1.1 equivalent. Filtration from water yielded the title compound melting at 48°–80° C. with decomposition.

Example 115

8-{3-[4-(2-Methoxyphenyl)-1-piperazinyl]propylcarbamoyl}-3-methyl-4-oxo-2-trifluoromethyl-4H-1-benzopyran methanesulfonate 2/3 $H_2O$ The title compound was obtained by the same method as described in Example 90, but starting from Intermediate C instead of 6-methoxy-3-methyl-4-oxo-2-phenyl-4H-1-benzopyran-8-carboxylic acid. After the usual workup by extraction with ethyl acetate, the residue was purified by column chromatography on silica gel eluting with ethyl acetate-methanol (9:1), yielding the title compound as a pure base, which was converted into its methanesulfonate by the usual procedure and recrystallized from ethyl acetate (m.p. 145°–148° C.).

Example 116

8-{N,3-[4-(2-methoxyphenyl)-1-piperazinyl]-propyl-N-methylcarbamoyl}-3-methyl-4-oxo-2-phenyl-4H-1-benzopyran hydrochloride. 0.66 $H_2O$ This compound was prepared according to Example 12, using Intermediate CI instead of 3-[4-(2-methoxyphenyl)-1-piperazinyl]propylamine. The crude base was purified by flash chromatography on silica gel, eluting with chloroform-5N ammonia in methanol (100:1) and transformed into the hydrochloride in the usual way. The obtained title compound melted at 195°–198° C., after crystallization from acetone.

Example 117

2-Benzoyl-3-ethyl-7-{3-[4-(2-methoxyphenyl)-1-piperazinyl]propylcarbamoyl}benzo[b]furan This compound was prepared according to Example 86, but using Intermediate CIII instead of 4-oxo-2-phenyl-4H-1-benzopyran-8-carboxylic acid, and completing the reaction at room temperature for 4 hours. It was purified by crystallization from ethanol (m.p. 165°–166° C.).

Example 118

2-(4-Biphenylyl)-8-{3-[4-(2-methoxyphenyl)-1-piperazinyl]-propylcarbamoyl}-3-methyl-4-oxo-4H-1-benzopyran The title compound was prepared according to Example 86, but using Intermediate CVI instead of 4-oxo-2-phenyl-4H-1-benzopyran-8-carboxylic acid. The reaction lasted 20 hours at room temperature. The base was purified by crystallization from ethanol (m.p. 164°–166° C.).

Example 119

8-{3-[4-(2-Methoxyphenyl)-1-piperazinyl]propylcarbamoyl}-3-methyl-4-oxo-2-(3-pyridyl)-4H-1-benzopyran A mixture of 6.2 g of methyl 3-propionylsalicylate and 5.8 g of nicotinoyl chloride hydrochloride in 18 ml of anhydrous pyridine was stirred and heated at 100° C. for 2 hours under nitrogen. After that, 16 ml of triethylamine was added and heating was continued for 1 hour at the same temperature. The reaction mixture was cooled to room temperature, poured into 600 ml of water and the precipitate was collected by suction and washed with water, yielding 5.4 g of methyl 2-hydroxy-3-(2-nicotinoyl)propionylbenzoate, which was used without purification in the next step. 3.4 g of this Intermediate was heated at 100° C. for 1.5 hours after dissolution in a mixture containing 15 ml of acetic acid and 1 ml of 37% hydrochloric acid. After cooling to room temperature, the mixture was poured into 150 ml of water and extracted with ethyl acetate. The organic phase was washed with 5% aqueous sodium hydrogen carbonate solution, followed by water, dried on sodium sulfate and evaporated in vacuo, yielding 1.3 g of crude methyl 3-methyl-4-oxo-2-(3-pyridyl)-4H-1-benzopyran-8-carboxylate. 1 g of the above ester was dissolved in 9 ml of methanol and 15 ml of 1,4-dioxane and slowly added with 1.7 ml of 10N sodium hydroxide, maintaining the temperature between 20 and 25° C. After 1 hour at 50° C., the reaction mixture was poured into 150 ml of water and extracted with ethyl acetate. The aqueous layer was acidified with 1n aqueous hydrochloric acid solution. The precipitate was collected by suction, yielding 0.6 g of 3-methyl-4-oxo-2-(3-pyridyl)-4H-1-benzopyran-8-carboxylic acid, which was used without purification in the next step. The title compound was prepared according to Example 86, but using the above Intermediate instead of 4-oxo-2-phenyl-4H-1-benzopyran-8-carboxylic acid and carrying out the reaction for 2 hours at room temperature. The base was purified by flash chromatography on silica gel eluting with a mixture of chloroform-methanol (98:2), followed by crystallization from acetone, yielding 0.15 g (m.p. 134.5°–137° C.).

Example 120

8-{3-[4-(2-Acetoxyphenyl)-1-piperazinyl]propylcarbamoyl}-3-methyl-4-oxo-2-phenyl-4H-1-benzopyran 1 g of compound of Example 59 and 0.32 g of 4-dimethylaminopyridine were dissolved in 10 ml of dichloromethane and slowly added with 0.15 ml of acetyl chloride, maintaining the temperature between 8° and 10° C. After 2 hours at room temperature, the reaction mixture was poured into 70 ml of water and extracted with dichloromethane. The organic layer was washed with 5% aqueous sodium hydrogen carbonate solution, followed by water, dried on anhydrous sodium sulfate and evaporated in vacuo. The crude base was purified by flash chromatography on silica gel eluting with a mixture of ethyl acetate-methanol (9:1), followed by crystallization from ethanol, yielding 0.74 g of the title compound (m.p. 120°–123° C.).

Example 121

3-Methyl-8-{3-[4-(2-methylaminocarbonyloxyphenyl)-1-piperazinyl]-propylcarbamoyl}-4-oxo-2-phenyl-4H-1-benzopyran 3 g of compound of Example 59 and 18 ml of methyl isocyanate were dissolved in 30 ml of dry N,N-dimethylformamide and stirred at room temperature for 24 hours. The mixture was diluted with water, stirred for 2 hours, then filtered by suction. The crude base was purified by flash chromatography on silica gel eluting with chloroform-5N ammonia in methanol (100:3). The title compound melted at 132°–135° C. after crystallization from ethanol.

Example 122

6-Acetoxy-8-{3-[4-(2-methoxyphenyl)-1-piperazinyl]propylcarbamoyl}-3-methyl-4-oxo-2-phenyl-4H-1-benzopyran 0.17 ml of acetyl chloride was added dropwise during 5 minutes, under stirring at 0° C., into a solution of 1 g of the compound of Example 91 and 0.32 ml of triethylamine in 36 ml of chloroform. After 2 hours stirring at the same temperature, the reaction mixture was diluted with dichloromethane and water; the organic layer was separated, washed with water, dried on sodium sulfate and evaporated to dryness in vacuo. Crystallization of the residue from acetonitrile yielded 0.8 g of the title compound, melting at 148°–149° C.

Example 123

(R,S)-2,3-dihydro-4-hydroxy-8-{3-[4-(2-methoxyphenyl)-1-piperazinyl]propylcarbamoyl}-4H-1-benzopyran methanesulfonate The title compound was prepared by the same method as described in Example 17 but starting from compound of Example 87 instead of compound of Example 1. The reaction mixture was diluted with water and stirred for 15 minutes. Thereafter, it was extracted with ethyl acetate. Usual work up gave a crude residue, which was purified by flash chromatography on silica gel eluting with dichloromethane-methanol (95:5). Evaporation in vacuo of the collected fractions yielded the pure base, which was converted into the methanesulfonate and crystallized from acetonitrile (m.p. 172°–175° C.).

Example 124

2-(4-Aminophenyl)-8-{3-[4-(2-methoxyphenyl)-1-piperazinyl]propylcarbamoyl}-3-methyl-4-oxo-4H-1-benzopyran 2.22 g of compound of Example 113 and 0.56 g of Raney-Nickel in 96 ml of ethanol and 4.8 ml of acetic acid was hydrogenated in a Parr apparatus (pH$_2$=1 atm) at room temperature. After 6 hours shaking, the catalyst was filtered off and the filtrate was alkalinized with 3N aqueous sodium hydroxide solution and diluted with water. After standing for 2 days at 0° C., the precipitated title compound was collected by suction, washed with water, desiccated and recrystallized firstly from ethyl acetate then from ethanol yielding 1.5 g of the title compound (m.p. 192°–194° C.).

Example 125

2-(4-Acetylaminophenyl)-8-{3-[4-(2-methoxyphenyl)-1piperazinyl]propylcarbamoyl}-3-methyl-4H-1-benzopyran The title compound was prepared by the same method as described for compound of Example 36, but using the compound prepared in Example 124 instead of compound of Example 33. It was purified by crystallization from 95% ethanol (m.p. 209°–211° C.).

Example 126

2-(4-Hydroxyphenyl)-8-{3-[4-(2-methoxyphenyl)-1-piperazinyl]propylcarbamoyl}-3-methyl-4H-1-benzopyran dihydrochloride monohydrate The title compound was prepared by the method described in Example 86 but using Intermediate CVII instead of 4-oxo-2-phenyl-4H-1-benzopyran-8-carboxylic acid, and carrying out the reaction for 14 hours at room temperature also in the presence of hexamethylphosphoramide as co-solvent. The isolated diethylphosphonyl ester of the title compound was hydrolyzed by alkaline treatment followed by neutralization with diluted hydrochloric acid. The crude base was extracted with chloroform and the organic layer washed with water and evaporated in vacuo. The salt was prepared by ethanolic hydrogen chloride addition to an acetone solution of the base, evaporating to dryness and rinsing with acetone (m.p. 193°–205° C.).

Example 127

8-{3-[4-(2-Methoxyphenyl)-1-piperazinyl]propylcarbamoyl}-2-phenyl-4, $N_1$, $N_4$-trioxo-4H-1-benzothiopyran monohydrate 0.8 g of compound of Example 107 and 15 ml of acetic acid were added with 0.32 ml of 30% hydrogen peroxide and stirred at 50° C. for 3 hours. Then 0.48 ml of 30% hydrogen peroxide (3×0.16 ml portions every 2 hours of heating) was added to the mixture. After cooling, the mixture was poured into 240 ml of water, neutralized at pH 7 with 5% aqueous sodium hydrogen carbonate solution and extracted with chloroform. The organic layer was washed with water, dried on anhydrous sodium sulfate and evaporated in vacuo, yielding 0.18 g of the title compound, melting at 172°–175° C. after crystallization from acetonitrile.

Example 128

7-{3-[4-(2-Methoxyphenyl)-1-piperazinyl]propylcarbamoyl}-2-phenylbenzo[b]furan

The title compound was prepared by the method described in Example 86 but using 2-phenylbenzo[b]furan-7-carboxylic acid (prepared as described in EP 306,226) instead of 4-oxo-2-phenyl-4H-1-benzopyran-8-carboxylic acid, and carrying out the reaction for 1.5 hours at room temperature. It was purified by crystallization from carbon tetrachloride (m.p. 132°–136° C.).

Example 129

8-{3-[4-(2-Methoxyphenyl)-1-piperazinyl]propyl-N-methylsulfamoyl}-3-methyl-4-oxo-2-phenyl-4H-1-benzopyran methanesulfonate 2.29 g of Intermediate VIII was added portionwise under stirring at 0° C. to a solution of 1.5 g of Intermediate CI and 0.95 ml of triethylamine in 30 ml of chloroform. After 2 additional hours stirring at room temperature, the reaction mixture was diluted with dichloromethane, water and 0.5N sodium hydroxide. The organic layer was washed with water, dried on sodium sulfate and evaporated to dryness in vacuo. The residue was purified by flash chromatography on silica gel eluting with ethyl acetate-methanol (96:4). Evaporation in vacuo of the collected fractions, yielded of the pure title compound as a base. This one was converted by the usual method into the methanesulfonate salt, which was crystallized from ethyl acetate yielding 2.75 g, melting at 135°–141° C. (dec.).

Example 130

8-{3-[4-(2-Methoxyphenyl)-1-piperazinyl]-butyl-N-methylsulphamoyl}-3-methyl-4-oxo-2-phenyl-4H-1-benzopyran methanesulfonate The title compound was obtained by the same method described in Example 129 but using Intermediate CVIII instead of Intermediate CI. The title compound was crystallized from acetonitrile (m.p. 173°–175° C.).

Example 131

2-(4-Dimethylaminophenyl)-8-{3-[4-(2-methoxyphenyl)-1-piperazinyl]propylcarbamoyl}-3-methyl-4-oxo-4H-1-benzopyran The title compound was prepared by the same method as described for compound of Example 97, but using the compound prepared in Example 124 instead of compound of Example 94. The reaction mixture was diluted with water and 3N aqueous sodium hydroxide solution, under vigorous stirring. The precipitated solid was filtered by suction, washed with water, desiccated and purified by flash chromatography on silica gel eluting with ethyl acetate - methanol (8.5:1.5). Evaporation in vacuo of the collected fractions yielded the title compound which melted at 146°–150 (164) ° C after crystallization from acetonitrile.

Example 132

3-Benzyloxy-8-{3-[4-(2-methoxyphenyl)-1-piperazinyl] propylcarbamoyl}-4-oxo-2-phenyl-4H-1-benzopyran The title compound was prepared according to the method described in Example 90, but using Intermediate CXI instead of 6-methoxy-3-methyl-4-oxo-2-phenyl-4H-1-benzopyran-8-carboxylic acid. The crude title compound was recovered by suction filtration and purified by flash chromatography on silica gel, eluting with chloroform-methanol (95:5). Evaporation in vacuo of the collected fractions gave the pure title compound, which was recrystallized twice from ethanol, m.p. 159°–161° C.

Example 133

8-{3-[4-(4-hydroxy-2-methoxyphenyl)-1-piperazinyl]propylcarbamoyl}-3-methyl-4-oxo-2-phenyl-4H-1-benzopyran methanesulfonate 0.25 $H_2O$ A homogeneous mixture of 0.59 g of 1-(4-hydroxy-2-methoxyphenyl)piperazine (prepared as described in J. C. Pascal et al, *Eur. J. Med. Chem.*, 25, 291 (1990)) 0.89 g of intermediate XXXVII and 0.35 g of anhydrous potassium carbonate was heated at 180° C. for 15 minutes. After cooling to room temperature, the reaction mixture solidified and was extracted with chloroform. After washing with water, the organic layer was dried on sodium sulfate and evaporated to dryness in vacuo. The crude material was purified by flash chromatography on silica gel eluting with ethyl acetate-methanol (9:1). Evaporation in vacuo of the collected fraction yielded 0.99 g of the pure title compound as a base, which was converted in the usual manner into the methanesulfonate salt. Recrystallization from acetonitrile yielded 0.85 g of the title compound, m.p. (147) 150°–186° C. with decomposition.

Example 134

8-{3-[2-(8-methoxy-1,4-benzodioxanyl)methylamino]propylcarbamoyl}-3-methyl-4-oxo-2-phenyl-4H-1-benzopyran A mixture of 5.52 g of 8-hydroxy-2-hydroxymethyl-1,4-benzodioxan (prepared as described in EP 210581), 4.2g of anhydrous potassium carbonate and 2.06 ml of methyl iodide in 75 ml of anhydrous dimethylformamide was stirred at 45° C. for 8 hours. Methyl iodide (1 ml) was added to the mixture and stirring continued at the same temperature. After 8 hours, 1 ml of methyl iodide and 2.1 g of potassium carbonate were further added, and the reaction mixture was stirred at 45° C. for 6 hours. Thereafter, the mixture was cooled to room temperature, poured into water and extracted with ethyl acetate. The organic layer was washed with 6N aqueous sodium hydroxide solution, water, then dried on sodium sulfate. Evaporation of the organic layer to dryness in vacuo afforded 5.35 g of 2-hydroxymethyl-8-methoxy-1, 4-benzodioxan, which was used in the next step without further purification.

$^1$H-NMR Spectrum at 200 MHz (CDCl$_3$ (δ)) 6.78 (1H, t, CH of benzodioxan ring in 6) 6.55, 6.48 (2H, 2dd, CHs of benzodioxan ring in 5 and 7) 4.20°–4.35 (2H, m, CH$_{eq}$ in 3 and CH in 2 of benzopyran ring) 4.11 (1H, q, CH$_{ax}$ in 3 of benzopyran ring) 3.80–3.95 (2H, m, CH$_2$O) 3.85 (3H, s, CH$_3$O) 3.00 (1H, bs, OH)

5.35 g of the above Intermediate and 5.2 g of p-toluenesulfonyl chloride in 55 ml of anhydrous pyridine was stirred at 0° C. for 3 hours. The reaction mixture was poured into water, containing 75 ml of 37% hydrochloric acid, and extracted with ethyl acetate. The organic layer was washed with water, dried on sodium sulfate and evaporated to dryness in vacuo. The residue was crystallized from cyclohexane-benzene to give 5.2 g of 8-methoxy-2-p-toluenesulfonyloxymethyl-1,4-benzodioxan.

$^1$H-NMR Spectrum at 60 MHz (CDCl$_3$ ($\delta$)) 7.55, 7.25 (4H, 2dd, CHs of toluene ring) 6.30–6.80 (3H, m, CHs of benzopyran ring) 4.00–4.50 (4H, m, CH$_2$OS, CH$_{eq}$ in 3 and CH in 2 of benzopyran) 3.80 (4H, bs, CH$_3$O and CH$_{eq}$ in 3 of benzopyran ring) 2.40 (3H, s, CH$_3$ of tosyl group)

The title compound was prepared according to the procedure described in Example 52, but using 1.2 molar equivalent of Intermediate XLIII and 1 molar equivalent of the above 8-methoxy-2-(p-toluensulfonyloxymethyl)-1,4-benzodioxan instead of 2-(p-toluenesulfonyloxymethyl)-1,4-benzodioxan.

The crude was purified by flash chromatography eluting with an ethyl acetate-methanol gradient (9:1 to 8:2). Evaporation in vacuo of the collected fractions, yielded the title compound, m.p. 63°–108° C. (with decomposition).

Example 135

8-{3-[4-(2-Methoxyphenyl)-1-piperazinyl]propylcarbamoyl}-2-phenyl-4-thioxo-4H-1-benzopyran methanesulfonate The title compound was obtained by the same method of compound described in Example 87, but starting from Intermediate CXIII instead of 2,3-dihydro-4-oxo-4H-1-benzopyran-8-carboxylic acid. The corresponding carbonyl chloride was obtained by stirring for three hours at room temperature and 0.5 hour at reflux instead of 1.5 hour at room temperature. The crude was purified by flash chromatography on silica gel eluting with ethyl acetate-methanol (98:2), giving the pure title compound as a base, which was converted in the usual manner into the methanesulfonate and recrystallized from acetonitrile, m.p.196°–198° C.

Example 136

8-{[2,2-Dimethyl-3-(4-(2-methoxyphenyl)-1-piperazinyl)propyl]carbamoyl}-3-methyl-4-oxo-2-phenyl-4H-1-benzopyran 0.3 g of sodium borohydride was added at 0° C. to a stirred solution of 1.54 g of Intermediate CXIV in 17 ml of ethanol. After 1 hour stirring at the same temperature, 1N aqueous hydrochloric acid solution was added dropwise to the mixture until pH=1. Thereafter, the reaction mixture was made basic by adding 1N aqueous sodium hydroxide solution and extracted with ethyl acetate. The organic layer was washed with water, dried on sodium sulfate and evaporated to dryness in vacuo, yielding 1.54 g of 2,2-dimethyl-3-[4-(2-methoxyphenyl)-1-piperazinyl]propanol as an oil. The alcohol was used in the next step without further purification.

$^1$H-NMR Spectrum at 60 MHz (CDCl3 ($\delta$)) 6.85 (4H, s, aromatic CHs) 3.80 (3H, s, OCH$_3$) 3.50 (2H, s, CH$_2$O) 2.50–3.20 (8H, m, CH$_2$ of piperazine ring) 2.40 (3 H, s, OH and CH$_2$N ) 0.95 (6H, s, (CH$_3$)$_2$C)

1.5 g of the above alcohol and 1.2 g of p-toluenesulfonyl chloride in 12 ml of anhydrous pyridine were stirred at 0° C.-room temperature for 2.5 hours. After standing for 2 days at 0° C., the reaction mixture was poured into 0.1N aqueous sodium hydroxide solution containing ice and extracted with ethyl acetate. The organic layer was repeatedly washed with water, dried on sodium sulfate and evaporated to dryness in vacuo to give 2.16 g of a crude. The above obtained crude, 2,2-dimethyl- 3-[4-(2-methoxyphenyl)-1-piperazinyl]propyl p-toluenesulfonate, and 1.1 g of potassium phthalimide in 15 ml of anhydrous dimethylformamide were stirred at 110° C. for 2 hours. The cooled reaction mixture was poured into water and extracted with ethyl acetate. Usual work up yielded 0.75 g of 1-[2,2-dimethyl-3-(1-phthalimidyl)propyl]-4-(2-methoxyphenyl)piperazine, as a crude material which was used in the next step without further purification. 0.2 ml of 100% hydrazine hydrate was added to a solution of 0.75 g of the above intermediate in 10 ml of 95% aqueous ethanol solution, which was then refluxed for 2 hours. The reaction mixture was cooled to room temperature, diluted with in aqueous hydrochloric acid and water, then filtered by suction. The filtrate was made alkaline with 1N aqueous sodium hydroxide solution and extracted with dichloromethane. The organic layer was washed with water, dried on sodium sulfate and evaporated to dryness in vacuo, yielding 0.45 g of 2,2-dimethyl-3-[4-(2-methoxyphenyl)-1-piperazinyl]propylamine, which was not further purified.

$^1$H-NMR spectrum at 60 MHz (CDCl3 ($\delta$)) 7.00 ( 4H, s, phenyl CHs) 3.90 (3H, s, OCH$_3$) 2.50–3.20 (10H, m, piperazine CH$_2$s, CH$_2$N) 2.30 (2H, s, $\underline{CH_2}$NH$_2$) 1.20–1.50 (2H, bs, NH$_2$) 0.90 (6H, s, (CH$_3$)$_2$C)

A solution of 0.43 g of 3-methyl-8-chlorocarbonyl-4-oxo-2-phenyl-4H-1-benzopyran in 8 ml of dichloromethane was added dropwise at 0° C. to a stirred solution of 0.4 g of the above intermediate and 0.2 ml of triethylamine in 4 ml of dichloromethane. After 30 minutes at room temperature, the reaction mixture was diluted with water and the organic layer was separated, dried on sodium sulfate and evaporated to dryness in vacuo. The resulting crude material was purified by flash chromatography on silica gel eluting with a petroleum ether-ethyl acetate gradient (5:5 to 3:7).

Evaporation in vacuo of the collected fractions yielded 0.32 g of the title compound, m.p. 62°–73° C.

Example 137

8-{3-[4-(2-Methoxyphenyl)-1-piperazinyl]propylcarbamoyl}-3-methyl-4-oxo-2-(2-phenylethyl)-4H-1-benzopyran This compound was prepared according to Example 86, but using Intermediate CXVI instead of 4-oxo-2-phenyl-4H-1-benzopyran-8-carboxylic acid. The crude was purified by crystallization from ethanol, m.p. 142°–146° C.

Example 138

8-{3-[4-(2-Methoxyphenyl)-1-piperazinyl]propylcarbamoyl}-2-phenyl-1,1,4-trioxo-4H-1-benzothiopyran hydrochloride A mixture of 0.4 g of Intermediate CXVIII and 0.29 g of 1-(3-aminopropyl)-4-(2-methoxyphenyl)piperazine in 3 ml of dimethylformamide was stirred at room temperature for 90 minutes, then it was poured into 100 ml of water. After extraction with chloroform and evaporation in vacuo of the organic layer, the crude material was purified by flash chromatography on silica gel eluting with chloroform-methanol (100:5). The oily base was dissolved in ethanol and an excess of 5N ethanolic hydrogen chloride was added to the solution, followed by diethyl ether addition until the title compound crystallized. Yield 0.2 g, m.p. 187°–189° C.

Example 139

8-{3-[4-(2-Methoxyphenyl)-1-piperazinyl]propylcarbamoyl}-3-methyl-4-oxo-2-phenyl-4H-1-benzopyran-N$_1$-oxide hydrate A solution of 2.05 g of magnesium peroxyphthalate in 25 ml of water was added dropwise at 15°–20° C. to a stirred mixture of 3.5 g of the compound prepared in Example 11 in 60 ml of methanol and 5 ml of chloroform. After stirring at room temperature for 3 hours, solvents were evaporated in vacuo and the residue was treated with 50 ml of water, made alkaline with aqueous 5% sodium hydrogen carbonate addition, then extracted with chloroform. The separated organic layer was dried over sodium sulfate, evaporated to dryness in vacuo, and the resulting residue was purified by flash chromatography on silica gel eluting with a dichloromethane-5N methanolic ammonia gradient (100:5 to 100:15). The purification was again repeated by flash chromatography on silica gel eluting with n-butyl alcohol saturated with water and acetic acid. The fractions containing the title compound were pooled, diluted with water and made alkaline (pH>10) by addition of 20% aqueous sodium carbonate solution. The mixture was extracted with chloroform, the separated organic layer was washed with water, dried over anhydrous sodium sulfate and the solvent was evaporated to dryness. 0.37 g of the title compound was obtained after crystallization from ethanol, m.p. 165°–167° C.

Example 140

8-{3-[4-(2-Methoxyphenyl)-1-piperazinyl]propylcarbamoyl}-3-methyl-4-oxo-2-phenyl-4H-1-benzopyran $N_1,N_4$-dioxide 0.25 hydrate The compound was isolated during the purification of the crude of Example 139. The last fractions, collected from purification by flash chromatography on silica gel eluting with a dichloromethane - 5N methanolic ammonia gradient (100:5 to 100:15), were evaporated to dryness and the residue was crystallized from acetonitrile, yielding 0.5 g of the title compound, m.p. 170°–172° C.

Example 141

8-{3-[4-(5-Fluoro-2-methoxyphenyl)-1-piperazinyl]propylcarbamoyl}-3-methyl-4-oxo-2-phenyl-4H-1-benzopyran This compound was prepared by the method described in Example 133, but using 1-(5-fluoro-2-methoxyphenyl)piperazine (prepared as described in GB 2,161,807) instead of 1-(4-hydroxy-2-methoxyphenyl)piperazine. The reaction lasted 30 minutes and the crude material was purified by flash chromatography on silica gel eluting with chloroform - 2N triethylamine in methanol (100:1). The title compound melted at 146°–148° C., after crystallization from acetonitrile.

Example 142

8-{3-[4-(2-Methoxyphenyl)-1-piperazinyl]propylcarbamoyl}-2-phenyl=4(1H)-quinolone A solution of 0.78 g of N,N'-dicyclohexylcarbodiimide in 8 ml of anhydrous dimethylformamide was added dropwise over 5 minutes at 4° C. to a stirred mixture of 1 g of 2-phenyl-4(1H)-quinolone-8-carboxylic acid (prepared as described in W. A. Denny et al., *J. Med. Chem.*, 32, 396 (1989)) and 0.43 g of N-hydroxysuccinimide in 12 ml of anhydrous dimethylformamide under nitrogen atmosphere. After 1 hour at room temperature, the insoluble N,N'-dicyclohexylurea was filtered off by suction and a solution of 1-(3-aminopropyl)-4-(2-methoxyphenyl)piperazine in 6 ml of anhydrous dimethylformamide was added dropwise, over 5 minutes, to the reaction solution. After 4 hours at room temperature, the mixture was poured into water, extracted with ethyl acetate and the crude obtained after evaporation of the organic layer was purified by flash chromatography on silica gel eluting with chloroform-methanol (100:5). 0.8 g of the title compound was obtained after crystallization from acetone, m.p. 135°–140° C.

Example 143

2-(4-Cyanophenyl)-8-{3-[4-(2-methoxyphenyl)-1-piperazinyl]propylcarbamoyl}-3-methyl-4-oxo-4H-1-benzopyran The title compound was prepared by the method described in Example 142, but using Intermediate CXX instead of 2-phenyl-4(1H)-quinolone-8-carboxylic acid. The crude material was purified by flash chromatography on silica gel eluting with chloroform-methanol (100:1). The title compound had a melting point of 167°–170° C., after crystallization from ethanol.

Example 144

6-Cyano-8-{3-[4-(2-methoxyphenyl)-1-piperazinyl]propylcarbamoyl}3-methyl-4-oxo-2-phenyl-4H-1-benzopyran The title compound was prepared by the method described in Example 142, but using Intermediate CXXII instead of 2-phenyl-4(1H)-quinolone-8-carboxylic acid. The crude material was purified by flash chromatography on silica gel eluting with dichloromethane-methanol (100:2). The title compound was obtained after crystallization from acetonitrile, m.p. 165.5°–167° C.

Example 145

8-{3-[4-(4-Fluoro-2-methoxyphenyl)-1-piperazinyl]propylcarbamoyl}-3-methyl-4-oxo-2-phenyl-4H-1-benzopyran The title compound was prepared by the method described in Example 133, but using 1-(4-fluoro-2-methoxyphenyl)piperazine (prepared as described in GB 2,161,807) instead of 1-(4-hydroxy-2-methoxy-phenyl)piperazine. The crude material was purified by flash chromatography on silica gel eluting with chloroform-2N methanolic triethylamine (100:1). The title compound was obtained after crystallization from acetonitrile, m.p. 169°–171° C.

Example 146

8-{3-[4-(3-Methoxyphenyl)-1-piperazinyl]-propylcarbamoyl}-3-methyl-4-oxo-2-phenyl-4H-1-benzopyran The title compound was prepared by the method described in Example 133, but using 1-(3-methoxyphenyl)piperazine instead of 1-(4-hydroxy-2-methoxyphenyl)piperazine. The crude material was purified by flash chromatography on silica gel eluting with dichloromethane-methanol gradient (100:2 to 100:3). The title compound was obtained after crystallization from acetonitrile, m.p. 130°–132.5° C.

Example 147

8-{3-[4-(4-Methoxyphenyl)-1-piperazinyl]-propylcarbamoyl}-3-methyl-4-oxo-2-phenyl-4H-1-benzopyran The title compound was prepared by the method described in Example 133, but using 1-(4-methoxyphenyl)piperazine instead of 1-(4-hydroxy-2-methoxyphenyl)piperazine. The crude material was purified by flash chromatography on silica gel eluting with dichloromethane-methanol (100:2). The title compound was obtained after crystallization from acetonitrile, m.p. 182°–184° C.

Example 148

3-Methoxy-8-{3-[4-(2-methoxyphenyl)-1-piperazinyl]propylcarbamoyl}-4-oxo-2-phenyl-4H-1-benzopyran The title compound was prepared following the procedure of Example 90, but using Intermediate CXXIV instead of 6-methoxy-4-oxo-2-phenyl-4H-1-benzopyran-8-carboxylic acid. The crude material was crystallized from ethanol, yielding the title compound, m.p. 145°–146° C.

Example 149

3-Hydroxy-8-{3-[4-(2-methoxyphenyl)-1-piperazinyl]propylcarbamoyl}-4-oxo-2-phenyl-4H-1-benzopyran The title compound was prepared according to Example 142, using Intermediate CXXXIII instead of 2-phenyl-4(1H)-quinolone-8-carboxylic acid. The crude product was recovered by filtration (in vacuo) was purified by flash chromatography on silica gel using dichloromethane/methanol (95:5) as the eluent. After evaporation to dryness, (in vacuo) of the solvent from the combined fractions, the residue was washed with hot acetone. The title compound was crystallized from acetonitrile, m.p. 196°–199° C.

Example 150

2-Cyclohexyl-3,4-dihydro-8-{3-[4-(2-methoxyphenyl)1-piperazinyl]propylcarbamoyl}-2H-1-benzopyran The title compound was obtained following the method described in Example 90 starting from 1.59 g of Intermediate CXXXVI instead of 6-methoxy-3-methyl-4-oxo-2-phenyl-4H-1-benzopyran- 8-carboxylic acid. The crude product was purified by flash chromatography eluting with an ethyl acetate/methanol (98:2) mixture. Evaporation of the solvent from (in vacuo) the collected fractions, was followed by crystallization from cyclohexane, to provide 1.5 g of the title compound, m.p. 79°–83° C.

Example 151

2-Benzyl-3-ethyl-7-{3-[4-(2-methoxyphenyl)-1-piperazinyl]propylcarbamoyl}benzo[b]furan This compound was prepared by the method described in Example 142, using Intermediate CXXVI instead of 2-phenyl-4-(1H)-quinolone-8-carboxylic acid. Crystallization from acetone/water (9:1) provided the title compound, m.p. 110°–112° C.

Example 152

8-{3-[4-(2-Isopropoxyphenyl)-1-piperazinyl]propylcarbamoyl}-3-methyl-4-oxo-2-phenyl-4H-1-benzopyran dihydrochloride This compound was prepared by the method described in Example 133, using 1-(2-isopropoxyphenyl)piperazine (prepared as described in Martin G. E. et al., *J. Med. Chem.*, 32, 1052 (1989)) instead of 1-(4-hydroxy-2-methoxyphenyl)piperazine. The reaction was conducted for 30 minutes. The crude product was purified by flash chromatography on silica gel eluting with dichloromethane/methanol (100:2). The pure title compound, obtained as a base, was converted in the usual manner into the dihydrochloride salt. The salt was crystallized from isopropanol/ethyl acetate (45:55), m p. 208°–212° C.

Example 153

8-{[3-[4-(2-Methoxyphenyl)-1-piperazinyl]propylcarbamoyl]methyl}-3-methyl-4-oxo-2-phenyl-4H-1-benzopyran This compound was prepared by the method described in Example 86, using Intermediate XLVII instead of 4-oxo-2-phenyl-4H-1-benzopyran-8-carboxylic acid. The title compound was purified by crystallization from ethyl acetate, m.p. 137°–140° C.

Example 154

8-{3-[4-[5-(1,4-Benzodioxanyl)]-1-piperazinyl]propylcarbamoyl}-3-methyl-4-oxo-2-phenyl-4H-1-benzopyran The title compound was obtained following the method described in Example 133, using 1-[5-(1,4-benzodioxanyl)]piperazine (prepared as described in EP 138,280) instead of 1-(4-hydroxy-2-methoxyphenyl)piperazine. The crude product was purified by flash chromatography (elution mixture chloroform/methanol 97:3). Crystallization from ethyl acetate/2-propanol (3:1) provided the title compound melting at 111°–117° C.

Example 155

3-Ethoxymethyl-8-{3-[4-(2-methoxyphenyl)-1-piperazinyl]propylcarbamoyl}-4-oxo-2-phenyl-4H-1-benzopyran This compound was prepared according to Example 142, using Intermediate CXLI instead of 2-phenyl-4(1H)-quinolone-8-carboxylic acid. The reaction was carried out for 3 hours. The crude product was purified by flash chromatography on silica gel eluting with dichloromethane/acetonitrile (100:2). Crystallization from acetonitrile provided the title compound, m.p. 129°–133° C.

Example 156

8-{[3-[4-(2-Methoxyphenyl)-1-piperazinyl]propylamino]methyl}-3-methyl-4-oxo-2-phenyl-4H-1-benzopyran trihydrochloride. 2.5 $H_2O$ To a mixture of 0.53 g of 8-formyl-3-methyl-4-oxo-2-phenyl-4H-1-benzopyran, 0.55 g of 3-[4-(2-methoxyphenyl)-1-piperazinyl]propylamine, 70 ml of 1,2-dichloroethane and 0.11 ml of acetic acid was added 0.64 g of sodium triacetoxyborohydride. The mixture was stirred at room temperature for 4.5 hours. The reaction mixture was poured into 100 ml of water and acidified with 37% hydrochloric acid. This was followed addition of cold 6N aqueous sodium hydroxide to make the solution alkaline. The mixture was extracted with ethyl acetate. The organic layer was washed with water and dried over anhydrous sodium sulfate. After evaporation of the solvent, (in vacuo) the residue was purified by flash chromatography on silica gel eluting with chloroform/methanol (100:5). The fractions containing the pure base were combined and the solvent was evaporated to dryness. The title compound, obtained as a base, was converted in the usual manner into the trihydrochloride salt, and crystallized from ethanol, m.p. 170°–176° C. (dec.).

Example 157

7-{3-[4-(2-Methoxyphenyl)-1-piperazinyl]propylcarbamoyl}-2-(4-nitrophenyl)indole A mixture of 2.2 g of methyl 2-(4-nitrophenyl)indol-7-carboxylate (prepared as described in Filacchioni G. et al., Il Farmaco Ed. Sci., 37, 353–365 (1982)), 1.4 g of potassium hydroxide, 20 ml of ethanol and 20 ml of water was stirred at reflux temperature for 1 hour. After cooling to room temperature, the mixture was poured into water and extracted with ethyl acetate. The aqueous layer was separated, acidified by addition 37% hydrochloric acid. The 2-(4-nitrophenyl)indole-7-carboxylic acid was collected by suction filtration and washed with water. The yield was 1.59 g.

The title compound was prepared by the method described in Example 142, using the indolecarboxylic acid prepared above instead of 2-phenyl-4(1H)-quinolone-8-carboxylic acid. The crude product was purified by flash chromatography on silica gel eluting with chloroform/methanol (98:2). Crystallization from ethyl acetate provided the title compound, m.p. 188°–191° C.

Example 158

8-{3-[4-(5-Hydroxy-2-methoxyphenyl)-1-piperazinyl]propylcarbamoyl}-3-methyl-4-oxo-2-phenyl-4H-1-benzopyran methanesulfonate. 0.75 $H_2O$.

A solution of 1.48 g of intermediate CXXXIV and 1.67 g of potassium carbonate in 10 ml of water was stirred at 100° C. in an open vessel until complete evaporation of the water was obtained. The residue was mixed with 1.42 g of Intermediate XXXVII. The mixture was warmed to 180° C. for 15 min. After cooling to room temperature, the vitreous mass was rinsed with dichloromethane, the inorganic materials filtered off and the solvent evaporated (in vacuo). The residue was purified by flash chromatography on silica gel eluting with an ethyl acetate/methanol mixture (95:5). This provided 0.69 g of the title compound as a base. The base was converted in the usual manner into its methanesulfonate, m.p. 207°–219° C. (acetonitrile).

Example 159

3-Ethyl-8-{3-[4-(2-methoxyphenyl)-1-piperazinyl]propylcarbamoyl}-4-oxo-2-phenyl-4H-1-benzopyran This compound was prepared according to Example 86, using 3-ethyl-4-oxo-2-phenyl-4H-1-benzopyran-8-carboxylic acid (prepared as described in Da Re et al., Chem. Ber. 99, 1962–1965 (1966)) instead of 4-oxo-2-phenyl-4H-1-benzopyran-8-carboxylic acid. Crystallization from ethanol provided the title compound, m.p. 133°–136° C.

Example 160

8-{3-[4-(2-Methoxyphenoxy)-1-piperidinyl]propylcarbamoyl}-3-methyl-4-oxo-2-phenyl-4H-1-benzopyran This compound was prepared by the method described in Example 133, using 4-(2-methoxyphenoxy)piperidine (prepared as described in Baswell R. F. Jr. et al., J. Med. Chem. 17, 1000°–1008 (1974)) instead of 1-(4-hydroxy-2-methoxyphenyl)piperazine. The reaction was carried out for 30 minutes. The crude product was purified by flash chromatography on silica gel eluting with gradient of chloroform/5N methanolic ammonia (100:2 to 100:3). Crystallization from 95% ethanol provided the title compound, m.p. 154°–156° C.

Example 161

8-{3-[4-(2,3-Dihydrobenzo[b]furan-7-yl)-1-piperazinyl]propylcarbamoyl}-3-methyl-4-oxo-2-phenyl-4H-1-benzopyran - 0.75 $H_2O$ This compound was prepared according to Example 133, using 1-(2,3-dihydrobenzo[b]furan-7-yl)piperazine (prepared in the same way as 1-[5-(1,4-benzodioxanyl)]piperazine, which is described in EP 138,280) instead of 1-(4-hydroxy-2-methoxy-phenyl)piperazine (reaction time; 30 minutes). The crude product was purified by flash chromatography on silica gel eluting with dichloromethane/5N methanolic ammonia (100:2). The pure title compound was stirred with a 1:1 mixture of water and diethyl ether and heated to 35°–45° C. until diethyl ether was distilled off. The product was collected by filtration, m.p. 94°–95° C.

Example 162

2-(2-Biphenylyl)-8-{3-[4-(2-methoxyphenyl)-1-piperazinyl]propylcarbamoyl}-3-methyl-4-oxo-4H-1-benzopyran dihydrochloride. 1.25 $H_2O$ This compound was prepared by the method described in Example 86, using Intermediate CXLIV instead of 4-oxo-2-phenyl-4H-1-benzopyran-8-carboxylic acid. The crude product was purified by flash chromatography on silica gel eluting with chloroform-5N methanolic ammonia (100:5). The pure base obtained was transformed, in the usual manner, into the dihydrochloride. Crystallization from ethanol/diethyl ether provided the title compound, m.p. 188°–194° C.

Example 163

8-{3-[4-(2-Methoxyphenyl)-1-piperazinyl]propylcarbamoyl}-3-methyl-2-(1-naphthyl)-4-oxo-4H-1-benzopyran This compound was prepared by the method described in Example 86, using Intermediate CXLIII instead of 4-oxo-2-phenyl-4H-1-benzopyran-8-carboxylic acid. The crude product was purified by flash chromatography on silica gel eluting with chloroform/5N methanolic ammonia (100:3). Crystallization from isopropanol provided the title compound, m.p. 134°–138° C.

Example 164

3-Benzyloxymethyl-8-{3-[4-(2-methoxyphenyl)-1-piperazinyl]propylcarbamoyl}- 2-phenyl-4H-1-benzopyran dihydrochloride This compound was prepared according to Example 84, using Intermediate CXLII instead of 4-oxo-2-phenyl-4H-1-benzopyran-8-carboxylic acid. The title compound, as the base, was dissolved in boiling ethanol and acidified with a solution of 3N ethanolic hydrogen chloride. The solid was collected by suction filtration and crystallized from ethanol m.p. 187°–192° C.

Example 165

3-Methyl-8-{3-[4-[2-[(4-morpholinylmethyl)benzoyloxy]phenyl]-1-piperazinyl]propylcarbamoyl}-4-oxo-2-phenyl-4H-1-benzopyran A mixture of 1.74 g of 8-{3-[4-(2-hydroxyphenyl)-1-piperazinyl]propylcarbamoyl}-3-methyl-4-oxo-2-phenyl-4H-1-benzopyran, prepared as described in Example 59, 2 ml of triethylamine and 70 ml of dichloromethane, was stirred and maintained at 0°–5° C. 4-(4-Morpholinylmethyl)benzoyl chloride, 1.22 g, (prepared as described in U.S. Pat. No. 4,623,486) was added, in portions, to the mixture. After 1 hour with the temperature maintained at 0°–5° C., the reaction was allowed to stand for 7 days at room temperature. The reaction mixture was extracted with water. The organic layer was dried over anhydrous sodium sulfate and evaporated to dryness (in vacuo). Crystallization from 96% ethanol provided 2 g of the title compound, m.p. 106°–108° C.

Example 166

8-{2-[4-(2-Methoxyphenyl)-1-piperazinyl]ethoxycarbonylamino}-3-methyl-4-oxo-2-phenyl-4H-1-benzopyran methanesulfonate A mixture of 2.8 g of 3-methyl-4-oxo-2-phenyl-4H-1-benzopyran-8-carboxylic acid, 2.2 ml of diphenylphosphorylazide, 1.4 ml of triethylamine and 2.6 g of 2-[4-(2-methoxyphenyl)-1-piperazinyl]ethanol in 30 ml of dioxane was stirred at reflux for 6 hours. The reaction was cooled to room temperature and filtered by suction. The filtrate was diluted with water (150 ml) and extracted with ethyl acetate. The organic layer was washed with water, dried on sodium sulfate and evaporated to dryness (in vacuo). The residue was purified by flash chromatography, eluting with an ethyl acetate/petroleum ether mixture (85:15). The pure title compound, yield 2 g, was converted into its methanesulfonate by the usual procedure, m.p. 177°–181° C., (ethyl acetate).

Example 167

8-{3-[4-(2-Methoxyphenyl)-1-piperazinyl]propylcarbamoyl]-3-methyl-2-(3-nitrophenyl)-4-oxo-4H-1-benzopyran A mixture of 5 g of Intermediate CXXX, 1.94 g of potassium tert-butoxide and 50 ml of anhydrous pyridine was stirred at 100° C. for 3 hours under nitrogen. After cooling to room temperature, the solvent was evaporated (in vacuo). The residue was diluted with water, acidified with dilute hydrochloric acid and extracted with ethyl acetate. The organic layer was washed with water, dried over anhydrous sodium sulfate and evaporated to dryness (in vacuo). The crude methyl 3-methyl-2-(3-nitrophenyl)-4-oxo-4H-1-benzopyran-8-carboxylate was crystallized from acetone. The yield was 0.69 g.

A mixture of the intermediate prepared above, 10 ml of 1,4-dioxane, 13 ml of methanol and 0.088 g of sodium hydroxide was stirred at 50° C. for 2 hours. After cooling to room temperature, the mixture was poured into water, acidified with 3N hydrochloric acid and concentrated (in vacuo). The solid was separated by filtration to provide 0.54 g of 3-methyl-2-(3-nitrophenyl)-4-oxo-4H-1-benzopyran-8-carboxylic acid.

The title compound was prepared according to Example 86, starting from the acid prepared above instead of 4-oxo-2-phenyl-4H-1-benzopyran-8-carboxylic acid. The crude product was purified by flash chromatography on silica gel eluting with chloroform/methanol (100:5). Crystallization from ethanol provided the title compound m.p. 135°–137° C.

Example 168

8-{3-[4-(2-Methoxyphenyl)-1-(1,4-diazepinyl)]propylcarbamoyl}-3-methyl-4-oxo-2-phenyl-4H-1-benzopyran The title compound was prepared according to the procedure reported in Example 133 using 1-(2-methoxyphenyl)-1,4-diazepine (prepared as described in W. ten Hoeve et al, J.O.C. 58, 5101–5106 (1993)) instead of 1-(4-hydroxy-2-methoxyphenyl)piperazine. The residue was purified by flash chromatography (elution mixture chloroform/4.8N methanolic ammonia; 96:4). This provided the pure title compound as a base, m.p. 123°–128° C. (ethyl acetate).

Example 169

2-Cyclohexyl-3,4-dihydro-4-hydroxy-8-{3-[4-(2-methoxyphenyl)-1-piperazinyl]-propylcarbamoyl}-2H-1-benzopyran and Example 170

3,4-Dihydro-4-hydroxy-8-{3-[4-(2-methoxyphenyl)1-piperazinyl]propylcarbamoyl}-2-phenyl-2H-1-benzopyran hydrochloride A solution of 7 g of 8-{3-[4-(2-Methoxyphenyl)-1-piperazinyl]propylcarbamoyl}-4-oxo-2-phenyl-4H-1-benzopyran, prepared in Example 86, in 350 ml of methanol was hydrogenated in a Parr apparatus in the presence of 2.3 g of 70% platinum dioxide at an hydrogen pressure of 40 psi. After 4 hours shaking and resting overnight, the catalyst was filtered off and the solvent evaporated (in vacuo). The oily residue was purified by flash chromatography by eluting with an ethyl acetate/methanol gradient of 99:1 up to 90:1.

The compound of Example 169 was eluted first (A fractions) followed by the compound of Example 170 (B fractions).

Evaporation (in vacuo) of the solvent from the A fractions and crystallization of the crude product from ethyl acetate provided 1.07 g of compound of Example 169. M.p. 128°–132° C.

The residue obtained from evaporation to dryness (in vacuo) of the B fractions was purified again by flash chromatography (eluant:ethyl acetate/methanol 98:2). The pure compound of Example 170 obtained as a base was dissolved in ethyl acetate and 1 equivalent of 0.92M ethanolic hydrogen chloride was added. The corresponding hydrochloride crystallized and was recovered by suction filtration. Recrystallization from 2-propanol provided 0.35 g of the compound of Example 170, m.p. 220°–222° C. The product contained 0.5 molar equivalents of 2-propanol.

Example 171

2-(1-Adamantyl)-8-{3-[4-(2-methoxyphenyl)-1-piperazinyl]propylcarbamoyl}-3-methyl-4-oxo-4H-1-benzopyran The title compound was prepared according to the method described in Example 90, starting from Intermediate CXXXVIII instead of 6-methoxy-3-methyl-4-oxo-2-phenyl-4H-1-benzopyran-8-carboxylic acid. The crude product was purified by flash chromatography eluting with an ethyl acetate/methanol mixture (9:1). Recrystallization from ethyl acetate/diisopropyl ether (1:2) provided the title compound, m.p. 141°–143° C.

Example 172

8-{5-[4-(2-Methoxyphenyl)-1-piperazinyl]pentylsulfonyl}-3-methyl-4-oxo-2-phenyl-4H-1-benzopyran The title compound was obtained following the procedure of Example 38, starting from Intermediate CXL instead of intermediate XLIV and stirring at 50° C. for 4 hours. The crude residue was crystallized from 95% ethanol, m.p. 120°–123° C.

Example 173

8-{3-[4-(2-Methoxyphenyl)-1-piperazinyl]propylcarbamoyl}-3-methyl-4-oxo-2-(3,4,5-triiodophenyl)-4H-1-benzopyran A mixture of 3.74 g of 2-hydroxy-N,3-[4-(2-methoxyphenyl)-1-piperazinyl]propyl-3-propionylbenzamide dihydrochloride, Intermediate CLXVIII, 35 ml of anhydrous pyridine and 7 g of 3,4,5-triiodobenzoyl chloride (prepared as described by Klemme C. L. et al, J. Org. Chem. 5, 508 (1940)) was stirred at reflux temperature for 13 hours. After cooling to room temperature, 6.8 g of 1,8-diazabicyclo[5.4.0]undec-7-ene was added to the mixture. Stirring was continued for 7 hours. The solvent was evaporated (in vacuo) and the residue rinsed with water, acidified to about pH 6 with 3N hydrochloric acid and extracted with chloroform. The organic layer was separated, washed with water, dried over anhydrous sodium sulfate and evaporated to dryness (in vacuo). The crude product was purified by flash chromatography on silica gel eluting with dichloromethane/isopropanol (95:5). The title compound, yield, 1.16 g, was characterized by NMR spectrum.

$^1$H-NMR spectrum at 200 MHz (CDCl$_3$, (δ)) 1.82 (q, 2H) NCH$_2$C̲H̲$_2$CH$_2$N 2.15 (s, 3H) CH$_3$ in 3, benzopyran ring 2.45–2.60 (m, 6H) NHCH$_2$CH$_2$C̲H̲$_2$N; piperazine ring, CH$_2$s in 2,6 2.75–2.90 (m, 4H) piperazine ring, CH$_2$s in 3,5 3.68 (q, 2H) NHC̲H̲$_2$CH$_2$CH$_2$N 3.84 (s, 3H) OCH$_3$ 6.70 (dd, 1H) methoxyphenyl ring, CH in 3 6.75–7.05 (m, 3H)

methoxyphenyl ring, CHs in 4,5,6 7.48 (dd, 1H) benzopyran ring, CH in 6 7.80–7.90 (bs, 1H) CONH 8.16 (s, 2H) phenyl ring, CHs in 2',6' 8.25–8.40 (m, 2H) benzopyran ring, CHs in 5,7

Example 174

2-Cyclopropyl-8-{3-[4-(2-methoxyphenyl)-1-piperazinyl]propylcarbamoyl}-3-methyl-4-oxo-4H-1-benzopyran This compound was prepared by the method described in Example 173, using cyclopropanecarbonyl chloride instead of 3,4,5-triiodobenzoyl chloride. After addition of 1,8-diazabicyclo[5.4.0]undec-7-ene, the reaction mixture was stirred at reflux temperature for 2 hours. The title compound was isolated in amorphous form melting at 139°–141° C.

Elemental analysis for $C_{28}H_{33}N_3O_4$: Calc. %: C, 70.71; H, 6.99; N, 8.83. Found %: C, 70.36; H, 6.99; N, 8.69.

Example 175

8-{5-[4-(2-Methoxyphenyl)-1-piperazinyl]pentyl}-3-methyl-4-oxo-2-phenyl-4H-1-benzopyran methanesulfonate The title compound was prepared as described in the third step of Example 53, starting from Intermediate CXLVII instead of 8-(4-oxobutyl)-3-methyl-4-oxo-2-phenyl-4H-1-benzopyran and using acetic acid instead of hydrochloric acid. The product was extracted with ethyl acetate. After removal of the solvent the crude product was purified by flash chromatography eluting with ethyl acetate/petroleum ether (8:2). The pure base was dissolved in ethyl acetate, and converted by the usual procedure into its methanesulfonate. The product was filtered and dried, to provide the title compound, m.p. 173°–178° C.

Example 176

8-{3-[4-(2-Methoxyphenyl)-1-piperazinyl]propylcarbamoyl}-3-methyl-2-(4-methylcyclohexyl)-4-oxo-4H-1-benzopyran The title compound was synthesized following the procedure described for Example 90, using Intermediate CXLIX instead of 6-methoxy-3-methyl-4-oxo-2-phenyl-4H-1-benzopyran-8-carboxylic acid. The reaction mixture was poured into water and the precipitated solid was filtered off. The product was recrystallized from ethyl acetate, m.p. 166°–167.5 C.

Example 177

2-Cyclopentyl-8-{3-[4-(2-methoxyphenyl)-1-piperazinyl]propylcarbamoyl}-3-methyl-4-oxo-4H-1-benzopyran This compound was prepared by the method described in Example 86, using Intermediate CLII instead of 4-oxo-2-phenyl-4H-1-benzopyran-8-carboxylic acid. The crude product was purified by flash chromatography on silica gel eluting with chloroform/methanol (98:2). Crystallization from acetonitrile provided the title compound, m.p. 135°–137° C.

Example 178

8-{3-[4-(2-Methoxyphenyl)-1-piperazinyl]propylcarbamoyl}-3-methyl-2-(1-phenylcyclopentyl)-4-oxo-4H-1-benzopyran This compound was prepared by the method described in Example 86, using Intermediate CLV instead of 4-oxo-2-phenyl-4H-1-benzopyran-8-carboxylic acid. Crystallization from ethanol provided the title compound, m.p. 171°–172° C.

Example 179

8-{3-[4-(2-Methoxyphenyl)-1-piperazinyl]propylcarbamoyl}-3-methyl-2-(1-methylcyclohexyl)-4-oxo-4H-1-benzopyran This compound was prepared by the method described in Example 86, using Intermediate CLVI instead of 4-oxo-2-phenyl-4H-1-benzopyran-8-carboxylic acid. Crystallization from acetonitrile provided the title compound, m.p. 120°–124° C.

Examples 180 and 181

2-(Bicyclo[2.2.1]hept-5-en-2-yl)-8-{3-[4-(2-methoxyphenyl)-1-piperazinyl]propylcarbamoyl}-3-methyl-4-oxo-4H-1-benzopyran Example 180 (exo isomer dihydrochloride)

Example 181 (endo isomer hydrochloride. 0.75 $H_2O$)

These compounds were prepared by the method described in Example 86, using Intermediate CLVIII instead of 4-oxo-2-phenyl-4H-1-benzopyran-8-carboxylic acid. The base was dissolved in ethanol and 2 equivalents of ethanolic hydrogen chloride were added to provide the title compound dihydrochloride as the exo isomer, m.p. 184°–188° C. after crystallization from ethanol and drying (in vacuo).

The amorphous material obtained by evaporation to dryness of the crystallization liquor was crystallized from acetone to provide 2-(bicyclo[2.2.1]hept-5-en-2-yl)-8-{3-[4-(2-methoxyphenyl)-1-piperazinyl]propylcarbamoyl}-3-methyl-4-oxo-4H-1-benzopyran hydrochloride. 0.5 $H_2O$ as 1:1 a mixture (endo-exo) of isomers (NMR), m.p. 171°–175° C. The base obtained from the above endo-exo mixture was purified by repeated flash chromatography on silica gel eluting with chloroform/3N methanolic ammonia (100:2). The fractions containing the first eluted substance were combined and the solvent were evaporated (in vacuo) to provide the crude base. The base was dissolved in chloroform and 1 equivalent of hydrogen chloride in isopropanol was added. After crystallization from acetonitrile the hydrochloride of the endo isomer was obtained, m.p. 178°–181° C.

Example 182

2-(Bicyclo[2.2.1]heptan-2-yl)-8-{3-[4-(2-methoxyphenyl)-1-piperazinyl]propylcarbamoyl}-3-methyl-4-oxo-4H-1-benzopyran hydrochloride hemi-hydrate The 1:1 mixture of endo-exo isomers 0.56 g from Examples 180 and 181, were combined with 30 ml of methanol and 0.15 g of 5% palladium on charcoal and reduced with hydrogen in a Parr apparatus at room temperature and 45 psi until the theoretical amount of hydrogen was absorbed. The catalyst was separated by filtration and the solvent was evaporated to dryness. The crude product was purified by crystallization from acetonitrile to provide 0.32 g of the title compound as a 1:1 mixture of endo-exo isomers, m.p. 172°–178° C.

Example 183

2-Cycloheptyl-8-{3-[4-(2-methoxyphenyl)-1-piperazinyl]propylcarbamoyl}-3-methyl-4-oxo-4H-1-benzopyran The title compound was prepared by the method described in Example 86, using Intermediate CLIX instead of 4-oxo-2-phenyl-4H-1-benzopyran-8-carboxylic acid. After quenching with water, the precipitate was extracted with chloroform. The organic layer was separated, dried over anhydrous sodium sulfate, and evaporated to dryness

Example 184

8-[3-[4-(2-Methoxyphenyl)-1-piperazinyl]propylcarbamoyl]-1-methyl-2-phenyl-1,2,3,4-tetrahydroquinoline This compound was prepared by the method described in Example 86, using Intermediate CLXIII instead of 4-oxo-2-phenyl-4H-1-benzopyran-8-carboxylic acid. The title compound was obtained as a thick oil and characterized by NMR spectrum.

$^1$H-NMR Spectrum at 200 MHz (CDCl3, ($\delta$) 1.75 (m, 2H) CONHCH$_2$CH$_2$CH$_2$ 1.95–2.30 (m, 2H) CH$_2$ in 3, tetrahydroquinoline ring 2.50 (m, 2H) CONHCH$_2$CH$_2$CH$_2$ 2.55–2.70 (m, 4H) CH$_2$s in 2 and 6, piperazine ring 2.72 (s, 3H) NCH$_3$ 2.75–2.90 (m, 2H) CH$_2$ in 4, tetrahydroquinoline ring 2.95–3.10 (m, 4H) CH$_2$ s in 3 and 5, piperazine ring 3.35–3.55 (m, 2H) CONHCH$_2$CH$_2$CH$_2$ 3.85 (s, 3H) OCH$_3$ 4.15 (dd, 1H) CH in 2, tetrahydroquinoline ring 6.80–6.95 (m, 4H) CHs of methoxyphenyl ring 7.05 ( dd, 1H) CH in 6, tetrahydroquinoline ring 7.25–7.40 (m, 6H) phenyl CHs in 2, tetrahydroquinoline and CH in 5, tetrahydroquinoline ring 7.65 (dd, 1H) CH in 7, tetrahydroquinoline ring 8.10 (m, 1H) CONH

Example 185

(Trans)-2-(4-methoxycyclohexyl)-8-{3-[4-(2-methoxyphenyl)-1-piperazinyl]propylcarbamoyl}-3-methyl-4-oxo-4H-1-benzopyran The title compound was synthesized according to the procedure described in example 90 using 0.73 g of Intermediate CLXVI instead of 6-methoxy-3-methyl-4-oxo-2-phenyl-4H-1-benzopyran-8-carboxylic acid. After the usual work up, crystallization from ethyl acetate provided 1.2 g of the title compound, m.p. 167.5°–169.5° C.

Example 186

(Cis)-2-(4-methoxycyclohexyl)-8-{3-[4-(2-methoxyphenyl)-1-piperazinyl]propylcarbamoyl}-3-methyl-4-oxo-4H-1-benzopyran The title compound was synthesized according to the procedure described in Example 90, using 0.65 g of Intermediate CLXVII instead of 6-methoxy-3-methyl-4-oxo-2-phenyl-4H-1-benzopyran-8-carboxylic acid. The usual work up provided 1 g of the title compound as solid, m.p. 121°–125° C.

$^1$H-NMR spectrum at 200 MHz (CDCl$_3$ ($\delta$)): 8.38–8.48 (m, 2H) benzopyran, CHs in 5 and 7 7.65–7.77 (bt, 1H) NHCO 7.42 (dd, 1H) benzopyran, CH in 6 6.53–7.03 (m, 4H) phenyl ring CHs 3.84 (s, 3H) aryl OCH$_3$ 3.51–3.75 (m, 2H) CH$_2$ NHCO 3.52–3.61 (m, 1H) CHOCH$_3$, eq. 3.37 ( s, 3H) CHOCH$_3$, ax. 2.90–3.16 (m, 5H) cyclohexyl CH in 1 and piperazine CH$_2$ 2.50–2.72 (m, 6H) CH$_2$N and piperazine CH$_2$ 1.97–2.25 (m, 9H) cyclohexyl CHs, CH$_3$C, CH$_2$–CH$_2$, -NHCO 1.40–1.80 (m, 4H) cyclohexyl CHs

Example 187

8-{3-[4-(7-Benzofuranyl)-1-piperazinyl]propylcarbamoyl}-3-methyl-4-oxo-2-phenyl-4H-1-benzopyran The title compound was synthesized following the method described in Example 133, using 1-(7-benzofuranyl)piperazine (prepared as described in I. van Wijngaarden et al, J. Med. Chem. 31, 1934–1940 (1988)). The crude product was purified by flash chromatography (eluent chloroform/methanol 97:3). Evaporation (in vacuo) to dryness of the combined fractions provided the title compound, m.p. 120°–121° C. (ethyl acetate/diisopropyl ether 1:1).

$^1$H-NMR Spectrum at 200 MHz (CDCl$_3$): 8.32–8.42 (m, 2H) benzopyran, CHs in 5 and 7 7.64–7.78 (m, 3H) NHCO and phenyl CHs in 2,6 7.50–7.62 (m, 4H) phenyl, CHs in 3,4,5 and benzofuran, CH in 2 7.47 (dd, 1H) benzopyran, CH in 6 7.10–7.25 (m, 2H) benzofuran, CHs in 4 and 5 6.75 (d, 1H) benzofuran CH in 3 6.63 (dd, 1H) benzofuran CH in 6 3.50–3.63 (m, 2H) CH$_2$NHCO 3.13–3.28 (m, 4H) piperazine CH$_2$s 2.51–2.63 (m, 4H) piperazine CH$_2$s 2.46 (t, 2H) CH$_2$N 2.19 (s, 3H) CH$_3$C 1.68–1.88 (m, 2H) C–CH$_2$C

Example 188

2-(Bicyclo[2.2.1]heptan-2-yl)-8-{3-[4-(2-methoxyphenyl)-1-piperazinyl]propylcarbamoyl}-3-methyl-4-oxo-4H-1-benzopyran hydrochloride hydrate (exo isomer).

A 97:3 mixture of exo:endo isomers, 0.68 g, from Examples 180 and 181, were combined with 40 mL of methanol and 0.2 g of 5% palladium on charcoal and reduced with hydrogen in a Parr apparatus at room temperature and 45 psi until the theoretical amount of hydrogen was absorbed. The catalyst was separated by filtration and the solvent was removed (in vacuo). The crude product was solidified by stirring with a minimum amount of acetone. Crystallization from acetonitrile provided the title compound, 0.35 g, as a 98:2 mixture of exo:endo isomers, m.p. 177°–181° C.

Example 189

8-{3-[4-(2-Chlorophenyl)-1-piperazinyl]propylcarbamoyl}-3-methyl-4-oxo-2-phenyl-4H-1-benzopyran.

The title compound was prepared according to Example 133, using 1-(2-chlorophenyl)piperazine instead of 1-(4-hydroxy-2-methoxyphenyl)piperazine. The reaction was conducted for 30 minutes. The crude product was purified by flash chromatography on silica gel eluting with ethyl acetate/methanol (gradient 100:0 to 100:2). Crystallization from ethanol provided the title compound, m.p. 149°–151° C.

Example 190

8-{3-[4-(4-Chlorophenyl)-1-piperazinyl]propylcarbamoyl}-3-methyl-4-oxo-2-phenyl-4H-1-benzopyran.

The title compound was prepared according to Example 133, using 1-(4-chlorophenyl)piperazine instead of 1-(4-hydroxy-2-methoxyphenyl)piperazine. The reaction was conducted for 30 minutes. The crude product was purified by flash chromatography on silica gel eluting with ethyl acetate/methanol (gradient 100:0 to 100:20). Crystallization from acetonitrile provided the title compound m.p. 200°–204° C.

PHARMACOLOGICAL DATA

Methodology

Male Sprague Dawley rats [Crl: CD'BR] of 175–300 g b.w., female Albino Swiss mice [Crl: CD-1 (ICR) BR] 20–30 g b.w., male Beagle dogs (8–12 kg b.w.) were obtained from Charles River, Italy and Nossan (Correzzana, Milan, Italy), respectively. Male white New-Zealand rabbits, weighing 3–3.5 kg, aging 6–8 months, were obtained from Conelli Allevamenti (Novara-Italy). Animals were housed with free access to food and water and maintained on forced light-dark cycle at 22°–24° C. until the day of experiments.

Acute toxicity

The acute toxicity of synthesized compounds was evaluated in female albino Swiss mice after intraperitoneal and oral administration. Four logarithmic scaled doses of the compounds were dissolved or suspended in 0.5% Methocel and administered in a volume of 10 ml/kg to groups of 4 mice/dose. Mortality was recorded 7 days after the administration. Data analysis: the $LD_{50}$ values and their fiducial limits were calculated according to the method of Weil (*Biometrics*, 8, 249, 1952).

Receptor Binding studies:

The following receptor binding studies, as well as the experimental data reported below, establish compounds of the invention as 1-blockers, i.e. to be within a class of substances widely used as antihypertensive and agents that can be used for the relief of symptoms associated with obstructive disorders of the lower urinary tract, including (but not limited to) benign prostatic hypertrophy (BPH). See, e.g., Frishman, W. H. et al., *Medical Clinics of N. America*, 72, 427, 1988 and references cited therein. Moreover, as phenylpiperazines (and many compounds containing this structure) can be good ligands for G protein coupled receptors such as the $\alpha 2$, $5\text{-HT}_{1a}$ and $D_2$ receptors (see for example: Russo F. et al. *J. Med. Chem.*, 34, 1850, 1991), the affinity of the compounds of the present invention for these different receptors has been evaluated, in vitro, utilizing the receptor binding technique.

Suzuki et al. *Jap. J. Pharmacol.* 58 (Suppl. 1):173P (1992) have characterized the subtype of the $\alpha_1$ receptor of human prostate as $\alpha_{1A}$. If this characterization is correct, then a high affinity for the $\alpha_{1A}$ receptor would be desirable for compounds active on the lower urinary tract and especially on the prostate.

What is undesirable for compounds selective for the lower urinary tract is an affinity for the $\alpha_2$ and $D_2$ receptor. Such affinity is also undesirable for compounds with selectivity for the $5HT_{1A}$ receptors and for compounds to be used as antihypertensives.

[$^3$H]prazosin binding ($\alpha_1$ receptors)

Rat cerebral cortices were homogenized in 50 volumes of original wet weight of ice-cold 50 mM Tris-HCl buffer pH 7.4. The homogenates were centrifuged at 48,000×g for 10 minutes, and the pellets were resuspended in the same volume of ice-cold buffer, centrifuged and resuspended two more times. The final pellets obtained were resuspended in 100 vols of 50 mM Tris-HCl buffer (containing 0.1% ascorbic acid and 10 μM pargyline) pH 7.4 and incubated (1 ml/sample) for 30 min at 25° C. with 0.35 nM [$^3$H]prazosin, in absence or presence of 5–10 concentrations of the displacing compound to be tested. Non specific binding was determined in the presence of 2 μM prazosin. h e incubations were terminated by rapid filtration through Whatman GF/B filters using a Brandel cell harvester and the filters were washed with 3×3 ml of ice-cold buffer. The radioactivity retained on the filters was determined by liquid scintillation counting.

[$^3$H]prazosin binding ($\alpha_{1A}$ receptors).

Rat hippocampi were homogenized in 50 volumes of original wet weight of ice-cold 50 mM Tris-HCl buffer pH 7.4. The homogenates were centrifuged at 48,000×g for 10 minutes, the pellets were resuspended in the same volume of ice-cold buffer and preincubated for 30 min at 37° C. with 10 μM chloroethylclonidine (CEC). The homogenates were centrifuged and resuspended in Tris-HCl buffer two more times. The final pellets obtained were resuspended in 80–120 vols of Tris-HCl buffer (containing 0.1% ascorbic acid and 10 μM pargyline) and incubated (2 ml/sample) for 30 min at 25° C. with 0.25–0.35 nM [$^3$H]prazosin, in absence or presence of 10 concentrations of the displacing compound to be tested. Non specific binding was determined in the presence of 10 μM phentolamine. The incubations were terminated by rapid filtration through Whatman GF/B filters using a Brandel cell harvester and the filters were washed with 3×3 ml of ice-cold buffer. The radioactivity retained on the filters was determined by liquid scintillation counting.

[$^3$H]prazosin binding ($\alpha_{1B}$ receptors).

Rat liver was homogenized in 50 volumes of original wet weight of ice-cold 50 mM Tris-HCl buffer pH 7.4 and filtered through four layers of cheesecloth. The homogenates were centrifuged at 48,000×g for 10 minutes, and the pellets were resuspended in the same volume of ice-cold buffer, incubated for 30 minutes at 37° C., centrifuged and resuspended two more times. The final pellets obtained were resuspended in the same volume of Tris-HCl buffer pH 7.4 (containing 0.1% ascorbic acid and 10 μM pargyline) and incubated (2 ml/sample) for 30 min at 25° C. with 0.4–0.6 nM [$^3$H]prazosin in absence or presence of 5–10 concentrations of the displacing compound to be tested. Non specific binding was determined in the presence of 10 μM phentolamine. The incubations were terminated by rapid filtration through Whatman GF/B filters using a Brandel cell harvester and the filters were washed with 3×3 ml of ice-cold buffer. The radioactivity retained on the filters was determined by liquid scintillation counting.

[$^3$H]rauwolscine binding ($\alpha_2$ receptors)

Rat cerebral cortices were homogenized in 50 volumes of original wet weight of ice-cold 50 mM Tris-HCl buffer pH 7.4. The homogenates were centrifuged at 48,000×g for 10 minutes, and the pellets were resuspended in the same volume of ice-cold buffer, incubated for 15 minutes at 37° C., centrifuged and resuspended two more times. The final pellets obtained were resuspended in 100 vols of 50mM Tris-HCl buffer (containing 0.1% ascorbic acid and 10 μM pargyline) pH 7.4 and incubated (1 ml/sample) for 30 min at 25° C. with 0.7–1.0 nM [$^3$H]rauwolscine, in absence or presence of 5–10 concentrations of the displacing compound to be tested. Non specific binding was determined in the presence of 10 μM phentolamine. The incubations were terminated by rapid filtration through Whatman GF/B filters using a Brandel cell harvester and the filters were washed with 3×3 ml of ice-cold buffer. The radioactivity retained on the filters was determined by liquid scintillation counting.

[$^3$H]spiperone binding ($D_2$ receptors)

Rat striata were homogenized in 20 volumes of original wet weight of ice-cold 50 mM Tris-HCl buffer pH 7.4, diluted to 30 vols and centrifuged at 48,000×g for 10 minutes. The pellets were resuspended in the 200 vols of 50 mM Tris-HCl buffer (containing: 120 mM NaCl, 5 mM KCl, 2 mM CaCl2, 1mM $MgCl_2$, 0.1% ascorbic acid and 10 μM pargyline) pH 7.4 and incubated (1 ml/sample) for 15 min at 25° C. with 0.3 nM [$^3$H]spiperone, in absence or presence of 5–10 concentrations of the displacing compound to be tested. Non specific binding was determined in the presence of 1 μM (+)butaclamol. The incubations were terminated by rapid filtration through Whatman GF/B filters using a Brandel cell harvester and the filters were washed with 3×3 ml of ice-cold buffer. The radioactivity retained on the filters was determined by liquid scintillation counting.

[$^3$H]8-OH-DPAT binding ($5HT_{1A}$ receptors)

Rat hippocampi were homogenized in 50 volumes of original wet weight of ice-cold 50 mM Tris-HCl buffer pH 7.4. The homogenates were centrifuged at 48,000×g for 10 minutes, and the pellets were resuspended in the same volume of ice-cold buffer, incubated for 10 minutes at 37° C., centrifuged and resuspended two more times. The final pellets obtained were resuspended in 100 vols of 50 mM Tris-HCl buffer (containing 0.1% ascorbic acid and 10 μM pargyline) pH 7.4 and incubated (1 ml/sample) for 30 min at 25° C. with 1 nM [$^3$H]8-OH-DPAT, in absence or presence of 5–10 concentrations of the displacing compound to be tested. Non specific binding was determined in the presence of 10 μM 5-HT. The incubations were terminated by rapid filtration through Whatman GF/B filters using a Brandel cell harvester and the filters were washed with 3×3 ml of ice-cold buffer. The radioactivity retained on the filters was determined by liquid scintillation counting. These receptor binding studies serve to establish compounds of the present invention as ligands for the $5HT_{1A}$ receptor. As previously reported, compounds that are $5HT_{1A}$ ligands exert anxiolytic and antidepressant effects in animals and humans (Hamon, M. et al., *Ann. N.Y. Acad. Sci.*, 600, 114, 1990; Traber J. et al., *T.I.P.S.*, 8, 437, 1987). In all binding studies the samples were run in triplicate. All the compounds were initially tested at $1\times10^{-6}$M concentration, and in presence of significant displacing activity, a complete competition curve was generated (down to a concentration of $10^{-11}$M). The competition curves were always analyzed (to evaluate the $IC_{50}$ values) by non linear curve fitting of the logistic equation according to the method reported by De Lean et al. (*Am. J. Physiol.*, 235, E97, 1978), utilizing the ALLFIT program (publicly available from the National Institute of Health (N.I.H.) Bethesda, Md., USA) written for the IBM PC.

$K^+$-induced contractions of rat bladder strips:

The whole bladder of the rat was removed and immediately placed in Krebs solution warmed at 37° C. Strips of detrusor muscle (20–30 mm long, 1–2 mm wide), were cut from the dome of the bladder. Each strip was placed in a 10 ml organ bath and connected, under a constant load of 1 g, to an isometric strain gauge (DY-1 Basile, Comerio, Varese, Italy). Contractions were recorded by means of a Basile 7070 polygraph. After a 60 minute equilibration period the strips were exposed to 80 mM KCl (final concentration). This produced a rapid phasic contraction followed by a slow ensuing and sustained tonic component. When the tonic contraction was stable, the strips were washed and 30 minutes later a new contraction was induced. After having recorded two or more reproducible responses, one concentration of the tested compounds was added to the bath and 30 minutes later a new contraction was induced. The experimental groups consisted of at least two preparations taken from different animals for each concentration of compound tested. The IC50 values of inhibition of agonist-induced contractions were evaluated by linear regression analysis.

Effects on noradrenaline-induced mortality in rats

Groups of 10 rats, fasted overnight, were intravenously (caudal vein) treated with different doses of the tested compounds, 30 minutes before the injection of 0.6 mg/kg i.v. noradrenaline (2 ml/kg). This dose of noradrenaline induced a 100% of mortality in the control animals within a few minutes. Survival rate after 24 hours was used as the evaluation criterium for efficacy of the test compound. ED50 values (compound's dose that prevent the death in the 50% of the animals treated with noradrenaline) and confidence limits were obtained by the method of Bliss (*Q. J. Pharm. Pharmacol.* 11, 192, 1935) by utilizing the percentage of survival for each dose-level of the compound tested. The aim of the study was to evaluate the in vivo alpha-antagonistic activity of the compounds by utilizing the inhibition of mortality induced by noradrenaline in rats as reported by Janssen et al. (*Arzneim. Forsch.*, 15, 104, 1965).

Hypotensive effect in normotensive rats

The animals were anaesthetized with pentobarbital sodium (50 mg/kg i.p. for induction and, 30 minutes later, 50 mg/kg s.c. for maintenance of anaesthesia). The left jugular vein was cannulated with a polyethylene cannula (PE 50) for the intravenous compound administration. The right carotid artery was cannulated with a polyethylene cannula, filled with heparin (50 U.I., 0.4 ml/rat), for the measurement of arterial blood pressure. In order to measure the systolic and diastolic blood pressure, the arterial catheter was connected to pressure transducer and recordings were made on a San-ei Rectigraph polygraph. After a stabilizing period following surgical procedure (30 min), in which arterial pressure was continuously monitored, the compounds were administered in single doses. Each dose of each compound was tested in a single animal. Groups of 3–4 animals for each dose were used. Systolic and diastolic blood pressure were continuously recorded before and after compound administration, and quantified manually from the polygraph tracing. All values were expressed as mean±S.E. The statistical significance of the difference in systolic and diastolic blood pressure (SBP, DBP) values before and after treatment was analyzed by Student's t test for paired data. In order to compare the effects of the compounds, dose-response curves (log dose transformation) were constructed by computing the percent decrease in diastolic blood pressure at the peak effect. Regression was considered significant when the correlation coefficient showed $P>0.01$, using analysis of variance. Linear regression equations were used in order to evaluate the theoretical effectiveness as $ED_{25}$ (the effective dose inducing a 25% decrease in diastolic blood pressure, with 95% confidence limits).

Effects on Urethral Contractions (induced by noradrenaline injection) and Blood Pressure in Dogs. after i.v. administration The experiments were performed according to the method of Imagawa et al. (*J. Pharmacol. Methods*, 22, 103–111, 1989), with substantial modifications, as follows: adult male beagle dogs, weighing 8–10 kg, were anaesthetized with pentobarbital sodium (30 mg/kg i.v. and 2 mg/kg/h i.v.), intubated and spontaneously ventilated with room air. In order to monitor systemic blood pressure (BP), a PE catheter was introduced into the aortic arch through the right common carotid artery. A collateral of the left femoral vein was cannulated for infusion of anaesthetic, and the right femoral vein was cannulated for administration of compounds. For intraarterial (i.a.) injection of noradrenaline (NA), a PE catheter was introduced into the lower portion of abdominal aorta via the right external iliac artery. Through such procedure, NA was selectively distributed to the lower urinary tract. Via a midline laparotomy, the urinary bladder and proximal urethra were exposed. In order to prevent the filling of the bladder, the two ureters were cannulated and the urine led outside. In order to record the prostatic urethral pressure, a Mikro-tip catheter (6F) was introduced into the bladder via the external urethral meatus, and withdrawn until the pressure transducer was positioned in the prostatic urethra. A ligature was secured between the neck of the bladder and urethra to isolate the response of the latter and avoid any interaction with the bladder. Another ligature was put around the Mikro-tip catheter at the external urethral meatus, to secure the catheter itself. After a stabilizing period following surgical procedure (30 min), in which arterial and prostatic urethral pressure were continuously monitored as basal values, i.a. administration of NA was made at intervals of 10 min. The dose of NA chosen was such to produce an increase of at least 100% in urethral pressure. The test compounds were administered i.v. in a cumulative manner with intervals of 15–20 min between administrations. I.a. injections of NA were repeated approximately 5 min. after every dosing of test compound. Dose response curves were constructed computing the percentage inhibition to the increase in urethral pressure (NA induced), and the percentage drop in blood pressure produced by the test compound. $ED_{25}$ for diastolic blood pressure (dose inducing a 25% decrease) and $ID_{50}$ (dose inducing a 50% inhibition of NA-induced increase in urethral pressure) were computed by means of linear regression analysis.

Effects on urethral contractions (induced by hypogastric nerve stimulation) and blood pressure in dogs after i.v. and i.d. administration The animals were anaesthetized with pentobarbital sodium (30 mg/kg i.v. for induction and 5 mg/kg/h i.v. for maintenance), intubated and spontaneously ventilated with air room. Systemic blood pressure was monitored via a Mikro-tip 6F pressure transducer introduced into the aortic arch through the right common carotid artery. A collateral of the left femoral vein was cannulated with a PE catheter for infusion of the anaesthetic. A paramedian vertical suprapubic incision extending from the base of the pelvis to the mid-abdominal region was made and the bladder and the prostate were exposed. The bladder was manually emptied with a syringe. The hypogastric nerve was freed from the surrounding tissue and cut 1 cm distal from the inferior mesenteric ganglion. The distal end of right or left branch of the nerve was placed on a bipolar platinum electrode. Prostatic urethral pressure was monitored with a Mikro-tip catheter (5F) introduced into the bladder via the external urethral meatus, and withdrawn until the pressure transducer was positioned in the prostatic region of the urethra. A ligature was secured between the neck of the bladder and urethra to isolate the response of the latter and to avoid any interaction with the bladder. Another ligature was put around the Mikro-tip catheter at the external meatus, to secure the catheter itself. For intravenous administration of test compounds a collateral of the right femoral vein was cannulated with PE catheter. For intraduodenal administration, the duodenum was isolated and exposed via a second abdominal laparotomy and cannulated for compound administration. Intravenous administration: hypogastric nerve stimulation were made with a train of rectangular pulses of 10–15 V, 10–30 Hz, width 5 msec, 8 sec duration. After a stabilizing period following surgical procedure (30 min.) in which both arterial and prostatic urethral pressure were continuously monitored, five or more stimulations of the hypogastric nerve were made at intervals of 10 min, and the mean of the urethral responses considered as basal increase of urethral pressure. The compounds were administered in cumulative way with intervals of 15 min among the doses. Hypogastric nerve stimulation was repeated 5 min after each dose. Intraduodenal administration: hypogastric nerve stimulation were made with a train of rectangular pulses of 10 V, 10–30 Hz, width 5 msec, 7 sec duration. After a stabilizing period following surgical procedure (30 min.) in which both arterial and prostatic urethral pressure were continuously monitored, five or more stimulations of hypogastric nerve were made at intervals of 15 min, and the means of urethral responses considered as basal increase of urethral pressure. After administration of the compounds, stimulations of urethra were performed from 15 up to 270 min, with intervals of 15 min in the first hour, and intervals of 30 min in the following hours. The statistical significance of the differences after treatments vs basal values was analyzed by one-way or two-way ANOVA and Dunnett's test. In order to compare the effects of the administered compound, dose response curves (log dose transformation) were constructed by computing, at the peak effect, the percent decrease in diastolic blood pressure and the percent inhibition of the increase in urethral pressure induced by hypogastric nerve stimulation. Linear regression equations were then used in order to evaluate the theoretical effectiveness as $ED_{25}$ (the effective dose inducing a 25% decrease in diastolic and systolic blood pressure with 95% confidence limits) and $ID_{50}$ (dose inhibiting by 50% the increase in urethral pressure, with 95% confidence limits). After the i.d. administration, in order to evaluate the time course of the effects on urethral and blood pressure, $AUC_{0-270\ min}$ (area under the inhibition curve for the urethral pressure) and $AOC_{0-270\ min}$ (area over the hypotensive curve for diastolic blood pressure), were computed by means of trapezoidal rule. For the urethral pressure the $ED_{50}\ AUC_{0-270\ min}$ was then computed by linear regression analysis. $ED_{50}\ AUC_{0-270\ min}$ represents the oral dose requested to produce a theoretical inhibition of 50% in area under the inhibition curve in the time considered.

Effects on noradrenaline-induced contractions of urethra and on blood pressure in rabbits after i.v. administration The animals were anaesthetized with pentobarbital sodium (20 mg/kg i.v.) and urethane (1.2 g/kg i.v.), intubated and spontaneously ventilated with air room. Systemic blood pressure was monitored via a Mikro-tip 6F pressure transducer introduced into the aortic arch through the right common carotid artery. A paramedian vertical suprapubic incision extending from the base of the pelvis to the mid-abdominal region was made and the bladder and the prostatic portion of the urethra were exposed. The bladder was manually emptied with a syringe. Prostatic urethral pressure was monitored with a Mikro-tip catheter (5F) introduced into the bladder via the external urethral meatus, and withdrawn until the pressure transducer was positioned in the prostatic region of the urethra. A ligature was secured between the neck of the bladder and urethra to isolate the response of the latter and to avoid any interaction with the bladder. Another ligature was put around the Mikro-tip catheter at the external meatus, to secure the catheter itself. The jugular vein was cannulated with a PE catheter for injection of the compound or noradrenaline. For intraarterial administration of noradrenaline the right femoral artery was cannulated with a PE catheter, advanced up to the lower portion of abdominal aorta. Intraarterial administration of noradrenaline: after a stabilizing period following surgical procedure (30 min) in which arterial and prostatic urethral pressure were continuously monitored, five or more injection of noradrenaline were made in the femoral artery at intervals of 15 min, and the mean of urethral responses was considered as basal increase of urethral pressure. Such procedure allows NA to be selectively distributed in the lower urinary tract, with very low effects on cardiovascular system. The dose of noradrenaline chosen (3–10 μg/kg) was such to produce an increase of at least 80–100% in urethral pressure. The compounds were administered in cumulative way with intervals of 15 min. among the doses; NA stimulations were repeated 5 min after every dose. Intravenous administration of noradrenaline: after a stabilizing period following surgical procedure (30 min.) in which arterial pressure was continuously monitored, five or more injections of noradrenaline in the jugular vein were made at intervals of 10 min, and the mean of systolic blood pressure responses considered as basal increase of systolic pressure. The compounds were administered in cumulative way with intervals of 15 min. among the doses. NA stimulation were repeated 5 min after every dose.

In this protocol, the urethral pressure was not recorded, but all the animals were submitted to the same surgical procedure as in previous protocol. Linear regression equations were used in order to evaluate the theoretical effectiveness as $ID_{50}$ (dose inhibiting 50% increase in urethral pressure and systolic blood pressure, with 95% confidence limits) and $ED_{25}$ (the effective dose inducing a 25% decrease in diastolic blood pressure, with 95% confidence limits). The effects on blood pressure ($ED_{25}$ on diastolic BP) were computed considering together the hypotensive effects obtained in the two protocols.

Results

Compounds as prepared in the Examples were tested according to the methods reported above, and the results are given in the Tables below, together with comparative results for the reference standards used. Compounds having receptor affinity ($IC_{50}$ values) lower than about 500 nM are generally considered to have good affinity. Compounds with $IC_{50}$ values less than 100 nM are generally preferred.

TABLE I

| Compound Example No. | Receptor Binding $IC_{50}$ (nM) | | Acute Toxicity in Mice $LD_{50}$ (mg/kg) | | K+ Stimulation of Rat Bladder $IC_{50}$ (µM) Contractions | |
|---|---|---|---|---|---|---|
| | $\alpha_1$ | 5-$HT_{1A}$ | i.p. | p.o | Phasic | Tonic |
| 4 | 550 | 55 | 346 | 732 | >10 | >10 |
| 5 | 20 | 19 | 621 | >3000 | >10 | >10 |
| 6 | 107 | 1000 | 233 | — | >10 | >10 |
| 7 | 86 | 155 | 384 | 1915 | — | — |
| 8 | 66 | 111 | >500 | 1915 | — | — |
| 9 | 27 | 18 | 620 | >3000 | — | — |
| 11 | 29 | 9 | 247 | 297 | 2.9 | 3.0 |
| 13 | 68 | 229 | >1000 | >3000 | 10.0 | 10.0 |
| 14 | 61 | 6 | 140 | 559 | <10 | <10 |
| 15 | 8 | 131 | 306 | 496 | — | — |
| 16 | 220 | 1050 | 345 | 778 | 1.6 | 2.2 |
| 17 | 59 | 910 | 299 | 608 | 8.8 | 3.8 |
| 18 | 270 | >1000 | 457 | 3000 | — | — |
| 19 | 165 | 340 | >1000 | >3000 | >10 | >10 |
| 20 | 169 | 85 | 297 | 594 | 2.7 | 2.5 |
| 21 | 17 | 33 | 297 | 566 | 1.7 | 1.7 |
| 22 | 117 | 48 | >500 | >2000 | — | — |
| 24 | 690 | 212 | >1000 | >3000 | <10 | <10 |
| 26 | 270 | >1000 | >500 | >2000 | <10 | <10 |
| 27 | 23 | 124 | 399 | >3000 | 1.0 | 0.8 |
| 28 | 120 | 96 | 203 | 1127 | <10 | <10 |
| 29 | 86 | 45 | 730 | >3000 | 10.0 | 10.0 |
| 32 | 119 | 46 | 301 | >2000 | 10.0 | >10 |
| 33 | 17 | 38 | 399 | >2000 | 10.0 | 10.0 |
| 34 | 30 | 34 | >500 | — | 2.8 | 3.6 |
| 35 | 15 | 8 | 329 | 959 | 10.0 | 10.0 |
| 36 | 18 | 54 | >500 | >2000 | — | — |
| 37 | 32 | 77 | >500 | >2000 | — | — |
| 38 | 20 | 344 | >500 | >2000 | <10 | <10 |
| 39 | 90 | 170 | >1000 | >3000 | — | — |
| 40 | 75 | 83 | 140 | 349 | 0.5 | 0.9 |
| 41 | 43 | 53 | 399 | 2241 | 0.7 | 1.4 |
| 42 | 7 | 39 | 459 | 2163 | 10.0 | 10.0 |
| 43 | 166 | >1000 | — | — | — | — |
| 44 | 685 | 201 | 84 | 399 | 0.6 | 0.5 |
| 45 | 15 | 106 | 329 | 1727 | <10 | <10 |
| 46 | 86 | 23 | — | — | — | — |
| 47 | 36 | 23 | 330 | 1047 | 2.7 | 5.2 |
| 48 | 104 | 5 | 500 | 1914 | <10 | <10 |
| 49 | 152 | 9 | 432 | >2000 | <10 | <10 |
| 50 | 39 | 300 | 211 | 299 | >10 | <10 |
| 51 | 22 | 84 | >500 | >2000 | — | — |
| 52 | 89 | 2 | 127 | 224 | <10 | <10 |
| 53 | 7 | 41 | 127 | 1020 | — | — |
| 54 | 35 | 143 | 106 | 421 | — | — |
| 55 | 291 | >1000 | 128 | >2000 | <10 | <10 |
| 56 | 25 | 748 | >500 | — | — | — |
| 57 | 69 | >1000 | 500 | >2000 | — | — |
| 59 | 5 | 9 | >500 | 278 | — | — |
| 60 | 25 | 45 | 203 | 329 | — | — |
| 61 | 36 | 11 | 315 | 592 | — | — |
| 62 | 252 | 278 | 128 | 344 | — | — |
| 63 | 194 | 99 | 309 | 479 | — | — |
| 64 | 40 | 11 | 231 | — | — | — |
| 65 | 113 | 26 | — | — | — | — |
| 66 | 57 | 56 | 404 | 601 | — | — |
| 67 | 4 | 4 | 508 | 1868 | — | — |
| 68 | 29 | 13 | — | — | — | — |
| 69 | 16 | 87 | 344 | — | — | — |
| 70 | 53 | 85 | >500 | 1868 | — | — |
| 71 | 108 | 69 | — | — | — | — |

TABLE I-continued

| Compound Example No. | Receptor Binding IC$_{50}$ (nM) | | Acute Toxicity in Mice LD$_{50}$ (mg/kg) | | K+ Stimulation of Rat Bladder IC$_{50}$ (μM) Contractions | |
|---|---|---|---|---|---|---|
| | $\alpha_1$ | 5-HT$_{1A}$ | i.p. | p.o | Phasic | Tonic |
| 72 | 145 | 111 | 479 | >2000 | — | — |
| 73 | 6 | 89 | 202 | 462 | — | — |
| 74 | 178 | 482 | — | — | — | — |
| 75 | 147 | 15 | — | — | — | — |
| 77 | 6 | 127 | >500 | >2000 | — | — |
| 78 | 18 | 116 | — | — | — | — |
| 79 | 77 | 141 | >500 | >2000 | — | — |
| 80 | 28 | 162 | 411 | — | — | — |
| 81 | 13 | 81 | 451 | — | — | — |
| 83 | 30 | 5 | — | — | — | — |
| 84 | 5 | 2 | 349 | — | — | — |
| 85 | 16 | 14 | >500 | 1138 | — | — |
| 86 | 48 | 20 | 101 | 451 | — | — |
| 87 | 119 | 107 | 237 | >500 | — | — |
| 88 | 216 | 11 | — | — | — | — |
| 89 | 101 | 50 | — | 43 | — | — |
| 90 | 54 | 18 | 388 | — | — | — |
| 91 | 71 | 60 | >500 | — | — | — |
| 92 | 67 | 28 | 223 | 646 | — | — |
| 93 | 47 | 38 | 375 | 2000 | — | — |
| 94 | 39 | 66 | >500 | — | — | — |
| 95 | 16 | 170 | >500 | — | — | — |
| 96 | 19 | 155 | >500 | 1434 | — | — |
| 97 | 30 | 37 | >500 | 1541 | — | — |
| 98 | 34 | 12 | >500 | >2000 | — | — |
| 99 | 44 | 5 | 310 | 2000 | — | — |
| 100 | 17 | 1 | 500 | >2000 | — | — |
| 101 | 46 | 35 | — | — | — | — |
| 102 | 56 | 18 | — | — | — | — |
| 103 | 31 | 33 | 91 | 206 | — | — |
| 104 | 9 | 15 | >500 | — | — | — |
| 105 | 9 | 31 | — | — | — | — |
| 106 | 9 | 12 | — | — | — | — |
| 107 | 37 | 16 | 262 | — | — | — |
| 108 | 26 | 52 | — | — | — | — |
| 109 | 10 | 32 | — | — | — | — |
| 110 | 26 | 15 | 327 | — | — | — |
| 111 | 8 | 11 | — | — | — | — |
| 112 | 88 | 233 | — | — | — | — |
| 113 | 16 | 1 | — | — | — | — |
| 115 | 10.5 | 2 | — | — | — | — |
| 116 | 39 | 95 | 121 | 252 | — | — |
| 117 | 47 | 134 | >500 | — | — | — |
| 118 | 148 | 28 | >500 | — | — | — |
| 119 | 51 | 36 | — | — | — | — |
| 120 | 5 | 5 | — | — | — | — |
| 122 | 138 | 90 | — | — | — | — |
| 123 | 588 | 241 | — | — | — | — |
| 124 | 60 | 7.5 | — | — | — | — |
| 125 | 72 | 16 | — | — | — | — |
| 126 | 11 | 2 | >500 | — | — | — |
| 128 | 74 | 739 | >500 | — | — | — |
| 129 | 59 | 37 | 299 | — | — | — |
| 130 | 8 | 7.5 | — | — | — | — |
| 131 | 18 | 46 | — | — | — | — |
| 132 | 96 | 300 | — | — | — | — |
| 134 | 43 | 1 | — | — | — | — |
| 135 | 80 | 1542 | — | — | — | — |
| 137 | 101 | 33 | — | — | — | — |
| 141 | 72 | 37 | — | — | — | — |
| 142 | 55 | 278 | — | — | — | — |
| 143 | 39 | 3 | >500 | — | — | — |
| 144 | 71 | 34 | >500 | — | — | — |
| 145 | 19 | 63 | >500 | 519 | — | — |
| 146 | 75 | 150 | >500 | — | — | — |
| 147 | 786 | >1000 | >500 | — | — | — |
| 148 | 24 | 29 | — | — | — | — |
| 149 | 20 | 27 | — | — | — | — |
| 150 | 17 | 73 | 500 | — | — | — |
| 151 | 21 | 868 | >500 | — | — | — |
| 152 | 13 | 18 | 306 | — | — | — |
| 153 | 43 | 27 | — | — | — | — |

TABLE I-continued

| Compound Example No. | Receptor Binding IC$_{50}$ (nM) | | Acute Toxicity in Mice LD$_{50}$ (mg/kg) | | K+ Stimulation of Rat Bladder IC$_{50}$ (μM) Contractions | |
|---|---|---|---|---|---|---|
| | α$_1$ | 5-HT$_{1A}$ | i.p. | p.o | Phasic | Tonic |
| 155 | 30 | 17 | >500 | 683 | — | — |
| 156 | 140 | 44 | — | — | — | — |
| 157 | 332 | 792 | — | — | — | — |
| 158 | 102 | 226 | — | — | — | — |
| 159 | 16 | 14 | — | — | — | — |
| 160 | 352 | 542 | — | — | — | — |
| 161 | 8 | 10 | — | — | — | — |
| 168 | 138 | 186 | — | — | — | — |
| 169 | 5 | 26 | >500 | — | — | — |
| Flavoxate | >>1000 | >>1000 | 385 | 808 | 13 | 13 |

TABLE II

| Compound Example No. | Receptor Binding IC$_{50}$ (nM) | | | |
|---|---|---|---|---|
| | α$_{1A}$ | α$_{1B}$ | α$_2$ | D$_2$ |
| 4 | — | — | — | 309 |
| 5 | 9 | 28 | — | 53 |
| 6 | — | — | — | 138 |
| 7 | 46 | 76 | — | 364 |
| 8 | 17 | 37 | — | 421 |
| 11 | 2 | 24 | 128 | 161 |
| 13 | 14.5 | 79 | 275 | 349 |
| 14 | 20 | 165 | — | 163 |
| 15 | 2 | 7 | — | 655 |
| 16 | — | — | — | 939 |
| 17 | 21 | 34 | 313 | 390 |
| 18 | — | — | — | 412 |
| 19 | — | — | — | 413 |
| 20 | — | 68 | — | 412 |
| 21 | 3 | 12 | 15 | 44 |
| 22 | — | — | — | 228 |
| 24 | — | — | — | 483 |
| 26 | — | — | — | >1000 |
| 27 | 5 | 31 | 18 | 83 |
| 28 | — | — | — | 72 |
| 29 | — | 125 | — | 92 |
| 32 | — | — | — | 236 |
| 33 | 8.5 | 178 | — | 60 |
| 34 | 32 | 62 | — | 42 |
| 35 | 12 | 14 | — | 97 |
| 36 | 8 | 74 | — | 562 |
| 37 | 5 | 5 | — | 187 |
| 38 | 15 | 49 | — | 460 |
| 39 | 39 | 311 | — | 483 |
| 40 | 5 | 25 | 53 | 60 |
| 41 | 10 | 39 | 64 | 46 |
| 42 | 6 | 16 | 73 | 67 |
| 43 | — | — | — | >1000 |
| 44 | — | — | — | 796 |
| 45 | — | 53 | — | 169 |
| 46 | 23 | 49 | — | 69 |
| 47 | 14 | 55 | 182 | 193 |
| 48 | 82 | 184 | — | 45 |
| 49 | 21 | 389 | — | 592 |
| 50 | 8.5 | 38 | — | 576 |
| 51 | 1.5 | 24 | 22 | 57 |
| 52 | 7.1 | 188 | — | 103 |
| 53 | 0.4 | 5.5 | 25 | 78 |
| 54 | 23 | 44 | — | 1054 |
| 55 | 322 | 291 | — | >1000 |
| 56 | 8 | 16 | — | 15 |
| 57 | 52 | 43 | — | 446 |
| 58 | — | — | — | 4419 |
| 59 | 0.5 | 5 | — | 1000 |
| 60 | 17 | 23 | — | 90 |
| 61 | 32 | 49 | — | 17 |
| 62 | — | — | — | >1000 |
| 63 | — | — | — | >1000 |
| 64 | 9 | 259 | — | 317 |
| 65 | 101 | 207 | — | 315 |
| 66 | 63 | 138 | — | 134 |
| 67 | 2 | 8 | — | 7 |
| 68 | — | 61 | — | 68 |
| 69 | 4 | 23 | — | 130 |
| 70 | — | 137 | — | 34 |
| 71 | 59 | 165 | — | 1000 |
| 72 | — | — | — | 106 |
| 73 | 2 | 18 | — | 83 |
| 74 | — | — | — | 1000 |
| 75 | — | — | — | 131 |
| 77 | 1 | 29 | — | 270 |
| 78 | 5 | 18 | — | 65 |
| 79 | 48 | 375 | — | 299 |
| 80 | 29 | 52 | — | 563 |
| 81 | 8 | 27 | — | 69 |
| 83 | 1 | 60 | — | 81 |
| 84 | 2 | 15 | — | 75 |
| 85 | 2 | 56 | — | 492 |
| 86 | 4 | 44 | — | 265 |
| 87 | 38 | 61 | — | 801 |
| 88 | 26 | 244 | — | 2223 |
| 89 | — | 43 | — | 281 |
| 90 | 13 | 33 | — | 201 |
| 91 | 8 | 50 | — | 117 |
| 92 | 16 | 49 | — | 222 |
| 93 | 23 | 41 | — | 238 |
| 94 | 3 | 25 | — | 195 |
| 95 | 11 | 32 | — | 209 |
| 96 | 7 | 51 | — | 158 |
| 97 | 6 | 74 | — | 287 |
| 98 | 4 | 69 | — | 59 |
| 99 | 52 | 36 | — | 781 |
| 100 | 1 | 145 | — | 455 |
| 101 | 3 | 283 | — | 548 |
| 102 | 11 | 48 | — | 1288 |
| 103 | 1.5 | 138 | — | 179 |
| 104 | 1 | 45 | 7 | 67 |
| 105 | 3 | 46 | — | 172 |
| 106 | 1 | 51 | — | 196 |
| 107 | 3 | 59 | — | 179 |
| 108 | 6 | 36 | — | 390 |
| 109 | 1 | 21 | — | 673 |
| 110 | 1 | 32 | — | 655 |
| 111 | 1 | 66 | — | 398 |
| 112 | — | 223 | — | 105 |
| 113 | 1 | 42 | — | 303 |
| 115 | 6 | 35 | 60.5 | 640 |

TABLE II-continued

| Compound Example No. | Receptor Binding IC$_{50}$ (nM) | | | |
|---|---|---|---|---|
| | $\alpha_{1A}$ | $\alpha_{1B}$ | $\alpha_2$ | $D_2$ |
| 116 | 29 | 42 | — | 224 |
| 117 | 8 | 17 | — | 349 |
| 118 | 18 | 304 | — | 526 |
| 119 | 3 | 167 | — | 2414 |
| 120 | 1 | 5.5 | — | 1627 |
| 122 | — | — | — | 73 |
| 123 | — | — | — | 1759 |
| 124 | 6 | 104 | — | 454 |
| 125 | 6.5 | 174 | — | 766 |
| 126 | 5 | 57 | — | 275 |
| 128 | 6 | 52 | — | 127 |
| 129 | 27 | 43 | — | 41 |
| 130 | 3 | 21 | — | 17 |
| 131 | 21 | 123 | — | 387 |
| 132 | — | 144 | — | 541 |
| 134 | 3.5 | 64 | — | 23 |
| 135 | — | — | — | 368 |
| 137 | 50 | — | 155 | |
| 141 | 1 | 51 | — | 225 |
| 142 | 45 | 89 | — | 183 |
| 143 | 16 | 23 | — | 878 |
| 144 | — | 63 | — | 287 |
| 145 | 13 | 19 | — | 1102 |
| 146 | 45 | 67 | — | 1421 |
| 147 | — | — | — | 3613 |
| 148 | 7 | 46 | — | 434 |
| 149 | — | 40 | — | 213 |
| 150 | — | 26 | — | 27 |
| 151 | — | 35 | — | 605 |
| 152 | 1 | 108 | — | 34 |
| 153 | — | 73 | — | 42 |
| 155 | — | 114 | — | 545 |
| 156 | — | 129 | — | 585 |
| 157 | — | — | — | 298 |
| 158 | 79 | 482 | — | 497 |
| 159 | — | 30 | — | 199 |
| 160 | — | 430 | — | 2012 |
| 161 | 3 | 7 | — | 207 |
| 168 | 67 | 560 | — | 789 |
| 169 | 3 | 13 | — | 37 |

TABLE III

| Compound Example No. | Na-induced mortality rat ED$_{50}$ (µg/kg i.v.) | Hypotensive effect normotensive rat ED$_{25}$ (µg/kg i.v.) |
|---|---|---|
| 5 | 1000 | 191 |
| 11 | 8 | 45 |
| 13 | 399 | 87 |
| 15 | 111 | 284 |
| 17 | 1260 | 81 |
| 21 | 75 | 73 |
| 27 | 240 | 99 |
| 35 | — | 198 |
| 36 | 148 | 32 |
| 37 | 312 | — |
| 38 | — | 44 |
| 40 | 170 | 69 |
| 41 | 766 | 543 |
| 42 | 171 | 1,33 |
| 45 | 548 | 513 |
| 47 | 3830 | 102 |
| 49 | 4220 | 415 |
| 50 | 212 | 125 |
| 51 | 410 | 100 |
| 53 | 77 | >1000 |
| 54 | — | 260 |
| 59 | 35 | 65 |
| 69 | 85 | 79 |
| 71 | 1000 | 400 |
| 73 | 15.5 | >3000 |
| 77 | 34 | — |
| 78 | 83 | 530 |
| 80 | 304 | 126 |
| 83 | 74 | 271 |
| 84 | 270 | >3000 |
| 85 | 24 | 44 |
| 86 | 33 | 216 |
| 93 | 457 | — |
| 94 | — | 22 |
| 99 | 194 | >1000 |
| 100 | 15.5 | — |
| 104 | 3 | 174 |
| 106 | — | 157 |
| 107 | 212 | 306 |
| 109 | — | 187 |
| 111 | 22 | 260 |
| 113 | 11 | — |
| 115 | 33 | 38 |
| 116 | 690 | 151 |
| 120 | 87 | 69 |
| 134 | 40 | — |
| 136 | >3000 | — |
| 141 | 7.5 | — |
| 145 | 27 | 146 |
| 152 | 6 | — |

TABLE IV

Effects on Urethal Contractility (NA-induced contraction) and Blood Pressure in Dogs

| Compound Example No. | Urethra ED$_{50}$ (µg/kg i.v.) | DBP ED$_{25}$ (µg/kg i.v.) | DBP/Urethra ratio |
|---|---|---|---|
| 5 | 37.0 | 1074 | 29.0 |
| 11 | 1.4 | 390 | 278.6 |
| 13 | 16.0 | 215 | 13.4 |
| 15 | 10.1 | 65.6 | 6.5 |
| 17 | 10.0 | 6.2 | 0.6* |
| 21 | 6.6 | 127 | 19.2 |
| 27 | 3.2 | 9.8 | 3.1* |
| 40 | 11.0 | 152 | 13.8 |
| 41 | 57.0 | 745 | 13.1 |
| 42 | 31.0 | 404 | 13.0 |
| 45 | 16.4 | 186 | 11.3 |
| 47 | 35.0 | 530 | 15.1 |
| 49 | 260.0 | 2150 | 8.3 |
| 51 | 8.6 | 327 | 38.0 |
| 53 | 8.1 | 113 | 13.9 |
| 59 | 5.7 | 141 | 24.7 |
| 69 | 14.7 | 156.5 | 10.4 |
| 73 | 3.5 | 110 | 31.4 |
| 83 | 9.7 | 134 | 13.8 |
| 100 | 9.2 | 296 | 32.2 |
| 104 | 1.8 | 96.7 | 53.7 |
| 113 | 6.9 | 113 | 16.4 |
| 115 | 1.4 | 126 | 90.0 |
| 116 | 21.0 | 264 | 12.6 |
| Prazosin | 3.6 | 6.6 | 1.8* |
| Terflavoxate | >10000 | 6060 | — |

Urethra: active dose in inhibiting by 50% the noradrenaline induced contraction of urethra
DBP: active dose in lowering diastolic blood pressure by 25%
DBP/urethra: ratio between the active doses (selectivity index)
*non-selective: substantial effect on both urethra and DBP.

TABLE V

Effects on Urethral Contractility (hypogastric nerve stimulation - induced contraction) and Blood Pressure in Dogs

| Compound Example No. | Urethra ED$_{50}$ (µg/kg i.v.) | DBP ED$_{25}$ (µg/kg i.v.) | DBP/Urethra ratio |
|---|---|---|---|
| 11 | 3.2 | 76.9 | 24.0 |
| Prazosin | 10.2 | 10.0 | 1.0 |

TABLE VI

Effects on Urethral Contractility (hypogastric nerve stimulation - induced contraction) and Blood Pressure in Dogs

| Compound Example No. | Urethra ED$_{50}$ (µg/kg i.v.) | DBP ED$_{25}$ (µg/kg i.v.) | DBP/Urethra ratio |
|---|---|---|---|
| 11 | 53.0 | 1652 | 31.2 |
| 104 | 16.0 | 706 | 44.1 |
| Tamsulosin | 12.9 | 50 | 3.8 |

TABLE VI bis

Effects on Urethral Contractility (hypogastric nerve stimulation - induced contraction) and Blood Pressure in Dogs: % effect after 100 µg/kg i.d. administration

| Compound Example No. | Urethra % peak | Urethra % AUC | DBP % peak | DBP % AOC |
|---|---|---|---|---|
| 11 | 63.4 | 47.6 | 6.6 | 3.6 |
| 59 | 68.9 | 43.2 | 7.7 | 5.0 |
| 77 | 42.8 | 21.6 | 4.9 | 2.4 |
| 80 | 62.9 | 36.2 | 7.4 | 3.4 |
| 85 | 66.5 | 44.4 | 7.5 | 5.8 |
| 111 | 82.7 | 52.9 | 6.9 | 4.0 |
| 115 | 78.3 | 56.1 | 7.9 | 8.2 |
| 120 | 43.8 | 17.5 | 4.6 | 1.3 |
| 141 | 69.8 | 52.5 | 7.6 | 2.9 |
| 145 | 61.1 | 35.4 | 6.2 | 3.7 |
| 152 | 67.1 | 52.3 | 12.0 | 9.0 |
| Tamsulosin | 94.0 | 86.8 | 34.4 | 25.2 |

TABLE VII

Effects on Urethral Contractility (NA-induced contraction) and Blood Pressure in Rabbits

| Compound Example No. | Urethra ED$_{50}$ (µg/kg i.v.) | DBP ED$_{25}$ (µg/kg i.v.) | DBP/Urethra ratio |
|---|---|---|---|
| 11 | 5.5 | 36.9 | 6.7 |
| tamsulosin | 1.5 | 1.1 | 0.7 |

Urethra: active dose in inhibiting by 50% the contraction of urethra induced by noradrenaline
DBP: active dose in lowering diastolic blood pressure by 25%
DBP/urethra: ratio between the active doses (selectivity index)

Effective Amounts

The following represent guidelines to effective oral, parenteral or intravenous dose ranges expressed in mg/kg of body weight per day for the following uses:

(a) In obstructive disorders of the lower urinary tract:

| | |
|---|---|
| General | 0.001–20 |
| Preferred | 0.05–1 |
| Most Preferred** | 0.3 |

(b) As antihypertensives:

| | |
|---|---|
| General | 0.01–20 |
| Preferred | 0.1–5 |
| Most Preferred** | 1 |

(c) As anxiolytics - antidepressants:

| | |
|---|---|
| General | 0.01–20 |
| Preferred | 0.05–5 |
| Most Preferred** | 0.5 |

(d) As bladder spasmolytics:

| | |
|---|---|
| General | 0.01–20 |
| Preferred | 0.02–10 |
| Most Preferred** | 2 |

**Most preferred values refer to oral dosing. Intravenous dosages should be 10 to 100 fold lower.

Patients in need of treatment by the present compounds and compositions also include humans that have one or more depression symptoms (as defined, e.g. in Harrison's Principles of Internal Medicine, XII Ed., McGraw-Hill, Inc., p.2124) or humans that display anxiety symptoms (Harrison's, supra, pp. 2131–2134). Selective use dosages, i.e. dosages that are active in the lower urinary tract without a substantial effect on the blood pressure, depend on the particular compound employed. Generally, in the case of a compound selective in inhibiting urethral contraction, up to four times the amount of the ED$_{50}$ used in inhibiting urethral contraction can be administered without substantial effect on blood pressure. Further refinements and optimization of dosages are possible using no more than routine experiments. The active compounds of the invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but the amount of active ingredient may be varied depending upon the particular form and may conveniently be between 5% to about 70% of the weight of the unit. The amount of active compound in such compositions is such that a suitable dosage will be obtained although the desired dosage can be obtained by administering a plurality of dosage forms. Preferred compositions and preparations according to the invention are prepared so that an oral dosage unit form contains between 1.0–300 milligrams of active compound. The tablets, pills, capsules, troches and the like may also contain for example the following ingredients: a binder such as micro-crystalline cellulose, gum tragacanth or gelatin; an excipient such as starch or lactose, a disintegrating agent such as alginic acid, sodium starch glycolate, cornstarch and the like; a lubricant such as magnesium stearate or hydrogenated castor oil, a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and nontoxic in the amounts used. For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.2 to 100 milligrams of active compound. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine tetraacetic acid; buffers such as acetates; citrates or phosphates and agents for the adjustment of tonicity such as sodium chloride or dextrose. The parenteral multiple dose vials may be of glass or plastics material.

Additional compositions suitable for administration by various routes and containing compounds according to the present invention are also within the scope of the invention. Dosage forms, additional ingredients and routes of administration contemplated herein include those disclosed in U.S. Pat. Nos. 4,089,969; and 5,091,182, all incorporated by reference in their entirety.

We claim:

1. A compound having the general formula I

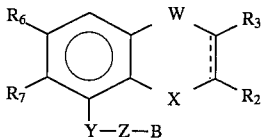

wherein

---- represents a single or double bond;

X represents a nitrogen, oxygen or sulfur atom, an amino or alkylamino, a sulfinyl or sulfonyl group;

W represents a carbonyl, thiocarbonyl, hydroxymethylene, a methylene group or a bond; or X is nitrogen and W is methine, and the fused rings represent quinolyl ring;

$R_2$ represents a hydrogen atom or an alkyl, alkenyl, alkynyl, carbocyclic or heterocyclic group, each of which groups may optionally be substituted by one or more substituents selected from the group consisting of alkyl, cyano, hydroxy, alkoxy, halogen, phenyl, phenoxy, trifluoromethyl, nitro, acylamino, alkylsulfonylamino and benzoyl; or $R_2$ itself represents a trifluoromethyl or an aroyl group; wherein the carbocyclic group may be substituted with amino, alkylamino or dialkylamino;

with the proviso that the heterocyclic group cannot be linked through a nitrogen atom;

$R_3$ represents a hydrogen atom or an alkyl, hydroxyalkyl, phenyl, hydroxy, O—$R_4$, or alkyl-O$R_4$ group, where $R_4$ represents an alkyl group optionally substituted with an aryl group;

$R_6$ represents a hydrogen or halogen atom or a nitro, amino, acetylamino, alkylamino, dialkylamino, cyano, hydroxy, alkoxy or alkyl group;

$R_7$ represents a hydrogen atom;

Y represents one of the following groups, each of which is depicted with its left hand end being the end which attaches to the heterobicyclic ring and its right hand end being the end which attaches to the group Z:

| | |
|---|---|
| —CO—, | (Y1) |
| —COO—, | (Y2) |
| —CONH—, | (Y3) |
| —CON(CH$_3$)—, | (Y4) |
| —CON(OH)—, | (Y5) |
| —CH(OH)—, | (Y6) |
| —CH(OAlkyl)—, | (Y7) |
| —CH=CH—, | (Y8) |
| —CH=CH—COO—, | (Y9) |
| —CH=CH—CONH—, | (Y10) |
| —CH=NO—, | (Y11) |
| —CH$_2$—, | (Y12) |
| —CH$_2$COO—, | (Y13) |
| —CH$_2$CONH—, | (Y14) |
| —CH$_2$NH—, | (Y15) |
| —CH$_2$N(CH$_3$)—, | (Y16) |
| —CH$_2$N(COCH$_3$)—, | (Y17) |
| —CH$_2$N(CONH$_2$)—, | (Y18) |
| —CH$_2$NHCO—, | (Y19) |
| —CH$_2$N(CH$_3$)CO—, | (Y20) |
| —CH$_2$NH—CONH—, | (Y21) |
| —CH$_2$NHSO$_2$—, | (Y22) |
| —CH$_2$O—, | (Y23) |
| —CH$_2$S—, | (Y24) |
| —CH$_2$SO—, | (Y25) |
| —CH$_2$SO$_2$—, | (Y26) |
| —CH$_2$SO$_2$NH—, | (Y27) |
| —CH$_2$SO$_2$N(CH$_3$)—, | (Y28) |
| —NH—, | (Y29) |
| —N(CH$_3$)—, | (Y30) |
| —N(COCH$_3$)—, | (Y31) |
| —N(CONH$_2$)—, | (Y32) |
| —NHCO—, | (Y33) |
| —N(CH$_3$)CO—, | (Y34) |

-continued

—NH—CONH—, (Y35)

—NHSO$_2$—, (Y36)

—O—, (Y37)

—S—, (Y38)

—SO—, (Y39)

—SO$_2$—, (Y40)

—SO$_2$NH—, (Y41)

—SO$_2$N(CH$_3$)—, (Y42)

—CONHO—, (Y43)

—CON(COCH$_3$)—, (Y44)

—CSNH—, (Y45)

—CSN(CH$_3$)—, (Y46)

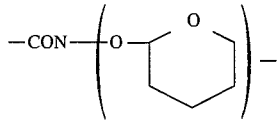 (Y47)

—NHCOO—, (Y48)

and

—COS— (Y49)

Z a linear or branched chain alkylene group having from 1 to 6 carbon atoms and optionally having one hydroxy substituent; and represents one of the following groups:

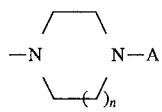 (B1)

wherein n is 1 or 2 and A represents a phenyl group; wherein said phenyl group is unsubstituted or substituted by one or more substituents selected from the group consisting of alkoxy, alkyl, halogen, hydroxy, or A represents a 2-pyrimidinyl group or a bicyclic ring of formula

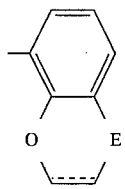

where ---- represents a single or double bond and E represents an oxygen atom or a bond;

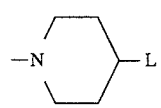 (B2)

wherein L represents one or two groups selected among phenyl, 4-fluorobenzoyl or a 2-oxo-1-benzimidozolinyl group or a group of the formula (CH$_2$)$_n$-O-A wherein n=0, 1, or 2 and A has the same meaning defined under B1,

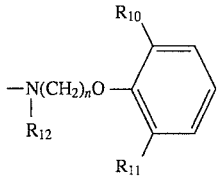 (B3)

wherein each of R$_{10}$ and R$_{11}$ independently represents a hydrogen atom or an alkoxy or alkylthio group, R$_{12}$ represents a hydrogen atom or an alkyl group and n is 2 or 3,

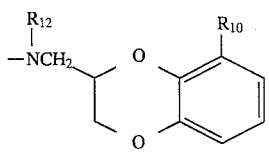 (B4)

wherein R$_{12}$ has the meaning defined under B3 and R$_{13}$ represents a hydrogen atom or a alkoxy group,

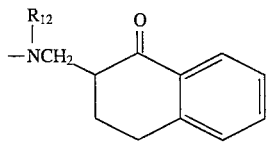 (B5)

wherein R$_{12}$ has the meaning defined under B3, or an enantiomer, a diastereomer, an N-oxide, a prodrug, a metabolite, a prodrug of a metabolite, or a pharmaceutically acceptable salt of said compound.

2. A compound according to claim 1, wherein Y represents one of the groups Y2, Y3, Y37, Y40 or Y41.

3. A compound according to claim 1, wherein B is B1 and A is a phenyl group substituted by one or more substituents.

4. A compound according to claim 1, wherein

---- represents a double bond,

W represents a carbonyl group,

X represents an oxygen atom,

R$_2$ represents a phenyl group,

R$_3$ represents a methyl group,

R$_6$ represents a hydrogen atom, and

R$_7$ represents a hydrogen atom.

5. A compound according to claim 4, wherein Y represents one of the groups Y2, Y3, Y37, Y40 or Y41.

6. A compound according to claim 5, wherein Z represents a trimethylene or tetramethylene group.

7. A compound according to claim 5, wherein B represents one of the groups B1 or B3.

8. A compound according to claim 6, wherein B represents one of the groups B1 or B3.

9. A compound according to claim 7, wherein B represents a 4-(2-methoxyphenyl)-1-piperazinyl group.

10. A compound according to claim 8, wherein B represents a 4-(2-methoxyphenyl)-1-piperazinyl group.

11. A compound according to claim 4, wherein B is B3 and at least one of R$_{10}$, R$_{11}$ is methoxy.

12. Compound selected from the group consisting of:

8-{2-[4-(2-methoxyphenyl)-1-piperazinyl]-1-oxoethyl}-3-methyl-4-oxo-2-phenyl-4H-1-benzopyran;

8-{2-[4-(2-methylphenyl)-1-piperazinyl]-1-oxoethyl}-3-methyl-4-oxo-2-phenyl-4H-1-benzopyran;

8-{2-[4-(2-ethoxyphenyl)-1-piperazinyl]-1-oxoethyl}-3-methyl-4-oxo-2-phenyl-4H-1-benzopyran;

8-{3-[4-(2-methoxy-phenyl)-1-piperazinyl]-1-oxopropyl}-3-methyl-4-oxo-2-phenyl-4H-1-benzopyran;

8-{3-[4-(2-methoxyphenyl)-1-piperazinyl]-propoxycarbonyl}-3-methyl-4-oxo-2-phenyl-4H-1-benzopyran;
8-{2-[4-(2-methoxyphenyl)-1-piperazinyl]-ethoxycarbonyl}-3-methyl-4-oxo-2-phenyl-4H-1-benzopyran;
8-{3-[4-(2-chlorophenyl)-1-piperazinyl]-propoxycarbonyl}-3-methyl-4-oxo-2-phenyl-4H-1-benzopyran;
8-[3-(4-phenyl-1-piperazinyl)-propoxycarbonyl]-3-methyl-4-oxo-2-phenyl-4H-1-benzopyran;
8-{3-[4-(2-methoxyphenyl)-1-piperazinyl]-2-methyl-2-propoxycarbonyl}-3-methyl-4-oxo-2-phenyl-4H-1-benzopyran;
8-{3-[4-(2-methoxyphenyl)-1-piperazinyl]-propylcarbamoyl}-3-methyl-4-oxo-2-phenyl-4H-1-benzopyran;
8-{2-[4-(2-methoxyphenyl)-1-piperazinyl]-ethyl-carbamoyl}-3-methyl-4-oxo-2-phenyl-4H-1-benzopyran;
8-{3-[2-(2-methoxyphenoxy)-ethylamino]-propylcarbamoyl}-3-methyl-4-oxo-2-phenyl-4H-1-benzopyran;
8-[3-(4-phenyl-1-piperazinyl)-propylcarbamoyl]-3-methyl-4-oxo-2-phenyl-4H-1-benzopyran;
8-{N-methyl-2-[4-(2-methoxyphenyl)-1-piperazinyl]-ethylcarbamoyl}-3-methyl-4-oxo-2-phenyl-4H-1-benzopyran;
8-{1-hydroxy-2-[4-(2-methoxyphenyl)-1-piperazinyl]-ethyl}-3-methyl-4-oxo-2-phenyl-4H-1-benzopyran;
8-{1-hydroxy-2-[4-(2-methylphenyl)-1-piperazinyl]-ethyl}-3-methyl-4-oxo-2-phenyl-4H-1-benzopyran;
8-{1-hydroxy-2-[4-(2-ethoxyphenyl)-1-piperazinyl]-ethyl}-3-methyl-4-oxo-2-phenyl-4H-1-benzopyran;
8-{1-hydroxy-3-[4-(2-methoxyphenyl)-1-piperazinyl]-propyl}-3-methyl-4-oxo-2-phenyl-4H-1-benzopyran;
8-{1-hydroxy-4-[4-(2-methoxyphenyl)-1-piperazinyl]-butyl}-3-methyl-4-oxo-2-phenyl-4H-1-benzopyran;
8-{1-ethoxy-2-[4-(2-methoxyphenyl)-1-piperazinyl]-ethyl}-3-methyl-4-oxo-2-phenyl-4H-1-benzopyran;
8-{N-methyl-2-[4-(2-methoxyphenyl)-1-piperazinyl]-ethylaminomethyl}-3-methyl-4-oxo-2-phenyl-4H-1-benzopyran;
8-{N-acetyl-2-[4-(2-methoxyphenyl)-1-piperazinyl]-ethylaminomethyl}-3-methyl-4-oxo-2-phenyl-4H-1-benzopyran;
8-[4-(2-methoxyphenyl)-1-piperazinylacetamidomethyl]-3-methyl-4-oxo-2-phenyl-4H-1-benzopyran;
8-{N-methyl-2-[4-(2-methoxyphenyl)-1-piperazinyl]-acetamidomethyl}-3-methyl-4-oxo-2-phenyl-4H-1-benzopyran;
8-{2-[4-(2-methoxyphenyl)-1-piperazinyl]-ethoxymethyl}-3-methyl-4-oxo-2-phenyl-4H-1-benzopyran;
8-{2-[2-(2-ethoxyphenoxy)-ethylamino]-ethoxymethyl}-3-methyl-4-oxo-2-phenyl-4H-1-benzopyran;
8-{2-[4-(2-methoxyphenyl)-1-piperazinyl]-ethylthiomethyl}-3-methyl-4-oxo-2-phenyl-4H-1-benzopyran;
8-{2-[4-(2-methoxyphenyl)-1-piperazinyl]-ethylsulfinylmethyl}-3-methyl-4-oxo-2-phenyl-4H-1-benzopyran;
8-{2-[4-(2-methoxyphenyl)-1-piperazinyl]-ethylsulfonylmethyl}-3-methyl-4-oxo-2-phenyl-4H-1-benzopyran;
8-{2-[4-(2-methoxyphenyl)-1-piperazinyl]-ethylamino}-3-methyl-4-oxo-2-phenyl-4H-1-benzopyran;
8-{3-[4-(2-methoxyphenyl)-1-piperazinyl]-propylamino}-3-methyl-4-oxo-2-phenyl-4H-1-benzopyran;
8-{4-[4-(2-methoxyphenyl)-1-piperazinyl]-butylamino}-3-methyl-4-oxo-2-phenyl-4H-1-benzopyran;
8-{N-methyl-3-[4-(2-methoxyphenyl)-1-piperazinyl]-propylamino}-3-methyl-4-oxo-2-phenyl-4H-1-benzopyran;
8-{N-acetyl-3-[4-(2-methoxyphenyl)-1-piperazinyl]-propylamino}-3-methyl-4-oxo-2-phenyl-4H-1-benzopyran;
8-{3-[4-(2-methoxyphenyl)-1-piperazinyl]-propionamido}-3-methyl-4-oxo-2-phenyl-4H-1-benzopyran;
8-{2-[4-(2-methoxyphenyl)-1-piperazinyl]-ethylureido}-3-methyl-4-oxo-2-phenyl-4H-1-benzopyran;
8-{2-[4-(2-methoxyphenyl)-1-piperazinyl]-ethoxy}-3-methyl-4-oxo-2-phenyl-4H-1-benzopyran;
8-{3-[4-(2-methoxyphenyl)-1-piperazinyl]-propoxy}-3-methyl-4-oxo-2-phenyl-4H-1-benzopyran;
8-{4-[4-(2-methoxyphenyl)-1-piperazinyl]-butoxy}-3-methyl-4-oxo-2-phenyl-4H-1-benzopyran;
8-{5-[4-(2-methoxyphenyl)-1-piperazinyl]-pentoxy}-3-methyl-4-oxo-2-phenyl-4H-1-benzopyran;
8-{3-[4-(2-methoxyphenyl)-1-oxo-1-piperazinyl]-propoxy}-3-methyl-4-oxo-2-phenyl-4H-1-benzopyran;
8-{2-[2-(2,6-dimethoxyphenoxy)-ethylamino]-ethoxy}-3-methyl-4-oxo-2-phenyl-4H-1-benzopyran;
8-{2-hydroxy-3-[4-(2-methoxyphenyl)-1-piperazinyl]-propoxy}-3-methyl-4-oxo-2-phenyl-4H-1-benzopyran;
8-{3-[4-(2-methoxyphenyl)-1-piperazinyl]-propylthio}-3-methyl-4-oxo-2-phenyl-4H-1-benzopyran;
8-{3-[4-(2-methoxyphenyl)-1-piperazinyl]-propylsulfonyl}-3-methyl-4-oxo-2-phenyl-4H-1-benzopyran;
8-{2-[4-(2-methoxyphenyl)-1-piperazinyl]-ethylsulfamyl}-3-methyl-4-oxo-2-phenyl-4H-1-benzopyran;
8-{N-methyl-2-[4-(2-methoxyphenyl)-1-piperazinyl]ethylsulfamyl}-3-methyl-4-oxo-2-phenyl-4H-1-benzopyran;
8-{N-aminocarbonyl-3-[4-(2-methoxyphenyl)-1-piperazinyl]propylamino}-3-methyl-4-oxo-2-phenyl-4H-1-benzopyran;
8-{4-[4-(2-methoxyphenyl)-1-piperazinyl]-1-oxobutyl}-3-methyl-4-oxo-2-phenyl-4H-1-benzopyran;
8-{3-[2-(1,4-benzodioxanyl)methylamino]propylcarbamoyl}-3-methyl-4-oxo-2-phenyl-4H-1-benzopyran;
8-{4-[4-(2-methoxyphenyl)-1-piperazinyl]butyl}-3-methyl-4-oxo-2-phenyl-4H-1-benzopyran;
8-[3-(4-phenyl-1-piperidinyl)propylcarbamoyl]-3-methyl-4-oxo-2-phenyl-4H-1-benzopyran;
8-[3-(4,4-Diphenyl-1-piperidinyl)propylcarbamoyl]-3-methyl-4-oxo-2-phenyl-4H-1-benzopyran;
8-{3-[4-(4-fluorobenzoyl)-1-piperidinyl]propylcarbamoyl}-3-methyl-4-oxo-2-phenyl-4H-1-benzopyran;
8-{3-[4-(2-oxo-1-benzimidazolinyl)-1-piperidinyl]propyl-carbamoyl}-3-methyl-4-oxo-2-phenyl-4H-1-benzopyran;
8-{3-[4-(2-pyrimidinyl)-1-piperazinyl]propylcarbamoyl}-3-methyl-4-oxo-2-phenyl-4H-1-benzopyran;
8-{3-[4-(2-hydroxyphenyl)-1-piperazinyl]propylcarbamoyl}-3-methyl-4-oxo-2-phenyl-4H-1-benzopyran;
8-{4-[4-(2-methoxyphenyl)-1-piperazinyl]butylcarbamoyl}-3-methyl-4-oxo-2-phenyl-4H-1-benzopyran;
8-{3-[4-(2-methoxyphenyl)-1-piperazinyl]propylsulfamyl}-3-methyl-4-oxo-2-phenyl-4H-1-benzopyran;
8-{3-[N-methyl-2-(2-methoxyphenoxy)-ethylamino]propylcarbamoyl}-3-methyl-4-oxo-2-phenyl-4H-1-benzopyran;
8-{N-methyl-3-[4-(2-methoxyphenyl)-1-piperazinyl]propionamido}-3-methyl-4-oxo-2-phenyl-4H-1-benzopyran;

8-{3-[4-(2-methoxyphenyl)-1-piperazinyl]propylcarbamoyl}-3-phenyl-4-oxo-4H-1-benzopyran;

8-{3-[2-(3,4-dihydro-1, (2H)-naphthalenonyl)methylamino]propylcarbamoyl}-3-methyl-4-oxo-2-phenyl-4H-1-benzopyran;

8-{2-[4-(2-methoxyphenyl)-1-piperazinyl]-ethoxycarbonylmethyl}-3-methyl-4-oxo-2-phenyl-4H-1-benzopyran;

8-{4-[4-(2-methoxyphenyl)-1-piperazinyl]butylsulfamyl}-3-methyl-4-oxo-2-phenyl-4H-1-benzopyran;

8-{N, 2-tetrahydropyranyloxy-3-[4-(2-methoxyphenyl)-1-piperazinyl]-propylcarbamoyl}-3-methyl-4-oxo-2-phenyl-4H-1-benzopyran;

8-{4-[4-(2-methoxyphenyl)-1-piperazinyl]butyramido}-3-methyl-4-oxo-2-phenyl-4H-1-benzopyran;

E-8-{2-[4-(2-methoxyphenyl)-1-piperazinyl]ethoxyiminomethyl}-3-methyl-4-oxo-2-phenyl-4H-1-benzopyran;

8-{N-hydroxy-3-[4-(2-methoxyphenyl)-1-piperazinyl]-propylcarbamoyl}-3-methyl-4-oxo-2-phenyl-4H-1-benzopyran;

E-8-{2-[2-[4-(2-methoxyphenyl)-1-piperazinyl]-ethylcarbamoyl]ethenyl}-3-methyl-4-oxo-2-phenyl-4H-1-benzopyran;

8-{4-[4-(2-methoxyphenyl)-1-piperazinyl]butylsulfinyl}-3-methyl-4-oxo-2-phenyl-4H-1-benzopyran;

8-{3-[3-(2-methoxyphenoxy)propylamino]propylcarbamoyl}-3-methyl-4-oxo-2-phenyl-4H-1-benzopyran;

3-methyl-8-{3-[2-(2-methylthiophenoxy)ethylamino]propyl carbamoyl}-4-oxo-2-phenyl-4H-1-benzopyran;

8-{3-[2-(2,6-dimethoxyphenoxy)ethylamino]propylcarbamoyl}-3-methyl-4-oxo-2-phenyl-4H-1-benzopyran;

8-{3-[4-(5-chloro-2-methoxyphenyl)-1-piperazinyl]propylcarbamoyl}-3-methyl-4-oxo-2-phenyl-4H-1-benzopyran;

(E)-8-{4-[4-(2-methoxyphenyl)-1-piperazinyl]-1-butenyl}-3-methyl-4-oxo-2-phenyl-4H-1-benzopyran;

(E)-8-{2-[2-[4-(2-methoxyphenyl)-1-piperazinyl]ethoxycarbonyl]ethenyl}-3-methyl-4-oxo-2-phenyl-4H-1-benzopyran;

8-{{2-[4-(2-methoxyphenyl)-1-piperazinyl]ethylcarbamoyl}methyl}-4-oxo-2-phenyl-4H-1-benzopyran;

8-{N-acetyl-N,3-[4-(2-methoxyphenyl)-1-piperazinyl]propylcarbamoyl}-3-methyl-4-oxo-2-phenyl-4H-1-benzopyran;

8-{2-[4-(2-methoxyphenyl)-1-piperazinyl]ethylsulfonylamino}-3-methyl-4-oxo-2-phenyl-4H-1-benzopyran;

8-{3-[4-(2-methoxyphenyl)-1-piperazinyl]propylthiocarbamoyl}-3-methyl-4-oxo-2-phenyl-4H-1-benzopyran;

8-{4-[4-(2-methoxyphenyl)-1-piperazinyl]butylsulfonyl}-3-methyl-4-oxo-2-phenyl-4H-1-benzopyran;

3-hydroxymethyl-8-{3-[4-(2-methoxyphenyl)-1-piperazinyl]propylcarbamoyl}-4-oxo-2-phenyl-4H-1-benzopyran;

8-{3-[4-(2-methoxyphenyl)-1-piperazinyl]propylcarbamoyl}-4-oxo-2-phenyl-4H-1-benzopyran;

2,3-dihydro-8-{3-[4-(2-methoxyphenyl)-1-piperazinyl]propylcarbamoyl}-4-oxo-4H-1-benzopyran;

8-{3-[4-(2-methoxyphenyl)-1-piperazinyl]propylcarbamoyl}-4-oxo-4H-1-benzopyran;

6-bromo-8-{3-[4-(2-methoxyphenyl)-1-piperazinyl]propylcarbamoyl}-3-methyl-4-oxo-2-phenyl-4H-1-benzopyran;

6-methoxy-8-{3-[4-(2-methoxyphenyl)-1-piperazinyl]propylcarbamoyl}-3-methyl-4-oxo-2-phenyl-4H-1-benzopyran;

6-hydroxy-8-{3-[4-(2-methoxyphenyl)-1-piperazinyl]propylcarbamoyl}-3-methyl-4-oxo-2-phenyl-4H-1-benzopyran;

3,6-dimethyl-8-{3-[4-(2-methoxyphenyl)-1-piperazinyl]propylcarbamoyl}-4-oxo-2-phenyl-4H-1-benzopyran;

8-{3-[4-(2-methoxyphenyl)-1-piperazinyl]propylcarbamoyl}-3-methyl-6-nitro-4-oxo-2-phenyl-4H-1-benzopyran;

6-amino-8-{3-[4-(2-methoxyphenyl)-1-piperazinyl]propylcarbamoyl}-3-methyl-4-oxo-2-phenyl-4H-1-benzopyran;

6-acetylamino-8-{3-[4-(2-methoxyphenyl)-1-piperazinyl]propylcarbamoyl}-3-methyl-4-oxo-2-phenyl-4H-1-benzopyran;

6-ethylamino-8-{3-[4-(2-methoxyphenyl)-1-piperazinyl]propylcarbamoyl}-3-methyl-4-oxo-2-phenyl-4H-1-benzopyran;

6-dimethylamino-8-{3-[4-(2-methoxyphenyl)-1-piperazinyl]propylcarbamoyl}-3-methyl-4-oxo-2-phenyl-4H-1-benzopyran;

7-methoxy-8-{3-[4-(2-methoxyphenyl)-1-piperazinyl]propylcarbamoyl}-3-methyl-4-oxo-2-phenyl-4H-1-benzopyran;

8-{3-[4-(2-methoxyphenyl)-1-piperazinyl]propylcarbamoyl}-3-methyl-4-oxo-2-(4-trifluoromethylphenyl)-4H-1-benzopyran;

2-(4-benzoylphenyl)-8-{3-[4-(2-methoxyphenyl)-1-piperazinyl]propylcarbamoyl}-3-methyl-4-oxo-4H-1-benzopyran;

8-{3-[4-(2-methoxyphenyl)-1-piperazinyl]propylcarbamoyl}-3-methyl-4-oxo-2-(4-phenoxyphenyl)-4H-1-benzopyran;

2,3-dimethyl-8-{3-[4-(2-methoxyphenyl)-1-piperazinyl]propylcarbamoyl}-4-oxo-4H-1-benzopyran;

2-tert-butyl-8-{3-[4-(2-methoxyphenyl)-1-piperazinyl]propylcarbamoyl}-3-methyl-4-oxo-4H-1-benzopyran;

2-cyclohexyl-8-{3-[4-(2-methoxyphenyl)-1-piperazinyl]propylcarbamoyl}-3-methyl-4-oxo-4H-1-benzopyran;

2-(2-furyl)-8-{3-[4-(2-methoxylphenyl)-1-piperazinyl]propylcarbamoyl}-3-methyl-4-oxo-4H-1-benzopyran;

8-{3-[4-(2-methoxyphenyl)-1-piperazinyl]propylcarbamoyl}-3-methyl-4-oxo-2-thienyl-4H-1-benzopyran;

8-{3-[4-(2-methoxyphenyl)-1-piperazinyl]propylcarbamoyl}-4-oxo-2-phenyl-4H-1-benzothiopyran;

(E)-8-{3-[4-(2-methoxyphenyl)-1-piperazinyl]propylcarbamoyl}-3-methyl-4-oxo-2-(2-phenylethenyl)-4H-1-benzopyran;

8-{3-[4-(2-methoxyphenyl)-1-piperazinyl]propylcarbamoyl}-3-methyl-2-(4-methylphenyl)-4-oxo-4H-1-benzopyran;

2-(4-methoxyphenyl)-8-{3-[4-(2-methoxyphenyl)-1-piperazinyl]propylcarbamoyl}-3-methyl-4-oxo-4H-1-benzopyran;

2-(4-fluorophenyl)-8-{3-[4-(2-methoxyphenyl)-1-piperazinyl]propyl carbamoyl}-3-methyl-4-oxo-4H-1-benzopyran;

8-{3-[4-(2-methoxyphenyl)-1-piperazinyl]-propylcarbamoyl}-3-methyl-6-methanesulfonylamino-4-oxo-2-phenyl-4H-1-benzopyran;

8-{3-[4-(2-methoxyphenyl)-1-piperazinyl]propylcarbamoyl}-3-methyl-2-(4-nitrophenyl)-4-oxo-4H-1-benzopyran;

6-diethoxyphosphonyloxy-8-{3-[4-(2-methoxyphenyl)-1-piperazinyl]propylcarbamoyl}-3-methyl-4-oxo-2-phenyl-4H-1-benzopyran;

8-{3-[4-(2-methoxyphenyl)-1-piperazinyl]propylcarbamoyl}-3-methyl-4-oxo-2-trifluoromethyl-4H-1-benzopyran;

8-{N,3-[4-(2-methoxyphenyl)-1-piperazinyl]propyl-N-methylcarbamoyl}-3-methyl-4-oxo-2-phenyl-4H-1-benzopyran;

2-benzoyl-3-ethyl-7-{3-[4-(2-methoxyphenyl)-1-piperazinyl]propcarbamoyl}benzo[b]furan;

2-(4-biphenylyl)-8-{3-[4-(2-methoxyphenyl)-1-piperazinyl]propylcarbamoyl}-3-methyl-4-oxo-4H-1-benzopyran;

8-{3-[4-(2-methoxyphenyl)-1-piperazinyl]propylcarbamoyl}-3-methyl-4-oxo-2-(3-pyridyl)-4H-1-benzopyran;

8-{3-[4-(2-acetoxyphenyl)-1-piperazinyl]propylcarbamoyl}-3-methyl-4-oxo-2-phenyl-4H-1-benzopyran;

3-methyl-8-{3-[4-(2-methylaminocarbonyloxyphenyl)-1-piperazinyl]propylcarbamoyl}-4-oxo-2-phenyl-4H-1-benzopyran;

6-acetoxy-8-{3-[4-(2-methoxyphenyl)-1-piperazinyl]propylcarbamoyl}-3-methyl-4-oxo-2-phenyl-4H-1-benzopyran;

(R,S)-2,3-dihydro-4-hydroxy-8-{3-[4-(2-methoxyphenyl)-1-piperazinyl]propylcarbamoyl}-4H-1-benzopyran;

2-(4-aminophenyl)-8-{3-[4-(2-methoxyphenyl)-1-piperazinyl]propylcarbamoyl}-3-methyl-4-oxo-4H-1-benzopyran;

2-(4-acetylaminophenyl)-8-{3-[4-(2-methoxyphenyl)-1-piperazinyl]-propylcarbamoyl}-3-methyl-4H-1-benzopyran;

2-(4-hydroxyphenyl)-8-{3-[4-(2-methoxyphenyl)-1-piperazinyl]-propylcarbamoyl}-3-methyl-4H-1-benzopyran;

8-{3-[4-(2-methoxyphenyl)-1-piperazinyl]-propylcarbamoyl}-2-phenyl-4, $N_1$, N4-trioxo-4H-1-benzothiopyran;

7-{3-[4-(2-methoxyphenyl)-1-piperazinyl]propylcarbamoyl}-2-phenylbenzo[b]furan;

8-{3-[4-(2-methoxyphenyl)-1-piperazinyl]propyl-N-methylsulfamoyl}-3-methyl-4-oxo-2-phenyl-4H-1-benzopyran;

8-{3-[4-(2-methoxyphenyl)-1-piperazinyl]butyl-N-methylsulphamoyl}-3-methyl-4-oxo-2-phenyl-4H-1-benzopyran;

2-(4-dimethylaminophenyl)-8-{3-[4-(2-methoxyphenyl)-1-piperazinyl]propylcarbamoyl}-3-methyl-4-oxo-4H-1-benzopyran;

3-benzyloxy-8-{3-[4-(2-methoxyphenyl)-1-piperazinyl]propylcarbamoyl}-4-oxo-2-phenyl-4H-1-benzopyran;

8-{3-[4-(4-hydroxy-2-methoxyphenyl)-1-piperazinyl]propylcarbamoyl}-3-methyl-4-oxo-2-phenyl-4H-1-benzopyran;

8-{3-[2-(8-methoxy-1,4-benzodioxanyl)methylamino]propylcarbamoyl}-3-methyl-4-oxo-2-phenyl-4H-1-benzopyran;

8-{3-[4-(2-methoxyphenyl)-1-piperazinyl]propylcarbamoyl}-2-phenyl-4-thioxo-4H-1-benzopyran;

8-{[2,2-dimethyl-3-(4-(2-methoxyphenyl)-1-piperazinyl)propyl]-carbamoyl}-3-methyl-4-oxo-2-phenyl-4H-1-benzopyran;

8-{3-[4-(2-methoxyphenyl)-1-piperazinyl]propylcarbamoyl}-3-methyl-4-oxo-2-(2-phenylethyl)-4H-1-benzopyran;

8-{3-[4-(2-methoxyphenyl)-1-piperazinyl]propylcarbamoyl}-2-phenyl-1,1,4-trioxo-4H-1-benzothiopyran;

8-{3-[4-(2-methoxyphenyl)-1-piperazinyl]propylcarbamoyl}-3-methyl-4-oxo-2-phenyl-4H-1-benzopyran-$N_1$-oxide;

8-{3-[4-(2-methoxyphenyl)-1-piperazinyl]propylcarbamoyl}-3-methyl-4-oxo-2-phenyl-4H-1-benzopyran $N_1$, $N_4$-dioxide;

8-{3-[4-(5-fluoro-2-methoxyphenyl)-1-piperazinyl]propylcarbamoyl}-3-methyl-4-oxo-2-phenyl-4H-1-benzopyran;

8-{3-[4-(2-methoxyphenyl)-1-piperazinyl]propylcarbamoyl}-2-phenyl-4(1H)-quinolone;

2-(4-cyanophenyl)-8-{3-[4-(2-methoxyphenyl)-1-piperazinyl]propylcarbamoyl}-3-methyl-4-oxo-4H-1-benzopyran;

6-cyano-8-{3-[4-(2-methoxyphenyl)-1-piperazinyl]propylcarbamoyl}-3-methyl-4-oxo-2-phenyl-4H-1-benzopyran;

8-{3-[4-(4-fluoro-2-methoxyphenyl)-1-piperazinyl]propylcarbamoyl}-3-methyl-4-oxo-2-phenyl-4H-1-benzopyran;

8-{3-[4-(3-methoxyphenyl)-1-piperazinyl]-propylcarbamoyl}-3-methyl-4-oxo-2-phenyl-4H-1-benzopyran;

8-{3-[4-(4-methoxyphenyl)-1-piperazinyl]-propylcarbamoyl}-3-methyl-4-oxo-2-phenyl-4H-1-benzopyran;

3-methoxy-8-{3-[4-(2-methoxyphenyl)-1-piperazinyl]propylcarbamoyl}-4-oxo-2-phenyl-4H-1-benzopyran;

3-Hydroxy-8-{3-[4-(2-methoxyphenyl)-1-piperazinyl]propylcarbamoyl}-4-oxo-2-phenyl-4H-1-benzopyran;

2-Cyclohexyl-3,4-dihydro-8-{3-[4-(2-methoxyphenyl)-1-piperazinyl]propylcarbamoyl}-2H-1-benzopyran;

2-benzyl-3-ethyl-7-{3-[4-(2-methoxyphenyl)-1-piperazinyl]propylcarbamoyl}benzo[b]furan;

8-{3-[4-(2-isopropoxyphenyl)-1-piperazinyl]propylcarbamoyl}-3-methyl-4-oxo-2-phenyl-4H-1-benzopyran;

8-{[3-[4-(2-methoxyphenyl)-1-piperazinyl]propylcarbamoyl]-methyl}3-methyl-4-oxo-2-phenyl-4H-1-benzopyran;

8-{3-[4-[5-(1,4-benzodioxanyl)]-1-piperazinyl]propylcarbamoyl}-3-methyl-4-oxo-2-phenyl-4H-1-benzopyran;

3-ethoxymethyl-8-{3-[4-(2-methoxyphenyl)-1-piperazinyl]propylcarbamoyl}-4-oxo-2-phenyl-4H-1-benzopyran;

8-{[3-[4-(2-methoxyphenyl)-1-piperazinyl]propylamino]methyl}-3-methyl-4-oxo-2-phenyl-4H-1-benzopyran;

7-{3-[4-(2-methoxyphenyl)-1-piperazinyl]propylcarbamoyl}-2-(4-nitrophenyl)indole;

8-{3-[4-(5-hydroxy-2-methoxyphenyl)-1-piperazinyl]propylcarbamoyl}-3-methyl-4-oxo-2-phenyl-4H-1-benzopyran;

3-ethyl-8-{3-[4-(2-methoxyphenyl)-1-piperazinyl]propylcarbamoyl}-4-oxo-2-phenyl-4H-1-benzopyran;

8-{3-[4-(2-methoxyphenoxy)-1-piperidinyl]propylcarbamoyl}-3-methyl-4-oxo-2-phenyl-4H-1-benzopyran;

8-{3-[4-(2,3-dihydrobenzo[b]furan-7-yl)-1-piperazinyl]propylcarbamoyl}-3-methyl-4-oxo-2-phenyl-4H-1-benzopyran;

2-(2-biphenylyl)-8-{3-[4-(2-methoxyphenyl)-1-piperazinyl]propylcarbamoyl}-3-methyl-4-oxo-4H-1-benzopyran;

8-{3-[4-(2-methoxyphenyl)-1-piperazinyl]propylcarbamoyl}-3-methyl-2-(1-naphthyl)-4-oxo-4H-1-benzopyran;

3-benzyloxymethyl-8-{3-[4-(2-methoxyphenyl)-1-piperazinyl]propylcarbamoyl}-2-phenyl-4H-1-benzopyran;

3-methyl-8-{3-[4-[2-[(4-morpholinylmethyl)benzoyloxy]phenyl]-1-piperazinyl]propylcarbamoyl}-4-oxo-2-phenyl-4H-1-benzopyran;

8-{2-[4-(2-methoxyphenyl)-1-piperazinyl]ethoxycarbonylamino]-3-methyl-4-oxo-2-phenyl-4H-1-benzopyran;

8-{3-[4-(2-methoxyphenyl)-1-piperazinyl]propylcarbamoyl]-3-methyl-2-(3-nitrophenyl)-4-oxo-4H-1-benzopyran;

8-{3-[4-(2-methoxyphenyl)-1-(1,4-diazepinyl)]propylcarbamoyl}-3-methyl-4-oxo-2-phenyl-4H-1-benzopyran;

2-cyclohexyl-3,4-dihydro-4-hydroxy-8-{3-[4-(2-methoxyphenyl)-1-piperazinyl]propylcarbamoyl}-2H-1-benzopyran;

3,4-dihydro-4-hydroxy-8-{3-[4-(2-methoxyphenyl)1-piperazinyl]propylcarbamoyl}-2-phenyl-2H-1-benzopyran;

2-(1-adamantyl)-8-{3-[4-(2-methoxyphenyl)-1-piperazinyl]propylcarbamoyl}-3-methyl-4-oxo-4H-1-benzopyran;

8-{5-[4-(2-methoxyphenyl)-1-piperazinyl]pentylsulfonyl}-3-methyl-4-oxo-2-phenyl-4H-1-benzopyran;

8-{3-[4-(2-methoxyphenyl)-1-piperazinyl]propylcarbamoyl}-3-methyl-4-oxo-2-(3,4,5-triiodophenyl)-4H-1-benzopyran;

2-cyclopropyl-8-{3-[4-(2-methoxyphenyl)-1-piperazinyl]propylcarbamoyl}-3-methyl-4-oxo-4H-1-benzopyran;

8-{5-[4-(2-methoxyphenyl)-1-piperazinyl]pentyl}-3-methyl-4-oxo-2-phenyl-4H-1-benzopyran;

8-{3-[4-(2-methoxyphenyl)-1-piperazinyl]propylcarbamoyl}-3-methyl-2-(4-methylcyclohexyl)-4-oxo-4H-1-benzopyran;

2-cyclopentyl-8-{3-[4-(2-methoxyphenyl)-1-piperazinyl]propylcarbamoyl}-3-methyl-4-oxo-4H-1-benzopyran;

8-{3-[4-(2-methoxyphenyl)-1-piperazinyl]propylcarbamoyl}-3-methyl-2-(1-phenylcyclopentyl)-4-oxo-4H-1-benzopyran;

8-{3-[4-(2-methoxyphenyl)-1-piperazinyl]propylcarbamoyl}-3-methyl-2-(1-methylcyclohexyl)-4-oxo-4H-1-benzopyran;

2-(bicyclo[2.2.1]hept-5-en-2-yl)-8-{3-[4-(2-methoxyphenyl)-1-piperazinyl]propylcarbamoyl}-3-methyl-4-oxo-4H-1-benzopyran, mixture of endo-exo isomers;

2-(bicyclo[2.2.1]hept-5-en-2-yl)-8-{3-[4-(2-methoxyphenyl)-1-piperazinyl]propylcarbamoyl}-3-methyl-4-oxo-4H-1-benzopyran, endo isomer;

2-(bicyclo[2.2.1]hept-5-en-2-yl)-8-{3-[4-(2-methoxyphenyl)-1-piperazinyl]propylcarbamoyl}-3-methyl-4-oxo-4H-1-benzopyran, exo isomer;

2-(bicyclo[2.2.1]heptan-2-yl)-8-{3-[4-(2-methoxyphenyl)-1-piperazinyl]propylcarbamoyl}-3-methyl-4-oxo-4H-1-benzopyran, mixture of endo-exo isomers;

2-(bicyclo[2.2.1]heptan-2-yl)-8-{3-[4-(2-methoxyphenyl)-1-piperazinyl]propylcarbamoyl}-3-methyl-4-oxo-4H-1-benzopyran, exo isomer;

2-cycloheptyl-8-{3-[4-(2-methoxyphenyl)-1-piperazinyl]-propylcarbamoyl}-3-methyl-4-oxo-4H-1-benzopyran;

8-[3-[4-(2-methoxyphenyl)-1-piperazinyl]propylcarbamoyl]-1-methyl-2-phenyl-1,2,3,4-tetrahydroquinoline;

(trans)-2-(4-methoxycyclohexyl)-8-{3-[4-(2-methoxyphenyl)-1-piperazinyl]propylcarbamoyl}-3-methyl-4-oxo-4H-1-benzopyran;

(cis)-2-(4-methoxycyclohexyl)-8-{3-[4-(2-methoxyphenyl)-1-piperazinyl]propylcarbamoyl}-3-methyl-4-oxo-4H-1-benzopyran;

8-{3-[4-(7-benzofuranyl)-1-piperazinyl]propylcarbamoyl}-3-methyl-4-oxo-2-phenyl-4H-1-benzopyran;

8-{3-[4-(2-chlorophenyl)-1-piperazinyl]propylcarbamoyl}-3-methyl-4-oxo-2-phenyl-4H-1-benzopyran;

8-{3-[4-(4-chlorophenyl)-1-piperazinyl]propylcarbamoyl}-3-methyl-4-oxo-2-phenyl-4H-1-benzopyran; or a pharmaceutically acceptable salt thereof.

13. A pharmaceutical composition comprising the compound of claim 1 or pharmaceutically acceptable salt thereof and a pharmaceutically acceptable diluent or carrier.

14. A pharmaceutical composition comprising the compound of claim 12 or an enantiomer, a diastereomer, an N-oxide, a prodrug, a metabolite, a prodrug of a metabolite, or a pharmaceutically acceptable salt of said compound and a pharmaceutically acceptable diluent or carrier.

15. A compound according to claim 1, having α1 adrenergic activity.

16. A compound according to claim 1, having 5-HT$_{1A}$ serotonergic activity.

17. A compound according to claim 1 wherein B is

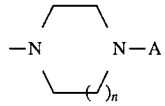

wherein n is 1 or 2, and A represents a phenyl group; wherein said phenyl group is unsubstituted or substituted by one or more substituents selected from the group consisting of alkoxy, alkyl, halogen, and hydroxy, or A represents a 2-pyrimidinyl group or a bicyclic ring of formula

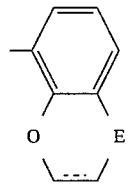

where ---- represents a single or double bond and E represents an oxygen atom or a bond.

18. A compound according to claim 1 wherein B is

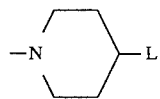

wherein L represents one or two groups selected among phenyl, 4-fluorobenzoyl or a 2-oxo-1-benzimidozolinyl group or a group of the formula (CH$_2$)$_n$-O-A wherein n=0, 1, or 2.

19. A compound according to claim 1 wherein B is

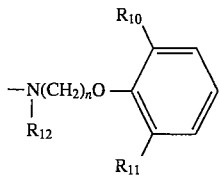

and each of $R_{10}$ and $R_{11}$ independently represents a hydrogen atom or an alkoxy or alkylthio group, $R_{12}$ represents a hydrogen atom or an alkyl group and n is 2 or 3.

20. A compound according to claim 1 wherein B is

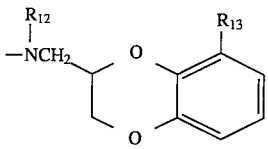

and $R_{13}$ represents a hydrogen atom or a alkoxy group.

21. A compound according to claim 1 wherein B is

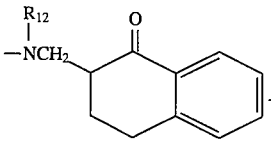

22. A compound according to claim 1 which is selected from the group consisting of:

8-[3-[4-(5-chloro-2-methoxyphenyl)-1-piperazinyl]propylcarbamoyl]-2-cyclohexyl-3-methyl-4-oxo-4H-1-benzopyran;

2-(4-chlorophenyl)-8-[3-[4-(2-methoxyphenyl)-1-piperazinyl]propylcarbamoyl]-3-methyl-4-oxo-4H-1-benzopyran;

2-(4-ethylaminophenyl)-8-[3-[4-(2-methoxyphenyl)-1-piperazinyl]propylcarbamoyl]-3-methyl-4-oxo-4H-1-benzopyran;

2-(4-methansulfonylaminophenyl)-8-[3-[4-(2-methoxyphenyl)-1-piperazinyl]propylcarbamoyl]-3-methyl-4-oxo-4H-1-benzopyran;

8-[3-[4-(5-chloro-2-methoxyphenyl)-1-piperazinyl]propylcarbamoyl]-2-(4-chlorophenyl)-3-methyl-4-oxo-4H-1-benzopyran;

2-(t-butyl)-7-[3-[4-(2-methoxyphenyl)-1-piperazinyl] propylcarbamoyl]benzofuran;

2-(t-butyl)-7-[3-[4-(5-chloro-2-methoxyphenyl)-1-piperazinyl]propylcarbamoyl]benzofuran;

8-[3-[4-[5-chloro-2-(1-methylethoxy)phenyl]-1-piperazinyl]propylcarbamoyl]-3-methyl-4-oxo-2-phenyl-4H-1-benzopyran;

8-[3-[4-(5-chloro-2-hydroxyphenyl)-1-piperazinyl]propylcarbamoyl]-3-methyl-4-oxo-2-phenyl-4-1-benzopyran;

8-[3-[4-(2,5-dimethoxyphenyl)-1-piperazinyl]propylcarbamoyl]-3-methyl-4-oxo-2-phenyl-4H-1-benzopyran;

8-[3-[4-(2-methoxyphenyl)-1-piperazinyl]propylcarbamoyl]-3-methyl-4-oxo-2-pentafluoroethyl-4H-1-benzopyran; and (cis)-2-(4-hydroxycyclohexyl)-8-[3-[4-(2-methoxyphenyl)-1-piperazinyl]propylcarbamoyl]-3-methyl-4-oxo-4H-1-benzopyran.

23. A compound according to claim 3, wherein ---- represents a double bond, W represents a carbonyl group, X represents an oxygen atom, Y represents —CONH—, Z is propyl, B is B1, n is 1, $R_2$ represents a phenyl group or a cycloalkyl group, $R_3$ represents a methyl group, $R_6$ represents a hydrogen atom, $R_7$ represents a hydrogen atom and A is a phenyl group substituted with a methoxy group and optionally a halogen.

24. A compound according to claim 23, which is selected from the group consisting of:

8-{3-[4-(5-chloro-2-methoxyphenyl)-1-piperazinyl]propylcarbamoyl}-3-methyl-4-oxo-2-phenyl-4H-1-benzopyran;

2-cyclohexyl-8-{3-[4-(2-methoxyphenyl)-1-piperazinyl] propylcarbamoyl}-3-methyl-4-oxo-4H-1-benzopyran; and 8-[3-[4-(5-chloro-2-methoxyphenyl)-1-piperazinyl]propylcarbamoyl]-2-cyclohexyl-3-methyl-4-oxo-4H-1-benzopyran.

* * * * *

UNITED STATES PATENT AND TRADEMARK OFFICE
CERTIFICATE OF CORRECTION

PATENT NO. : 5,605,896
DATED : February 25, 1997
INVENTOR(S) : Amedeo LEONARDI et al.

It is certified that error appears in the above-identified patent and that said Letters Patent is hereby corrected as shown below:

On the title page, item [30], add the following:

--Feb. 22, 1993  [EPO]  European Pat. Off. ..... EP 93 301 264.3--.

Signed and Sealed this

Twenty-seventh Day of October, 1998

Attest:

BRUCE LEHMAN

*Attesting Officer*  *Commissioner of Patents and Trademarks*